United States Patent
Hachtel et al.

(10) Patent No.: US 8,283,479 B2
(45) Date of Patent: Oct. 9, 2012

(54) CXCR2 INHIBITORS

(75) Inventors: Stephanie Hachtel, Frankfurt (DE); Juergen Dedio, Mainz-Kastel (DE); Holger Heitsch, Mainz-Kastel (DE); Werngard Czechtizky, Frankfurt (DE); Sven Grueneberg, Kelkheim (DE); Stephen J. Shimshock, Hillsborough, NJ (US); Raymond W. Kosley, Jr., Bridgewater, NJ (US); Carolina L. Lanter, Audubon, PA (US); Hui Li, Neshanic Station, NJ (US); Rosy Sher, Bridgewater, NJ (US); Aleksandra Weichsel, Tucson, AZ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/079,522

(22) Filed: Apr. 4, 2011

(65) Prior Publication Data

US 2011/0184177 A1 Jul. 28, 2011

Related U.S. Application Data

(60) Division of application No. 11/771,958, filed on Jun. 29, 2007, now Pat. No. 7,919,628, which is a continuation of application No. PCT/EP2005/013624, filed on Dec. 17, 2005.

(30) Foreign Application Priority Data

Dec. 30, 2004 (EP) .................................... 04031009

(51) Int. Cl.
*C07D 333/66* (2006.01)
*C07D 409/12* (2006.01)
*A61K 31/44* (2006.01)
(52) U.S. Cl. ..................... 549/55; 546/281.1; 514/338
(58) Field of Classification Search ................ 549/55; 546/281.1; 514/338
See application file for complete search history.

(56) References Cited

U.S. PATENT DOCUMENTS

| | | | |
|---|---|---|---|
| 4,962,224 A | 10/1990 | Wrobel et al. | |
| 4,994,477 A | 2/1991 | Kempf et al. | |
| 7,919,628 B2 | 4/2011 | Hachtel et al. | |
| 2002/0123522 A1 | 9/2002 | Fritz et al. | |
| 2004/0204417 A1 | 10/2004 | Perez et al. | |
| 2005/0059705 A1 | 3/2005 | Mjalli et al. | |
| 2008/0090854 A1 | 4/2008 | Hachtel et al. | |

FOREIGN PATENT DOCUMENTS

| | | |
|---|---|---|
| EP | 1 676 834 A1 | 7/2006 |
| FR | 2 825 706 A1 | 12/2002 |
| WO | WO 99/07351 | 2/1999 |
| WO | WO 01/58852 A2 | 4/2001 |
| WO | WO 2004/108681 A1 | 12/2004 |
| WO | WO 2005/023818 A2 | 3/2005 |
| WO | WO 2005/033102 A2 | 4/2005 |
| WO | WO 2005/051940 A2 | 6/2005 |
| WO | WO 2005/070906 A1 | 8/2005 |
| WO | WO 2006/040646 A1 | 4/2006 |
| WO | WO 2006/052722 A1 | 5/2006 |
| WO | WO 2006/099610 A2 | 9/2006 |

OTHER PUBLICATIONS

Kubinyi (3D QSAR in Drug Design: Ligand-Protein Interactions and Molecular Similarity, vol. 2-3, Springer, 1998, 800 pages).*
Wermuth, The Practice of Medicinal Chemsitry, 2d ed. (2003), 768 pages. Chapters 9-10 provided.*
Boschelli et al. (J. Med. Chem., vol. 38, p. 4597-4614 (1995).*
Boschelli D. et al., "Inhibition of E-Selectin-ICAM-1-, and VCAM-1-Mediated Cell Adhesion by Benzo(b)Thiophene-, Benzofuran-, Indole-, and Naphthalene-2-Carboxamides: Identification of PD 144795 as a Antiinflammatory Agent", *Journal of Medicinal Chemistry* 38:4597-4614 (1995), XP002286757.
CAPLUS Abstract of: Jodlbauer et al., *J. Chromatography, A 945* (1-2):45-63 (2002).
Kubinyi (3D QSAR in Drug Design: Ligand-Protein Interactions and Molecular Similarity, *Springer 2-3*:243-244 (1998).
Final Official Action dated May 7, 2010 received in U.S. Appl. No. 11/771,958.
Official Action dated Mar. 27, 2009 received in U.S. Appl. No. 11/771,958.
International Search Report dated Mar. 29, 2006 received from the European Patent Office issued in corresponding International Application No. PCT/EP2005/013624.
International Search Report dated Oct. 2, 2007 corresponding to International Application No. PCT/EP2007/005576 from related U.S. Appl. No. 12/337,040.
PCT International Publication No. WO 2005/023818 A2, published March 17, 2005.
European Patent Application No. EP 1 676 834 A1, dated Jul. 5, 2006.
French Patent Application No. 2 825 706 Al, dated Dec. 13, 2002.
PCT International Publication No. WO 2004/108681 A1, published Dec. 16, 2004.

(Continued)

*Primary Examiner* — Robert Havlin
(74) *Attorney, Agent, or Firm* — Scully, Scott, Murphy & Presser, P.C.

(57) ABSTRACT

The invention relates to compounds of the formula I:

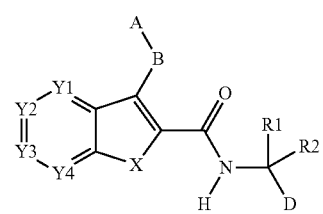

in which R1, R2, X, A, B, D and Y1 to Y4 have the meanings indicated in the claims, and/or a pharmaceutically acceptable salt and/or a prodrug thereof. Because of their properties as inhibitors of chemokine receptors, especially as CXCR2 inhibitors, the compounds of the formula I and the pharmaceutically acceptable salts and prodrugs thereof are suitable for the prevention and treatment of chemokine mediated diseases.

2 Claims, No Drawings

OTHER PUBLICATIONS

PCT International Publication No. WO 01/58852 A2, published Aug. 16, 2001.
U.S. Office Action dated Jan. 12, 2012 received in related U.S. Appl. No. 12/337,040.
PCT International Publication No. WO 2006/099610 A2, published Sep. 21, 2006.
PCT International Publication No. WO 2005/033102 A2, published Apr. 14, 2005.
PCT International Publication No. WO 2005/051940 A2, published Jun. 9, 2005.
PCT International Publication No. WO 2005/070906 A1, published Aug. 4, 2005.
PCT International Publication No. WO 2006/040646 A1, published Apr. 20, 2006.
PCT International Publication No. WO 2006/052722 A1, published May 18, 2006.
U.S. Office Action dated Sep. 26, 2011 received in related U.S. Appl. No. 12/337,040.
Van den Eynde et al., Database Caplus Chemical Abstracts Service, Columbus, Ohio, US; Database Accession No. 1972:47393, Abstract, DE 2108189, Sep. 9, 1971.
International Search Report dated Sep. 14, 2007 corresponding to International Application No. PCT/EP2007/005574 from related U.S. Appl. No. 12/337,107.
U.S. Final Office Action dated Feb. 29, 2012 received in related U.S. Appl. No. 12/337,107.
Huff J.R., "HIV Protease: A Novel Chemotherapeutic Target for AIDS", *Journal of Medicinal Chemistry*, 34(8):2305-2314 (Aug. 1991).
The Merck Manual of Diagnosis and Therapy (16$^{th}$ Ed., pp. 52-55) (1999).
Johnson J. et al., "Relationships Between Drug Activity in NCI Preclinical In Vitro and In Vivo Models and Early Clinical Trials", *British Journal of Cancer*, 84(10):1424-1431 (2001).
Lala P.K. et al., "Role of Nitric Oxide in Tumor Progression: Lessons from Experimental Tumors", *Cancer and Metastasis Reviews*, 17:91-106 (1998).
Sausville E.A. et al., "Contributions of Human Tumor Xenografts to Anticancer Drug Development", *Cancer Research* 66(7):3351-3354 (Apr. 1, 2006).
Golub T.R. et al., "Molecular Classification of Cancer: Class Discovery and Class Prediction by Gene Expression Monitoring", *Science*, 286:531-537 (1999).
U.S. Office Action dated Jul. 12, 2011 received in related U.S. Appl. No. 12/337,107.
International Search Report dated Sep. 3, 2007 corresponding to International Application No. PCT/EP2007/005575 from related U.S. Appl. No. 12/337,970.
U.S. Final Office Action dated Feb. 8, 2012 received in related U.S. Appl. No. 12/337,970.
U.S. Office Action dated Sep. 15, 2011 received in related U.S. Appl. No. 12/337,970.
International Search Report dated Sep. 3, 2007 corresponding to International Application No. PCT/EP2007/005577 from related U.S. Appl. No. 12/337,980.
U.S. Final Office Action dated Mar. 22, 2012 received in related U.S. Appl. No. 12/337,980.
U.S. Office Action dated Nov. 2, 2011 received in related U.S. Appl. No. 12/337,980.

* cited by examiner

CXCR2 INHIBITORS

CROSS REFERENCE TO RELATED APPLICATIONS

This application is a divisional of copending application Ser. No. 11/771,958 filed Jun. 29, 2007, which is a continuation of International Application Serial No. PCT/EP05/13624 filed Dec. 17, 2005, which claims benefit of European Patent Application No. 04031009.6 filed Dec. 30, 2004, the entire contents of which are incorporated herein by reference.

FIELD OF THE INVENTION

The present invention is directed to novel compounds represented by the formula I and pharmaceutically acceptable salts, solvates, isomers or prodrugs thereof, which are inhibitors of chemokine receptors, in particular of CXC-chemokine receptors, more particular of CXCR2, and therefore useful for the prevention and treatment of chemokine mediated diseases.

BACKGROUND OF THE INVENTION

Chemokines are a family of low molecular weight proteins (8-13 kDa) that are classified into four distinct groups depending on the positioning of the cysteine motif at the amino terminus. The family members comprise CXC, CC, XC, and CX3C chemokines of which CXC and CC are the largest and most characterized. The CXC chemokines include interleukin-8 (IL-8), neutrophil-activating protein-2 (NAP-2), growth-related oncogenes GRO-α, GRO-β, GRO-γ, epithelial cell-derived neutrophil activating factor-78 (ENA-78), granulocyte chemoattractant protein-2 (GCP-2), γ-interferon-inducible protein-10 (γIP-10), interferon-inducible T cell α-chemoattractant (I-TAC), monokine induced by γ-interferon (Mig) and platelet factor-4 (PF-4). CC chemokines include RANTES (regulated on activation normal T cell expressed and secreted), macrophage inflammatory proteins MIP-1α, MIP-1β, monocyte chemoattractant proteins MCP-1, MCP-2, MCP-3 and eotaxin. The XC family comprises two members, lymphotactin-α and lymphotactin-β, and the CX3C family consists only of a single chemokine named fractalkine (Murphy et al., Pharmacol. Rev. 52: 145-176, 2000).

Chemokines mediate their biological effects by binding to cell surface molecules, which belong to the superfamily of seven-transmembrane spanning receptors that signal through coupling to heterotrimeric G proteins. Although most chemokine receptors recognize more than one chemokine, they are almost always restricted to a single subclass. Chemokine receptor binding initiates a cascade of intracellular events of which the first step is the binding of the receptor by its high-affinity ligand. This induces a conformational change leading to a dissociation of the receptor-associated heterotrimeric G proteins into α and βγ subunits. These G protein subunits are able to activate various effector proteins, including phospholipases leading to generation of inositol trisphosphate, an increase in cytosolic calcium, and activation of protein kinases. This cascade of intracellular events mediates a wide range of functions in different leukocytes such as chemotaxis, degranulation, oxidative burst, phagocytosis, and lipid mediator synthesis.

Interleukin-8 (IL-8) is a key mediator of immunological reactions in inflammatory disorders such as atherosclerosis, ischemia/reperfusion injury, rheumatoid arthritis, chronic obstructive pulmonary disease, respiratory distress syndrome, asthma, cystic fibrosis, and psoriasis (Bizarri et al., Curr. Med. Chem. 2: 67-79, 2003). IL-8 is the most characterized member of the CXC subfamily of chemokines. Leukocyte responses to IL-8 are mediated via specific cell surface receptors, CXCR1 and CXCR2. Whereas CXCR1 is selectively activated by IL-8, CXCR2 responds to several additional chemokines including growth-related oncogenes GRO-α, GRO-β, GRO-γ, neutrophil-activating protein-2 (NAP-2), epithelial cell-derived neutrophil activating factor-78 (ENA-78), and granulocyte chemoattractant protein-2 (GCP-2). The common denominator shared by all chemokines that activate CXCR2 is a Glu-Leu-Arg (ELR) sequence in the amino terminus, which appears to serve as a recognition sequence for receptor binding and activation (Herbert et al., J. Biol. Chem. 266: 18989-18994, 1991).

Early investigations concentrated on the effect of IL-8 on neutrophils, which respond to IL-8 with calcium mobilization, actin polymerization, enzyme release, chemotaxis, and the respiratory burst. Despite similar affinities for IL-8 and similar receptor numbers of CXCR1 and CXCR2 on neutrophils, both receptors are functionally different. Responses such as calcium mobilization and the release of granule enzymes are mediated through both receptors, whereas the respiratory burst and the activation of phospholipase D depend exclusively on stimulation of CXCR1 (Jones et al., Proc. Natl. Acad. Sci. USA 93: 6682-6686, 1996). Due to their prominent role in neutrophil recruitment, CXCR1 and CXCR2 are thought to be important in several acute neutrophil-mediated diseases such as acute respiratory distress syndrome and ischemia/reperfusion injuries, as well as in chronic diseases such as asthma, psoriasis, dermatitis, and arthritis.

It has been shown that CXCR2 is also expressed by monocytes. Despite IL-8's inactivity in monocyte chemotaxis assay, this factor induces calcium flux and respiratory burst in monocytes and enhances adhesion of monocytes in static assays. Similarly, GRO-α enhances adhesion of monocytes to stimulated endothelial cells. Moreover, IL-8 is able to induce firm arrest of monocytes on endothelial cells under conditions of physiological flow (Gerszten et al., Nature 398: 718-723, 1999). Since CXCR2 is strongly expressed on monocytes and macrophages in atherosclerotic lesions where it is suggested to play a key role in chemoattraction, retension, expansion, and activation of monocytes and macrophages, this strongly suggests that CXCR2 and one or more of its ligands (IL-8, GRO-α) play a pathophysiological role in atherosclerosis (Huo et al., J. Clin. Invest. 108: 1307-1314, 2001).

Apart from neutrophils and monocytes, numerous cell types have been shown to express IL-8 receptors. These cell types include neurons, various cancer cells, keratinocytes, and endothelial cells. Several lines of evidence indicate that IL-8 plays a direct role in angiogenesis via stimulation of CXCR2 expressed on endothelial cells. IL-8 has been shown to bind specifically to endothelial cells and induce chemotaxis. IL-8 is able to induce neovascularization in the absence of inflammatory responses (Koche et al., Science 258: 1798-1801, 1992). Moreover, there is accumulating evidence that IL-8 could play a key role in melanoma progression and metastasis as patients with melanoma metastases have elevated serum levels of IL-8. IL-8 is supposed to act as an autocrine growth and metastatic factor for melanoma cells (Schadendorf et al., J. Immunol: 151-157, 1993).

Due to the wide range of actions of IL-8, such as attraction and activation of neutrophils and monocytes/macrophages as well as promotion of endothelial cell proliferation and cancer cell growth, the inhibition of chemokine receptors CXCR1 and CXCR2 is expected to be beneficial in the prevention and treatment of numerous diseases. Besides acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases include adult respiratory distress syndrome, inflammatory bowel disease, ulcerative colitis, Crohn's disease, atopic dermatitis, cystic fibrosis, psoriasis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

SUMMARY OF THE INVENTION

The invention provides novel compounds represented by the formula I and pharmaceutically acceptable salts, solvates, isomers or prodrugs thereof, which are inhibitors of chemokine receptors, in particular of CXC-chemokine receptors, more particular of CXCR2, and therefore useful for the prevention and treatment of chemokine mediated diseases.

DETAILED DESCRIPTION OF THE INVENTION

The invention relates to a compound of formula I

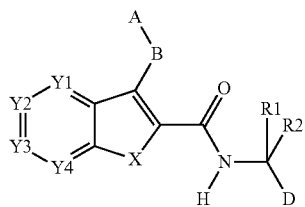

I wherein
X is —CR3=CR4-, —CR5=N—, —N=CR6-, —NR7- or —S—;
R3, R4, R5 and R6
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, NO$_2$, NR27R28, C(O)R29, C(O)NR30R31, S(O)$_o$R32, S(O)$_p$NR33R34, aryl, heteroaryl, arylalkyl with alkyl having 1, 2, 3 or 4 carbon atoms or heteroarylalkyl with alkyl having 1, 2, 3 or 4 carbon atoms;
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34
are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl;
o and p
are, independently of one another, 1 or 2;
R7 is hydrogen, alkyl having 1, 2, 3 or 4 carbon atoms or C(O)R35;
R35 is hydrogen, alkyl with 1, 2, 3 or 4 carbon atoms or aryl;
Y1, Y2, Y3 and Y4
are, independently of one another, —CR8- or Nitrogen, with the proviso that at least two of Y1, Y2, Y3 and Y4 are defined as —CR8-;
R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, NO$_2$, NR36R37, C(O)R38, C(O)NR39R40, S(O)$_q$R41, S(O)$_r$NR42R43, aryl, heteroaryl, arylalkyl with alkyl having 1, 2, 3 or 4 carbon atoms or heteroarylalkyl with alkyl having 1, 2, 3 or 4 carbon atoms;
R36 is hydrogen or alkyl having 1, 2, 3 or 4 carbon atoms
R37 is hydrogen, alkyl having 1, 2, 3 or 4 carbon atoms, aryl, C(O)H, C(O)alkyl with alkyl having 1, 2, 3 or 4 carbon atoms or C(O)aryl;
R38 is hydrogen, OH, alkyl with 1,2,3 or 4 carbon atoms, alkoxy with 1, 2, 3 or 4 carbon atoms or aryl;
R39, R40, R42 and R43
are, independently of one another, hydrogen, alkyl having 1, 2, 3 or 4 carbon atoms or aryl;
R41 is OH, alkyl having 1, 2, 3 or 4 carbon atoms, alkoxy with 1, 2, 3 or 4 carbon atoms or aryl;
q and r
are, independently of one another, 1 or 2;
A is cycloalkyl having 3, 4, 5, 6, 7 or 8 carbon atoms, heterocycle, aryl or heteroaryl;
in which the cycloalkyl or heterocycle radical can be condensed to an aryl or heteroaryl radical and in which the cycloalkyl or heterocycle radical and the optionally condensed aryl or heteroaryl radical are unsubstituted or substituted by 1, 2, 3 or 4 radicals selected from the group consisting of F, Cl, Br, I, OH, CN, NO$_2$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, S(O)$_s$R47, S(O)$_t$NR48R49, —(CH$_2$)$_k$-aryl or —(CH$_2$)$_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a$—$(CH_2)_b$—$(CF_2)_c$—$CF_3$;

R9 is hydrogen or alkyl having 1, 2, 3 or 4 carbon atoms

R10 is hydrogen, alkyl having 1, 2, 3 or 4 carbon atoms, aryl, C(O)H, C(O)alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49
are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

a is zero or 1;

b, c, k and l
are, independently of one another, zero, 1, 2 or 3;

s and t
are, independently of one another, 1 or 2;

in which the aryl or heteroaryl radical can be condensed to an cycloalkyl or heterocycle radical and in which the aryl or heteroaryl radical and the optionally condensed cycloalkyl or heterocycle radical are unsubstituted or substituted by 1, 2, 3 or 4 radicals selected from the group consisting of F, Cl, Br, I, OH, CN, $NO_2$, SF5, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, $S(O)_sR47$, $S(O)_tNR48R49$, —$(CH_2)_k$-aryl or —$(CH_2)_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a$—$(CH_2)_b$—$(CF_2)_c$—$CF_3$;

R9 is hydrogen or alkyl having 1, 2, 3 or 4 carbon atoms

R10 is hydrogen, alkyl having 1, 2, 3 or 4 carbon atoms, aryl, C(O)H, C(O)alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49
are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

a is zero or 1;

b, c, k and l
are, independently of one another, zero, 1, 2 or 3;

s and t
are, independently of one another, 1 or 2;

B is —O—C(R11R12)-, —C(R50R51)-O—, —C≡C—, —CR52=CR53-, —C(R13R14)-C(R15R16)-, —NR17—C(R18R19)-, —C(R54R55)-NR56-, —NR20-C(O)— or —C(O)—NR57-;

R11, R12, R13, R14, R15, R16, R17, R18, R19, R20, R50, R51, R52, R53, R54, R55, R56 and R57 are, independently of one another, hydrogen or alkyl having 1, 2, 3 or 4 carbon atoms, in which 1, 2, 3, 4, 5, 6, 7, 8 or 9 hydrogen atoms may be substituted by fluorine atoms;

D is C(O)OH, C(O)NHR21 or C(=NR58)NHR22;

R21 and R22
are, independently of one another, hydrogen, —$SO_2$-alkyl having 1, 2, 3 or 4 carbon atoms, —$SO_2$-aryl, —C(O)-alkyl with alkyl having 1, 2, 3 or 4 carbon atoms, —C(O)-aryl, —C(O)OR23, —C(O)NR24R25 or —CN, R23 is alkyl having 1,2,3 or 4 carbon atoms or aryl, R24 and R25
are, independently of one another, hydrogen, alkyl having 1, 2, 3 or 4 carbon atoms or aryl;

R58 is hydrogen, OH, CN, alkyl having 1, 2, 3 or 4 carbon atoms or alkoxy having 1, 2, 3 or 4 carbon atoms or aryl;

R1 and R2
are, independently of one another, alkyl having 1, 2, 3, 4, 5 or 6 carbon atoms;
in which the alkyl radicals are unsubstituted or substituted by 1, 2 or 3 radicals selected from the group consisting of F, Cl, Br, I, —SH, —S— alkyl having 1, 2, 3 or 4 carbon atoms, —C(O)OH, —C(O)$NH_2$, NH2, —NH—C(=NH)$NH_2$ or —$O_m$—$(CH_2)_n$—R26;

m is zero or 1;

n is zero, 1, 2 or 3;

R26 is hydrogen, aryl or heteroaryl, in which the aryl or heteroaryl radical is unsubstituted or substituted by F, Cl, Br, I, OH or alkyl having 1, 2, 3 or 4 carbon atoms;

or

R1 and R2
form, together with the carbon atom to which they are attached, a 3-, 4-, 5- or 6-membered carbon ring, in which the formed carbon ring can be condensed to an aryl or heteroaryl radical;
wherein the formed carbon ring and the condensed aryl or heteroaryl radical can be unsubstituted or substituted by 1, 2 or 3 radicals selected form the group consisting of F, Cl, Br, I or alkyl having 1, 2, 3 or 4 carbon atoms;

and/or a pharmaceutically acceptable salt and/or a prodrug thereof.

Preference is given to a compound of the formula I, in which:

X is —CR3=CR4-, —CR5=N—, —N=CR6-, —NR7- or —S—;

R3, R4, R5 and R6
are, independently of one another, hydrogen, F, Cl, Br, I, alkyl having 1, 2, 3 or 4 carbon atoms or alkoxy having 1, 2, 3 or 4 carbon atoms;

R7 is hydrogen or alkyl having 1, 2, 3 or 4 carbon atoms;

Y1, Y2, Y3 and Y4
are, independently of one another, —CR8- or Nitrogen, with the proviso that at least two of Y1, Y2, Y3 and Y4 are defined as —CR8-;

R8 is hydrogen, F, Cl, Br, I or alkyl having 1, 2, 3 or 4 carbon atoms;

A is cycloalkyl having 3, 4, 5, 6, 7 or 8 carbon atoms, heterocycle, aryl or heteroaryl;
in which the cycloalkyl or heterocycle radical can be condensed to an aryl radical and in which the cycloalkyl or heterocycle radical is unsubstituted or substituted by 1, 2 or 3 radicals selected from the group consisting of F, Cl, Br, I or alkyl having 1, 2, 3 or 4 carbon atoms, —C(O)-alkyl having 1, 2, 3 or 4 carbon atoms, —C(O)-cycloalkyl having 3, 4, 5 or 6 carbon atoms or —C(O)O-alkyl having 1, 2, 3 or 4 carbon atoms;
in which the aryl or heteroaryl radical can be condensed to an cycloalkyl or heterocycle radical and in which the aryl or heteroaryl radical is unsubstituted or substituted by 1, 2, 3 or 4 radicals selected from the group consisting of F, Cl, Br, I, CN, $NO_2$, $SF_5$, —NR9R10, alkoxy having 1, 2, 3 or 4 carbon atoms, alkyl having 1, 2, 3, 4, 5 or 6 carbon atoms, —$O_a$—$(CH_2)_b$—$(CF_2)_c$—$CF_3$, —$O_d$—$CHF_2$, —$O_e$—$CH_2F$, —$SO_f$-alkyl having 1, 2, 3 or 4 carbon atoms, S—$(CH_2)_g$—$(CF_2)_h$—$CF_3$, —$(CH_2)_k$-aryl or —$(CH_2)_l$-heteroaryl, in which the aryl and heteroaryl radicals can be substituted by F, Cl, Br, I, $CF_3$, alkoxy having 1, 2, 3 or 4 carbon atoms or alkyl having 1, 2, 3 or 4 carbon atoms;
R9 and R10
are, independently of one another, hydrogen or alkyl having 1, 2, 3 or 4 carbon atoms;
a, d and e
are, independently of one another, zero or 1;
b, c, g, h, k and l
are, independently of one another, zero, 1, 2 or 3;
f is zero, 1 or 2;
B is —O—(CR11R12)-, —C≡C—, —C(R13R14)-C(R15R16)-, —NR17-C(R18R19)- or —NR20C(O)—;
R11, R12, R13, R14, R15, R16, R17, R18, R19 and R20
are, independently of one another, hydrogen or alkyl having 1, 2, 3 or 4 carbon atoms;
D is C(O)OH, C(O)NHR21 or C(N—OH)NHR22;
R21 and R22
are, independently of one another, hydrogen, —$SO_2$-alkyl having 1, 2, 3 or 4 carbon atoms, —$SO_2$-aryl —C(O)-alkyl with alkyl having 1, 2, 3 or 4 carbon atoms, —C(O)-aryl, —C(O)OR23, —C(O)NR24R25 or —CN,
R23 is alkyl having 1,2,3 or 4 carbon atoms or aryl,
R24 and R25
are, independently of one another, hydrogen, alkyl having 1, 2, 3 or 4 carbon atoms or aryl;
R1 and R2
are, independently of one another, alkyl having 1, 2, 3, 4, 5 or 6 carbon atoms;
in which the alkyl radicals are unsubstituted or substituted by 1, 2 or 3 radicals selected from the group consisting of F, Cl, Br, I, —S-alkyl having, 1, 2, 3 or 4 carbon atoms or —$O_m$—$(CH_2)_n$—R26;
m is zero or 1;
n is zero, 1, 2 or 3;
R26 is hydrogen, aryl or heteroaryl, in which the aryl or heteroaryl radical is unsubstituted or substituted by F, Cl, Br, I, OH or alkyl having 1, 2, 3 or 4 carbon atoms;
or
R1 and R2
form, together with the carbon atom to which they are attached, a 3-, 4-, 5- or 6-membered carbon ring;
and/or a pharmaceutically acceptable salt and/or a prodrug thereof.
Particular preference is given to a compound of the formula I in which:
X is —CR3=CR4-, —CR5=N—, —N=CR6-, —NH— or —S—;
R3, R4, R5 and R6
are, independently of one another, hydrogen, F, Cl or Br;

Y1, Y2, Y3 and Y4
are, independently of one another, —CR8- or Nitrogen, with the proviso that at least three of Y1, Y2, Y3 and Y4 are defined as —CR8-;
R8 is hydrogen, F or Cl;
A is cyclohexyl, piperidyl, phenyl, naphthyl, indanyl, 2,3-dihydro-benzo[1,4]dioxanyl, benzo[1,3]dioxolyl, furyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl, benzimidazolyl, benzoxadiazolyl, benzotriazolyl, benzo-1,1-dioxid-thiophenyl or quinolyl;
in which cyclohexyl is unsubstituted or substituted by 1, 2 or 3 methyl radicals;
in which piperidyl is unsubstituted or substituted by alkyl having 1, 2, 3 or 4 carbon atoms, —C(O)$CH_3$, —C(O)$CH_2CH_3$, —C(O)— cyclopropyl, —C(O)$CF_3$, —C(O)OC$(CH_3)_3$;
in which the aryl or heteroaryl radical is unsubstituted or substituted by 1, 2 or 3 radicals selected from the group consisting of F, Cl, Br, CN, $NO_2$, $SF_5$, —N$(CH_3)_2$, methoxy, ethoxy, alkyl having 1, 2, 3 or 4 carbon atoms, $CF_3$, $OCF_3$, $OCH_2CF_3$, $OCHF_2$, $SCH_3$, $SOCH_3$, $SO_2CH_3$, $SCF_3$, phenyl, benzyl, pyrazolyl, pyrrolyl and triazolyl, in which phenyl can be substituted by Cl;
B is —O—C(R11R12)-; —C≡C—, —C(R13R14)-C(R15R16)-, —NR17-C(R18R19)- or —NR20-C(O)—;
R11, R13, R14, R15, R16, R18 and R19
are hydrogen;
R12, R17 and R20
are hydrogen or methyl;
D is C(O)OH, C(O)NHR21 or C(N—OH)NHR22,
R21 is —$SO_2$-alkyl having 1, 2, 3 or 4 carbon atoms or —$SO_2$— phenyl;
R22 is hydrogen
R1 and R2
are, independently of one another, alkyl having 1, 2 or 3 carbon atoms; or
R1 and R2
form, together with the carbon atom to which they are attached, a 3-, 4-, or 5-membered carbon ring;
and/or a pharmaceutically acceptable salt and/or prodrug thereof.
Special preference is given to a compound of the formula I, in which
X is —CR3=CR4- or —S—;
R3 and R4
are, independently of one another, hydrogen, F, Cl or Br;
Y1, Y2, Y3 and Y4
are, independently of one another, —CR8-;
R8 is hydrogen, F or Cl;
A is cyclohexyl, piperidyl, phenyl, naphthyl, indanyl, 2,3-dihydro-benzo[1,4]dioxanyl, benzo[1,3]dioxolyl, furyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl, benzimidazolyl, benzoxadiazolyl, benzotriazolyl, benzo-1,1-dioxid-thiophenyl or quinolyl;
in which cyclohexyl is unsubstituted or substituted by 1, 2 or 3 methyl radicals;
in which piperidyl is unsubstituted or substituted by alkyl having 1, 2, 3 or 4 carbon atoms, —C(O)$CH_3$, —C(O)$CH_2CH_3$, —C(O)— cyclopropyl, —C(O)$CF_3$, —C(O)OC$(CH_3)_3$;
in which the aryl or heteroaryl radical is unsubstituted or substituted by 1, 2 or 3 radicals selected from the group consisting of F, Cl, Br, CN, $NO_2$, $SF_5$, —N$(CH_3)_2$, methoxy, ethoxy, alkyl having 1, 2, 3 or 4 carbon atoms, CF$_3$, OCF$_3$, OCH$_2$CF$_3$, OCHF$_2$, SCH$_3$, SOCH$_3$, SO$_2$CH$_3$, SCF$_3$, phenyl, benzyl, pyrazolyl, pyrrolyl and triazolyl, in which phenyl can be substituted by Cl;

B is —O—C(R11R12)-;

R11 is hydrogen;

R12 is hydrogen or methyl;

D is C(O)OH;

R1 and R2
are, independently of one another, alkyl having 1, 2 or 3 carbon atoms; or R1 and R2
form, together with the carbon atom to which they are attached, a 3-, 4-, or 5-membered carbon ring;

and/or a pharmaceutically acceptable salt and/or a prodrug thereof.

In one embodiment X in compounds of formula I is described by —CR3=CR4-, —CR5=N—, —N=CR6-, —NR7- or —S—, wherein R3, R4, R5 and R6 are independently of one another, hydrogen, F, Cl, Br, I, alkyl having 1, 2, 3 or 4 carbon atoms or alkoxy having 1, 2, 3 or 4 carbon atoms, and R7 is hydrogen or alkyl having 1, 2, 3 or 4 carbon atoms, preferably hydrogen; preference is given to compounds, in which X is described by —CR3=CR4-, —CR5=N—, —N=CR6-, —NH— or —S—, wherein R3, R4, R5 and R6 are, independently of one another, hydrogen, F, Cl, Br, I or alkyl having 1, 2, 3 or 4 carbon atoms, preferably R3, R4, R5 and R6 are, independently of one another, hydrogen, F, Cl or Br; particular preference is given to compounds, in which X is described as —CR3=CH—, —CH=N—, —N=CH, NH or —S—, wherein R3 is defined as hydrogen, F, Cl or Br; more particular preference is given to compounds, in which X is described as —CR3=CH— or —S—, wherein R3 is defined as hydrogen, F, Cl or Br.

Linker X is attached with its left hand side to the carbon atom in the six-membered ring and with its right hand side to the other carbon atom.

In a further embodiment Y1, Y2, Y3 and Y4 in compounds of formula I are, independently of one another, described by —CR8- or Nitrogen, with the proviso that at least two of Y1, Y2, Y3 and Y4 are defined as —CR8-, wherein R8 is hydrogen, F, Cl, Br, I or alkyl having 1, 2, 3 or 4 carbon atoms; preferably at least three of Y1, Y2, Y3 and Y4 are defined as —CR8-, wherein R8 is hydrogen, F, Cl, Br, I or alkyl having 1, 2, 3 or 4 carbon atoms, preferably hydrogen or Cl, for example hydrogen; for example Y1, Y2 and Y3 are CH and Y4 is N or Y1, Y2, Y3 and Y4 are CR8, wherein R8 is hydrogen, F or Cl, in particular hydrogen.

In a further embodiment A in compounds of formula I is described by cycloalkyl having 3, 4, 5, 6, 7 or 8 carbon atoms, heterocycle, aryl or heteroaryl, wherein the cycloalkyl or heterocycle radical can be condensed to an aryl radical and wherein the cycloalkyl or heterocycle radical is unsubstituted or substituted by 1, 2 or 3 radicals selected from the group consisting of F, Cl, Br, I, alkyl having 1, 2, 3 or 4 carbon atoms, —C(O)-alkyl having 1, 2, 3 or 4 carbon atoms, —C(O)-cycloalkyl having 3, 4, 5 or 6 carbon atoms or —C(O)O-alkyl having 1, 2, 3 or 4 carbon atoms and wherein the aryl or heteroaryl radical can be condensed to an cycloalkyl or heterocycle radical and wherein the aryl or heteroaryl radical is unsubstituted or substituted by 1, 2, 3 or 4 radicals selected from the group consisting of F, Cl, Br, I, CN, NO$_2$, SF$_5$, —NR9R10, alkoxy having 1, 2, 3 or 4 carbon atoms, alkyl having 1, 2, 3, 4, 5 or 6 carbon atoms, —O$_a$—(CH$_2$)$_b$—(CF$_2$)$_c$—CF$_3$, —O$_d$—CHF$_2$, —O$_e$—CH$_2$F, —SO$_f$-alkyl having 1, 2, 3 or 4 carbon atoms, S—(CH$_2$)$_g$—(CF$_2$)$_h$—CF$_3$, —(CH$_2$)$_k$-aryl or —(CH$_2$)$_l$-heteroaryl, in which the aryl and heteroaryl radicals can be substituted by F, Cl, Br, I, alkoxy having 1, 2, 3 or 4 carbon atoms or alkyl having 1, 2, 3 or 4 carbon atoms, wherein R9 and R10 are, independently of one another, hydrogen or alkyl having 1, 2, 3 or 4 carbon atoms, a, d and e are, independently of one another, zero or 1, b, c, g, h, k and l are, independently of one another, zero, 1, 2 or 3 and f is zero, 1 or 2; preference is given to compounds, wherein A is described by cyclohexyl, piperidyl, phenyl, naphthyl, indanyl, 2,3-dihydro-benzo[1,4]dioxanyl, benzo[1,3]dioxolyl, furyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl, benzimidazolyl, benzoxadiazolyl, benzotriazolyl, benzo-1,1-dioxid-thiophenyl or quinolyl, wherein cyclohexyl is unsubstituted or substituted by 1, 2 or 3 radicals selected from the group consisting of alkyl having 1, 2, 3 or 4 carbon atoms, in particular methyl, wherein piperidyl is unsubstituted or substituted by alkyl having 1, 2, 3 or 4 carbon atoms, —C(O)CH$_3$, —C(O)CH$_2$CH$_3$, —C(O)-cyclopropyl, —C(O)CF$_3$, —C(O)OC(CH$_3$)$_3$, and wherein the aryl or heteroaryl radical is unsubstituted or substituted by 1, 2 or 3 radicals selected from the group consisting of F, Cl, Br, CN, NO$_2$, SF$_5$, —N(CH$_3$)$_2$, methoxy, ethoxy, alkyl having 1, 2, 3 or 4 carbon atoms, CF$_3$, OCF$_3$, OCH$_2$CF$_3$, OCHF$_2$, SCH$_3$, SOCH$_3$, SO$_2$CH$_3$, SCF$_3$, phenyl, benzyl, pyrazolyl, pyrrolyl and triazolyl, wherein phenyl can be substituted by Cl; particular preference is given to compounds of formula I, in which A is described by:

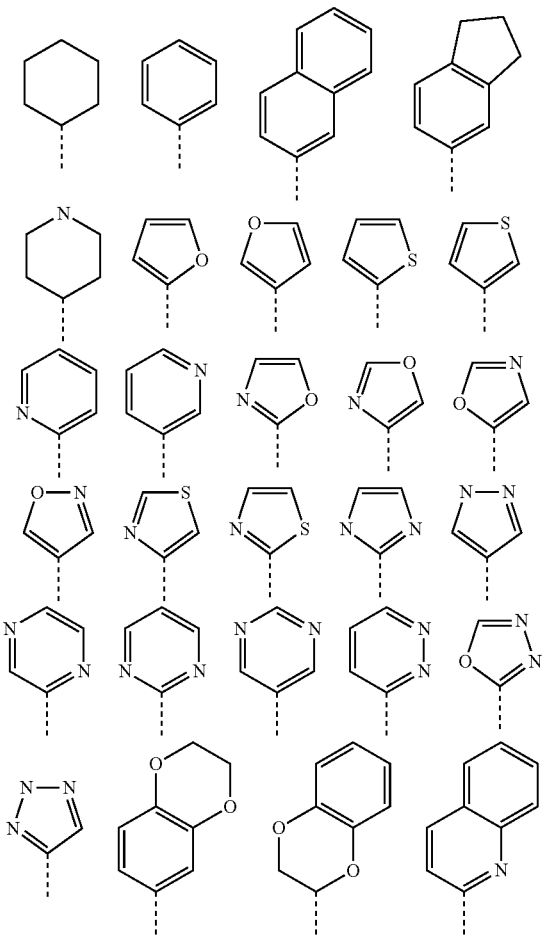

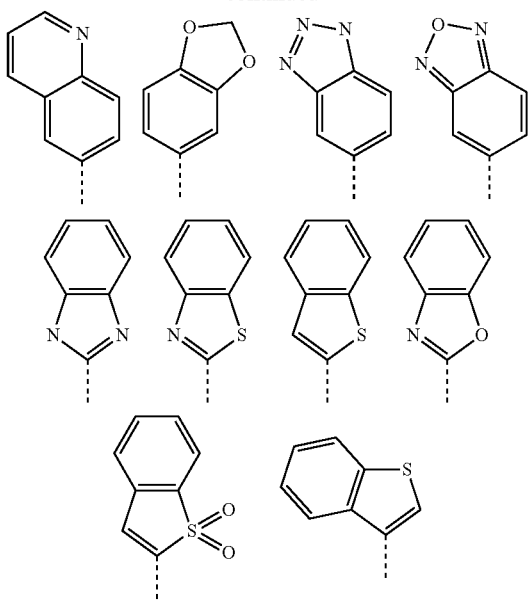

wherein 2,3-Dihydro-benzo[1,4]dioxanyl is unsubstituted, cyclohexyl is unsubstituted or substituted by 1, 2 or 3 radicals selected from the group consisting of alkyl having 1, 2, 3 or 4 carbon atoms, in particular methyl, and wherein piperidyl is unsubstituted or substituted by alkyl having 1, 2, 3 or 4 carbon atoms, —C(O)CH$_3$, —C(O)CH$_2$CH$_3$, —C(O)-cyclopropyl, —C(O)CF$_3$, —C(O)OC(CH$_3$)$_3$, and wherein the aryl or heteroaryl radical is unsubstituted or substituted by 1, 2 or 3 radicals selected from the group consisting of F, Cl, Br, CN, NO$_2$, SF$_5$, —N(CH$_3$)$_2$, methoxy, ethoxy, alkyl having 1, 2, 3 or 4 carbon atoms, CF$_3$, OCF$_3$, OCH$_2$CF$_3$, OCHF$_2$, SCH$_3$, SOCH$_3$, SO$_2$CH$_3$, SCF$_3$, phenyl, benzyl, pyrazolyl, pyrrolyl and triazolyl, wherein phenyl can be substituted by Cl;

In another embodiment particular preference is given to compounds of formula I, in which A is described by:

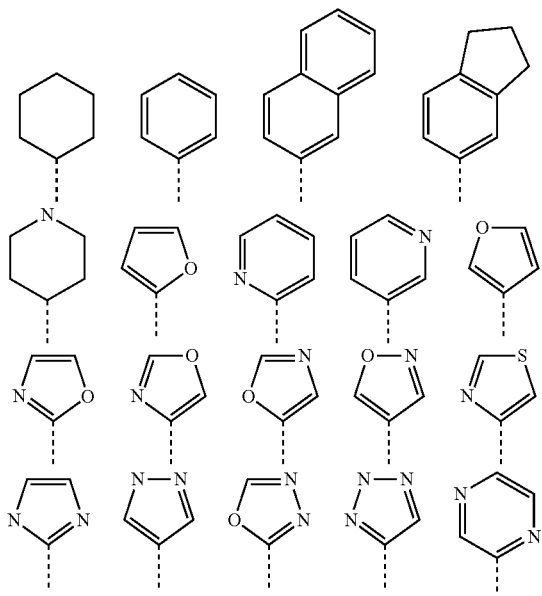

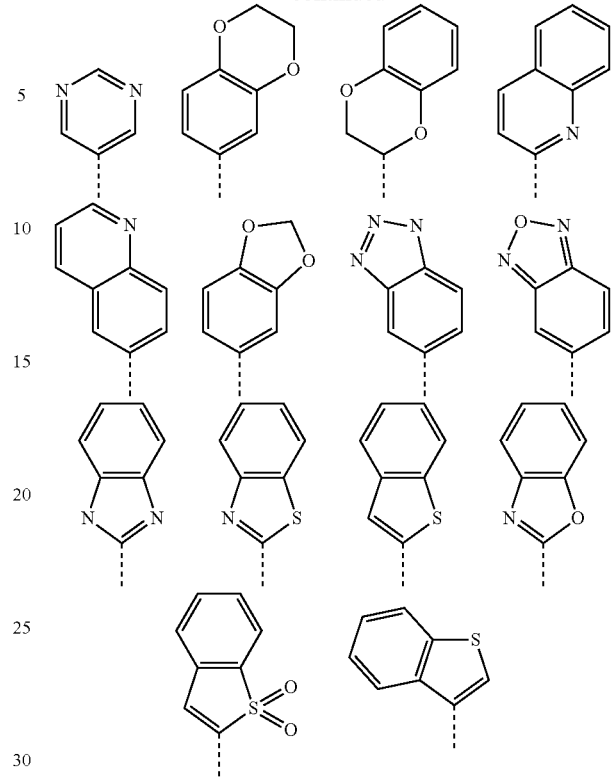

wherein 2,3-Dihydro-benzo[1,4]dioxanyl is unsubstituted, cyclohexyl is unsubstituted or substituted by 1, 2 or 3 radicals selected from the group consisting of alkyl having 1, 2, 3 or 4 carbon atoms, in particular methyl, and wherein piperidyl is unsubstituted or substituted by alkyl having 1, 2, 3 or 4 carbon atoms, —C(O)CH$_3$, —C(O)CH$_2$CH$_3$, —C(O)-cyclopropyl, —C(O)CF$_3$, —C(O)OC(CH$_3$)$_3$, and wherein the aryl or heteroaryl radical is unsubstituted or substituted by 1, 2 or 3 radicals selected from the group consisting of F, Cl, Br, CN, NO$_2$, SF$_5$, —N(CH$_3$)$_2$, methoxy, ethoxy, alkyl having 1, 2, 3 or 4 carbon atoms, CF$_3$, OCF$_3$, OCH$_2$CF$_3$, OCHF$_2$, SCH$_3$, SOCH$_3$, SO$_2$CH$_3$, SCF$_3$, phenyl, benzyl, pyrazolyl, pyrrolyl and triazolyl, wherein phenyl can be substituted by Cl.

In another embodiment A in compounds of formula I is described by unsubstituted cycloalkyl having 3, 4, 5, 6, 7 or 8 carbon atoms, heterocycle, aryl or heteroaryl, in which the cycloalkyl or heterocycle radical can be condensed to an aryl radical and in which the aryl or heteroaryl radical can be condensed to an cycloalkyl or heterocycle radical.

In another embodiment A in compounds of formula I is described by cycloalkyl having 3, 4, 5, 6, 7 or 8 carbon atoms, heterocycle, aryl or heteroaryl, wherein the cycloalkyl or heterocycle radical can be condensed to an aryl radical and wherein the cycloalkyl or heterocycle radical is substituted by 1, 2 or 3 radicals and wherein the aryl or heteroaryl radical can be condensed to an cycloalkyl or heterocycle radical and wherein the aryl or heteroaryl radical is unsubstituted or substituted by 1, 2, 3 or 4 radicals; preference is given to compounds of the formula I in which A is described by a monocyclic ring compound, for example a monocyclic cycloalkyl having 3, 4, 5, 6, 7 or 8 carbon atoms, heterocycle, aryl or heteroaryl, which is at least substituted once in a position not near to the binding site of the cycloalkyl, heterocycle, aryl or heteroaryl to the linker B, for example phenyl or cyclohexyl radicals are at least substituted in position 4 and are optionally additionally substituted by additional radicals; preference is further given to compounds of the formula I in which A is described by a bicyclic ring compound, for example a bicyclic aryl, a bicyclic heteroaryl, a cycloalkyl or heterocycle radical to which an aryl or heteroaryl radical is condensed or an aryl or heteroaryl radical to which an cycloalkyl or heterocycle is condensed, where this bicyclic ring compound is unsubstituted or substituted with small substituents, in particular with F, Cl, CF3, CN or methoxy, preferably in a position not near the binding site of the cycloalkyl, heterocycle, aryl or heteroaryl to the linker B, for example in 2-benzthiazolyl radicals in position 6 and/or 7 and in 2-naphthalene radicals in position 6.

In a further embodiment B in compounds of formula I is described as —O—C(R11R12)-, —C≡C—, —C(R13R14)-C(R15R16)-, —NR17-C(R18R19)- or —NR20-C(O)—, wherein R11, R12, R13, R14, R15, R16, R17, R18, R19 and R20 are, independently of one another, hydrogen or alkyl having 1, 2, 3 or 4 carbon atoms; preference is given to compounds, wherein B is —O—(CR11R12)-, —C≡C— or —CR13R14CR15R16-, wherein R11, R12, R13, R14, R15 and R16 are, independently of one another, hydrogen or alkyl having 1, 2, 3 or 4 carbon atoms, preferably when R11, R13, R14, R15 and R16 are hydrogen and R12 is hydrogen or alkyl having 1, 2, 3 or 4 carbon atoms, for example methyl; more preference is given to compounds, wherein B is —O—(CR11R12)-, preferably when R11 is hydrogen and R12 is hydrogen or alkyl having 1, 2, 3 or 4 carbon atoms, for example methyl.

Linker B is attached with its left hand side to the ring system and with its right hand side to the residue A.

In a further embodiment D in compounds of formula I is described by C(O)OH, C(O)NHR21 or C(N—OH)NHR22, wherein R21 and R22 are, independent of one another, hydrogen, —SO$_2$-alkyl having 1, 2, 3 or 4 carbon atoms or —SO$_2$-aryl, —C(O)-alkyl having 1, 2, 3 or 4 carbon atoms, —C(O)-aryl, —C(O)OR23, —C(O)NR24R25 or CN, wherein R23 is alkyl having 1, 2, 3 or 4 carbon atoms or aryl and R24 and R25 are, independently of one another, hydrogen, alkyl having 1, 2, 3 or 4 carbon atoms or aryl; preference is given to compounds wherein D is C(O)OH, C(O)NHR21 or C(N—OH)NHR22, wherein R22 is hydrogen and R21 is hydrogen, —SO$_2$-alkyl having 1, 2, 3 or 4 carbon atoms, for example —SO$_2$CH$_3$ or —SO$_2$C(CH$_3$)$_3$, or —SO$_2$-aryl, for example —SO$_2$-phenyl, preferably R21 is —SO$_2$CH$_3$ or —SO$_2$C(CH$_3$)$_3$, or —SO$_2$-phenyl; particular preference is given to compounds wherein D is C(O)OH.

In a further embodiment R1 and R2 are, independently of one another, alkyl having 1, 2, 3, 4, 5 or 6 carbon atoms, in which the alkyl radicals are unsubstituted or substituted by 1, 2 or 3 radicals selected from the group consisting of F, Cl, Br, I, —S-alkyl having, 1, 2, 3 or 4 carbon atoms or —O$_m$—(CH$_2$)$_n$≧R26, wherein m is zero or 1, n is zero, 1, 2 or 3 and R26 is hydrogen, aryl or heteroaryl, in which the aryl or heteroaryl radicals are unsubstituted or substituted by F, Cl, Br, I, OH or alkyl having 1, 2, 3 or 4 carbon atoms, or R1 and R2 form, together with the carbon atom to which they are attached, a 3-, 4-, 5- or 6-membered carbon ring; preference is given to compounds of formula I in which R1 is alkyl having 1, 2 or 3 carbon atoms and R2 is alkyl having 1, 2, 3 or 4 carbon atoms, for example 1, 2 or 3 carbon atoms, in which the alkyl radicals are unsubstituted or substituted by a radical selected from the group consisting of SCH$_3$, —O$_m$—(CH$_2$)$_n$—R26, wherein m is zero or 1, n is zero, 1, 2 or 3 and R26 is hydrogen, phenyl, thienyl, imidazolyl or indolyl, in which the aryl or heteroaryl radicals are unsubstituted or substituted by F, OH or methyl, or R1 and R2 form, together with the carbon atom to which they are attached, a 3-, 4-, or 5-membered carbon ring; particular preference is given to compounds of formula I in which R1 is alkyl having 1, 2 or 3 carbon atoms and R2 is alkyl having 1, 2, 3 or 4 carbon atoms or where R1 and R2 form, together with the carbon atom to which they are attached, a 3-, 4-, or 5-membered carbon ring.

Special preference is given to the following compounds of the formula I, selected from the group consisting of:

2-[(1-Benzyloxy-naphthalene-2-carbonyl)-amino]-2-methyl-propionic acid;

2-Methyl-2-{[1-(pyridin-2-ylmethoxy)-naphthalene-2-carbonyl]-amino}-propionic acid;

2-[(1-Cyclohexylmethoxy-naphthalene-2-carbonyl)-amino]-2-methyl-propionic acid;

2-Methyl-2-{[1-(4-methyl-benzyloxy)-naphthalene-2-carbonyl]-amino}-propionic acid;

2-Methyl-2-{[1-(6-methyl-pyridin-2-ylmethoxy)-naphthalene-2-carbonyl]-amino}-propionic acid;

2-Methyl-2-{[1-(4-methyl-cyclohexylmethoxy)-naphthalene-2-carbonyl]-amino}-propionic acid;

2-Methyl-2-{[1-(4-methyl-cyclohexylmethoxy)-naphthalene-2-carbonyl]amino}-propionic acid;

2-{[1-(4-Ethyl-benzyloxy)-naphthalene-2-carbonyl]-amino}-2-methyl-propionic acid;

2-{[1-(6-Methoxy-pyridin-3-ylmethoxy)-naphthalene-2-carbonyl]-amino}-2-methyl-propionic acid;

2-{[1-(4-Chloro-benzyloxy)-naphthalene-2-carbonyl]-amino}-2-methyl-propionic acid;

2-{[1-(6-Chloro-pyridin-3-ylmethoxy)-naphthalene-2-carbonyl]-amino}-2-methyl-propionic acid;

2-{[1-(1H-Benzoimidazol-2-ylmethoxy)-naphthalene-2-carbonyl]-amino}-2-methyl-propionic acid;

2-{[1-(Indan-5-ylmethoxy)-naphthalene-2-carbonyl]-amino}-2-methyl-propionic acid;

2-{[1-(Benzo[1,2,5]oxadiazol-5-ylmethoxy)-naphthalene-2-carbonyl]-amino}-2-methyl-propionic acid;

2-{[1-(4-Isopropyl-benzyloxy)-naphthalene-2-carbonyl]-amino}-2-methyl-propionic acid;

2-Methyl-2-{[1-(2,4,6-trimethyl-benzyloxy)-naphthalene-2-carbonyl]-amino}-propionic acid;

2-Methyl-2-{[1-(4-nitro-benzyloxy)-naphthalene-2-carbonyl]-amino}-propionic acid;

2-{[1-(6-Methoxy-pyridin-3-ylmethoxy)-naphthalene-2-carbonyl]-amino}-2-methyl-butyric acid;

2-Methyl-2-{[1-(4-methylsulfanyl-benzyloxy)-naphthalene-2-carbonyl]-amino}-propionic acid;

2-Methyl-2-{[1-(2,4,6-trimethyl-cyclohexylmethoxy)-naphthalene-2-carbonyl]-amino}-propionic acid;

2-({1-[1-(4-Chloro-phenyl)-ethoxy]-naphthalene-2-carbonyl}-amino)-2-methyl-propionic acid;

2-Methyl-2-{[1-(naphthalen-2-ylmethoxy)-naphthalene-2-carbonyl]-amino}-propionic acid;

2-Methyl-2-{[1-(quinolin-2-ylmethoxy)-naphthalene-2-carbonyl]-amino}-propionic acid;

2-{[1-(4-Chloro-2-fluoro-benzyloxy)-naphthalene-2-carbonyl]-amino}-2-methyl-propionic acid;

2-{[1-(4-Chloro-3-fluoro-benzyloxy)-naphthalene-2-carbonyl]-amino}-2-methyl-propionic acid;

2-Methyl-2-{[1-(1-methyl-1H-benzotriazol-5-ylmethoxy)-naphthalene-2-carbonyl]-amino}-propionic acid;

2-{[1-(Benzo[b]thiophen-2-ylmethoxy)-naphthalene-2-carbonyl]-amino}-2-methyl-propionic acid;

2-{[1-(Benzo[b]thiophen-3-ylmethoxy)-naphthalene-2-carbonyl]-amino}-2-methyl-propionic acid;

2-{[1-(4-tert-Butyl-benzyloxy)-naphthalene-2-carbonyl]-amino}-2-methyl-propionic acid;

2-{[1-(4-Butyl-benzyloxy)-naphthalene-2-carbonyl]-amino}-2-methyl-propionic acid;

2-{[1-(Benzothiazol-2-ylmethoxy)-naphthalene-2-carbonyl]-amino}-2-methyl-propionic acid;

2-Methyl-2-{[3-(quinolin-2-ylmethoxy)-benzo[b]thiophene-2-carbonyl]-amino}-propionic acid;

2-{[1-(2,3-Dihydro-benzo[1,4]dioxin-2-ylmethoxy)-naphthalene-2-carbonyl]-amino}-2-methyl-propionic acid;

2-{[1-(2,3-Dihydro-benzo[1,4]dioxin-6-ylmethoxy)-naphthalene-2-carbonyl]-amino}-2-methyl-propionic acid;

2-{[1-(6-Methanesulfinyl-pyridin-3-ylmethoxy)-naphthalene-2-carbonyl]-amino}-2-methyl-propionic acid;

2-{[3-(Benzothiazol-2-ylmethoxy)-benzo[b]thiophene-2-carbonyl]-amino}-2-methyl-propionic acid;

2-{[3-(Benzothiazol-2-ylmethoxy)-thieno[2,3-b]pyridine-2-carbonyl]-amino}-2-methyl-propionic acid;

2-Methyl-2-{[1-(3-pyrrol-1-yl-benzyloxy)-naphthalene-2-carbonyl]-amino}-propionic acid;

2-{[1-(5-Chloro-6-methoxy-pyridin-3-ylmethoxy)-naphthalene-2-carbonyl]-amino}-2-methyl-propionic acid;

2-{[1-(4-Difluoromethoxy-benzyloxy)-naphthalene-2-carbonyl]-amino}-2-methyl-propionic acid;

2-Methyl-2-{[1-(4-pyrazol-1-yl-benzyloxy)-naphthalene-2-carbonyl]-amino}-propionic acid;

2-Methyl-2-{[1-(2-phenyl-oxazol-4-ylmethoxy)-naphthalene-2-carbonyl]-amino}-propionic acid;

2-Methyl-2-{[1-(4-[1,2,4]triazol-1-yl-benzyloxy)-naphthalene-2-carbonyl]-amino}-propionic acid;

2-Methyl-2-{[1-(4-trifluoromethyl-benzyloxy)-naphthalene-2-carbonyl]-amino}-propionic acid;

2-Methyl-2-{[1-(3-trifluoromethyl-benzyloxy)-naphthalene-2-carbonyl]-amino}-propionic acid;

2-Methyl-2-{[1-(5-phenyl-[1,3,4]oxadiazol-2-ylmethoxy)-naphthalene-2-carbonyl]-amino}-propionic acid;

2-{[1-(2,4-Dichloro-benzyloxy)-naphthalene-2-carbonyl]-amino}-2-methyl-propionic acid;

2-{[1-(3,4-Dichloro-benzyloxy)-naphthalene-2-carbonyl]-amino}-2-methyl-propionic acid;

2-Methyl-2-{[1-(6-trifluoromethyl-pyridin-3-ylmethoxy)-naphthalene-2-carbonyl]-amino}-propionic acid;

2-Methyl-2-{[4-(4-trifluoromethyl-benzyloxy)-isoquinoline-3-carbonyl]-amino}-propionic acid;

1-{[1-(Benzothiazol-2-ylmethoxy)-naphthalene-2-carbonyl]-amino}-cyclobutanecarboxylic acid;

2-{[1-(5,6-Dichloro-pyridin-3-ylmethoxy)-naphthalene-2-carbonyl]-amino}-2-methyl-propionic acid;

2-{[1-(Benzo[b]thiophen-2-ylmethoxy)-naphthalene-2-carbonyl]-amino}-2-methyl-butyric acid;

2-{[1-(Benzo[b]thiophen-3-ylmethoxy)-naphthalene-2-carbonyl]-amino}-2-methyl-butyric acid;

2-{[1-(Benzothiazol-2-ylmethoxy)-naphthalene-2-carbonyl]-amino}-2-methyl-butyric acid;

2-{[1-(1-Benzothiazol-2-yl-ethoxy)-naphthalene-2-carbonyl]-amino}-2-methyl-propionic acid;

2-Methyl-2-{[3-(quinolin-2-ylmethoxy)-benzo[b]thiophene-2-carbonyl]-amino}-butyric acid;

2-{[1-(2,3-Dihydro-benzo[1,4]dioxin-2-ylmethoxy)-naphthalene-2-carbonyl]-amino}-2-methyl-butyric acid;

2-Methyl-2-{[3-(4-trifluoromethyl-benzyloxy)-benzo[b]thiophene-2-carbonyl]-amino}-propionic acid;

2-Methyl-2-{[3-(6-trifluoromethyl-pyridin-3-ylmethoxy)-benzo[b]thiophene-2-carbonyl]-amino}-propionic acid;

2-{[1-(5-Fluoro-benzothiazol-2-ylmethoxy)-naphthalene-2-carbonyl]-amino}-2-methyl-propionic acid;

2-{[1-(6-Chloro-benzooxazol-2-ylmethoxy)-naphthalene-2-carbonyl]-amino}-2-methyl-propionic acid;

2-{[1-(5-Chloro-benzooxazol-2-ylmethoxy)-naphthalene-2-carbonyl]-amino}-2-methyl-propionic acid;

2-{[1-(Biphenyl-4-ylmethoxy)-naphthalene-2-carbonyl]-amino}-2-methyl-propionic acid;

2-{[3-(Benzothiazol-2-ylmethoxy)-benzo[b]thiophene-2-carbonyl]-amino}-2-methyl-butyric acid;

2-{[1-(4-Methanesulfonyl-benzyloxy)-naphthalene-2-carbonyl]-amino}-2-methyl-propionic acid;

2-{[1-(6-Chloro-benzo[1,3]dioxol-5-ylmethoxy)-naphthalene-2-carbonyl]-amino}-2-methyl-propionic acid;

2-{[1-(4-Bromo-benzyloxy)-naphthalene-2-carbonyl]-amino}-2-methyl-propionic acid;

2-{[1-(3-Bromo-benzyloxy)-naphthalene-2-carbonyl]-amino}-2-methyl-propionic acid;

2-{[1-(6-Methanesulfonyl-pyridin-3-ylmethoxy)-naphthalene-2-carbonyl]-amino}-2-methyl-propionic acid;

2-{[1-(5-Chloro-6-ethoxy-pyridin-3-ylmethoxy)-naphthalene-2-carbonyl]-amino}-2-methyl-propionic acid;

2-{[1-(6-Bromo-pyridin-3-ylmethoxy)-naphthalene-2-carbonyl]-amino}-2-methyl-propionic acid;

2-{[1-(4-Difluoromethoxy-benzyloxy)-naphthalene-2-carbonyl]-amino}-2-methyl-butyric acid;

2-Methyl-2-{[1-(5-methyl-2-phenyl-2H-[1,2,3]triazol-4-ylmethoxy)-naphthalene-2-carbonyl]-amino}-propionic acid;

2-{[1-(5-Cyano-benzo[b]thiophen-2-ylmethoxy)-naphthalene-2-carbonyl]-amino}-2-methyl-propionic acid;

2-Methyl-2-({1-[1-(4-trifluoromethyl-phenyl)-ethoxy]-naphthalene-2-carbonyl}-amino)-propionic acid;

2-Methyl-2-{[1-(4-trifluoromethyl-benzyloxy)-naphthalene-2-carbonyl]-amino}-butyric acid;

(R)-2-Methyl-2-{[1-(4-trifluoromethyl-benzyloxy)-naphthalene-2-carbonyl]-amino}-butyric acid;

2-Methyl-2-({1-[(S)-1-(4-trifluoromethyl-phenyl)-ethoxy]-naphthalene-2-carbonyl}-amino)-propionic acid;

2-Methyl-2-({1-[(R)-1-(4-trifluoromethyl-phenyl)-ethoxy]-naphthalene-2-carbonyl}-amino)-propionic acid;

(S)-2-Methyl-2-{[1-(4-trifluoromethyl-benzyloxy)-naphthalene-2-carbonyl]-amino}-butyric acid;

2-Methyl-2-({1-[1-(2-trifluoromethyl-phenyl)-ethoxy]-naphthalene-2-carbonyl}-amino)-propionic acid;

2-Methyl-2-({1-[1-(3-trifluoromethyl-phenyl)-ethoxy]-naphthalene-2-carbonyl}-amino)-propionic acid;

2-({1-[1-(3,4-Dichloro-phenyl)-ethoxy]-naphthalene-2-carbonyl}-amino)-2-methyl-propionic acid;

(S)-2-Methyl-2-{[1-(6-trifluoromethyl-pyridin-3-ylmethoxy)-naphthalene-2-carbonyl]-amino}-butyric acid;

2-Methyl-2-{[1-(6-trifluoromethyl-pyridin-3-ylmethoxy)-naphthalene-2-carbonyl]-amino}-butyric acid;

(R)-2-Methyl-2-{[1-(6-trifluoromethyl-pyridin-3-ylmethoxy)-naphthalene-2-carbonyl]-amino}-butyric acid;

1-(6-Trifluoromethyl-pyridin-3-ylmethoxy)-naphthalene-2-carboxylic acid [1-(N-hydroxycarbamimidoyl)-1-methyl-ethyl]-amide;

1-{[1-(Benzothiazol-2-ylmethoxy)-naphthalene-2-carbonyl]-amino}-cyclopentanecarboxylic acid;

2-Methyl-2-{[1-(2-phenyl-thiazol-4-ylmethoxy)-naphthalene-2-carbonyl]-amino}-propionic acid;

1-{[3-(Quinolin-2-ylmethoxy)-benzo[b]thiophene-2-carbonyl]-amino}-cyclopentanecarboxylic acid;

2-Methyl-2-{[1-(4-trifluoromethoxy-benzyloxy)-naphthalene-2-carbonyl]-amino}-propionic acid;

2-Methyl-2-{[1-(3-trifluoromethoxy-benzyloxy)-naphthalene-2-carbonyl]-amino}-propionic acid;

1-{[1-(2,3-Dihydro-benzo[1,4]dioxin-2-ylmethoxy)-naphthalene-2-carbonyl]-amino}-cyclopentanecarboxylic acid;

2-{[4-Chloro-1-(quinolin-2-ylmethoxy)-naphthalene-2-carbonyl]-amino}-2-methyl-propionic acid;
2-{[4-Fluoro-1-(4-trifluoromethyl-benzyloxy)-naphthalene-2-carbonyl]-amino}-2-methyl-propionic acid;
2-{[1-(2-Fluoro-4-trifluoromethyl-benzyloxy)-naphthalene-2-carbonyl]-amino}-2-methyl-propionic acid;
2-Methyl-2-({3-[1-(4-trifluoromethyl-phenyl)-ethoxy]-benzo[b]thiophene-2-carbonyl}-amino)-propionic acid;
2-Methyl-2-{[3-(4-trifluoromethyl-benzyloxy)-benzo[b]thiophene-2-carbonyl]-amino}-butyric acid;
2-Methyl-2-{[3-(6-trifluoromethyl-pyridin-3-ylmethoxy)-benzo[b]thiophene-2-carbonyl]-amino}-butyric acid;
2-{[1-(5-Fluoro-benzothiazol-2-ylmethoxy)-naphthalene-2-carbonyl]-amino}-2-methyl-butyric acid;
2-Methyl-2-{[3-(4-trifluoromethoxy-benzyloxy)-benzo[b]thiophene-2-carbonyl]-amino}-propionic acid;
2-{[1-(5-Chloro-benzo[b]thiophen-3-ylmethoxy)-naphthalene-2-carbonyl]-amino}-2-methyl-propionic acid;
2-{[1-(5-Chloro-benzothiazol-2-ylmethoxy)-naphthalene-2-carbonyl]-amino}-2-methyl-propionic acid;
2-{[1-(Benzothiazol-2-ylmethoxy)-4-chloro-naphthalene-2-carbonyl]-amino}-2-methyl-propionic acid;
2-{[1-(4-Methanesulfonyl-benzyloxy)-naphthalene-2-carbonyl]-amino}-2-methyl-butyric acid;
2-{[4-Chloro-1-(5-trifluoromethyl-furan-2-ylmethoxy)-naphthalene-2-carbonyl]-amino}-2-methyl-propionic acid;
2-({1-[1-(4-Bromo-phenyl)-ethoxy]-naphthalene-2-carbonyl}-amino)-2-methyl-propionic acid;
2-({1-[1-(3-Bromo-phenyl)-ethoxy]-naphthalene-2-carbonyl}-amino)-2-methyl-propionic acid;
2-{[1-(5,6-Difluoro-benzothiazol-2-ylmethoxy)-naphthalene-2-carbonyl]-amino}-2-methyl-propionic acid;
1-{[1-(4-Trifluoromethyl-benzyloxy)-naphthalene-2-carbonyl]-amino}-cyclopentanecarboxylic acid;
1-{[1-(6-Trifluoromethyl-pyridin-3-ylmethoxy)-naphthalene-2-carbonyl]-amino}-cyclopentanecarboxylic acid;
2,3-Dimethyl-2-{[1-(4-trifluoromethyl-benzyloxy)-naphthalene-2-carbonyl]-amino}-butyric acid;
2-{[4-Chloro-1-(5-cyclopropyl-[1,3,4]thiadiazol-2-ylmethoxy)-naphthalene-2-carbonyl]-amino}-2-methyl-butyric acid;
2-{[1-(4-Bromo-2-fluoro-benzyloxy)-naphthalene-2-carbonyl]-amino}-2-methyl-propionic acid;
2-{[1-(5-tert-Butyl-benzooxazol-2-ylmethoxy)-naphthalene-2-carbonyl]-amino}-2-methyl-propionic acid;
2-Methyl-2-{[1-(4-trifluoromethoxy-benzyloxy)-naphthalene-2-carbonyl]-amino}-butyric acid;
2-Methyl-2-{[1-(3-trifluoromethoxy-benzyloxy)-naphthalene-2-carbonyl]-amino}-butyric acid;
2-{[1-(4-Methoxy-3-trifluoromethyl-benzyloxy)-naphthalene-2-carbonyl]-amino}-2-methyl-propionic acid;
2-Methyl-2-({1-[6-(2,2,2-trifluoro-ethoxy)-pyridin-3-ylmethoxy]-naphthalene-2-carbonyl}-amino)-propionic acid;
(S)-2-{[1-(2-Fluoro-4-trifluoromethyl-benzyloxy)-naphthalene-2-carbonyl]-amino}-2-methyl-butyric acid;
2-{[1-(2-Fluoro-4-trifluoromethyl-benzyloxy)-naphthalene-2-carbonyl]-amino}-2-methyl-butyric acid;
(R)-2-{[1-(2-Fluoro-4-trifluoromethyl-benzyloxy)-naphthalene-2-carbonyl]-amino}-2-methyl-butyric acid;
2-Methyl-2-{[1-(4-trifluoromethylsulfanyl-benzyloxy)-naphthalene-2-carbonyl]-amino}-propionic acid;
1-{[3-(4-Trifluoromethyl-benzyloxy)-benzo[b]thiophene-2-carbonyl]-amino}-cyclopentanecarboxylic acid;
2-({1-[2-(4-Chloro-phenyl)-oxazol-5-ylmethoxy]-naphthalene-2-carbonyl}-amino)-2-methyl-propionic acid;
2-({1-[5-(4-Chloro-phenyl)-oxazol-2-ylmethoxy]-naphthalene-2-carbonyl}-amino)-2-methyl-propionic acid;
2-Methyl-2-({3-[1-(4-trifluoromethyl-phenyl)-ethoxy]-benzo[b]thiophene-2-carbonyl}-amino)-butyric acid;
2,3-Dimethyl-2-{[3-(4-trifluoromethyl-benzyloxy)-benzo[b]thiophene-2-carbonyl]-amino}-butyric acid;
2-{[4-Chloro-1-(4-trifluoromethyl-benzyloxy)-naphthalene-2-carbonyl]-amino}-2-methyl-propionic acid;
2-{[4-Chloro-1-(5-trifluoromethyl-pyridin-2-ylmethoxy)-naphthalene-2-carbonyl]-amino}-2-methyl-propionic acid;
2-{[4-Chloro-1-(6-trifluoromethyl-pyridin-3-ylmethoxy)-naphthalene-2-carbonyl]-amino}-2-methyl-propionic acid;
2-{[1-(2,3-Difluoro-4-trifluoromethyl-benzyloxy)-naphthalene-2-carbonyl]-amino}-2-methyl-propionic acid;
2-Methyl-2-{[3-(4-trifluoromethoxy-benzyloxy)-benzo[b]thiophene-2-carbonyl]-amino}-butyric acid;
(S)-2-{[1-(Benzothiazol-2-ylmethoxy)-4-chloro-naphthalene-2-carbonyl]-amino}-2-methyl-butyric acid;
(R)-2-{[1-(Benzothiazol-2-ylmethoxy)-4-chloro-naphthalene-2-carbonyl]-amino}-2-methyl-butyric acid;
2-{[1-(Benzothiazol-2-ylmethoxy)-4-chloro-naphthalene-2-carbonyl]-amino}-2-methyl-butyric acid;
2-{[1-(5,6-Difluoro-benzothiazol-2-ylmethoxy)-naphthalene-2-carbonyl]-amino}-2-methyl-butyric acid;
2-Methyl-2-{[1-(6-trifluoromethyl-1H-benzoimidazol-2-ylmethoxy)-naphthalene-2-carbonyl]-amino}-propionic acid;
2-{[4-Chloro-1-(3-thiophen-2-yl-[1,2,4]oxadiazol-5-ylmethoxy)-naphthalene-2-carbonyl]-amino}-2-methyl-propionic acid;
2-{[4-Chloro-1-(5-thiophen-2-yl-[1,2,4]oxadiazol-3-ylmethoxy)-naphthalene-2-carbonyl]-amino}-2-methyl-propionic acid;
2-{[1-(5,6-Dichloro-1H-benzoimidazol-2-ylmethoxy)-naphthalene-2-carbonyl]-amino}-2-methyl-propionic acid;
1-{[1-(4-Trifluoromethoxy-benzyloxy)-naphthalene-2-carbonyl]-amino}-cyclopentanecarboxylic acid;
2-{[1-(4-Bromo-2-fluoro-benzyloxy)-naphthalene-2-carbonyl]-amino}-2-methyl-butyric acid;
2,3-Dimethyl-2-{[1-(4-trifluoromethoxy-benzyloxy)-naphthalene-2-carbonyl]-amino}-butyric acid;
2-Methyl-2-({1-[6-(2,2,2-trifluoro-ethoxy)-pyridin-3-ylmethoxy]-naphthalene-2-carbonyl}-amino)-butyric acid;
2-Methyl-2-({1-[3-methyl-4-(2,2,2-trifluoro-ethoxy)-pyridin-2-ylmethoxy]-naphthalene-2-carbonyl}-amino)-propionic acid;
(S)-2-Methyl-2-{[1-(4-trifluoromethylsulfanyl-benzyloxy)-naphthalene-2-carbonyl]-amino}-butyric acid;
(R)-2-Methyl-2-{[1-(4-trifluoromethylsulfanyl-benzyloxy)-naphthalene-2-carbonyl]-amino}-butyric acid;
2-Methyl-2-{[1-(4-trifluoromethylsulfanyl-benzyloxy)-naphthalene-2-carbonyl]-amino}-butyric acid;
2-{[1-(5-Bromo-pyridin-2-ylmethoxy)-4-chloro-naphthalene-2-carbonyl]-amino}-2-methyl-propionic acid;
2-{[1-(6-Bromo-pyridin-3-ylmethoxy)-4-chloro-naphthalene-2-carbonyl]-amino}-2-methyl-propionic acid;
1-{[3-(4-Trifluoromethoxy-benzyloxy)-benzo[b]thiophene-2-carbonyl]-amino}-cyclopentanecarboxylic acid;
2-{[4-Chloro-1-(4-trifluoromethyl-benzyloxy)-naphthalene-2-carbonyl]-amino}-2-methyl-butyric acid;
2-({4-Chloro-1-[1-(4-trifluoromethyl-phenyl)-ethoxy]-naphthalene-2-carbonyl}-amino)-2-methyl-propionic acid;

2-({4-Chloro-1-[1-(6-trifluoromethyl-pyridin-3-yl)-ethoxy]-naphthalene-2-carbonyl}-amino)-2-methyl-propionic acid;

2-{[4-Chloro-1-(6-trifluoromethyl-pyridin-3-ylmethoxy)-naphthalene-2-carbonyl]-amino}-2-methyl-butyric acid;

(S)-2-{[4-Chloro-1-(6-trifluoromethyl-pyridin-3-ylmethoxy)-naphthalene-2-carbonyl]-amino}-2-methyl-butyric acid;

(R)-2-{[4-Chloro-1-(6-trifluoromethyl-pyridin-3-ylmethoxy)-naphthalene-2-carbonyl]-amino}-2-methyl-butyric acid;

1-{[1-(Benzothiazol-2-ylmethoxy)-4-chloro-naphthalene-2-carbonyl]-amino}-cyclopentanecarboxylic acid;

2-{[1-(2,3-Difluoro-4-trifluoromethyl-benzyloxy)-naphthalene-2-carbonyl]-amino}-2-methyl-butyric acid;

2,3-Dimethyl-2-{[3-(4-trifluoromethoxy-benzyloxy)-benzo[b]thiophene-2-carbonyl]-amino}-butyric acid;

2-{[4-Chloro-1-(4-trifluoromethoxy-benzyloxy)-naphthalene-2-carbonyl]-amino}-2-methyl-propionic acid;

2-{[1-(3-Chloro-4-trifluoromethoxy-benzyloxy)-naphthalene-2-carbonyl]-amino}-2-methyl-propionic acid;

2-{[4-Chloro-1-(2-fluoro-4-trifluoromethyl-benzyloxy)-naphthalene-2-carbonyl]-amino}-2-methyl-propionic acid;

2-Methyl-2-{[1-(5-trifluoromethyl-benzothiazol-2-ylmethoxy)-naphthalene-2-carbonyl]-amino}-propionic acid;

2-{[1-(4-Pentafluorothio-benzyloxy)-naphthalene-2-carbonyl]-amino}-2-methyl-propionic acid;

1-{[4-Chloro-1-(4-trifluoromethyl-benzyloxy)-naphthalene-2-carbonyl]-amino}-cyclopentanecarboxylic acid;

2-({1-[3-Methoxy-4-(2,2,2-trifluoro-ethoxy)-pyridin-2-ylmethoxy]-naphthalene-2-carbonyl}-amino)-2-methyl-propionic acid;

1-{[4-Chloro-1-(6-trifluoromethyl-pyridin-3-ylmethoxy)-naphthalene-2-carbonyl]-amino}-cyclopentanecarboxylic acid;

2-{[4-Chloro-1-(4-trifluoromethoxy-benzyloxy)-naphthalene-2-carbonyl]-amino}-2-methyl-butyric acid;

2-{[1-(3-Chloro-4-trifluoromethoxy-benzyloxy)-naphthalene-2-carbonyl]-amino}-2-methyl-butyric acid;

2-{[4-Chloro-1-(6-chloro-quinolin-2-ylmethoxy)-naphthalene-2-carbonyl]-amino}-2-methyl-butyric acid;

2-{[4-Chloro-1-(2-fluoro-4-trifluoromethyl-benzyloxy)-naphthalene-2-carbonyl]-amino}-2-methyl-butyric acid;

2-{[4-Chloro-1-(4-trifluoromethylsulfanyl-benzyloxy)-naphthalene-2-carbonyl]-amino}-2-methyl-propionic acid;

2-{[1-(2,4-Bis-trifluoromethyl-benzyloxy)-naphthalene-2-carbonyl]-amino}-2-methyl-propionic acid;

2-Methyl-2-{[1-(5-trifluoromethyl-benzothiazol-2-ylmethoxy)-naphthalene-2-carbonyl]-amino}-butyric acid;

2-{[4-Chloro-1-(5,6-difluoro-benzothiazol-2-ylmethoxy)-naphthalene-2-carbonyl]-amino}-2-methyl-butyric acid;

2-[(5-Benzyloxy-2,2-dimethyl-2H-chromene-6-carbonyl)-amino]-2-methyl-propionic acid; compound with trifluoro-acetic acid;

2-{[4-Bromo-1-(4-trifluoromethyl-benzyloxy)-naphthalene-2-carbonyl]-amino}-2-methyl-propionic acid;

2-{[4-Chloro-1-(4-trifluoromethylsulfanyl-benzyloxy)-naphthalene-2-carbonyl]-amino}-2-methyl-butyric acid;

2-{[1-(4-Methoxy-2-trifluoromethyl-quinolin-6-ylmethoxy)-naphthalene-2-carbonyl]-amino}-2-methyl-propionic acid;

2-{[1-(4-Dimethylamino-2-trifluoromethyl-quinolin-6-ylmethoxy)-naphthalene-2-carbonyl]-amino}-2-methyl-propionic acid;

2-{[4-Bromo-1-(4-trifluoromethoxy-benzyloxy)-naphthalene-2-carbonyl]-amino}-2-methyl-propionic acid;

1-(6-Trifluoromethyl-pyridin-3-ylmethoxy)-naphthalene-2-carboxylic acid [1,1-dimethyl-2-(2-methyl-propane-2-sulfonylamino)-2-oxo-ethyl]-amide;

3-(3-Hydroxy-phenyl)-2-methyl-2-{[1-(4-trifluoromethyl-benzyloxy)-naphthalene-2-carbonyl]-amino}-propionic acid;

2-{[4-Chloro-1-(piperidin-4-ylmethoxy)-naphthalene-2-carbonyl]-amino}-2-methyl-butyric acid;

1-{[1-(Quinolin-2-ylmethoxy)-naphthalene-2-carbonyl]-amino}-cyclopentanecarboxylic acid;

2-{[1-(1-Acetyl-piperidin-4-ylmethoxy)-4-chloro-naphthalene-2-carbonyl]-amino}-2-methyl-butyric acid;

2-{[4-Chloro-1-(1-isopropyl-piperidin-4-ylmethoxy)-naphthalene-2-carbonyl]-amino}-2-methyl-butyric acid;

1-{[4-Chloro-1-(quinolin-2-ylmethoxy)-naphthalene-2-carbonyl]-amino}-cyclopentanecarboxylic acid;

2-{[4-Chloro-1-(1-propionyl-piperidin-4-ylmethoxy)-naphthalene-2-carbonyl]-amino}-2-methyl-butyric acid;

2-{[4-Chloro-1-(1-cyclopropanecarbonyl-piperidin-4-ylmethoxy)-naphthalene-2-carbonyl]-amino}-2-methyl-butyric acid;

2-({4-Chloro-1-[1-(2,2,2-trifluoro-acetyl)-piperidin-4-ylmethoxy]-naphthalene-2-carbonyl}-amino)-2-methyl-butyric acid;

4-[2-(1-Carboxy-1-methyl-propylcarbamoyl)-4-chloro-naphthalen-1-yloxymethyl]-piperidine-1-carboxylic acid tert-butyl ester;

2-{[4-Chloro-1-(2-thiophen-2-yl-pyrimidin-5-ylmethoxy)-naphthalene-2-carbonyl]-amino}-2-methyl-propionic acid;

1-{[4-Chloro-1-(5-trifluoromethyl-pyridin-2-ylmethoxy)-naphthalene-2-carbonyl]-amino}-cyclopentanecarboxylic acid;

1-{[1-(5-Trifluoromethyl-pyridin-2-ylmethoxy)-naphthalene-2-carbonyl]-amino}-cyclopentanecarboxylic acid;

2-{[1-(5-Chloro-6-methoxy-pyridin-3-ylmethoxy)-naphthalene-2-carbonyl]-amino}-2-methyl-propionic acid;

2-{[1-(5-Chloro-6-ethoxy-pyridin-3-ylmethoxy)-naphthalene-2-carbonyl]-amino}-2-methyl-propionic acid;

2-({1-[6-(2,2,2-trifluoro-ethoxy)-pyridin-3-ylmethoxy]-naphtha-lene-2-carbonyl}-amino)-2-methyl-propionic acid;

2-Methyl-2-({1-[6-(2,2,2-trifluoro-ethoxy)-pyridin-3-ylmethoxy]-naphtha-lene-2-carbonyl}-amino)-butyric acid;

2-{[1-(6-Methoxy-pyridin-3-ylmethoxy)-naphthalene-2-carbonyl]-amino}-2-methyl-propionic acid;

2-{[1-(6-Methoxy-pyridin-3-ylmethoxy)-naphthalene-2-carbonyl]-amino}-2-methyl-propionic acid;

2-{[1-(1-Benzothiazol-2-yl-ethoxy)-naphthalene-2-carbonyl]-amino}-2-methyl-propionic acid;

1-(6-Trifluoromethyl-pyridin-3-ylmethoxy)-naphthalene-2-carboxylic acid [1-(N-hydroxycarbamimidoyl)-1-methyl-ethyl]-amide;

2-{[1-(4-Dimethylamino-2-trifluoromethyl-quinolin-6-ylmethoxy)-naphthalene-2-carbonyl]-amino}-2-methyl-propionic acid;

2-{[1-(4-methoxy-2-trifluoromethyl-quinolin-6-ylmethoxy)-naphthalene-2-carbonyl]-amino}-2-methyl-propionic acid;

2-{[3-(Benzothiazol-2-ylmethoxy)-5-fluoro-benzo[b]thiophene-2-carbonyl]-amino}-2-methyl-propionic acid;

2-{[5-Fluoro-3-(6-trifluoromethyl-pyridin-3-ylmethoxy)-benzo[b]thio-phene-2-carbonyl]-amino}-2-methyl-propionic acid;

2-{[1-(1-Acetyl-piperidin-4-ylmethoxy)-4-chloro-naphthalene-2-carbonyl]-amino}-2-methyl-butyric acid;

2-{[4-Chloro-1-(1-propionyl-piperidin-4-yl-methoxy)-naphthalene-2-carbonyl]-amino}-2-methyl-butyric acid;

2-{[4-Chloro-1-(1-cyclopropanecarbonyl-piperidin-4-yl-methoxy)-naphthalene-2-carbonyl]-amino}-2-methyl-butyric acid;

4-[2-(1-Carboxy-1-methyl-propylcarbamoyl)-4-chloro-naphthalen-1-yloxymethyl]-piperidine-1-carboxylic acid tert-butyl ester;

2-{[4-Chloro-1-(piperidin-4-yl-methoxy)-naphthalene-2-carbonyl]-amino}-2-methyl-butyric acid;

2-({4-Chloro-1-[1-(2,2,2-trifluoro-acetyl)-piperidin-4-yl-methoxy]-naphthalene-2-carbonyl}-amino)-2-methyl-butyric acid;

2-{[4-Chloro-1-(1-isopropyl-piperidin-4-ylmethoxy)-naphthalene-2-carbonyl]-amino}-2-methyl-butyric acid;

2-{[4-Chloro-1-(1-cyclopentyl-piperidin-4-yl-methoxy)-naphthalene-2-carbonyl]-amino}-2-methyl-butyric acid;

1-{[1-(6-Trifluoromethyl-pyridin-3-ylmethoxy)-naphthalene-2-carbonyl]-amino}-cyclobutanecarboxylic acid;

1-{[1-(6-Chloro-pyridin-3-ylmethoxy)-naphthalene-2-carbonyl]-amino}-cyclobutanecarboxylic acid;

1-{[1-(Quinolin-2-ylmethoxy)-naphthalene-2-carbonyl]-amino}-cyclobutanecarboxylic acid;

1-{[1-(2-Thiophen-2-yl-thiazol-4-ylmethoxy)-naphthalene-2-carbonyl]-amino}-cyclobutanecarboxylic acid;

1-{[1-(4-Trifluoromethyl-benzyloxy)-naphthalene-2-carbonyl]-amino}-cyclobutanecarboxylic acid;

1-{[1-(2-Fluoro-4-trifluoromethyl-benzyloxy)-naphthalene-2-carbonyl]-amino}-cyclobutanecarboxylic acid, 1-{[1-(2,4-Bis-trifluoromethyl-benzyloxy)-naphthalene-2-carbonyl]-amino}-cyclobutanecarboxylic acid;

1-{[1-(4-Trifluoromethoxy-benzyloxy)-naphthalene-2-carbonyl]-amino}-cyclobutanecarboxylic acid;

1-[(1-Benzyloxy-naphthalene-2-carbonyl)-amino]-cyclobutanecarboxylic acid;

1-{[1-(4-Trifluoromethylsulfanyl-benzyloxy)-naphthalene-2-carbonyl]-amino}-cyclobutanecarboxylic acid;

1-{[1-(4-Chloro-benzyloxy)-naphthalene-2-carbonyl]-amino}-cyclobutanecarboxylic acid;

1-{[1-(4-Chloro-2-fluoro-benzyloxy)-naphthalene-2-carbonyl]-amino}-cyclobutanecarboxylic acid;

1-{[1-(4-Isopropyl-benzyloxy)-naphthalene-2-carbonyl]-amino}-cyclobutanecarboxylic acid;

1-{[1-(4-Pyrazol-1-yl-benzyloxy)-naphthalene-2-carbonyl]-amino}-cyclobutanecarboxylic acid;

1-{[1-(2-Phenyl-thiazol-4-ylmethoxy)-naphthalene-2-carbonyl]-amino}-cyclobutanecarboxylic acid;

1-{[1-(2,4-Difluoro-benzyloxy)-naphthalene-2-carbonyl]-amino}-cyclobutanecarboxylic acid;

1-{[1-(4-Fluoro-benzyloxy)-naphthalene-2-carbonyl]-amino}-cyclobutanecarboxylic acid;

1-[(1-Cyclohexylmethoxy-naphthalene-2-carbonyl)-amino]-cyclobutanecarboxylic acid;

1-{[4-Chloro-1-(6-chloro-pyridin-3-ylmethoxy)-naphthalene-2-carbonyl]-amino}-cyclobutanecarboxylic acid;

1-{[4-Chloro-1-(quinolin-2-ylmethoxy)-naphthalene-2-carbonyl]-amino}-cyclobutanecarboxylic acid;

1-{[4-Chloro-1-(2-thiophen-2-yl-thiazol-4-ylmethoxy)-naphthalene-2-carbonyl]-amino}-cyclobutanecarboxylic acid;

1-{[4-Chloro-1-(4-trifluoromethyl-benzyloxy)-naphthalene-2-carbonyl]-amino}-cyclobutanecarboxylic acid;

1-{[4-Chloro-1-(2-fluoro-4-trifluoromethyl-benzyloxy)-naphthalene-2-carbonyl]-amino}-cyclobutanecarboxylic acid;

1-{[1-(2,4-Bis-trifluoromethyl-benzyloxy)-4-chloro-naphthalene-2-carbonyl]-amino}-cyclobutanecarboxylic acid;

1-{[4-Chloro-1-(4-trifluoromethoxy-benzyloxy)-naphthalene-2-carbonyl]-amino}-cyclobutanecarboxylic acid;

1-[(1-Benzyloxy-4-chloro-naphthalene-2-carbonyl)-amino]-cyclobutanecarboxylic acid;

1-{[4-Chloro-1-(4-difluoromethoxy-benzyloxy)-naphthalene-2-carbonyl]-amino}-cyclobutanecarboxylic acid;

1-{[4-Chloro-1-(4-trifluoromethylsulfanyl-benzyloxy)-naphthalene-2-carbonyl]-amino}-cyclobutanecarboxylic acid;

1-{[1-(4-Bromo-2-fluoro-benzyloxy)-4-chloro-naphthalene-2-carbonyl]-amino}-cyclobutanecarboxylic acid;

1-{[1-(4-Bromo-2-fluoro-benzyloxy)-4-chloro-naphthalene-2-carbonyl]-amino}-cyclobutanecarboxylic acid;

1-{[4-Chloro-1-(4-chloro-2-fluoro-benzyloxy)-naphthalene-2-carbonyl]-amino}-cyclobutanecarboxylic acid;

1-{[4-Chloro-1-(4-isopropyl-benzyloxy)-naphthalene-2-carbonyl]-amino}-cyclobutanecarboxylic acid;

1-{[4-Chloro-1-(4-pyrazol-1-yl-benzyloxy)-naphthalene-2-carbonyl]-amino}-cyclobutanecarboxylic acid;

1-{[4-Chloro-1-(2-phenyl-thiazol-4-ylmethoxy)-naphthalene-2-carbonyl]-amino}-cyclobutanecarboxylic acid;

1-{[4-Chloro-1-(2,4-difluoro-benzyloxy)-naphthalene-2-carbonyl]-amino}-cyclobutanecarboxylic acid;

1-{[4-Chloro-1-(4-fluoro-benzyloxy)-naphthalene-2-carbonyl]-amino}-cyclobutanecarboxylic acid;

2-{[1-(Benzothiazol-2-ylmethoxy)-naphthalene-2-carbonyl]-amino}-2-ethyl-hexanoic acid;

2-Ethyl-2-{[1-(6-trifluoromethyl-pyridin-3-ylmethoxy)-naphthalene-2-carbonyl]-amino}-hexanoic acid;

2-{[1-(6-Chloro-pyridin-3-ylmethoxy)-naphthalene-2-carbonyl]-amino}-2-ethyl-hexanoic acid;

2-Ethyl-2-{[1-(quinolin-2-ylmethoxy)-naphthalene-2-carbonyl]-amino}-hexanoic acid;

2-Ethyl-2-{[1-(2-thiophen-2-yl-thiazol-4-ylmethoxy)-naphthalene-2-carbonyl]-amino}-hexanoic acid;

2-Ethyl-2-{[1-(4-trifluoromethyl-benzyloxy)-naphthalene-2-carbonyl]-amino}-hexanoic acid;

2-Ethyl-2-{[1-(2-fluoro-4-trifluoromethyl-benzyloxy)-naphthalene-2-carbonyl]-amino}-hexanoic acid;

2-{[1-(2,4-Bis-trifluoromethyl-benzyloxy)-naphthalene-2-carbonyl]-amino}-2-ethyl-hexanoic acid;

2-Ethyl-2-{[1-(4-trifluoromethoxy-benzyloxy)-naphthalene-2-carbonyl]-amino}-hexanoic acid;

2-[(1-Benzyloxy-naphthalene-2-carbonyl)amino]-2-ethyl-hexanoic acid;

2-{[1-(4-Difluoromethoxy-benzyloxy)-naphthalene-2-carbonyl]-amino}-2-ethyl-hexanoic acid;

2-Ethyl-2-{[1-(4-trifluoromethylsulfanyl-benzyloxy)-naphthalene-2-carbonyl]-amino}-hexanoic acid;

2-{[1-(4-Bromo-benzyloxy)-naphthalene-2-carbonyl]-amino}-2-ethyl-hexanoic acid;

2-{[1-(4-Bromo-2-fluoro-benzyloxy)-naphthalene-2-carbonyl]-amino}-2-ethyl-hexanoic acid;

2-{[1-(4-Chloro-benzyloxy)-naphthalene-2-carbonyl]-amino}-2-ethyl-hexanoic acid;

2-{[1-(4-Chloro-2-fluoro-benzyloxy)-naphthalene-2-carbonyl]-amino}-2-ethyl-hexanoic acid;

2-Ethyl-2-{[1-(4-isopropyl-benzyloxy)-naphthalene-2-carbonyl]-amino}-hexanoic acid;

2-Ethyl-2-{[1-(4-pyrazol-1-yl-benzyloxy)-naphthalene-2-carbonyl]-amino}-hexanoic acid;

2-Ethyl-2-{[1-(2-phenyl-thiazol-4-ylmethoxy)-naphthalene-2-carbonyl]-amino}-hexanoic acid;

2-{[1-(2,4-Difluoro-benzyloxy)-naphthalene-2-carbonyl]-amino}-2-ethyl-hexanoic acid;

2-{[1-(1H-Benzoimidazol-2-ylmethoxy)-naphthalene-2-carbonyl]-amino}-2-methyl-propionic acid;

2-{[1-(6-Chloro-benzooxazol-2-ylmethoxy)-naphthalene-2-carbonyl]-amino}-2-methyl-propionic acid;

2-{[1-(5-tert-Butyl-benzooxazol-2-ylmethoxy)-naphthalene-2-carbonyl]-amino}-2-methyl-propionic acid;

2-{[1-(5-Chloro-benzooxazol-2-ylmethoxy)-naphthalene-2-carbonyl]-amino}-2-methyl-propionic acid;

2-{[1-(5-Chloro-benzothiazol-2-ylmethoxy)-naphthalene-2-carbonyl]-amino}-2-methyl-propionic acid;

2-Methyl-2-{[1-(1-methyl-1H-benzoimidazol-2-ylmethoxy)-naphthalene-2-carbonyl]-amino}-propionic acid;

2-{[1-(5,6-Dichloro-1H-benzoimidazol-2-ylmethoxy)-naphthalene-2-carbonyl]-amino}-2-methyl-propionic acid;

2-{[1-(5-Chloro-1H-benzoimidazol-2-ylmethoxy)-naphthalene-2-carbonyl]-amino}-2-methyl-propionic acid;

2-Methyl-2-{[1-(5-phenyl-[1,3,4]oxadiazol-2-ylmethoxy)-naphthalene-2-carbonyl]-amino}-propionic acid;

2-{[1-(5-Chloro-benzothiazol-2-ylmethoxy)-4-fluoro-naphthalene-2-carbonyl]-amino}-2-methyl-propionic acid;

2-{[4-Fluoro-1-(5-fluoro-benzothiazol-2-ylmethoxy)-naphthalene-2-carbonyl]-amino}-2-methyl-propionic acid;

2-{[4-Fluoro-1-(2-phenyl-thiazol-4-ylmethoxy)-naphthalene-2-carbonyl]-amino}-2-methyl-propionic acid;

2-{[4-Fluoro-1-(5-thiophen-2-yl-[1,2,4]oxadiazol-3-ylmethoxy)-naphthalene-2-carbonyl]-amino}-2-methyl-propionic acid;

2-{[4-Chloro-1-(2-trifluoromethyl-pyrimidin-5-ylmethoxy)-naphthalene-2-carbonyl]-amino}-2-methyl-propionic acid;

2-{[4-Chloro-1-(2-methylsulfanyl-pyrimidin-5-ylmethoxy)-naphthalene-2-carbonyl]-amino}-2-methyl-propionic acid;

2-{[4-Chloro-1-(2-cyclopropyl-pyrimidin-5-ylmethoxy)-naphthalene-2-carbonyl]-amino}-2-methyl-propionic acid;

2-{[4-Chloro-1-(2-isopropyl-pyrimidin-5-ylmethoxy)-naphthalene-2-carbonyl]-amino}-2-methyl-propionic acid;

(R)-2-Methyl-2-{[1-(4-trifluoromethyl-benzyloxy)-naphthalene-2-carbonyl]-amino}-butyric acid;

(S)-2-Methyl-2-{[1-(4-trifluoromethyl-benzyloxy)-naphthalene-2-carbonyl]-amino}-butyric acid;

(R)-2-Methyl-2-{[1-(6-trifluoromethyl-pyridin-3-ylmethoxy)-naphthalene-2-carbonyl]-amino}-butyric acid;

(S)-2-Methyl-2-{[1-(6-trifluoromethyl-pyridin-3-ylmethoxy)-naphthalene-2-carbonyl]-amino}-butyric acid;

(R)-2-{[4-Chloro-1-(6-trifluoromethyl-pyridin-3-ylmethoxy)-naphthalene-2-carbonyl]-amino}-2-methyl-butyric acid;

(S)-2-{[4-Chloro-1-(6-trifluoromethyl-pyridin-3-ylmethoxy)-naphthalene-2-carbonyl]-amino}-2-methyl-butyric acid;

(R)-2-{[1-(2-Fluoro-4-trifluoromethyl-benzyloxy)-naphthalene-2-carbonyl]-amino}-2-methyl-butyric acid;

(S)-2-{[1-(2-Fluoro-4-trifluoromethyl-benzyloxy)-naphthalene-2-carbonyl]-amino}-2-methyl-butyric acid;

(R)-2-Methyl-2-{[1-(4-trifluoromethylsulfanyl-benzyloxy)-naphthalene-2-carbonyl]-amino}-butyric acid;

(S)-2-Methyl-2-{[1-(4-trifluoromethylsulfanyl-benzyloxy)-naphthalene-2-carbonyl]-amino}-butyric acid;

(R)-2-{[1-(5-Fluoro-benzothiazol-2-ylmethoxy)-naphthalene-2-carbonyl]-amino}-2-methyl-butyric acid;

(S)-2-{[1-(5-Fluoro-benzothiazol-2-ylmethoxy)-naphthalene-2-carbonyl]-amino}-2-methyl-butyric acid;

(R)-2-({4-Chloro-1-[1-(6-trifluoromethyl-pyridin-3-yl)-ethoxy]-naphthalene-2-carbonyl}-amino)-2-methyl-propionic acid;

(S)-2-({4-Chloro-1-[1-(6-trifluoromethyl-pyridin-3-yl)-ethoxy]-naphthalene-2-carbonyl}-amino)-2-methyl-propionic acid;

2-Methyl-3-phenyl-2-{[1-(4-trifluoromethyl-benzyloxy)-naphthalene-2-carbonyl]-amino}-propionic acid;

2-{[1-(Benzothiazol-2-ylmethoxy)-naphthalene-2-carbonyl]-amino}-2-methyl-3-phenyl-propionic acid;

2-Methyl-2-{[1-(6-trifluoromethyl-1H-benzoimidazol-2-ylmethoxy)-naphthalene-2-carbonyl]-amino}-propionic acid;

2-{[1-(4-Chloro-6-trifluoromethyl-1H-benzoimidazol-2-ylmethoxy)-naphthalene-2-carbonyl]-amino}-2-methyl-propionic acid;

2-{[1-(6-Cyano-1H-benzoimidazol-2-ylmethoxy)-naphthalene-2-carbonyl]-amino}-2-methyl-propionic acid;

2-({4-Chloro-1-[1-(4-trifluoromethyl-phenyl)-ethoxy]-naphthalene-2-carbonyl}-amino)-2-methyl-propionic acid;

2-{[4-Chloro-1-(quinolin-2-ylmethoxy)-naphthalene-2-carbonyl]-amino}-2-methyl-propionic acid;

2-{[4-Chloro-1-(5-thiophen-2-yl-[1,2,4]oxadiazol-3-ylmethoxy)-naphthalene-2-carbonyl]-amino}-2-methyl-propionic acid;

2-({4-Chloro-1-[5-(4-trifluoromethyl-phenyl)-[1,2,4]oxadiazol-3-ylmethoxy]-naphthalene-2-carbonyl}-amino)-2-methyl-propionic acid;

2-{[4-Chloro-1-(3-thiophen-2-yl-[1,2,4]oxadiazol-5-ylmethoxy)-naphthalene-2-carbonyl]-amino}-2-methyl-propionic acid;

(R)-2-{[1-(Benzothiazol-2-ylmethoxy)-4-chloro-naphthalene-2-carbonyl]-amino}-2-methyl-butyric acid;

(S)-2-{[1-(Benzothiazol-2-ylmethoxy)-4-chloro-naphthalene-2-carbonyl]-amino}-2-methyl-butyric acid;

2-{[4-Chloro-1-(5-cyclopropyl-[1,3,4]thiadiazol-2-ylmethoxy)-naphthalene-2-carbonyl]-amino}-2-methyl-butyric acid;

1-{[4-Chloro-1-(6-trifluoromethyl-pyridin-3-ylmethoxy)-naphthalene-2-carbonyl]-amino}-cyclopentanecarboxylic acid;

1-{[1-(Benzothiazol-2-ylmethoxy)-4-chloro-naphthalene-2-carbonyl]-amino}-cyclopentanecarboxylic acid;

1-{[4-Chloro-1-(quinolin-2-ylmethoxy)-naphthalene-2-carbonyl]-amino}-cyclopentanecarboxylic acid;

2-{[4-Chloro-1-(2-thiophen-2-yl-pyrimidin-5-ylmethoxy)-naphthalene-2-carbonyl]-amino}-2-methyl-propionic acid;

1-{[4-Chloro-1-(5-trifluoromethyl-pyridin-2-ylmethoxy)-naphthalene-2-carbonyl]-amino}-cyclopentanecarboxylic acid;

1-{[1-(5-Trifluoromethyl-pyridin-2-ylmethoxy)-naphthalene-2-carbonyl]-amino}-cyclopentanecarboxylic acid;

2-Methyl-2-{[1-(5-trifluoromethyl-pyridin-2-ylmethoxy)-naphthalene-2-carbonyl]-amino}-butyric acid;

1-{[1-(4-Trifluoromethylsulfanyl-benzyloxy)-naphthalene-2-carbonyl]-amino}-cyclopentanecarboxylic acid;

1-{[1-(2-Fluoro-4-trifluoromethyl-benzyloxy)-naphthalene-2-carbonyl]-amino}-cyclopentanecarboxylic acid;

1-{[4-Chloro-1-(4-trifluoromethylsulfanyl-benzyloxy)-naphthalene-2-carbonyl]-amino}-cyclopentanecarboxylic acid;

1-{[4-Chloro-1-(2-fluoro-4-trifluoromethyl-benzyloxy)-naphthalene-2-carbonyl]-amino}-cyclopentanecarboxylic acid;

1-({4-Chloro-1-[1-(4-trifluoromethyl-phenyl)-ethoxy]-naphthalene-2-carbonyl}-amino)-cyclopentanecarboxylic acid;

1-{[4-Chloro-1-(2-isopropyl-pyrimidin-5-ylmethoxy)-naphthalene-2-carbonyl]-amino}-cyclopentanecarboxylic acid;

(S)-2-{[4-Fluoro-1-(4-trifluoromethyl-benzyloxy)-naphthalene-2-carbonyl]-amino}-2-methyl-butyric acid;

2-{[1-(4-Bromo-benzyloxy)-4-fluoro-naphthalene-2-carbonyl]-amino}-2-methyl-propionic acid;

2-{[1-(2,4-Dichloro-benzyloxy)-4-fluoro-naphthalene-2-carbonyl]-amino}-2-methyl-propionic acid;

2-{[4-Fluoro-1-(quinolin-2-ylmethoxy)-naphthalene-2-carbonyl]-amino}-2-methyl-propionic acid;

2-{[1-(4-Bromo-benzyloxy)-4-fluoro-naphthalene-2-carbonyl]-amino}-2-methyl-butyric acid;

2-{[1-(4-Difluoromethoxy-benzyloxy)-4-fluoro-naphthalene-2-carbonyl]-amino}-2-methyl-butyric acid;

2-{[4-Fluoro-1-(quinolin-2-ylmethoxy)-naphthalene-2-carbonyl]-amino}-2-methyl-butyric acid;

2-{[1-(2,4-Dichloro-benzyloxy)-4-fluoro-naphthalene-2-carbonyl]-amino}-2-methyl-butyric acid;

2-{[4-Fluoro-1-(2-phenyl-thiazol-4-ylmethoxy)-naphthalene-2-carbonyl]-amino}-2-methyl-butyric acid;

(R)-2-{[4-Fluoro-1-(4-trifluoromethyl-benzyloxy)-naphthalene-2-carbonyl]-amino}-2-methyl-butyric acid;

2-{[4-Fluoro-1-(4-pyrrol-1-yl-benzyloxy)-naphthalene-2-carbonyl]-amino}-2-methyl-propionic acid;

1-{[1-(Benzothiazol-2-ylmethoxy)-4-fluoro-naphthalene-2-carbonyl]-amino}-cyclobutanecarboxylic acid;

1-{[4-Fluoro-1-(6-trifluoromethyl-pyridin-3-ylmethoxy)-naphthalene-2-carbonyl]-amino}-cyclobutanecarboxylic acid;

1-{[4-Fluoro-1-(4-trifluoromethyl-benzyloxy)-naphthalene-2-carbonyl]-amino}-cyclobutanecarboxylic acid 1-{[4-Fluoro-1-(5-trifluoromethyl-pyridin-2-ylmethoxy)-naphthalene-2-carbonyl]-amino}-cyclobutanecarboxylic acid;

2-{[4-Fluoro-1-(2-fluoro-4-trifluoromethyl-benzyloxy)-naphthalene-2-carbonyl]-amino}-2-methyl-propionic acid;

2-{[1-(4-Chloro-benzyloxy)-4-fluoro-naphthalene-2-carbonyl]-amino}-2-methyl-propionic acid;

2-[(1-Cyclohexylmethoxy-4-fluoro-naphthalene-2-carbonyl)-amino]-2-methyl-propionic acid;

2-{[4-Fluoro-1-(4-fluoro-benzyloxy)-naphthalene-2-carbonyl]-amino}-2-methyl-propionic acid;

2-{[4-Fluoro-1-(4-trifluoromethoxy-benzyloxy)-naphthalene-2-carbonyl]-amino}-2-methyl-propionic acid;

2-{[4-Fluoro-1-(tetrahydro-pyran-4-ylmethoxy)-naphthalene-2-carbonyl]-amino}-2-methyl-propionic acid;

2-{[4-Fluoro-1-(4-isopropyl-benzyloxy)-naphthalene-2-carbonyl]-amino}-2-methyl-propionic acid;

2-{[1-(4-Ethyl-benzyloxy)-4-fluoro-naphthalene-2-carbonyl]-amino}-2-methyl-propionic acid;

2-Methyl-2-{[3-(6-trifluoromethyl-pyridin-3-ylmethoxy)-1H-indole-2-carbonyl]-amino}-propionic acid;

2-{[1-(6-Methanesulfonyl-pyridin-3-ylmethoxy)-naphthalene-2-carbonyl]-amino}-2-methyl-propionic acid;

2-{[1-(6-Methanesulfinyl-pyridin-3-ylmethoxy)-naphthalene-2-carbonyl]-amino}-2-methyl-propionic acid;

2-({4-Chloro-1-[1-(6-trifluoromethyl-pyridin-3-yl)-ethoxy]-naphthalene-2-carbonyl}-amino)-2-methyl-propionic acid;

2-{[1-(6-Bromo-pyridin-3-ylmethoxy)-4-chloro-naphthalene-2-carbonyl]-amino}-2-methyl-propionic acid;

2-{[4-Chloro-1-(4-pentafluorothio-benzyloxy)-naphthalene-2-carbonyl]-amino}-2-methyl-butyric acid;

2-{[1-(Benzothiazol-2-ylmethoxy)-4-fluoro-naphthalene-2-carbonyl]-amino}-2-methyl-butyric acid;

2-{[4-Fluoro-1-(5-trifluoromethyl-pyridin-2-ylmethoxy)-naphthalene-2-carbonyl]-amino}-2-methyl-butyric acid;

2-{[4-Fluoro-1-(6-trifluoromethyl-pyridin-3-ylmethoxy)-naphthalene-2-carbonyl]-amino}-2-methyl-butyric acid;

2-{[4-Fluoro-1-(4-trifluoromethyl-benzyloxy)-naphthalene-2-carbonyl]-amino}-2-methyl-butyric acid;

2-{[4-Fluoro-1-(5-trifluoromethyl-pyridin-2-ylmethoxy)-naphthalene-2-carbonyl]-amino}-2-methyl-propionic acid;

1-{[4-Fluoro-1-(5-trifluoromethyl-pyridin-2-ylmethoxy)-naphthalene-2-carbonyl]-amino}-cyclopentanecarboxylic acid;

(R)-2-{[4-Fluoro-1-(5-trifluoromethyl-pyridin-2-ylmethoxy)-naphthalene-2-carbonyl]-amino}-2-methyl-butyric acid;

(S)-2-{[4-Fluoro-1-(5-trifluoromethyl-pyridin-2-ylmethoxy)-naphthalene-2-carbonyl]-amino}-2-methyl-butyric acid;

(S)-2-{[1-(Benzothiazol-2-ylmethoxy)-4-fluoro-naphthalene-2-carbonyl]-amino}-2-methyl-butyric acid;

(R)-2-{[1-(Benzothiazol-2-ylmethoxy)-4-fluoro-naphthalene-2-carbonyl]-amino}-2-methyl-butyric acid;

2-{[4-Fluoro-1-(6-trifluoromethyl-pyridin-3-ylmethoxy)-naphthalene-2-carbonyl]-amino}-2-methyl-propionic acid;

(S)-2-{[4-Fluoro-1-(6-trifluoromethyl-pyridin-3-ylmethoxy)-naphthalene-2-carbonyl]-amino}-2-methyl-butyric acid;

(R)-2-{[4-Fluoro-1-(6-trifluoromethyl-pyridin-3-ylmethoxy)-naphthalene-2-carbonyl]-amino}-2-methyl-butyric acid;

2-{[4-Fluoro-1-(4-pentafluorothio-benzyloxy)-naphthalene-2-carbonyl]-amino}-2-methyl-butyric acid;

2-{[1-(4-Chloro-3-fluoro-benzyloxy)-4-fluoro-naphthalene-2-carbonyl]-amino}-2-methyl-propionic acid;

2-{[1-(4-Chloro-2-fluoro-benzyloxy)-4-fluoro-naphthalene-2-carbonyl]-amino}-2-methyl-propionic acid;

2-{[1-(Benzothiazol-2-ylmethoxy)-4-fluoro-naphthalene-2-carbonyl]-amino}-2-methyl-propionic acid;

2-{[4-Fluoro-1-(4-trifluoromethylsulfanyl-benzyloxy)-naphthalene-2-carbonyl]-amino}-2-methyl-butyric acid;

2-{[4-Fluoro-1-(2-fluoro-4-trifluoromethyl-benzyloxy)-naphthalene-2-carbonyl]-amino}-2-methyl-butyric acid;

2-{[4-Fluoro-1-(4-pentafluorothio-benzyloxy)-naphthalene-2-carbonyl]-amino}-2-methyl-propionic acid;

2-{[5-Fluoro-1-(6-trifluoromethyl-pyridin-3-ylmethoxy)-naphthalene-2-carbonyl]-amino}-2-methyl-propionic acid;

2-{[4-Chloro-1-(4-chloro-pyridin-2-ylmethoxy)-naphthalene-2-carbonyl]-amino}-2-methyl-propionic acid;

2-{[4-Fluoro-1-(4-trifluoromethyl-thiazol-2-ylmethoxy)-naphthalene-2-carbonyl]-amino}-2-methyl-propionic acid;

2-{[1-(4-Chloro-pyridin-2-ylmethoxy)-4-fluoro-naphthalene-2-carbonyl]-amino}-2-methyl-propionic acid;

2-Methyl-2-{[1-(6-methyl-pyridin-2-ylmethoxy)-naphthalene-2-carbonyl]-amino}-propionic acid;

2-{[4-Chloro-1-(4-trifluoromethylsulfanyl-benzyloxy)-naphthalene-2-carbonyl]-amino}-2-methyl-propionic acid;

2-{[4-Chloro-1-(4-trifluoromethylsulfanyl-benzyloxy)-naphthalene-2-carbonyl]-amino}-2-methyl-butyric acid;

2-{[1-(5-Bromo-pyridin-2-ylmethoxy)-4-chloro-naphthalene-2-carbonyl]-amino}-2-methyl-propionic acid;

2-{[4-Chloro-1-(5-trifluoromethyl-pyridin-2-ylmethoxy)-naphthalene-2-carbonyl]-amino}-2-methyl-propionic acid;

2-{[4-Chloro-1-(5-methyl-isoxazol-3-ylmethoxy)-naphthalene-2-carbonyl]-amino}-2-methyl-propionic acid;

2-Methyl-2-{[1-(5-trifluoromethyl-pyridin-2-ylmethoxy)-naphthalene-2-carbonyl]-amino}-butyric acid;
2-{[4-Chloro-1-(5-trifluoromethyl-pyridin-2-ylmethoxy)-naphthalene-2-carbonyl]-amino}-2-methyl-butyric acid;
2-({4-Fluoro-1-[1-(4-trifluoromethyl-phenyl)-ethoxy]-naphthalene-2-carbonyl}-amino)-2-methyl-propionic acid;
2-{[1-(4-Pentafluorothio)-benzyloxy)-naphthalene-2-carbonyl]-amino}-2-methyl-propionic acid;
1-{[3-(Benzothiazol-2-ylmethoxy)-benzo[b]thiophene-2-carbonyl]-amino}-cyclobutanecarboxylic acid;
2-{[3-(5-Fluoro-benzothiazol-2-ylmethoxy)-benzo[b]thiophene-2-carbonyl]-amino}-2-methyl-propionic acid;
2-{[3-(Imidazo[1,2-a]pyridin-2-ylmethoxy)-benzo[b]thiophene-2-carbonyl]-amino}-2-methyl-propionic acid;
2-Methyl-2-({3-[1-(4-trifluoromethyl-phenyl)-ethoxy]-benzo[b]thiophene-2-carbonyl}-amino)-propionic acid;
2-Methyl-2-({3-[1-(4-trifluoromethyl-phenyl)-ethoxy]-benzo[b]thiophene-2-carbonyl}-amino)-butyric acid;
2-{[1-(Benzothiazol-2-ylmethoxy)-4-chloro-naphthalene-2-carbonyl]-amino}-2-ethyl-butyric acid;
2-{[1-(Benzothiazol-2-ylmethoxy)-naphthalene-2-carbonyl]-amino}-2-ethyl-butyric acid;
2-{[4-Chloro-1-(2-fluoro-4-trifluoromethyl-benzyloxy)-naphthalene-2-carbonyl]-amino}-2-methyl-butyric acid;
2-{[4-Chloro-1-(6-trifluoromethyl-pyridin-3-ylmethoxy)-naphthalene-2-carbonyl]-amino}-2-ethyl-butyric acid;
2-Ethyl-2-{[1-(6-trifluoromethyl-pyridin-3-ylmethoxy)-naphthalene-2-carbonyl]-amino}-butyric acid;
2-{[4-Fluoro-1-(4-trifluoromethylsulfanyl-benzyloxy)-naphthalene-2-carbonyl]-amino}-2-methyl-propionic acid;
2-{[1-(Phenylethynyl)-naphthalene-2-carbonyl]-amino}-2-methyl-propionic acid;
2-{[1-(4-Chloro-phenylethynyl)-naphthalene-2-carbonyl]-amino}-2-methyl-propionic acid;
2-{[1-(4-Fluoro-phenylethynyl)-naphthalene-2-carbonyl]-amino}-2-methyl-propionic acid;
2-{[1-(4-Methoxy-phenylethynyl)-naphthalene-2-carbonyl]-amino}-2-methyl-propionic acid;
1-{[1-(4-Chloro-phenylethynyl)-naphthalene-2-carbonyl]-amino}-cyclopentanecarboxylic acid;
1-[(1-Phenylethynyl-naphthalene-2-carbonyl)-amino]-cyclopentanecarboxylic acid;
1-{[1-(4-Methoxy-phenylethynyl)-naphthalene-2-carbonyl]-amino}-cyclopentanecarboxylic acid;
2-Methyl-2-[(1-phenethyl-naphthalene-2-carbonyl)-amino]-propionic acid;
1-[(1-Phenethyl-naphthalene-2-carbonyl)-amino]-cyclopentanecarboxylic acid;
2-({1-[2-(4-Methoxy-phenyl)-ethyl]-naphthalene-2-carbonyl}-amino)-2-methyl-propionic acid;
2-({1-[(E)-2-(4-Chloro-phenyl)-vinyl]-naphthalene-2-carbonyl}-amino)-2-methyl-propionic acid;
2-({1-[(E)-2-(4-Fluoro-phenyl)-vinyl]-naphthalene-2-carbonyl}-amino)-2-methyl-propionic acid;
2-({1-[(E)-2-(4-Isopropyl-phenyl)-vinyl]-naphthalene-2-carbonyl}-amino)-2-methyl-propionic acid;
2-({1-[(E)-2-(4-Methoxy-phenyl)-vinyl]-naphthalene-2-carbonyl}-amino)-2-methyl-propionic acid;
2-({1-[(E)-2-(4-Ethoxy-phenyl)-vinyl]-naphthalene-2-carbonyl}-amino)-2-methyl-propionic acid;
2-Methyl-2-({1-[(E)-2-(4-trifluoromethyl-phenyl)-vinyl]-naphthalene-2-carbonyl}-amino)-propionic acid;
2-Methyl-2-{[1-(4-trifluoromethyl-phenylethynyl)-naphthalene-2-carbonyl]-amino}-propionic acid;

and/or a pharmaceutically acceptable salt and/or a prodrug thereof.

Particular preference is given to the following compounds of the formula I, selected from the group consisting of:
2-[(1-Cyclohexylmethoxy-naphthalene-2-carbonyl)-amino]-2-methyl-propionic acid;
2-Methyl-2-{[1-(4-methyl-benzyloxy)-naphthalene-2-carbonyl]-amino}-propionic acid;
2-Methyl-2-{[1-(4-methyl-cyclohexylmethoxy)-naphthalene-2-carbonyl]-amino}-propionic acid;
2-Methyl-2-{[1-(4-methyl-cyclohexylmethoxy)-naphthalene-2-carbonyl]-amino}-propionic acid;
2-{[1-(4-Ethyl-benzyloxy)-naphthalene-2-carbonyl]-amino}-2-methyl-propionic acid;
2-{[1-(6-Methoxy-pyridin-3-ylmethoxy)-naphthalene-2-carbonyl]-amino}-2-methyl-propionic acid;
2-{[1-(4-Chloro-benzyloxy)-naphthalene-2-carbonyl]-amino}-2-methyl-propionic acid;
2-{[1-(6-Chloro-pyridin-3-ylmethoxy)-naphthalene-2-carbonyl]-amino}-2-methyl-propionic acid;
2-{[1-(Indan-5-ylmethoxy)-naphthalene-2-carbonyl]-amino}-2-methyl-propionic acid;
2-{[1-(Benzo[1,2,5]oxadiazol-5-ylmethoxy)-naphthalene-2-carbonyl]-amino}-2-methyl-propionic acid;
2-{[1-(4-Isopropyl-benzyloxy)-naphthalene-2-carbonyl]-amino}-2-methyl-propionic acid;
2-Methyl-2-{[1-(4-nitro-benzyloxy)-naphthalene-2-carbonyl]-amino}-propionic acid;
2-{[1-(6-Methoxy-pyridin-3-ylmethoxy)-naphthalene-2-carbonyl]-amino}-2-methyl-butyric acid;
2-Methyl-2-{[1-(4-methylsulfanyl-benzyloxy)-naphthalene-2-carbonyl]-amino}-propionic acid;
2-({1-[1-(4-Chloro-phenyl)-ethoxy]-naphthalene-2-carbonyl}-amino)-2-methyl-propionic acid;
2-Methyl-2-{[1-(naphthalen-2-ylmethoxy)-naphthalene-2-carbonyl]-amino}-propionic acid;
2-Methyl-2-{[1-(quinolin-2-ylmethoxy)-naphthalene-2-carbonyl]-amino}-propionic acid;
2-{[1-(4-Chloro-2-fluoro-benzyloxy)-naphthalene-2-carbonyl]-amino}-2-methyl-propionic acid;
2-{[1-(4-Chloro-3-fluoro-benzyloxy)-naphthalene-2-carbonyl]-amino}-2-methyl-propionic acid;
2-{[1-(Benzo[b]thiophen-2-ylmethoxy)-naphthalene-2-carbonyl]-amino}-2-methyl-propionic acid;
2-{[1-(Benzo[b]thiophen-3-ylmethoxy)-naphthalene-2-carbonyl]-amino}-2-methyl-propionic acid;
2-{[1-(4-tert-Butyl-benzyloxy)-naphthalene-2-carbonyl]-amino}-2-methyl-propionic acid;
2-{[1-(4-Butyl-benzyloxy)-naphthalene-2-carbonyl]-amino}-2-methyl-propionic acid;
2-{[1-(Benzothiazol-2-ylmethoxy)-naphthalene-2-carbonyl]-amino}-2-methyl-propionic acid;
2-Methyl-2-{[3-(quinolin-2-ylmethoxy)-benzo[b]thiophene-2-carbonyl]-amino}-propionic acid;
2-{[1-(2,3-Dihydro-benzo[1,4]dioxin-2-ylmethoxy)-naphthalene-2-carbonyl]-amino}-2-methyl-propionic acid;
2-{[1-(2,3-Dihydro-benzo[1,4]dioxin-6-ylmethoxy)-naphthalene-2-carbonyl]-amino}-2-methyl-propionic acid;
2-{[3-(Benzothiazol-2-ylmethoxy)-benzo[b]thiophene-2-carbonyl]-amino}-2-methyl-propionic acid;
2-Methyl-2-{[1-(3-pyrrol-1-yl-benzyloxy)-naphthalene-2-carbonyl]-amino}-propionic acid;
2-{[1-(4-Difluoromethoxy-benzyloxy)-naphthalene-2-carbonyl]-amino}-2-methyl-propionic acid;
2-Methyl-2-{[1-(4-pyrazol-1-yl-benzyloxy)-naphthalene-2-carbonyl]-amino}-propionic acid;

2-Methyl-2-{[1-(2-phenyl-oxazol-4-ylmethoxy)-naphthalene-2-carbonyl]-amino}-propionic acid;
2-Methyl-2-{[1-(4-trifluoromethyl-benzyloxy)-naphthalene-2-carbonyl]-amino}-propionic acid;
2-{[1-(2,4-Dichloro-benzyloxy)-naphthalene-2-carbonyl]-amino}-2-methyl-propionic acid;
2-{[1-(3,4-Dichloro-benzyloxy)-naphthalene-2-carbonyl]-amino}-2-methyl-propionic acid;
2-Methyl-2-{[1-(6-trifluoromethyl-pyridin-3-ylmethoxy)-naphthalene-2-carbonyl]-amino}-propionic acid;
2-Methyl-2-{[4-(4-trifluoromethyl-benzyloxy)-isoquinoline-3-carbonyl]-amino}-propionic acid;
1-{[1-(Benzothiazol-2-ylmethoxy)-naphthalene-2-carbonyl]-amino}-cyclobutanecarboxylic acid;
2-{[1-(5,6-Dichloro-pyridin-3-ylmethoxy)-naphthalene-2-carbonyl]-amino}-2-methyl-propionic acid;
2-{[1-(Benzo[b]thiophen-2-ylmethoxy)-naphthalene-2-carbonyl]-amino}-2-methyl-butyric acid;
2-{[1-(Benzo[b]thiophen-3-ylmethoxy)-naphthalene-2-carbonyl]-amino}-2-methyl-butyric acid;
2-{[1-(Benzothiazol-2-ylmethoxy)-naphthalene-2-carbonyl]-amino}-2-methyl-butyric acid;
2-{[1-(1-Benzothiazol-2-yl-ethoxy)-naphthalene-2-carbonyl]-amino}-2-methyl-propionic acid;
2-Methyl-2-{[3-(quinolin-2-ylmethoxy)-benzo[b]thiophene-2-carbonyl]-amino}-butyric acid;
2-{[1-(2,3-Dihydro-benzo[1,4]dioxin-2-ylmethoxy)-naphthalene-2-carbonyl]-amino}-2-methyl-butyric acid;
2-Methyl-2-{[3-(4-trifluoromethyl-benzyloxy)-benzo[b]thiophene-2-carbonyl]-amino}-propionic acid;
2-Methyl-2-{[3-(6-trifluoromethyl-pyridin-3-ylmethoxy)-benzo[b]thiophene-2-carbonyl]-amino}-propionic acid;
2-{[1-(5-Fluoro-benzothiazol-2-ylmethoxy)-naphthalene-2-carbonyl]-amino}-2-methyl-propionic acid;
2-{[1-(6-Chloro-benzooxazol-2-ylmethoxy)-naphthalene-2-carbonyl]-amino}-2-methyl-propionic acid;
2-{[1-(5-Chloro-benzooxazol-2-ylmethoxy)-naphthalene-2-carbonyl]-amino}-2-methyl-propionic acid;
2-{[1-(Biphenyl-4-ylmethoxy)-naphthalene-2-carbonyl]-amino}-2-methyl-propionic acid;
2-{[3-(Benzothiazol-2-ylmethoxy)-benzo[b]thiophene-2-carbonyl]-amino}-2-methyl-butyric acid;
2-{[1-(4-Methanesulfonyl-benzyloxy)-naphthalene-2-carbonyl]-amino}-2-methyl-propionic acid;
2-{[1-(4-Bromo-benzyloxy)-naphthalene-2-carbonyl]-amino}-2-methyl-propionic acid;
2-{[1-(3-Bromo-benzyloxy)-naphthalene-2-carbonyl]-amino}-2-methyl-propionic acid;
2-{[1-(6-Bromo-pyridin-3-ylmethoxy)-naphthalene-2-carbonyl]-amino}-2-methyl-propionic acid;
2-{[1-(4-Difluoromethoxy-benzyloxy)-naphthalene-2-carbonyl]-amino}-2-methyl-butyric acid;
2-{[1-(5-Cyano-benzo[b]thiophen-2-ylmethoxy)-naphthalene-2-carbonyl]-amino}-2-methyl-propionic acid;
2-Methyl-2-({1-[1-(4-trifluoromethyl-phenyl)-ethoxy]-naphthalene-2-carbonyl}-amino)-propionic acid;
2-Methyl-2-{[1-(4-trifluoromethyl-benzyloxy)-naphthalene-2-carbonyl]-amino}-butyric acid;
(R)-2-Methyl-2-{[1-(4-trifluoromethyl-benzyloxy)-naphthalene-2-carbonyl]-amino}-butyric acid;
2-Methyl-2-({1-[(S)-1-(4-trifluoromethyl-phenyl)-ethoxy]-naphthalene-2-carbonyl}-amino)-propionic acid;
2-Methyl-2-({1-[(R)-1-(4-trifluoromethyl-phenyl)-ethoxy]-naphthalene-2-carbonyl}-amino)-propionic acid;
(S)-2-Methyl-2-{[1-(4-trifluoromethyl-benzyloxy)-naphthalene-2-carbonyl]-amino}-butyric acid;
2-Methyl-2-({1-[1-(2-trifluoromethyl-phenyl)-ethoxy]-naphthalene-2-carbonyl}-amino)-propionic acid;
2-({1-[1-(3,4-Dichloro-phenyl)-ethoxy]-naphthalene-2-carbonyl}-amino)-2-methyl-propionic acid;
(S)-2-Methyl-2-{[1-(6-trifluoromethyl-pyridin-3-ylmethoxy)-naphthalene-2-carbonyl]-amino}-butyric acid;
2-Methyl-2-{[1-(6-trifluoromethyl-pyridin-3-ylmethoxy)-naphthalene-2-carbonyl]-amino}-butyric acid;
(R)-2-Methyl-2-{[1-(6-trifluoromethyl-pyridin-3-ylmethoxy)-naphthalene-2-carbonyl]-amino}-butyric acid;
1-{[1-(Benzothiazol-2-ylmethoxy)-naphthalene-2-carbonyl]-amino}-cyclopentanecarboxylic acid;
2-Methyl-2-{[1-(2-phenyl-thiazol-4-ylmethoxy)-naphthalene-2-carbonyl]-amino}-propionic acid;
1-{[3-(Quinolin-2-ylmethoxy)-benzo[b]thiophene-2-carbonyl]-amino}-cyclopentanecarboxylic acid;
2-Methyl-2-{[1-(4-trifluoromethoxy-benzyloxy)-naphthalene-2-carbonyl]-amino}-propionic acid;
2-Methyl-2-{[1-(3-trifluoromethoxy-benzyloxy)-naphthalene-2-carbonyl]-amino}-propionic acid;
1-{[1-(2,3-Dihydro-benzo[1,4]dioxin-2-ylmethoxy)-naphthalene-2-carbonyl]-amino}-cyclopentanecarboxylic acid;
2-{[4-Chloro-1-(quinolin-2-ylmethoxy)-naphthalene-2-carbonyl]-amino}-2-methyl-propionic acid;
2-{[4-Fluoro-1-(4-trifluoromethyl-benzyloxy)-naphthalene-2-carbonyl]-amino}-2-methyl-propionic acid;
2-{[1-(2-Fluoro-4-trifluoromethyl-benzyloxy)-naphthalene-2-carbonyl]-amino}-2-methyl-propionic acid;
2-Methyl-2-({3-[1-(4-trifluoromethyl-phenyl)-ethoxy]-benzo[b]thiophene-2-carbonyl}-amino)-propionic acid;
2-Methyl-2-{[3-(4-trifluoromethyl-benzyloxy)-benzo[b]thiophene-2-carbonyl]-amino}-butyric acid;
2-Methyl-2-{[3-(6-trifluoromethyl-pyridin-3-ylmethoxy)-benzo[b]thiophene-2-carbonyl]-amino}-butyric acid;
2-{[1-(5-Fluoro-benzothiazol-2-ylmethoxy)-naphthalene-2-carbonyl]-amino}-2-methyl-butyric acid;
2-Methyl-2-{[3-(4-trifluoromethoxy-benzyloxy)-benzo[b]thiophene-2-carbonyl]-amino}-propionic acid;
2-{[1-(5-Chloro-benzothiazol-2-ylmethoxy)-naphthalene-2-carbonyl]-amino}-2-methyl-propionic acid;
2-{[1-(Benzothiazol-2-ylmethoxy)-4-chloro-naphthalene-2-carbonyl]-amino}-2-methyl-propionic acid;
2-{[4-Chloro-1-(5-trifluoromethyl-furan-2-ylmethoxy)-naphthalene-2-carbonyl]-amino}-2-methyl-propionic acid;
2-({1-[1-(4-Bromo-phenyl)-ethoxy]-naphthalene-2-carbonyl}-amino)-2-methyl-propionic acid;
2-{[1-(5,6-Difluoro-benzothiazol-2-ylmethoxy)-naphthalene-2-carbonyl]-amino}-2-methyl-propionic acid;
1-{[1-(4-Trifluoromethyl-benzyloxy)-naphthalene-2-carbonyl]-amino}-cyclopentanecarboxylic acid;
1-{[1-(6-Trifluoromethyl-pyridin-3-ylmethoxy)-naphthalene-2-carbonyl]-amino}-cyclopentanecarboxylic acid;
2,3-Dimethyl-2-{[1-(4-trifluoromethyl-benzyloxy)-naphthalene-2-carbonyl]-amino}-butyric acid;
2-{[4-Chloro-1-(5-cyclopropyl-[1,3,4]thiadiazol-2-ylmethoxy)-naphthalene-2-carbonyl]-amino}-2-methyl-butyric acid;
2-{[1-(4-Bromo-2-fluoro-benzyloxy)-naphthalene-2-carbonyl]-amino}-2-methyl-propionic acid;
2-Methyl-2-{[1-(4-trifluoromethoxy-benzyloxy)-naphthalene-2-carbonyl]-amino}-butyric acid;
2-Methyl-2-{[1-(3-trifluoromethoxy-benzyloxy)-naphthalene-2-carbonyl]-amino}-butyric acid;
2-Methyl-2-({1-[6-(2,2,2-trifluoro-ethoxy)-pyridin-3-ylmethoxy]-naphthalene-2-carbonyl}-amino)-propionic acid;

(S)-2-{[1-(2-Fluoro-4-trifluoromethyl-benzyloxy)-naphthalene-2-carbonyl]-amino}-2-methyl-butyric acid;

2-{[1-(2-Fluoro-4-trifluoromethyl-benzyloxy)-naphthalene-2-carbonyl]-amino}-2-methyl-butyric acid;

(R)-2-{[1-(2-Fluoro-4-trifluoromethyl-benzyloxy)-naphthalene-2-carbonyl]-amino}-2-methyl-butyric acid;

2-Methyl-2-{[1-(4-trifluoromethylsulfanyl-benzyloxy)-naphthalene-2-carbonyl]-amino}-propionic acid;

1-{[3-(4-Trifluoromethyl-benzyloxy)-benzo[b]thiophene-2-carbonyl]-amino}-cyclopentanecarboxylic acid;

2-({1-[2-(4-Chloro-phenyl)-oxazol-5-ylmethoxy]-naphthalene-2-carbonyl}-amino)-2-methyl-propionic acid;

2-Methyl-2-({3-[1-(4-trifluoromethyl-phenyl)-ethoxy]-benzo[b]thiophene-2-carbonyl}-amino)-butyric acid;

2,3-Dimethyl-2-{[3-(4-trifluoromethyl-benzyloxy)-benzo[b]thiophene-2-carbonyl]-amino}-butyric acid;

2-{[4-Chloro-1-(4-trifluoromethyl-benzyloxy)-naphthalene-2-carbonyl]-amino}-2-methyl-propionic acid;

2-{[4-Chloro-1-(5-trifluoromethyl-pyridin-2-ylmethoxy)-naphthalene-2-carbonyl]-amino}-2-methyl-propionic acid;

2-{[4-Chloro-1-(6-trifluoromethyl-pyridin-3-ylmethoxy)-naphthalene-2-carbonyl]-amino}-2-methyl-propionic acid;

2-{[1-(2,3-Difluoro-4-trifluoromethyl-benzyloxy)-naphthalene-2-carbonyl]-amino}-2-methyl-propionic acid;

2-Methyl-2-{[3-(4-trifluoromethoxy-benzyloxy)-benzo[b]thiophene-2-carbonyl]-amino}-butyric acid;

(S)-2-{[1-(Benzothiazol-2-ylmethoxy)-4-chloro-naphthalene-2-carbonyl]-amino}-2-methyl-butyric acid;

(R)-2-{[1-(Benzothiazol-2-ylmethoxy)-4-chloro-naphthalene-2-carbonyl]-amino}-2-methyl-butyric acid;

2-{[1-(Benzothiazol-2-ylmethoxy)-4-chloro-naphthalene-2-carbonyl]-amino}-2-methyl-butyric acid;

2-{[1-(5,6-Difluoro-benzothiazol-2-ylmethoxy)-naphthalene-2-carbonyl]-amino}-2-methyl-butyric acid;

2-{[4-Chloro-1-(3-thiophen-2-yl-[1,2,4]oxadiazol-5-ylmethoxy)-naphthalene-2-carbonyl]-amino}-2-methyl-propionic acid;

2-{[4-Chloro-1-(5-thiophen-2-yl-[1,2,4]oxadiazol-3-ylmethoxy)-naphthalene-2-carbonyl]-amino}-2-methyl-propionic acid;

1-{[1-(4-Trifluoromethoxy-benzyloxy)-naphthalene-2-carbonyl]-amino}-cyclopentanecarboxylic acid;

2-{[1-(4-Bromo-2-fluoro-benzyloxy)-naphthalene-2-carbonyl]-amino}-2-methyl-butyric acid;

2,3-Dimethyl-2-{[1-(4-trifluoromethoxy-benzyloxy)-naphthalene-2-carbonyl]-amino}-butyric acid;

2-Methyl-2-({1-[6-(2,2,2-trifluoro-ethoxy)-pyridin-3-ylmethoxy]-naphthalene-2-carbonyl}-amino)-butyric acid;

2-Methyl-2-({1-[3-methyl-4-(2,2,2-trifluoro-ethoxy)-pyridin-2-ylmethoxy]-naphthalene-2-carbonyl}-amino)-propionic acid;

(S)-2-Methyl-2-{[1-(4-trifluoromethylsulfanyl-benzyloxy)-naphthalene-2-carbonyl]-amino}-butyric acid;

(R)-2-Methyl-2-{[1-(4-trifluoromethylsulfanyl-benzyloxy)-naphthalene-2-carbonyl]-amino}-butyric acid;

2-Methyl-2-{[1-(4-trifluoromethylsulfanyl-benzyloxy)-naphthalene-2-carbonyl]-amino}-butyric acid;

2-{[1-(5-Bromo-pyridin-2-ylmethoxy)-4-chloro-naphthalene-2-carbonyl]-amino}-2-methyl-propionic acid;

2-{[1-(6-Bromo-pyridin-3-ylmethoxy)-4-chloro-naphthalene-2-carbonyl]-amino}-2-methyl-propionic acid;

1-{[3-(4-Trifluoromethoxy-benzyloxy)-benzo[b]thiophene-2-carbonyl]-amino}-cyclopentanecarboxylic acid;

2-{[4-Chloro-1-(4-trifluoromethyl-benzyloxy)-naphthalene-2-carbonyl]-amino}-2-methyl-butyric acid;

2-({4-Chloro-1-[1-(4-trifluoromethyl-phenyl)-ethoxy]-naphthalene-2-carbonyl}-amino)-2-methyl-propionic acid;

2-({4-Chloro-1-[1-(6-trifluoromethyl-pyridin-3-yl)-ethoxy]-naphthalene-2-carbonyl}-amino)-2-methyl-propionic acid;

2-{[4-Chloro-1-(6-trifluoromethyl-pyridin-3-ylmethoxy)-naphthalene-2-carbonyl]-amino}-2-methyl-butyric acid;

(S)-2-{[4-Chloro-1-(6-trifluoromethyl-pyridin-3-ylmethoxy)-naphthalene-2-carbonyl]-amino}-2-methyl-butyric acid;

(R)-2-{[4-Chloro-1-(6-trifluoromethyl-pyridin-3-ylmethoxy)-naphthalene-2-carbonyl]-amino}-2-methyl-butyric acid;

1-{[1-(Benzothiazol-2-ylmethoxy)-4-chloro-naphthalene-2-carbonyl]-amino}-cyclopentanecarboxylic acid;

2-{[1-(2,3-Difluoro-4-trifluoromethyl-benzyloxy)-naphthalene-2-carbonyl]-amino}-2-methyl-butyric acid;

2,3-Dimethyl-2-{[3-(4-trifluoromethoxy-benzyloxy)-benzo[b]thiophene-2-carbonyl]-amino}-butyric acid;

2-{[4-Chloro-1-(4-trifluoromethoxy-benzyloxy)-naphthalene-2-carbonyl]-amino}-2-methyl-propionic acid;

2-{[1-(3-Chloro-4-trifluoromethoxy-benzyloxy)-naphthalene-2-carbonyl]-amino}-2-methyl-propionic acid;

2-{[4-Chloro-1-(2-fluoro-4-trifluoromethyl-benzyloxy)-naphthalene-2-carbonyl]-amino}-2-methyl-propionic acid;

2-Methyl-2-{[1-(5-trifluoromethyl-benzothiazol-2-ylmethoxy)-naphthalene-2-carbonyl]-amino}-propionic acid;

2-{[1-(4-Pentafluorothio-benzyloxy)-naphthalene-2-carbonyl]-amino}-2-methyl-propionic acid;

1-{[4-Chloro-1-(4-trifluoromethyl-benzyloxy)-naphthalene-2-carbonyl]-amino}-cyclopentanecarboxylic acid;

2-({1-[3-Methoxy-4-(2,2,2-trifluoro-ethoxy)-pyridin-2-ylmethoxy]-naphthalene-2-carbonyl}-amino)-2-methyl-propionic acid;

1-{[4-Chloro-1-(6-trifluoromethyl-pyridin-3-ylmethoxy)-naphthalene-2-carbonyl]-amino}-cyclopentanecarboxylic acid;

2-{[4-Chloro-1-(4-trifluoromethoxy-benzyloxy)-naphthalene-2-carbonyl]-amino}-2-methyl-butyric acid;

2-{[1-(3-Chloro-4-trifluoromethoxy-benzyloxy)-naphthalene-2-carbonyl]-amino}-2-methyl-butyric acid;

2-{[4-Chloro-1-(6-chloro-quinolin-2-ylmethoxy)-naphthalene-2-carbonyl]-amino}-2-methyl-butyric acid;

2-{[4-Chloro-1-(2-fluoro-4-trifluoromethyl-benzyloxy)-naphthalene-2-carbonyl]-amino}-2-methyl-butyric acid;

2-{[4-Chloro-1-(4-trifluoromethylsulfanyl-benzyloxy)-naphthalene-2-carbonyl]-amino}-2-methyl-propionic acid;

2-{[1-(2,4-Bis-trifluoromethyl-benzyloxy)-naphthalene-2-carbonyl]-amino}-2-methyl-propionic acid;

2-Methyl-2-{[1-(5-trifluoromethyl-benzothiazol-2-ylmethoxy)-naphthalene-2-carbonyl]-amino}-butyric acid;

2-{[4-Chloro-1-(5,6-difluoro-benzothiazol-2-ylmethoxy)-naphthalene-2-carbonyl]-amino}-2-methyl-butyric acid;

2-{[4-Bromo-1-(4-trifluoromethyl-benzyloxy)-naphthalene-2-carbonyl]-amino}-2-methyl-propionic acid;

2-{[4-Chloro-1-(4-trifluoromethylsulfanyl-benzyloxy)-naphthalene-2-carbonyl]-amino}-2-methyl-butyric acid;

2-{[1-(4-Methoxy-2-trifluoromethyl-quinolin-6-ylmethoxy)-naphthalene-2-carbonyl]-amino}-2-methyl-propionic acid;

2-{[4-Bromo-1-(4-trifluoromethoxy-benzyloxy)-naphthalene-2-carbonyl]-amino}-2-methyl-propionic acid;

1-{[4-Chloro-1-(5-trifluoromethyl-pyridin-2-yl-methoxy)-naphthalene-2-carbonyl]-amino}-cyclopentanecarboxylic acid;

1-{[1-(5-Trifluoromethyl-pyridin-2-ylmethoxy)-naphthalene-2-carbonyl]-amino}-cyclopentanecarboxylic acid;

2-{[1-(5-Chloro-6-methoxy-pyridin-3-ylmethoxy)-naphthalene-2-carbonyl]-amino}-2-methyl-propionic acid;

2-{[1-(5-Chloro-6-ethoxy-pyridin-3-ylmethoxy)-naphthalene-2-carbonyl]-amino}-2-methyl-propionic acid;

2-({1-[6-(2,2,2-trifluoro-ethoxy)-pyridin-3-ylmethoxy]-naphtha-lene-2-carbonyl}-amino)-2-methyl-propionic acid;

2-Methyl-2-({1-[6-(2,2,2-trifluoro-ethoxy)-pyridin-3-ylmethoxy]-naphtha-lene-2-carbonyl}-amino)-butyric acid;

2-{[1-(6-Methoxy-pyridin-3-ylmethoxy)-naphthalene-2-carbonyl]-amino}-2-methyl-propionic acid;

2-{[1-(6-Methoxy-pyridin-3-ylmethoxy)-naphthalene-2-carbonyl]-amino}-2-methyl-propionic acid;

2-{[1-(1-Benzothiazol-2-yl-ethoxy)-naphthalene-2-carbonyl]-amino}-2-methyl-propionic acid;

2-{[1-(4-Dimethylamino-2-trifluoromethyl-quinolin-6-ylmethoxy)-naphthalene-2-carbonyl]-amino}-2-methyl-propionic acid;

2-{[1-(4-methoxy-2-trifluoromethyl-quinolin-6-yl-methoxy)-naphthalene-2-carbonyl]-amino}-2-methyl-propionic acid;

2-{[3-(Benzothiazol-2-ylmethoxy)-5-fluoro-benzo[b]thiophene-2-carbonyl]-amino}-2-methyl-propionic acid;

2-{[5-Fluoro-3-(6-trifluoromethyl-pyridin-3-ylmethoxy)-benzo[b]thio-phene-2-carbonyl]-amino}-2-methyl-propionic acid;

2-({4-Chloro-1-[1-(2,2,2-trifluoro-acetyl)-piperidin-4-ylmethoxy]-naphthalene-2-carbonyl}-amino)-2-methyl-butyric acid;

1-{[1-(6-Trifluoromethyl-pyridin-3-ylmethoxy)-naphthalene-2-carbonyl]-amino}-cyclobutanecarboxylic acid;

1-{[1-(2-Thiophen-2-yl-thiazol-4-ylmethoxy)-naphthalene-2-carbonyl]-amino}-cyclobutanecarboxylic acid;

1-{[1-(4-Trifluoromethyl-benzyloxy)-naphthalene-2-carbonyl]-amino}-cyclobutanecarboxylic acid;

1-{[1-(2-Fluoro-4-trifluoromethyl-benzyloxy)-naphthalene-2-carbonyl]-amino}-cyclobutanecarboxylic acid;

1-{[1-(2,4-Bis-trifluoromethyl-benzyloxy)-naphthalene-2-carbonyl]-amino}-cyclobutanecarboxylic acid;

1-{[1-(4-Trifluoromethoxy-benzyloxy)-naphthalene-2-carbonyl]-amino}-cyclobutanecarboxylic acid;

1-{[1-(4-Trifluoromethylsulfanyl-benzyloxy)-naphthalene-2-carbonyl]-amino}-cyclobutanecarboxylic acid;

1-{[1-(4-Isopropyl-benzyloxy)-naphthalene-2-carbonyl]-amino}-cyclobutanecarboxylic acid;

1-{[1-(2-Phenyl-thiazol-4-ylmethoxy)-naphthalene-2-carbonyl]-amino}-cyclobutanecarboxylic acid;

1-{[4-Chloro-1-(2-thiophen-2-yl-thiazol-4-ylmethoxy)-naphthalene-2-carbonyl]-amino}-cyclobutanecarboxylic acid;

1-{[4-Chloro-1-(4-trifluoromethyl-benzyloxy)-naphthalene-2-carbonyl]-amino}-cyclobutanecarboxylic acid;

1-{[4-Chloro-1-(4-trifluoromethoxy-benzyloxy)-naphthalene-2-carbonyl]-amino}-cyclobutanecarboxylic acid;

2-Ethyl-2-{[1-(6-trifluoromethyl-pyridin-3-ylmethoxy)-naphthalene-2-carbonyl]-amino}-hexanoic acid;

2-{[1-(6-Chloro-pyridin-3-ylmethoxy)-naphthalene-2-carbonyl]-amino}-2-ethyl-hexanoic acid;

2-Ethyl-2-{[1-(quinolin-2-ylmethoxy)-naphthalene-2-carbonyl]-amino}-hexanoic acid;

2-Ethyl-2-{[1-(2-thiophen-2-yl-thiazol-4-ylmethoxy)-naphthalene-2-carbonyl]-amino}-hexanoic acid;

2-Ethyl-2-{[1-(4-trifluoromethyl-benzyloxy)-naphthalene-2-carbonyl]-amino}-hexanoic acid;

2-Ethyl-2-{[1-(2-fluoro-4-trifluoromethyl-benzyloxy)-naphthalene-2-carbonyl]-amino}-hexanoic acid;

2-{[1-(2,4-Bis-trifluoromethyl-benzyloxy)-naphthalene-2-carbonyl]-amino}-2-ethyl-hexanoic acid;

2-Ethyl-2-{[1-(4-trifluoromethoxy-benzyloxy)-naphthalene-2-carbonyl]-amino}-hexanoic acid;

2-{[1-(4-Difluoromethoxy-benzyloxy)-naphthalene-2-carbonyl]-amino}-2-ethyl-hexanoic acid;

2-Ethyl-2-{[1-(4-trifluoromethylsulfanyl-benzyloxy)-naphthalene-2-carbonyl]-amino}-hexanoic acid;

2-{[1-(4-Bromo-benzyloxy)-naphthalene-2-carbonyl]-amino}-2-ethyl-hexanoic acid;

2-{[1-(4-Bromo-2-fluoro-benzyloxy)-naphthalene-2-carbonyl]-amino}-2-ethyl-hexanoic acid;

2-{[1-(4-Chloro-benzyloxy)-naphthalene-2-carbonyl]-amino}-2-ethyl-hexanoic acid;

2-{[1-(4-Chloro-2-fluoro-benzyloxy)-naphthalene-2-carbonyl]-amino}-2-ethyl-hexanoic acid;

2-Ethyl-2-{[1-(4-isopropyl-benzyloxy)-naphthalene-2-carbonyl]-amino}-hexanoic acid;

2-Ethyl-2-{[1-(4-pyrazol-1-yl-benzyloxy)-naphthalene-2-carbonyl]-amino}-hexanoic acid;

2-Ethyl-2-{[1-(2-phenyl-thiazol-4-ylmethoxy)-naphthalene-2-carbonyl]-amino}-hexanoic acid;

2-{[1-(1H-Benzoimidazol-2-ylmethoxy)-naphthalene-2-carbonyl]-amino}-2-methyl-propionic acid;

2-{[1-(6-Chloro-benzooxazol-2-ylmethoxy)-naphthalene-2-carbonyl]-amino}-2-methyl-propionic acid;

2-{[1-(5-tert-Butyl-benzooxazol-2-ylmethoxy)-naphthalene-2-carbonyl]-amino}-2-methyl-propionic acid;

2-{[1-(5-Chloro-benzooxazol-2-ylmethoxy)-naphthalene-2-carbonyl]-amino}-2-methyl-propionic acid;

2-{[1-(5-Chloro-benzothiazol-2-ylmethoxy)-naphthalene-2-carbonyl]-amino}-2-methyl-propionic acid;

2-{[1-(5,6-Dichloro-1H-benzoimidazol-2-ylmethoxy)-naphthalene-2-carbonyl]-amino}-2-methyl-propionic acid;

2-Methyl-2-{[1-(5-phenyl-[1,3,4]oxadiazol-2-ylmethoxy)-naphthalene-2-carbonyl]-amino}-propionic acid;

2-{[1-(5-Chloro-benzothiazol-2-ylmethoxy)-4-fluoro-naphthalene-2-carbonyl]-amino}-2-methyl-propionic acid;

2-{[4-Fluoro-1-(5-fluoro-benzothiazol-2-ylmethoxy)-naphthalene-2-carbonyl]-amino}-2-methyl-propionic acid;

2-{[4-Fluoro-1-(2-phenyl-thiazol-4-ylmethoxy)-naphthalene-2-carbonyl]-amino}-2-methyl-propionic acid;

2-{[4-Fluoro-1-(5-thiophen-2-yl-[1,2,4]oxadiazol-3-ylmethoxy)-naphthalene-2-carbonyl]-amino}-2-methyl-propionic acid;

2-{[4-Chloro-1-(2-trifluoromethyl-pyrimidin-5-ylmethoxy)-naphthalene-2-carbonyl]-amino}-2-methyl-propionic acid;

2-{[4-Chloro-1-(2-methylsulfanyl-pyrimidin-5-ylmethoxy)-naphthalene-2-carbonyl]-amino}-2-methyl-propionic acid;

(R)-2-Methyl-2-{[1-(4-trifluoromethyl-benzyloxy)-naphthalene-2-carbonyl]-amino}-butyric acid;

(S)-2-Methyl-2-{[1-(4-trifluoromethyl-benzyloxy)-naphthalene-2-carbonyl]-amino}-butyric acid;

(R)-2-Methyl-2-{[1-(6-trifluoromethyl-pyridin-3-ylmethoxy)-naphthalene-2-carbonyl]-amino}-butyric acid;

(S)-2-Methyl-2-{[1-(6-trifluoromethyl-pyridin-3-ylmethoxy)-naphthalene-2-carbonyl]-amino}-butyric acid;

(R)-2-{[4-Chloro-1-(6-trifluoromethyl-pyridin-3-ylmethoxy)-naphthalene-2-carbonyl]-amino}-2-methyl-butyric acid;

(S)-2-{[4-Chloro-1-(6-trifluoromethyl-pyridin-3-yl-methoxy)-naphthalene-2-carbonyl]-amino}-2-methyl-butyric acid;

(R)-2-{[1-(2-Fluoro-4-trifluoromethyl-benzyloxy)-naphthalene-2-carbonyl]-amino}-2-methyl-butyric acid;

(S)-2-{[1-(2-Fluoro-4-trifluoromethyl-benzyloxy)-naphthalene-2-carbonyl]-amino}-2-methyl-butyric acid;

(R)-2-Methyl-2-{[1-(4-trifluoromethylsulfanyl-benzyloxy)-naphthalene-2-carbonyl]-amino}-butyric acid;

(S)-2-Methyl-2-{[1-(4-trifluoromethylsulfanyl-benzyloxy)-naphthalene-2-carbonyl]-amino}-butyric acid;

(R)-2-{[1-(5-Fluoro-benzothiazol-2-ylmethoxy)-naphthalene-2-carbonyl]-amino}-2-methyl-butyric acid;

(S)-2-{[1-(5-Fluoro-benzothiazol-2-ylmethoxy)-naphthalene-2-carbonyl]-amino}-2-methyl-butyric acid;

(R)-2-({4-Chloro-1-[1-(6-trifluoromethyl-pyridin-3-yl)-ethoxy]-naphthalene-2-carbonyl}-amino)-2-methyl-propionic acid;

(S)-2-({4-Chloro-1-[1-(6-trifluoromethyl-pyridin-3-yl)-ethoxy]-naphthalene-2-carbonyl}-amino)-2-methyl-propionic acid;

2-Methyl-3-phenyl-2-{[1-(4-trifluoromethyl-benzyloxy)-naphthalene-2-carbonyl]-amino}-propionic acid;

2-{[1-(Benzothiazol-2-ylmethoxy)-naphthalene-2-carbonyl]-amino}-2-methyl-3-phenyl-propionic acid;

2-({4-Chloro-1-[1-(4-trifluoromethyl-phenyl)-ethoxy]-naphthalene-2-carbonyl}-amino)-2-methyl-propionic acid;

2-{[4-Chloro-1-(quinolin-2-ylmethoxy)-naphthalene-2-carbonyl]-amino}-2-methyl-propionic acid;

2-{[4-Chloro-1-(5-thiophen-2-yl-[1,2,4]oxadiazol-3-yl-methoxy)-naphthalene-2-carbonyl]-amino}-2-methyl-propionic acid;

2-{[4-Chloro-1-(3-thiophen-2-yl-[1,2,4]oxadiazol-5-yl-methoxy)-naphthalene-2-carbonyl]-amino}-2-methyl-propionic acid;

(R)-2-{[1-(Benzothiazol-2-ylmethoxy)-4-chloro-naphthalene-2-carbonyl]-amino}-2-methyl-butyric acid;

(S)-2-{[1-(Benzothiazol-2-ylmethoxy)-4-chloro-naphthalene-2-carbonyl]-amino}-2-methyl-butyric acid;

2-{[4-Chloro-1-(5-cyclopropyl-[1,3,4]thiadiazol-2-ylmethoxy)-naphthalene-2-carbonyl]-amino}-2-methyl-butyric acid;

1-{[4-Chloro-1-(6-trifluoromethyl-pyridin-3-yl-methoxy)-naphthalene-2-carbonyl]-amino}-cyclopentanecarboxylic acid;

1-{[1-(Benzothiazol-2-ylmethoxy)-4-chloro-naphthalene-2-carbonyl]-amino}-cyclopentanecarboxylic acid;

1-{[4-Chloro-1-(quinolin-2-ylmethoxy)-naphthalene-2-carbonyl]-amino}-cyclopentanecarboxylic acid;

2-{[4-Chloro-1-(2-thiophen-2-yl-pyrimidin-5-yl-methoxy)-naphthalene-2-carbonyl]-amino}-2-methyl-propionic acid;

1-{[4-Chloro-1-(5-trifluoromethyl-pyridin-2-yl-methoxy)-naphthalene-2-carbonyl]-amino}-cyclopentanecarboxylic acid;

1-{[1-(5-Trifluoromethyl-pyridin-2-ylmethoxy)-naphthalene-2-carbonyl]-amino}-cyclopentanecarboxylic acid;

2-Methyl-2-{[1-(5-trifluoromethyl-pyridin-2-yl-methoxy)-naphthalene-2-carbonyl]-amino}-butyric acid;

1-{[1-(4-Trifluoromethylsulfanyl-benzyloxy)-naphthalene-2-carbonyl]-amino}-cyclopentanecarboxylic acid;

1-{[1-(2-Fluoro-4-trifluoromethyl-benzyloxy)-naphthalene-2-carbonyl]-amino}-cyclopentanecarboxylic acid;

1-{[4-Chloro-1-(4-trifluoromethylsulfanyl-benzyloxy)-naphthalene-2-carbonyl]-amino}-cyclopentanecarboxylic acid;

1-{[4-Chloro-1-(2-fluoro-4-trifluoromethyl-benzyloxy)-naphthalene-2-carbonyl]-amino}-cyclopentanecarboxylic acid;

1-({4-Chloro-1-[1-(4-trifluoromethyl-phenyl)-ethoxy]-naphthalene-2-carbonyl}-amino)-cyclopentanecarboxylic acid;

(S)-2-{[4-Fluoro-1-(4-trifluoromethyl-benzyloxy)-naphthalene-2-carbonyl]-amino}-2-methyl-butyric acid;

2-{[1-(4-Bromo-benzyloxy)-4-fluoro-naphthalene-2-carbonyl]-amino}-2-methyl-propionic acid;

2-{[1-(2,4-Dichloro-benzyloxy)-4-fluoro-naphthalene-2-carbonyl]-amino}-2-methyl-propionic acid;

2-{[4-Fluoro-1-(quinolin-2-ylmethoxy)-naphthalene-2-carbonyl]-amino}-2-methyl-propionic acid;

2-{[1-(4-Bromo-benzyloxy)-4-fluoro-naphthalene-2-carbonyl]-amino}-2-methyl-butyric acid;

2-{[1-(4-Difluoromethoxy-benzyloxy)-4-fluoro-naphthalene-2-carbonyl]-amino}-2-methyl-butyric acid;

2-{[4-Fluoro-1-(quinolin-2-ylmethoxy)-naphthalene-2-carbonyl]-amino}-2-methyl-butyric acid;

2-{[1-(2,4-Dichloro-benzyloxy)-4-fluoro-naphthalene-2-carbonyl]-amino}-2-methyl-butyric acid;

2-{[4-Fluoro-1-(2-phenyl-thiazol-4-ylmethoxy)-naphthalene-2-carbonyl]-amino}-2-methyl-butyric acid;

(R)-2-{[4-Fluoro-1-(4-trifluoromethyl-benzyloxy)-naphthalene-2-carbonyl]-amino}-2-methyl-butyric acid;

2-{[4-Fluoro-1-(4-pyrrol-1-yl-benzyloxy)-naphthalene-2-carbonyl]-amino}-2-methyl-propionic acid;

1-{[1-(Benzothiazol-2-ylmethoxy)-4-fluoro-naphthalene-2-carbonyl]-amino}-cyclobutanecarboxylic acid;

1-{[4-Fluoro-1-(6-trifluoromethyl-pyridin-3-ylmethoxy)-naphthalene-2-carbonyl]-amino}-cyclobutanecarboxylic acid;

1-{[4-Fluoro-1-(4-trifluoromethyl-benzyloxy)-naphthalene-2-carbonyl]-amino}-cyclobutanecarboxylic acid;

1-{[4-Fluoro-1-(5-trifluoromethyl-pyridin-2-ylmethoxy)-naphthalene-2-carbonyl]-amino}-cyclobutanecarboxylic acid;

2-{[4-Fluoro-1-(2-fluoro-4-trifluoromethyl-benzyloxy)-naphthalene-2-carbonyl]-amino}-2-methyl-propionic acid;

2-{[1-(4-Chloro-benzyloxy)-4-fluoro-naphthalene-2-carbonyl]-amino}-2-methyl-propionic acid;

2-[(1-Cyclohexylmethoxy-4-fluoro-naphthalene-2-carbonyl)-amino]-2-methyl-propionic acid;

2-{[4-Fluoro-1-(4-fluoro-benzyloxy)-naphthalene-2-carbonyl]-amino}-2-methyl-propionic acid;

2-{[4-Fluoro-1-(4-trifluoromethoxy-benzyloxy)-naphthalene-2-carbonyl]-amino}-2-methyl-propionic acid;

2-{[4-Fluoro-1-(tetrahydro-pyran-4-ylmethoxy)-naphthalene-2-carbonyl]-amino}-2-methyl-propionic acid;

2-{[4-Fluoro-1-(4-isopropyl-benzyloxy)-naphthalene-2-carbonyl]-amino}-2-methyl-propionic acid;

2-{[1-(4-Ethyl-benzyloxy)-4-fluoro-naphthalene-2-carbonyl]-amino}-2-methyl-propionic acid;

2-{[1-(6-Methanesulfonyl-pyridin-3-ylmethoxy)-naphthalene-2-carbonyl]-amino}-2-methyl-propionic acid;

2-({4-Chloro-1-[1-(6-trifluoromethyl-pyridin-3-yl)-ethoxy]-naphthalene-2-carbonyl}-amino)-2-methyl-propionic acid;

2-{[1-(6-Bromo-pyridin-3-ylmethoxy)-4-chloro-naphthalene-2-carbonyl]-amino}-2-methyl-propionic acid;

2-{[4-Chloro-1-(4-pentafluorothio-benzyloxy)-naphthalene-2-carbonyl]-amino}-2-methyl-butyric acid;

2-{[1-(Benzothiazol-2-ylmethoxy)-4-fluoro-naphthalene-2-carbonyl]-amino}-2-methyl-butyric acid;

2-{[4-Fluoro-1-(5-trifluoromethyl-pyridin-2-ylmethoxy)-naphthalene-2-carbonyl]-amino}-2-methyl-butyric acid;

2-{[4-Fluoro-1-(6-trifluoromethyl-pyridin-3-ylmethoxy)-naphthalene-2-carbonyl]-amino}-2-methyl-butyric acid;
2-{[4-Fluoro-1-(4-trifluoromethyl-benzyloxy)-naphthalene-2-carbonyl]-amino}-2-methyl-butyric acid;
2-{[4-Fluoro-1-(5-trifluoromethyl-pyridin-2-ylmethoxy)-naphthalene-2-carbonyl]-amino}-2-methyl-propionic acid;
1-{[4-Fluoro-1-(5-trifluoromethyl-pyridin-2-ylmethoxy)-naphthalene-2-carbonyl]-amino}-cyclopentanecarboxylic acid;
(R)-2-{[4-Fluoro-1-(5-trifluoromethyl-pyridin-2-ylmethoxy)-naphthalene-2-carbonyl]-amino}-2-methyl-butyric acid;
(S)-2-{[4-Fluoro-1-(5-trifluoromethyl-pyridin-2-ylmethoxy)-naphthalene-2-carbonyl]-amino}-2-methyl-butyric acid;
(S)-2-{[1-(Benzothiazol-2-ylmethoxy)-4-fluoro-naphthalene-2-carbonyl]-amino}-2-methyl-butyric acid;
(R)-2-{[1-(Benzothiazol-2-ylmethoxy)-4-fluoro-naphthalene-2-carbonyl]-amino}-2-methyl-butyric acid;
2-{[4-Fluoro-1-(6-trifluoromethyl-pyridin-3-ylmethoxy)-naphthalene-2-carbonyl]-amino}-2-methyl-propionic acid;
(S)-2-{[4-Fluoro-1-(6-trifluoromethyl-pyridin-3-yl-methoxy)-naphthalene-2-carbonyl]-amino}-2-methyl-butyric acid;
(R)-2-{[4-Fluoro-1-(6-trifluoromethyl-pyridin-3-yl-methoxy)-naphthalene-2-carbonyl]-amino}-2-methyl-butyric acid;
2-{[4-Fluoro-1-(4-pentafluorothio-benzyloxy)-naphthalene-2-carbonyl]-amino}-2-methyl-butyric acid;
2-{[1-(4-Chloro-3-fluoro-benzyloxy)-4-fluoro-naphthalene-2-carbonyl]-amino}-2-methyl-propionic acid;
2-{[1-(4-Chloro-2-fluoro-benzyloxy)-4-fluoro-naphthalene-2-carbonyl]-amino}-2-methyl-propionic acid;
2-{[1-(Benzothiazol-2-ylmethoxy)-4-fluoro-naphthalene-2-carbonyl]-amino}-2-methyl-propionic acid;
2-{[4-Fluoro-1-(4-trifluoromethylsulfanyl-benzyloxy)-naphthalene-2-carbonyl]-amino}-2-methyl-butyric acid;
2-{[4-Fluoro-1-(2-fluoro-4-trifluoromethyl-benzyloxy)-naphthalene-2-carbonyl]-amino}-2-methyl-butyric acid;
2-{[4-Fluoro-1-(4-pentafluorothio-benzyloxy)-naphthalene-2-carbonyl]-amino}-2-methyl-propionic acid;
2-{[5-Fluoro-1-(6-trifluoromethyl-pyridin-3-ylmethoxy)-naphthalene-2-carbonyl]-amino}-2-methyl-propionic acid;
2-{[4-Fluoro-1-(4-trifluoromethyl-thiazol-2-ylmethoxy)-naphthalene-2-carbonyl]-amino}-2-methyl-propionic acid;
2-{[4-Chloro-1-(4-trifluoromethylsulfanyl-benzyloxy)-naphthalene-2-carbonyl]-amino}-2-methyl-propionic acid;
2-{[4-Chloro-1-(4-trifluoromethylsulfanyl-benzyloxy)-naphthalene-2-carbonyl]-amino}-2-methyl-butyric acid;
2-{[1-(5-Bromo-pyridin-2-ylmethoxy)-4-chloro-naphthalene-2-carbonyl]-amino}-2-methyl-propionic acid;
2-{[4-Chloro-1-(5-trifluoromethyl-pyridin-2-ylmethoxy)-naphthalene-2-carbonyl]-amino}-2-methyl-propionic acid;
2-Methyl-2-{[1-(5-trifluoromethyl-pyridin-2-ylmethoxy)-naphthalene-2-carbonyl]-amino}-butyric acid;
2-{[4-Chloro-1-(5-trifluoromethyl-pyridin-2-ylmethoxy)-naphthalene-2-carbonyl]-amino}-2-methyl-butyric acid;
2-({4-Fluoro-1-[1-(4-trifluoromethyl-phenyl)-ethoxy]-naphthalene-2-carbonyl}-amino)-2-methyl-propionic acid;
2-{[1-(4-Pentafluorothio)-benzyloxy)-naphthalene-2-carbonyl]-amino}-2-methyl-propionic acid;
1-{[3-(Benzothiazol-2-ylmethoxy)-benzo[b]thiophene-2-carbonyl]-amino}-cyclobutanecarboxylic acid;
2-{[3-(5-Fluoro-benzothiazol-2-ylmethoxy)-benzo[b]thiophene-2-carbonyl]-amino}-2-methyl-propionic acid;
2-Methyl-2-({3-[1-(4-trifluoromethyl-phenyl)-ethoxy]-benzo[b]thiophene-2-carbonyl}-amino)-propionic acid;
2-Methyl-2-({3-[1-(4-trifluoromethyl-phenyl)-ethoxy]-benzo[b]thiophene-2-carbonyl}-amino)-butyric acid;
2-{[1-(Benzothiazol-2-ylmethoxy)-4-chloro-naphthalene-2-carbonyl]-amino}-2-ethyl-butyric acid;
2-{[1-(Benzothiazol-2-ylmethoxy)-naphthalene-2-carbonyl]-amino}-2-ethyl-butyric acid;
2-{[4-Chloro-1-(2-fluoro-4-trifluoromethyl-benzyloxy)-naphthalene-2-carbonyl]-amino}-2-methyl-butyric acid;
2-{[4-Chloro-1-(6-trifluoromethyl-pyridin-3-ylmethoxy)-naphthalene-2-carbonyl]-amino}-2-ethyl-butyric acid;
2-Ethyl-2-{[1-(6-trifluoromethyl-pyridin-3-ylmethoxy)-naphthalene-2-carbonyl]-amino}-butyric acid;
2-{[4-Fluoro-1-(4-trifluoromethylsulfanyl-benzyloxy)-naphthalene-2-carbonyl]-amino}-2-methyl-propionic acid;
2-{[1-(Phenylethynyl)-naphthalene-2-carbonyl]-amino}-2-methyl-propionic acid;
2-{[1-(4-Chloro-phenylethynyl)-naphthalene-2-carbonyl]-amino}-2-methyl-propionic acid;
2-{[1-(4-Fluoro-phenylethynyl)-naphthalene-2-carbonyl]-amino}-2-methyl-propionic acid;
2-{[1-(4-Methoxy-phenylethynyl)-naphthalene-2-carbonyl]-amino}-2-methyl-propionic acid;
1-{[1-(4-Chloro-phenylethynyl)-naphthalene-2-carbonyl]-amino}-cyclopentanecarboxylic acid;
1-{[1-(4-Methoxy-phenylethynyl)-naphthalene-2-carbonyl]-amino}-cyclopentanecarboxylic acid;
2-({1-[(E)-2-(4-Chloro-phenyl)-vinyl]-naphthalene-2-carbonyl}-amino)-2-methyl-propionic acid;
2-({1-[(E)-2-(4-Fluoro-phenyl)-vinyl]-naphthalene-2-carbonyl}-amino)-2-methyl-propionic acid;
2-({1-[(E)-2-(4-Isopropyl-phenyl)-vinyl]-naphthalene-2-carbonyl}-amino)-2-methyl-propionic acid;
2-({1-[(E)-2-(4-Methoxy-phenyl)-vinyl]-naphthalene-2-carbonyl}-amino)-2-methyl-propionic acid;
2-({1-[(E)-2-(4-Ethoxy-phenyl)-vinyl]-naphthalene-2-carbonyl}-amino)-2-methyl-propionic acid;
2-Methyl-2-({1-[(E)-2-(4-trifluoromethyl-phenyl)-vinyl]-naphthalene-2-carbonyl}-amino)-propionic acid;
2-Methyl-2-{[1-(4-trifluoromethyl-phenylethynyl)-naphthalene-2-carbonyl]-amino}-propionic acid;
and/or a pharmaceutically acceptable salt and/or a prodrug thereof.

The compounds of the formula I can be present in the form of their salts. An overview of pharmaceutically employed salts can be found in the "Handbook of Pharmaceutical Salts", edited by P. Heinrich Stahl, Camille G. Wermuth, Verlag Helvetica Chimica Acta, Switzerland, 2002. Suitable base addition salts are salts of all pharmacologically acceptable bases, for example alkali metal, earth alkali metal or metal salts, preferably sodium, potassium, magnesium, calcium or zinc salts, or as ammonium salts, for example as salts with ammonia or organic amines or amino acids, preferably as salts formed with ammonia, arginine, benethamine, benzathine, choline, deanol, diethanolamine, ditehylamine, 2-(diethylamino)-ethanol, ethanolamine, ethylendiamine, N-methyl-glucamine, hydrabamine, 1H-imidazole, lysine, 4-(2-hydroxyethyl)-morpholine, piperazine, 1-(2-hydroxyethyl)-pyrrolidine, triethanolamine or tromethamine; If the compounds contain a basic group, they are capable of forming salts with acid, for example halides, in particular hydrochlorides, hydrobromides, lactates, sulfates, citrates, tartrates, acetates, phosphates, methylsulfonates, benzenesulfonates, p-toluenesulfonates, adipinates, fumarates, gluconates, glutamates, glycerolphosphates, maleates, benzoates, oxalates and pamoates. This group also corresponds to the physiologically acceptable anions; but also trifluoroacetates. They can also be present as zwitterions.

If the inventive compounds contain one or more centers of asymmetry, these may independently of one another have the S and the R configuration. The compounds may be in the form of optical isomers, of diastereomers, of racemates or of mixtures thereof in any ratio.

The compounds of the formula I according to the invention can contain mobile hydrogen atoms, that is be present in various tautomeric forms. The present invention relates to all the tautomers of the compounds of the formula I.

The present invention furthermore encompasses derivatives of compounds of the formula I, for example solvates, such as hydrates and adducts with alcohols, esters, prodrugs and other physiologically tolerated derivatives of compounds of the formula I, and also active metabolites of compounds of the formula I. Further the invention contains all crystal modifications of compounds of formula I.

The invention relates, in particular, to prodrugs of the compounds of the formula I which are not necessarily pharmacologically active in vitro but which are converted in vivo, under physiological conditions, into active compounds of the formula I, for example by hydrolysis in blood. The skilled person is familiar with suitable prodrugs for the compounds of the formula I, that is chemically modified derivatives of the compounds of the formula I possessing properties which have been improved in a desired manner. Further details with regard to prodrugs can be found, for example, in Fleisher et al., Advanced Drug Delivery Reviews 19 (1996) 115-130; Design of Prodrugs, H. Bundgaard, Ed., Elsevier, 1985; or H. Bundgaard, Drugs of the Future 16 (1991) 443. Prodrugs which are especially suitable for the compounds of the formula I are ester prodrugs of carboxylic acid groups, amide prodrugs of carboxylic acid groups and alcohol prodrugs of carboxylic acid groups as well as acyl prodrugs and carbamate prodrugs of acylatable nitrogen-containing groups such as amino groups, amidino groups and guanidino groups. In the acyl prodrugs or carbamate prodrugs, a hydrogen atom which is located on a nitrogen atom is replaced with an acyl group or carbamate group. Suitable acyl groups and carbamate groups for the acyl prodrugs and carbamate prodrugs are, for example, the group D. Examples of ester prodrugs and amide prodrugs which may be mentioned are $(C_1-C_4)$-alkyl esters such as methyl esters, ethyl esters, n-propyl esters, isopropyl esters, n-butyl esters and isobutyl esters, substituted alkyl esters such as hydroxyalkyl esters, acyloxyalkyl esters, aminoalkyl esters, acylaminoalkyl esters and dialkylaminoalkyl esters, unsubstituted amides and N—$(C_1-C_4)$-alkylamides, such as methylamides or ethylamides. For example the methyl and ethyl esters of the compounds listed above are included.

Alkyl radicals may be straight-chain or branched. This also applies if they carry substituents or occur as substituents of other radicals, for example in alkylamino, alkoxy, arylalkyl, heteroarylalkyl, fluoroalkyl or —$SO_f$-alkyl radicals. Examples of alkyl radicals are methyl, ethyl, n-propyl, iso-propyl (=1-methylethyl), n-butyl, isobutyl (=2-methylpropyl), sec-butyl (=1-methylpropyl), tert-butyl (=1,1-dimethylethyl), pentyl or hexyl. Preferred alkyl radicals are methyl, ethyl, n-propyl, isopropyl, tert-butyl and isobutyl. One or more, for example 1, 2, 3, 4, 5, 6, 7, 8, 9, 10, 11, 12 or 13, hydrogen atoms in alkyl radicals may be replaced by fluorine atoms to form fluoroalkyl radicals. Examples of such radicals are difluoromethyl, trifluoromethyl, pentafluoroethyl, 2,2,2-trifluoroethyl; 3,3,3-trifluoropropyl; 3,3,3-trifluorobutyl, 4,4,4-trifluorbutyl.

Examples of cycloalkyl radicals are cyclopropyl, cyclobutyl, cyclopentyl, cyclohexyl, cycloheptyl or cyclooctyl, in particular cyclopentyl or cyclohexyl. Cycloalkyl radicals can be saturated or partly unsaturated, especially when they are condensed to an aryl or heteroaryl radical. For example a cycloalkyl radicals may contain zero, one or two double bonds. This also applies if they carry substituents or occur as substituents of other radicals, for example in the radical cycloalkylalkyl. One or more, for example 1, 2, 3, 4, 5, 6, 7, 8, 9, 10, 11, 12 or 13, hydrogen atoms in cycloalkyl radicals may be replaced by fluorine atoms to form fluorocycloalkyl radicals. Substituted cycloalkyl radicals may be substituted in identical or different positions.

Heterocycle radicals are monocyclic or bicyclic saturated or partly unsaturated 5, 6, 7, 8, 9 or 10-membered ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms, in particular two oxygen atoms. Heterocycle radicals includes heterocycloalkyls and heterocycloalkenyls and, therefore, they can be saturated or partly unsaturated, especially when they are condensed to an aryl or heteroaryl radical, for example to form 2,3-Dihydro-benzo[1,4]dioxine. For example a heterocycle radicals may contain zero, one or two double bonds. The heterocycle radicals may be attached by all positions, for example by the 1 position, 2 position, 3 position, 4 position, 5 position, 6 position, 7 position or 8 position. Heterocycle radicals may be unsubstituted or be substituted one or more times, for example once, twice or three times, by identical or different radicals in identical or different positions. This applies likewise to heterocycle radicals such as, for example, in the radical heterocycloalkyl. Examples of heterocycles are oxirane, aziridine, tetrahydrofurane, tetrahydropyrane, dioxolane, for example 1,3-dioxolane, dioxane, for example 1,4-dioxan, piperidine, pyrrolidin, imidazolidine, triazolidine, hexahydropyrimidine, piperazine, tetrahydropyridazine, triazinane, for example, 1,3,5-triazinane, 1,2,3-triazinane or 1,2,4-triazinane, tetrahydrothiophene, tetrahydrothiopyrane, dithiolane, for example 1,3-dithiolane, dithiane, thiazolidine, oxazolidine, oxathiolane, for example 1,3-oxathiolane, morpholine or thiomorpholine, in particular piperidine, 1,3-dioxolane and 1,4-dioxane.

The aryl radicals are chosen from phenyl, 1-naphthyl, 2-naphthyl and indenyl. Aryl radicals may be unsubstituted or be substituted one or more times, for example once, twice or three times, by identical or different radicals. If a aryl radical is substituted, it preferably has one, Two or three identical or different substituents. This likewise applies to substituted aryl radicals in groups such as, for example, arylalkyl or aryloxy. Aryl radicals may be condensed to a cycloalkyl or heterocycle radical, for example to form 2,3-Dihydro-benzo[1,4]dioxine, Benzo[1,3]dioxole or indane.

Heteroaryl radicals are monocyclic or bicyclic aromatic 5, 6, 7, 8, 9 or 10-membered ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or substituted one or more times, for example once, twice or three times, by identical or different radicals. This applies likewise to heteroaryl radicals such as, for example, in the radical heteroarylalkyl. Aryl radicals may be condensed to a cycloalkyl or heterocycle radical. Examples of heteroaryl are furyl, thienyl, pyrrolyl, imidazolyl, pyrazolyl, oxazolyl, isoxazolyl, thiazolyl, isothiazolyl, pyridyl, triazolyl, oxadiazolyl, thiadiazolyl, pyrazinyl, pyrimidinyl, pyridazinyl, tetrazolyl, benzothiophenyl, benzofuranyl, indolyl, isoindolyl, indazolyl, quinolyl, isoquinolyl, benzimidazolyl, benzothiazolyl, benzoxazolyl, benzotriazolyl, benzoxadiazolyl, benzothiadiazolyl, quinoxalinyl, quinazolinyl, cinnolinyl, phthalazinyl, quinolizinyl, purinyl, pteridinyl and thienothiazolyl. Also encompassed are the corresponding N-oxides and S-dioxides of these compounds, i.e. for example.

In one embodiment heteroaromatic radicals are furyl, thienyl, imidazolyl, pyrazolyl, oxazolyl, isoxazolyl, thiazolyl, pyridyl, triazolyl, oxadiazolyl, pyrazinyl, pyrimidinyl, pyridazinyl, benzthiophenyl, quinolyl, benzimidazolyl, benzothiazolyl, benzoxazolyl, benzotriazolyl, benzoxadiazolyl.

When any variable (e. g. aryl, R1) occurs more than one time in any constituent, its definition on each occurrence is independent of its definition at every other occurrence. Also, combinations of substituents and/or variables are permissible only if such combinations result in stable compounds.

The invention further relates to the following processes for preparing the compounds of the formula I.

Compounds of formula I can be prepared as described in Scheme 1 c) converting an ester of formula VI to an acid of formula Ia and optionally converting an acid of formula Ia to a compound of formula I
or
converting an ester of formula VI to a compound of formula I;
wherein in the compounds of the formulae Ia, III, IV, V and VI
X, Y1 to Y4, R1 and R2 are defined as in formula I,
R is —C(R11R12)-A, wherein R11, R12 and A are defined as in formula I and B is —O—(CR11R12)-,
Z is OH or L, wherein L is a leaving group, which can undergo nucleophilic substitution with an amine, and
R' is alkyl having 1, 2, 3, 4, 5 or 6 carbon atoms.

The procedure for preparing the compounds of the formula I is initially a coupling of an amino compound of formula IV with an acid of formula III for preparing the compound of formula V generally in the presence of an coupling agent, for example EDC, DIC or HATU and optionally an additional base, for example triethylamine or Hünig's base, can be used in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The

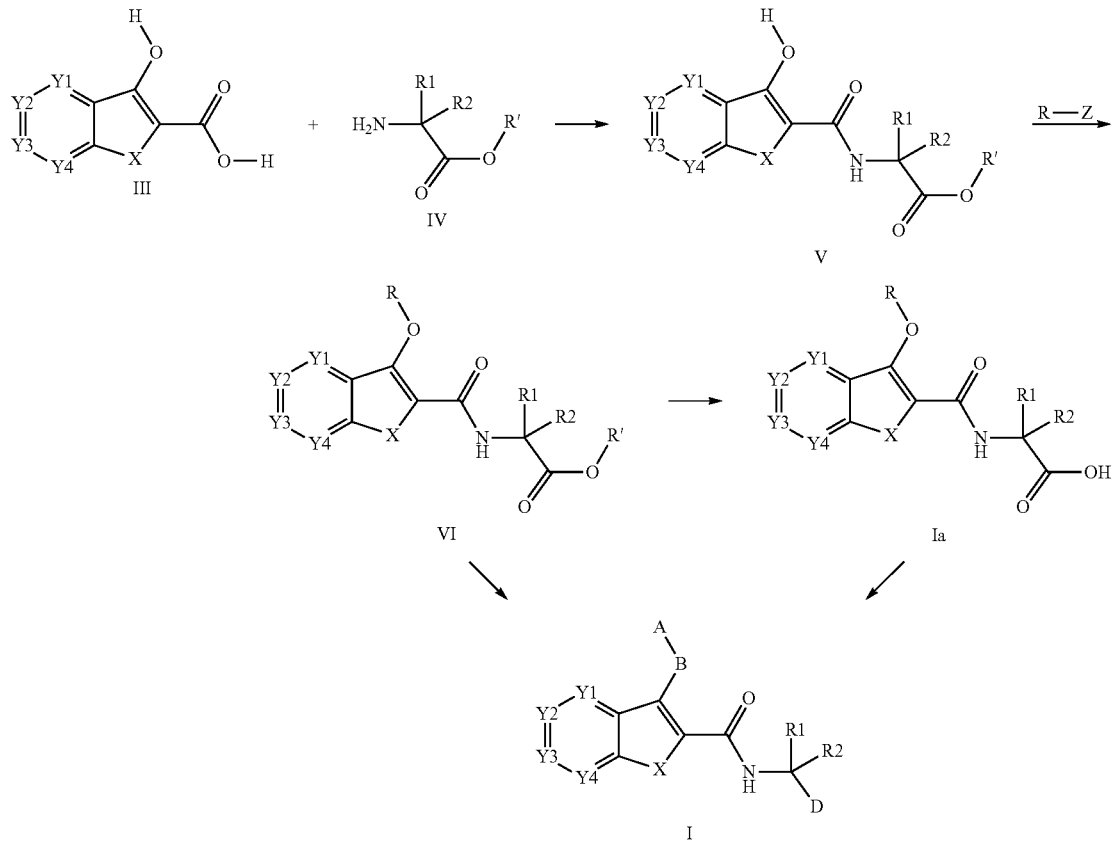

Scheme 1 which comprises
a) coupling of an acid of formula III with an amino compound of formula IV to an amide of formula V,
b) reacting a compound of formula V with an reagent R-L to an compound of formula VI, reaction time is generally from 15 min to 6 days, preferably from 15 min to 16 h depending on the composition of the mixture and the chosen temperature range.

Subsequently, the transformation of the compound of formula V to the compound of formula VI can be achieved by adding the reagent R-L (Z=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range.

analogy to the processes which are described in the literature and are known to those skilled in the art, for example by reaction of compounds of formula Ia with oxalyl chloride followed by the reaction with a sulfonamide in the presence of a suitable base like sodium hydride.

Alternatively compounds of formula I can be prepared as described in Scheme 2

Scheme 2

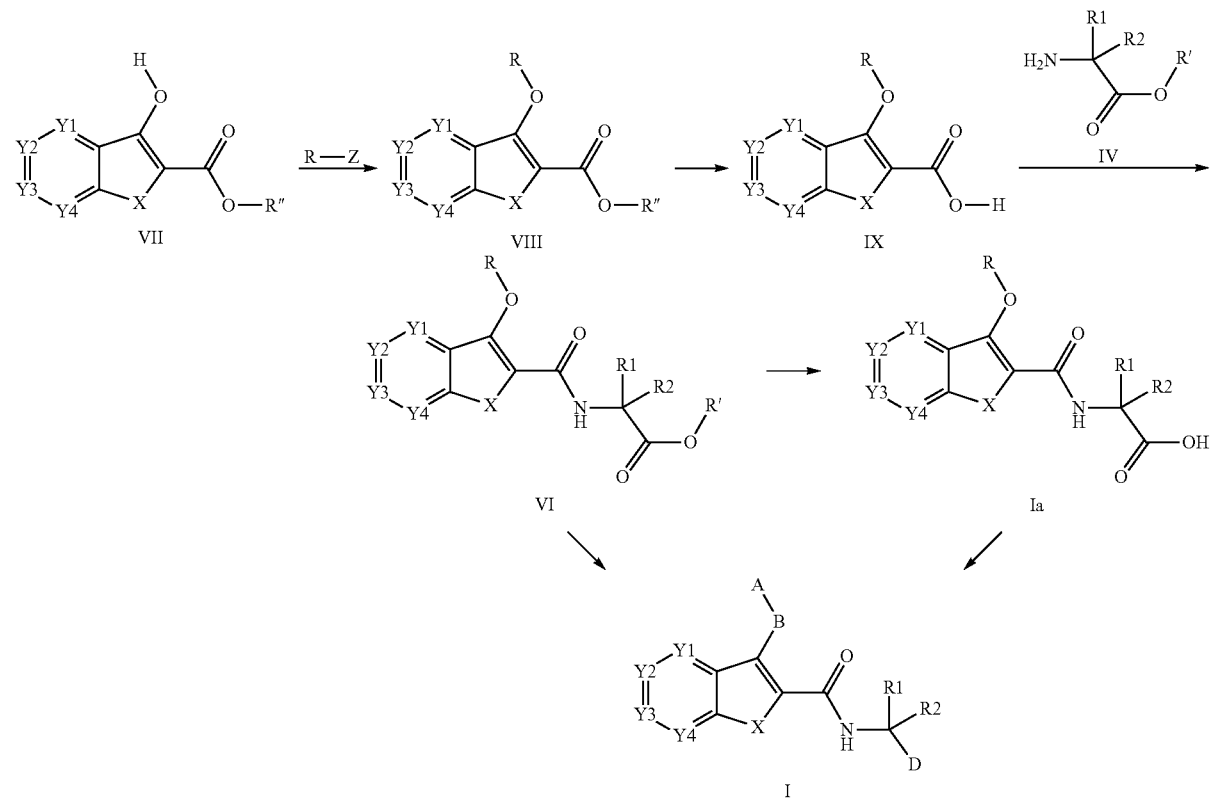

Alternatively the reaction of the compound of formula V with R—OH (Z=L) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range.

The cleavage of the ester of formula VI to the acid of formula Ia in can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range. The optional derivatisation of the compounds of the formulae VI or Ia to compounds of formula I, in which D is not defined as C(O)OH, can be carried out in which comprises a) reacting a compound of formula VII with an reagent R-L to a compound of formula VIII b) converting an ester of formula VIII to an acid of formula IX c) coupling of an acid of formula IX with an amino compound of formula IV to an amide of formula VI d) converting an ester of formula VI to an acid of formula Ia and optionally converting an acid of formula Ia to a compound of formula I or converting an ester of formula VI to a compound of formula I;

wherein in the compounds of the formulae Ia, IV, VI, VII, VIII and IX

X, Y1 to Y4, R1 and R2 are defined as in formula I,

R is —(CR11R12)-A, wherein R11, R12 and A are defined as in formula I and B is —O—(CR11R12)-, Z is OH or L, wherein L is a leaving group, which can undergo nucleophilic substitution with an amine, R' is alkyl having 1, 2, 3, 4, 5 or 6 carbon atoms, and R" is alkyl having 1, 2, 3, 4, 5 or 6 carbon atoms or aryl.

The procedure for preparing the compounds of the formula I is initially a transformation of the compound of formula VII to the compound of formula VIII which can be achieved by adding the reagent R-L (Z=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h depending on the composition of the mixture and the chosen temperature range Alternatively the reaction of the compound of formula V with R—OH (Z=L) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range.

The subsequent cleavage of the ester of formula VIII to the acid of formula IX can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

The resulting compound of formula IX can be coupled with the amino compound of formula IV to form the compound of formula VI generally in the presence of an coupling agent, for example EDC, DIC or HATU and optionally an additional base, for example triethylamine or Hünig's base, in an appropriate solvent, in particular in an aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range.

The optional cleavage of the ester of formula VI to the acid of formula Ia in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range.

The optional derivatisation of the compounds of the formulae VI or Ia to compounds of formula I, in which D is not defined as C(O)OH, can be carried out in analogy to the processes which are described in the literature and are known to those skilled in the art, for example by reaction of compounds of formula Ia with oxalyl chloride followed by the reaction with a sulfonamide in the presence of a suitable base like sodium hydride.

Alternatively, compounds of formula I can be prepared as described in Scheme 3

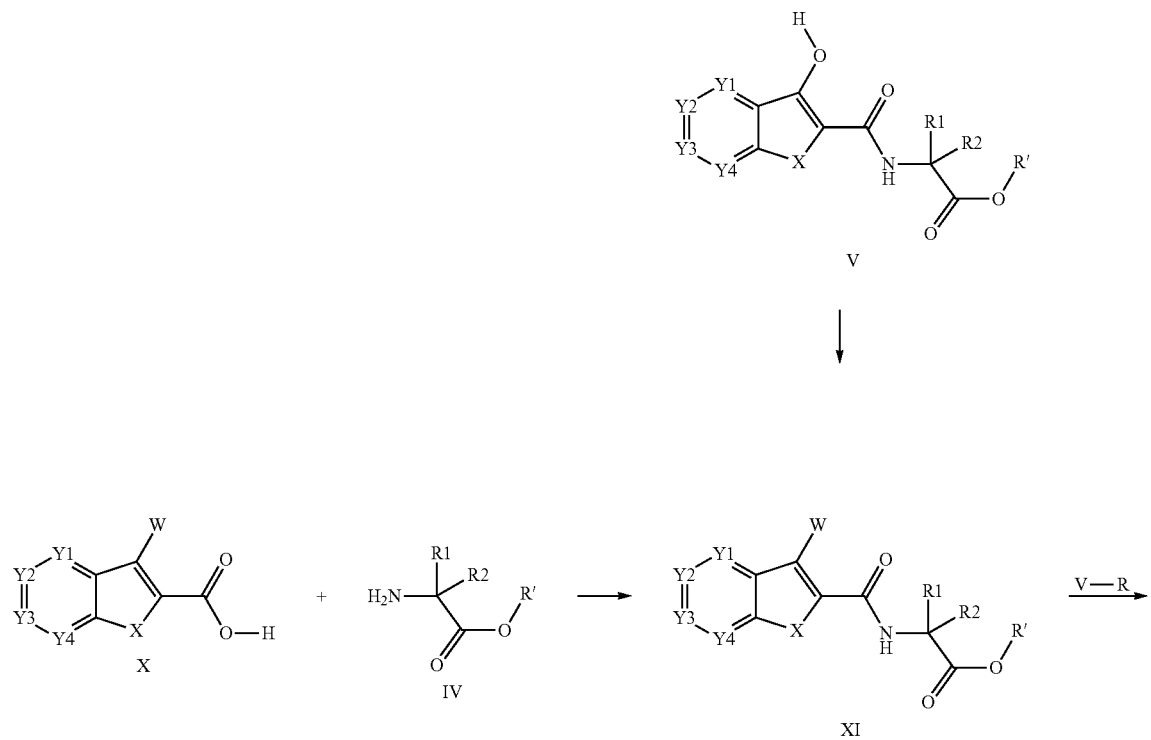

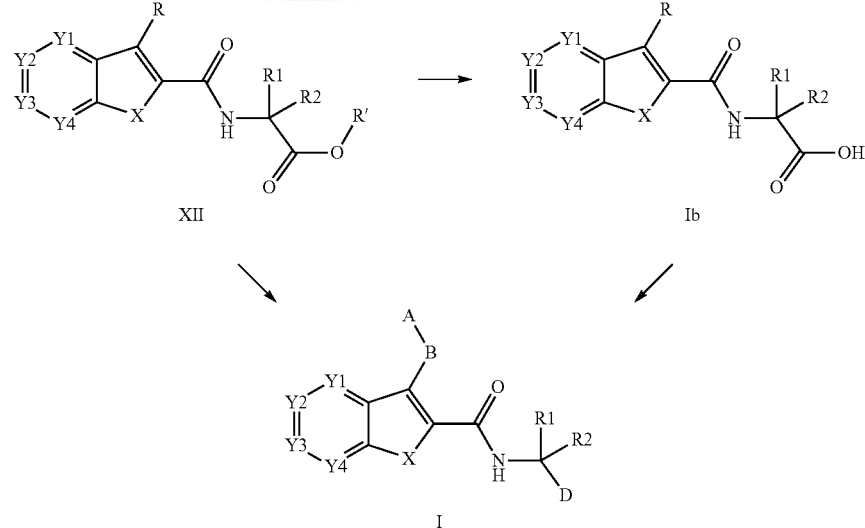

which comprises a) coupling of an acid of formula X with an amino compound of formula IV to an amide of formula XI, or, alternatively, the conversion of a compound of formula V to a compound of formula XI (if W is triflate, mesylate or tosylate), b) reacting a compound of formula XI with an reagent V—R to an compound of formula XII, c) converting an ester of formula XII to an acid of formula Ib and optionally converting an acid of formula Ib to a compound of formula I or, alternatively, converting an ester of formula XII to a compound of formula I;

converting an ester of formula XII to a compound of formula I;

wherein in the compounds of the formulae Ib, IV, V, X, XI and XII

X, Y1 to Y4, R1 and R2 are defined as in formula I,

V—R is HC≡C-A and R is —C≡C-A, or V—R is HCR52=CR53-A and R is —CR52=CR53-A, or V—R is (R'''O)$_2$BCR52=CR53-A and R is —CR52=CR53-A, or V—R is (R'''')$_3$SnCR52=CR53-A and R is —(R'''')$_3$SnCR52=CR53-A, or V—R is HalZnCR52=CR53-A and R is —CR52=CR53-A, or V—R is HNR17-C(R18R19)-A and R is —NR17-C(R18R19)-A, or V—R is HNR20-C(O)-A and R is —NR20-C(O)-A, wherein R17, R18, R19, R20, R52, R53 and A are defined as in formula I, W is halogen, for example I, Br or Cl, or triflate, mesylate or tosylate, R' is alkyl having 1, 2, 3, 4, 5 or 6 carbon atoms, R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups, R'''' is alkyl having 1, 2, 3, 4, 5 or 6 carbon atoms, Hal is halogen, for example I, Br or Cl.

The procedure for preparing the compounds of the formula I is initially a coupling of an amino compound of formula IV with an acid of formula X for preparing the compound of formula XI generally in the presence of an coupling agent, for example EDC, DIC or HATU and optionally an additional base, for example triethylamine or Hünig's base, can be used in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Alternatively, a compound of formula V can be converted into a compound of formula XI, in which W is defined as triflate, tosylate or mesylate, by reacting it with an anhydride or chloride of trifluoromethane sulfonic acid para-toluene sulfonic acid or methyl sulfonic acid in the presence of a suitable base, for example triethylamine in an appropriate solvent, for example dichloromethane. The reaction temperature in this case is generally from −80° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range. Subsequently, the transformation of the compound of formula XI to the compound of formula XII can be achieved by reacting with a reagent V—R, often under inert conditions and in an appropriate solvent, in the presence of a suitable catalytic system, which can contain a palladium and/or copper complex and/or salt, for example Pd$_2$dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range.

The cleavage of the ester of formula XII to the acid of formula Ib can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range. One optional derivatisation of the compounds of the formulae XII or Ib to compounds of formula I, in which D is not defined as C(O)OH, can be carried known to those skilled in the art, for example by (partial) hydrogenation of compounds of formula Ib in the presence of homogenous or heterogenous catalyst or by (partial) hydrogenation of compounds of formula XII in the presence of homogenous or heterogenous catalyst of, followed by an ester cleavage as described above.

Alternatively compounds of formula I can be prepared as described in Scheme 4

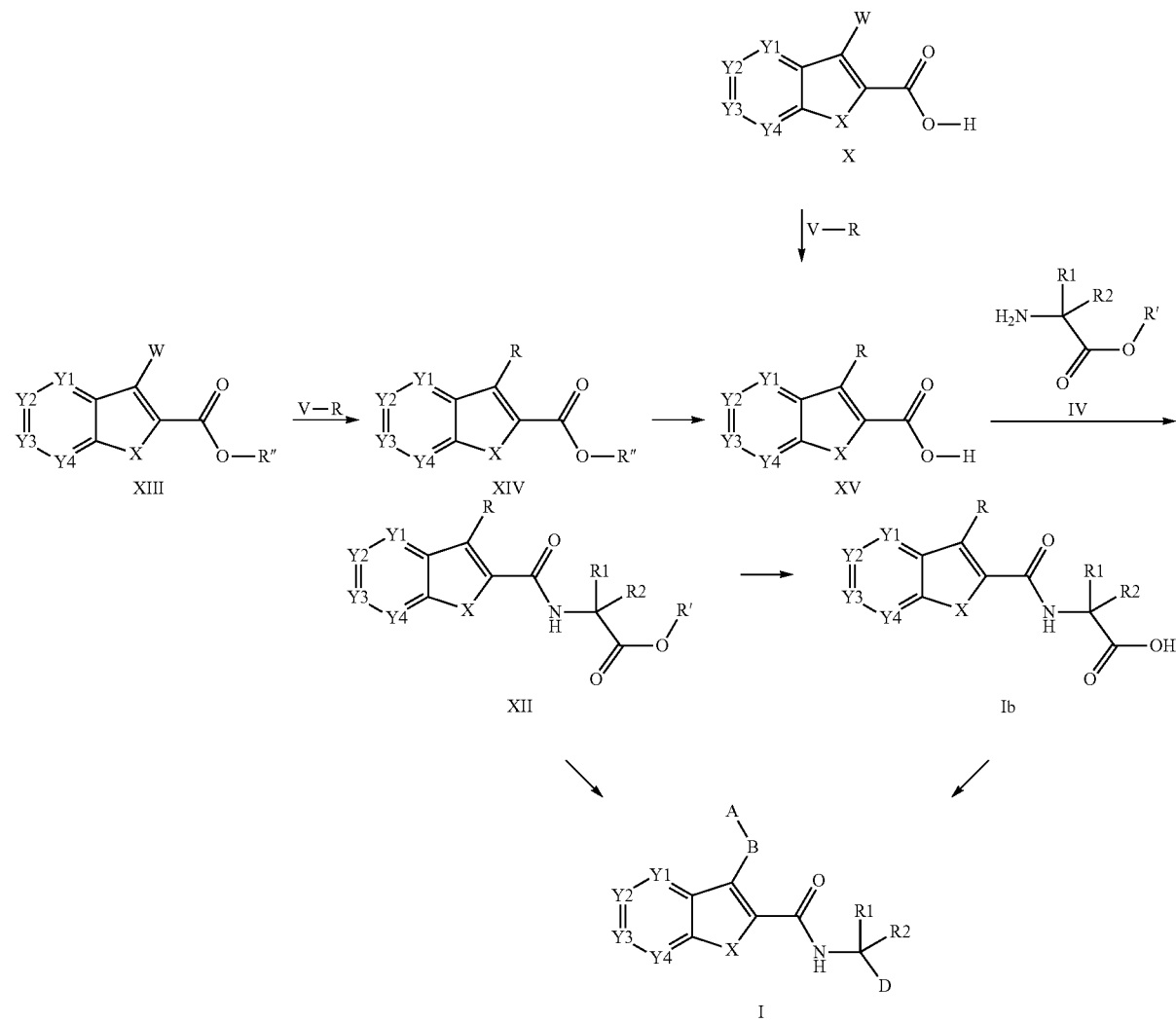

out in analogy to the processes which are described in the literature and are known to those skilled in the art, for example by reaction of compounds of formula Ib with oxalyl chloride followed by the reaction with a sulfonamide in the presence of a suitable base like sodium hydride.

Another optional derivatisation of the compounds of the formulae XII or Ib, in which R is defined as —C≡C-A to compounds of formula I, in which D is defined as C(O)OH and in which R is defined as —CR52=CR53-A or —C(R13R14)-C(R15R16)-A can be carried out in analogy to the processes which are described in the literature and are which comprises a) reacting a compound of formula XIII with a reagent V—R to a compound of formula XIV b) converting an ester of formula XIV to an acid of formula XV or, alternatively, reacting a compound of formula X with a reagent V—R to a compound of formula XV c) coupling of an acid of formula XV with an amino compound of formula IV to an amide of formula XII d) converting an ester of formula XII to an acid of formula Ib and optionally converting an acid of formula Ib to a compound of formula I or, alternatively, converting an ester of formula XII to a compound of formula I;

wherein in the compounds of the formulae Ib, IV, X, XII, XIII, XIV and XV X, Y1 to Y4, R1 and R2 are defined as in formula I, V—R is HC≡C-A and R is —C≡C-A, or V—R is HCR52=CR53-A and R is —CR52=CR53-A, or V—R is (R'''O)$_2$BCR52=CR53-A and R is —CR52=CR53-A, or V—R is (R'''')$_3$SnCR52=CR53-A and R is —(R'''')$_3$SnCR52=CR53-A, or V—R is HalZnCR52=CR53-A and R is —CR52=CR53-A, or V—R is HNR17-C(R18R19)-A and R is —NR17-C(R18R19)-A, or V—R is HNR20-C(O)-A and R is —NR20-C(O)-A, wherein R17, R18, R19, R20, R52, R53 and A are defined as in formula I, W is halogen, for example I, Br or Cl, or triflate, mesylate or tosylate, R' is alkyl having 1, 2, 3, 4, 5 or 6 carbon atoms, R'' is alkyl having 1, 2, 3, 4, 5 or 6 carbon atoms or aryl, R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups, R'''' is alkyl having 1, 2, 3, 4, 5 or 6 carbon atoms, Hal is halogen, for example I, Br or Cl.

The procedure for preparing the compounds of the formula I is initially a transformation of the compound of formula XIII to the compound of formula XIV which can be achieved by reacting with a reagent V—R, often under inert conditions and in an appropriate solvent, in the presence of a suitable catalytic system, which can contain a palladium and/or copper complex and/or salt, for example Pd$_2$dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range. The subsequent cleavage of the ester of formula XIV to the acid of formula XV can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

Alternatively, a transformation of a compound of formula X to the compound of formula XV can be achieved by reacting with a reagent V—R, often under inert conditions and in an appropriate solvent, in the presence of a suitable catalytic system, which can contain a palladium and/or copper complex and/or salt, for example Pd$_2$dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range. The resulting compound of formula XV can be coupled with the amino compound of formula IV to form the compound of formula XII generally in the presence of a coupling agent, for example EDC, DIC or HATU and optionally an additional base, for example triethylamine or Hünig's base, in an appropriate solvent, in particular in aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range.

The cleavage of the ester of formula XII to the acid of formula Ib in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range.

The optional derivatisation of the compounds of the formulae XII or Ib to compounds of formula I, in which D is not defined as C(O)OH, can be carried out in analogy to the processes which are described in the literature and are known to those skilled in the art, for example by reaction of compounds of formula Ia with oxalyl chloride followed by the reaction with a sulfonamide in the presence of a suitable base like sodium hydride.

Optionally, compounds of formulae XIV, XV, XII and Ib, in which R is defined as —C≡C-A, can be (partially) hydrogenated to compounds of formulae XIV, XV, XII and Ib, in which R is defined as —CH=CH-A or —CH$_2$—CH$_2$-A, and compounds of formulae XIV, XV, XII and Ib, in which R is defined as —CR52=CR53-A, can be hydrogenated to compounds of formulae XIV, XV, XII and Ib, in which R is defined —CHR52-CHR53-A, and these compounds can be transformed according to the reaction sequence described above to compounds of the formulae Ib or I, in which R is defined as —CH=CH-A or —CH$_2$—CH$_2$-A, or —CR52=CR53-A.

The compounds of formula Ia and Ib are contained in the compound of formula I. The starting compounds of the formulae III, IV, V, VII, X and XIII are commercially available or can be prepared by a skilled artisan according to procedures described in the literature.

The workup and optionally the purification of the products and/or intermediates are effected by the customary methods such as extraction, chromatography or crystallization and the customary dryings.

Alternative processes for preparing the compounds are described in the examples and are also part of the invention.

Functional groups in the starting compounds may be present in protected form or in the form of precursors, and then be converted into the desired groups in the compounds of the formula I prepared by the process described above.

Corresponding protective group techniques are known to the skilled worker. It is likewise possible for appropriate functional groups to be derivatized by methods known to the skilled worker.

Another aspect of the invention is the use of a compound of the formula I and/or a pharmaceutically acceptable salt and/or a prodrug thereof alone or in combination with other medicaments or active ingredients as for producing a medicament for the treatment or prophylaxis of chemokine mediated diseases. The invention further relates to the use of a compound of the formula I and/or a pharmaceutically acceptable salt and/or a prodrug thereof alone or in combination with other medicaments or active ingredients as for producing a medicament for the treatment or prophylaxis of a chemokine mediated disease, wherein the chemokine binds to a CXC receptor.

Another aspect of the invention is the use of a compound of the formula I and/or the pharmaceutically acceptable salt and/or a prodrug thereof alone or in combination with other medicaments or active ingredients as for producing a medicament for the treatment or prophylaxis of a chemokine mediated disease, wherein the chemokine binds to a CXCR2 and/or CXCR1 receptor, in particular to a CXCR2 receptor.

The invention further relates to the use of a compound of the formula I and/or a pharmaceutically acceptable salt and/or a prodrug thereof alone or in combination with other medicaments or active ingredients as for producing a medicament for the treatment or prophylaxis of rheumatoid arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multiorgan dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovasularization, tumor angiogenesis, cancer and metastasis.

In particular, the invention further relates to the use of a compound of the formula I and/or a pharmaceutically acceptable salt and/or a prodrug thereof alone or in combination with other medicaments or active ingredients as for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

A further aspect of the present invention is the use of a compound of the formula II

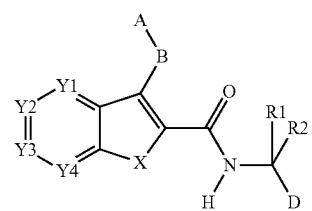

wherein
X is —CR3=CR4-, —CR5=N—, —N=CR6-, —NR7- or —S—;
R3, R4, R5 and R6
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, NO$_2$, NR27R28, C(O)R29, C(O)NR30R31, S(O)$_o$R32, S(O)$_p$NR33R34, aryl, heteroaryl, arylalkyl with alkyl having 1, 2, 3 or 4 carbon atoms or heteroarylalkyl with alkyl having 1, 2, 3 or 4 carbon atoms;
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34
are, independently of one another, hydrogen, alkyl having 1, 2, 3 or 4 carbon atoms or aryl;

R32 is OH, alkyl having 1, 2, 3 or 4 carbon atoms, alkoxy with 1, 2, 3 or 4 carbon atoms or aryl;

o and p
are, independently of one another, 1 or 2;

R7 is hydrogen, alkyl having 1, 2, 3 or 4 carbon atoms or C(O)R35;

R35 is hydrogen, alkyl with 1, 2, 3 or 4 carbon atoms or aryl;

Y1, Y2, Y3 and Y4
are, independently of one another, —CR8- or Nitrogen, with the proviso that at least two of Y1, Y2, Y3 and Y4 are defined as —CR8-;

R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR36R37, C(O)R38, C(O)NR39R40, $S(O)_q$R41, $S(O)_r$NR42R43, aryl, heteroaryl, arylalkyl with alkyl having 1, 2, 3 or 4 carbon atoms or heteroarylalkyl with alkyl having 1, 2, 3 or 4 carbon atoms;

R36 is hydrogen or alkyl having 1, 2, 3 or 4 carbon atoms

R37 is hydrogen, alkyl having 1, 2, 3 or 4 carbon atoms, aryl, C(O)H, C(O)alkyl with alkyl having 1, 2, 3 or 4 carbon atoms or C(O)aryl;

R38 is hydrogen, OH, alkyl with 1,2,3 or 4 carbon atoms, alkoxy with 1, 2, 3 or 4 carbon atoms or aryl;

R39, R40, R42 and R43
are, independently of one another, hydrogen, alkyl having 1, 2, 3 or 4 carbon atoms or aryl;

R41 is OH, alkyl having 1, 2, 3 or 4 carbon atoms, alkoxy with 1, 2, 3 or 4 carbon atoms or aryl;

q and r
are, independently of one another, 1 or 2;

A is cycloalkyl having 3, 4, 5, 6, 7 or 8 carbon atoms, heterocycle, aryl or heteroaryl;
in which the cycloalkyl or heterocycle radical can be condensed to an aryl or heteroaryl radical and in which the cycloalkyl or heterocycle radical and the optionally condensed aryl or heteroaryl radical are unsubstituted or substituted by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, $S(O)_s$R47, $S(O)_t$NR48R49, —$(CH_2)_k$-aryl or —$(CH_2)_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a$—$(CH_2)_b$—$(CF_2)_c$—$CF_3$;

R9 is hydrogen or alkyl having 1, 2, 3 or 4 carbon atoms

R10 is hydrogen, alkyl having 1, 2, 3 or 4 carbon atoms, aryl, C(O)H, C(O)alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49
are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

a is zero or 1;

b, c, k and l
are, independently of one another, zero, 1, 2 or 3;

s and t
are, independently of one another, 1 or 2;

in which the aryl or heteroaryl radical can be condensed to an cycloalkyl or heterocycle radical and in which the aryl or heteroaryl radical and the optionally condensed cycloalkyl or heterocycle radical are unsubstituted or substituted by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, $S(O)_s$R47, $S(O)_t$NR48R49, —$(CH_2)_k$-aryl or —$(CH_2)_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a$—$(CH_2)_b$—$(CF_2)_c$—$CF_3$;

R9 is hydrogen or alkyl having 1, 2, 3 or 4 carbon atoms

R10 is hydrogen, alkyl having 1, 2, 3 or 4 carbon atoms, aryl, C(O)H, C(O)alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49
are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

a is zero or 1;

b, c, k and l
are, independently of one another, zero, 1, 2 or 3;

s and t
are, independently of one another, 1 or 2;

B is —O—C(R11R12)-, —C(R50R51)-O—, —C≡C—, —CR52=CR53-, —C(R13R14)-C(R15R16)-, —NR17-C(R18R19)-, —C(R54R55)-NR56-, —NR20-C(O)— or —C(O)—NR57-;

R11, R12, R13, R14, R15, R16, R17, R18, R19, R20, R50, R51, R52, R53, R54, R55, R56 and R57
are, independently of one another, hydrogen or alkyl having 1, 2, 3 or 4 carbon atoms, in which 1, 2, 3, 4, 5, 6, 7, 8 or 9 hydrogen atoms may be substituted by fluorine atoms;

D is C(O)OH, C(O)NHR21 or C(=NR58)NHR22;
  R21 and R22
    are, independently of one another, hydrogen, —SO$_2$-alkyl having 1, 2, 3 or 4 carbon atoms, —SO$_2$-aryl, —C(O)-alkyl with alkyl having 1, 2, 3 or 4 carbon atoms, —C(O)-aryl, —C(O)OR23, —C(O)NR24R25 or —CN,
      R23 is alkyl having 1, 2, 3 or 4 carbon atoms or aryl,
      R24 and R25
        are, independently of one another, hydrogen, alkyl having 1, 2, 3 or 4 carbon atoms or aryl;
  R58 is hydrogen, OH, CN, alkyl having 1, 2, 3 or 4 carbon atoms or alkoxy having 1, 2, 3 or 4 carbon atoms or aryl;
  R1 and R2
    are, independently of one another, hydrogen, alkyl having 1, 2, 3, 4, 5 or 6 carbon atoms, with the proviso that at least one of R1 and R2 is not hydrogen;
      in which the alkyl radicals are unsubstituted or substituted by 1, 2 or 3 radicals selected from the group consisting of F, Cl, Br, I, —SH, —S-alkyl having 1, 2, 3 or 4 carbon atoms, —C(O)OH, —C(O)NH2, NH2, —NH—C(=NH)NH$_2$ or —O$_m$—(CH$_2$)$_n$—R26;
      m is zero or 1;
      n is zero, 1, 2 or 3;
      R26 is hydrogen, aryl or heteroaryl, in which the aryl or heteroaryl radical is unsubstituted or substituted by F, Cl, Br, I, OH or alkyl having 1, 2, 3 or 4 carbon atoms;
or
R1 and R2
  form, together with the carbon atom to which they are attached, a 3-, 4-, 5- or 6-membered carbon ring, in which the formed carbon ring can be condensed to an aryl or heteroaryl radical;
    wherein the formed carbon ring and the condensed aryl or heteroaryl radical can be unsubstituted or substituted by 1, 2 or 3 radicals selected form the group consisting of F, Cl, Br, I or alkyl having 1, 2, 3 or 4 carbon atoms;
and/or pharmaceutically acceptable salt and/or a prodrug thereof alone or in combination with other medicaments or active ingredients for producing a medicament for the treatment or prophylaxis of chemokine mediated diseases.

The invention further relates to the use of a compound of the formula II and/or a pharmaceutically acceptable salt and/or a prodrug thereof alone or in combination with other medicaments or active ingredients as for producing a medicament for the treatment or prophylaxis of a chemokine mediated disease, wherein the chemokine binds to a CXC receptor, for example wherein the chemokine binds to a CXCR2 and/or CXCR1 receptor, in particular to a CXCR2 receptor.

Another aspect of the invention is the use of a compound of the formula II and/or a pharmaceutically acceptable salt and/or a prodrug thereof alone or in combination with other medicaments or active ingredients as for producing a medicament for the treatment or prophylaxis of arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multi-organ dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovasularization, tumor angiogenesis, cancer and metastasis.

In particular, the invention further relates to the use of a compound of the formula II and/or a pharmaceutically acceptable salt and/or a prodrug thereof alone or in combination with other medicaments or active ingredients as for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

Examples no. 110, 203, 204, 238, 239, 308, 359, 360, 361, 362, 364, 366, 370, 371 vide infra represent compounds of the formula II in the context of the above described uses. All other example compounds exemplify compounds of the formula I.

As a further aspect of the present invention, certain compounds of formula I or formula II may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

Also claimed is a medicine or pharmaceutical composition for human or veterinary use, comprising an effective amount of a compound of the formula I and/or a pharmaceutically acceptable salt and/or a prodrug thereof, together with pharmaceutically acceptable carriers and additives, alone or in combination with other active pharmaceutical ingredients or medicaments.

Medicaments which comprise a compound of the formula I and/or a pharmaceutically acceptable salt and/or a prodrug thereof can in this connection be administered, for example, orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine. The medicaments generally comprise active ingredients of the formula I and/or a pharmaceutically acceptable salt and/or a prodrug thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or a pharmaceutically acceptable salt and/or a prodrug thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or a pharmaceutically acceptable salt and/or a prodrug thereof for a patient weighing about 75 kg is at least 0.001 mg/kg, preferably 0.01 mg/kg, to a maximum of 50 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

| List of abbreviations: | |
|---|---|
| O-(7-Azabenzotriazol-1-yl)-N,N,N',N'-tetramethyluronium Hexafluorophosphate | HATU |
| [2-(1H)-benzotriazol-1yl]-1,1,3,3-tetramethyluronium tetra-fluoroborate | TBTU |
| N-Brom-succinimide | NBS |
| Dichloromethane | DCM |
| 4-Dimethylaminopyridine | DMAP |
| Diethylazodicarboxylate | DEAD |
| Diisoppropylazodicarboxylate | DIAD |
| N,N'-Diisopropylcarbodiimid | DIC |
| 1-(3-Dimethylaminopropyl)-3-ethylcarbodiimide-Hydrochloride | EDC |
| N,N-Dimethylformamide | DMF |
| Electron spray ionisation Positive mode | ESI+ or ESI |
| Electron spray ionisation Negative mode | ESI- |
| Tetrahydrofuran | THF |
| N,N,N',N'-Tetramethylethylendiamine | TMEDA |
| Retention time | Rt |

Description of the Experiments and Examples

EXAMPLES

Example 1

2-{[4-Bromo-1-(4-trifluoromethyl-benzyloxy)-naphthalene-2-carbonyl]-amino}-2-methyl-propionic acid

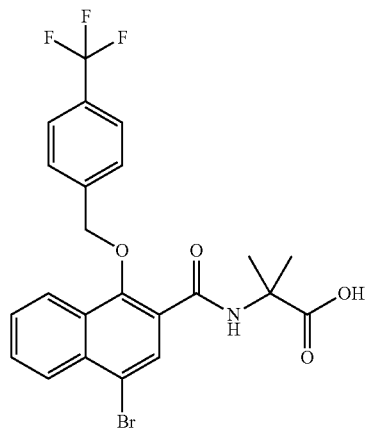

a) 2-[(4-Bromo-1-hydroxy-naphthalene-2-carbonyl)-amino]-2-methyl-propionic acid methyl ester To a solution of 1.5 g 4-bromo-1-hydroxy-2-naphthoic acid in 20 ml abs. DMF under inert atmosphere 0.84 g 1-hydroxybenzotriazole, 1.18 g 1-ethyl-3-(3-dimethylaminopropyl)carbodiimide hydrochloride and 1.1 ml of N,N-diisopropylethylamine were added. After 15 minutes 0.86 g of 2-amino-2-methyl-propionic acid methyl ester hydrochloride, followed by 1.1 ml of N,N-diisopropylethylamine were added. After 24 h at room temperature and 2 h at 50° C. the reaction mixture was concentrated, the residue was taken up in ethyl acetate and washed with 2 M HCl, aqueous sodium carbonate solution (10%) and brine. The organic layer was dried over magnesium sulphate, and concentrated to yield 1.44 g of 2-[(4-bromo-1-hydroxy-naphthalene-2-carbonyl)-amino]-2-methyl-propionic acid methyl ester.

$C_{16}H_{16}BrNO_4$ (366.21), LCMS (ESI): 368.00 (MH$^+$).

b) 2-{[4-Bromo-1-(4-trifluoromethyl-benzyloxy)-naphthalene-2-carbonyl]-amino}-2-methyl-propionic acid methyl ester To 90 mg cesium carbonate and 92 mg 2-[(4-bromo-1-hydroxy-naphthalene-2-carbonyl)-amino]-2-methyl-propionic acid methyl ester in 1 ml abs. DMF 67 mg 4-trifluoromethylbenzylbromide was added. After 16 h at room temperature the reaction was poured unto ice-water and extracted with ethyl acetate twice. The combined organic layers were washed with brine, dried over magnesium sulphate and concentrated in vacuo to yield 97 mg of 2-{[4-bromo-1-(4-trifluoromethyl-benzyloxy)-naphthalene-2-carbonyl]-amino}-2-methyl-propionic acid methyl ester.
$C_{24}H_{21}BrF_3NO_4$ (524.34), LCMS (ESI): 526.00 (MH$^+$).

c) 2-{[4-Bromo-1-(4-trifluoromethyl-benzyloxy)-naphthalene-2-carbonyl]-amino}-2-methyl-propionic acid 96 mg 2-{[4-bromo-1-(4-trifluoromethyl-benzyloxy)-naphthalene-2-carbonyl]-amino}-2-methyl-propionic acid methyl ester in 0.5 ml THF, 0.56 ml of 2 M sodium hydroxide and 1.4 ml methanol were reacted in a microwave at 120° C. for 6 min. The reaction was then acidified with 2 M hydrochloric acid and extracted with ethyl acetate twice. The combined organic layers were dried over magnesium sulphate, and concentrated. After purification of the residue by RP-HPLC 11 mg of 2-{[4-Bromo-1-(4-trifluoromethyl-benzyloxy)-naphthalene-2-carbonyl]-amino}-2-methyl-propionic acid were obtained.
$C_{23}H_{19}BrF_3NO_4$ (510.31), LCMS (ESI): 512.05 (MH$^+$).

Example 2

2-{[1-(4-Bromo-benzyloxy)-naphthalene-2-carbonyl]-amino}-2-methyl-propionic acid

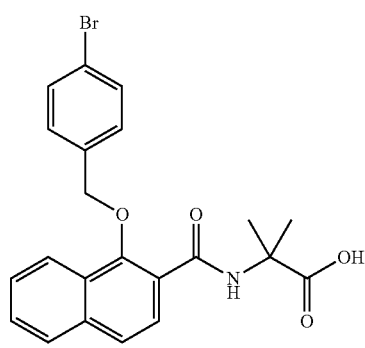

a) 2-[(1-Hydroxy-naphthalene-2-carbonyl)-amino]-2-methyl-propionic acid methyl To a solution of 4.70 g 1-hydroxy-2-naphthalene carboxylic acid in 40 ml abs. DMF under inert atmosphere 3.72 g 1-hydroxybenzotriazole and 8.89 g N,N'-diisopropyl carbodiimide and 7 ml of N,N-diisopropylethylamine were added at 0° C. After 30 minutes at 0° C. 4.22 g of methyl 2-aminoisobutyrate hydrochloride, followed by 5 ml of N,N-diisopropylethylamine were added. After 16 h at room temperature the reaction mixture was concentrated, the residue was taken up in ethyl acetate and washed with 2 M HCl and brine. The organic layer was dried over magnesium sulphate, and concentrated and the resulting residue was crystallized from toluene to yield 4.18 g of 2-[(1-hydroxy-naphthalene-2-carbonyl)-amino]-2-methyl-propionic acid methyl ester.
$C_{16}H_{17}NO_4$ (287.12), LCMS (ESI): 287.97 (MH$^+$).

b) 2-{[1-(4-Bromo-benzyloxy)-naphthalene-2-carbonyl]-amino}-2-methyl-propionic acid methyl ester To a solution of 80 mg of 2-[(1-hydroxy-naphthalene-2-carbonyl)-amino]-2-methyl-propionic acid methyl ester, 52 mg 4-bromobenzyl alcohol and 73 mg triphenyl phosphine in 3 ml of dry THF 56 mg of diisopropylazodicarboxylate were added. After 2 h at room temperature 36 mg of triphenylphosphine and 25 mg of diisopropylazodicarboxylate were added, and after 16 h again 36 mg of triphenylphosphine and 25 mg of diisopropylazodicarboxylate were added. After additional 24 h the reaction was concentrated in vacuo and after chromatography on silica (ethyl acetate/heptane) 96 mg of 2-{[1-(4-bromo-benzyloxy)-naphthalene-2-carbonyl]-amino}-2-methyl-propionic acid methyl ester were obtained.
$C_{23}H_{22}BrNO_4$ (455.07), LCMS (ESI): 456.18 (MH$^+$).

c) 2-{[1-(4-Bromo-benzyloxy)-naphthalene-2-carbonyl]-amino}-2-methyl-propionic acid A solution of 96 mg 2-{[1-(4-bromo-benzyloxy)-naphthalene-2-carbonyl]-amino}-2-methyl-propionic acid methyl ester in 1 ml dry THF was treated with 0.2 ml of 2 M aqueous sodium hydroxide. After 4 h at 60° C. the reaction was concentrated, the residue was taken up in 3 ml of water, treated with 2 M hydrochloric acid, and the resulting precipitate was collected by filtration and purified by RP-HPLC to yield 70 mg 2-{[1-(4-bromo-benzyloxy)-naphthalene-2-carbonyl]-amino}-2-methyl-propionic acid.
$C_{22}H_{20}BrNO_4$ (442.31), LCMS (ESI−): 441.00 (M-H$^+$).

Example 3

1-{[1-(2,3-Dihydro-benzo[1,4]dioxin-2-ylmethoxy)-naphthalene-2-carbonyl]-amino}-cyclopentanecarboxylic acid

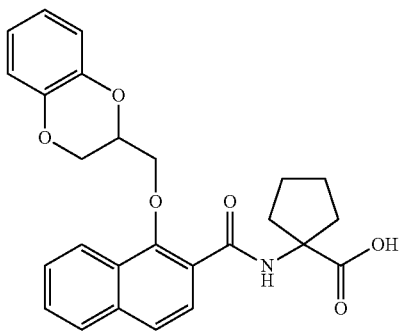

a) 1-(2,3-Dihydro-benzo[1,4]dioxin-2-ylmethoxy)-naphthalene-2-carboxylic acid methyl ester To 4.19 g cesium carbonate and 1.37 g methyl 1-hydroxy-2-naphthoate in 25 ml abs. DMF was added 1.62 g 2-bromomethyl-2,3-dihydro-benzo[1,4]dioxine and the mixture was reacted for 16 h at 50° C. The reaction was poured unto ice, the resulting precipitate was isolated by filtration, dissolved in ethyl acetate and washed with brine. The organic phase was dried over magnesium sulphate and concentrated in vacuo. The resulting residue was purified by flash chromatography (silica, heptane/ethyl acetate) to yield 1.31 g of 1-(2,3-dihydro-benzo[1,4]dioxin-2-ylmethoxy)-naphthalene-2-carboxylic acid methyl ester.

$C_{21}H_{18}O_5$ (350.37), LCMS (ESI): 351.05 (MH$^+$).

b) 1-(2,3-Dihydro-benzo[1,4]dioxin-2-ylmethoxy)-naphthalene-2-carboxylic acid To 1.31 g of 1-(2,3-dihydro-benzo[1,4]dioxin-2-ylmethoxy)-naphthalene-2-carboxylic acid methyl ester in 95 ml of THF were added 5.62 ml of 2 M aqueous sodium hydroxide and 30 ml of methanol. After 1 h at reflux and 16 h at room temperature the organic solvents were removed in vacuo. The residue was treated with 2 M hydrochloric acid, and three times extracted with ethyl acetate. The combined organic layers were dried over magnesium sulphate, and concentrated and dried in vacuo to yield 0.94 g of 1-(2,3-dihydro-benzo[1,4]dioxin-2-ylmethoxy)-naphthalene-2-carboxylic acid.

$C_{20}H_{16}O_5$ (336.35), LCMS (ESI): 319.00 (MH$^+$-H$_2$O).

c) 1-{[1-(2,3-Dihydro-benzo[1,4]dioxin-2-ylmethoxy)-naphthalene-2-carbonyl]-amino}-cyclopentanecarboxylic acid methyl ester To a solution of 84 mg 1-(2,3-dihydro-benzo[1,4]dioxin-2-ylmethoxy)-naphthalene-2-carboxylic acid in 1 ml abs. DMF under inert atmosphere 42 mg 1-hydroxybenzotriazole and 60 mg 1-ethyl-3-(3-dimethylaminopropyl)carbodiimide hydrochloride and 0.65 µl of N,N-diisopropylethylamine were added at 0° C. After 30 minutes at 0° C. 42 mg of 1-amino-cyclopentanecarboxylic acid methyl ester hydrochloride, followed by 0.65 µl of N,N-diisopropylethylamine were added. After 48 h at room temperature the reaction mixture was concentrated, the residue was taken up in ethyl acetate and washed with 2 M HCl, aqueous sodium carbonate solution (10%) and brine. The organic layer was dried over magnesium sulphate, and concentrated to yield 96 mg of 1-{[1-(2,3-dihydro-benzo[1,4]dioxin-2-ylmethoxy)-naphthalene-2-carbonyl]-amino}-cyclopentanecarboxylic acid methyl ester.

$C_{27}H_{27}NO_6$ (461.52), LCMS (ESI): 462.15 (MH$^+$).

d) 1-{[1-(2,3-Dihydro-benzo[1,4]dioxin-2-ylmethoxy)-naphthalene-2-carbonyl]-amino}-cyclopentanecarboxylic acid 96 mg 1-{[1-(2,3-dihydro-benzo[1,4]dioxin-2-ylmethoxy)-naphthalene-2-carbonyl]-amino}-cyclopentanecarboxylic acid methyl ester in 0.5 ml THF, 0.62 ml of 2 M sodium hydroxide and 1.4 ml methanol were reacted in a microwave at 120° C. for 6 min. The reaction was then acidified with 2 M hydrochloric acid and extracted with ethyl acetate twice. The combined organic layers were dried over magnesium sulphate, and concentrated to yield 47 mg of 1-{[1-(2,3-dihydro-benzo[1,4]dioxin-2-ylmethoxy)-naphthalene-2-carbonyl]-amino}-cyclopentanecarboxylic acid.

$C_{26}H_{25}NO_6$ (447.49), LCMS (ESI): 448.13 (MH$^+$).

The following examples were prepared in analogy to example 1:

| No. | Chemical Name | Structure | ESI+ or ESI− |
|---|---|---|---|
| 4 | 2-{[1-(3,5-Dimethyl-isoxazol-4-ylmethoxy)-naphthalene-2-carbonyl]-amino}-2-methyl-propionic acid | 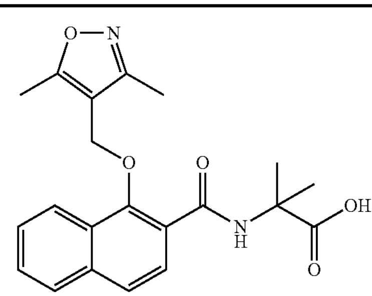 | 383.27 |
| 5 | 2-{[1-(Benzo[1,2,5]oxadiazol-5-ylmethoxy)-naphthalene-2-carbonyl]-amino}-2-methyl-propionic acid | 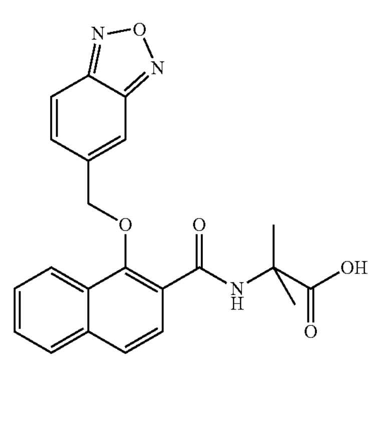 | 406.15 |

-continued

| No. | Chemical Name | Structure | ESI+ or ESI– |
|---|---|---|---|
| 6 | 2-Methyl-2-{[1-(quinolin-2-ylmethoxy)-naphthalene-2-carbonyl]-amino}-propionic acid | 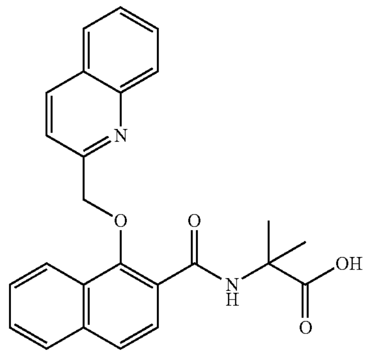 | 415.16 |
| 7 | 2-Methyl-2-{[1-(1-methyl-1H-benzotriazol-5-ylmethoxy)-naphthalene-2-carbonyl]-amino}-propionic acid | 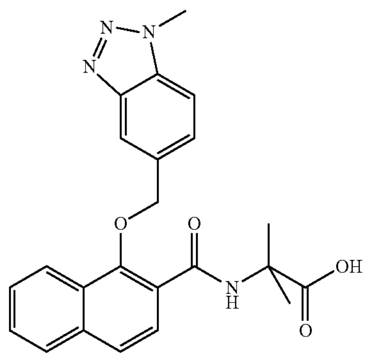 | 419.25 |
| 8 | 2-{[1-(Benzothiazol-2-ylmethoxy)-naphthalene-2-carbonyl]-amino}-2-methyl-propionic acid | 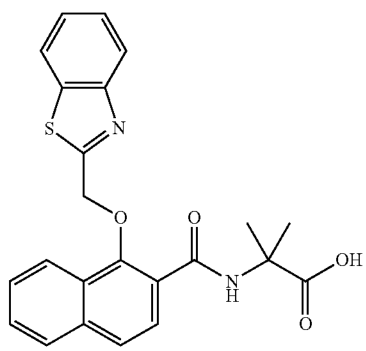 | 421.17 |
| 9 | 2-Methyl-2-{[1-(4-pyrazol-1-yl-benzyloxy)-naphthalene-2-carbonyl]-amino}-propionic acid | 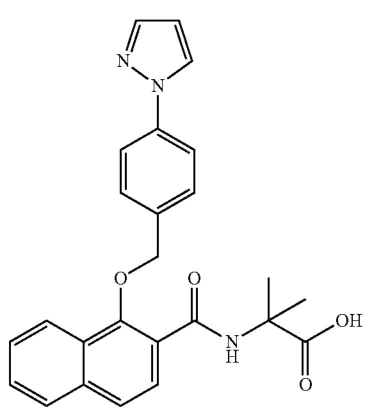 | 430.18 |

| No. | Chemical Name | Structure | ESI+ or ESI− |
|---|---|---|---|
| 10 | 2-Methyl-2-{[1-(3-pyrrol-1-yl-benzyloxy)-naphthalene-2-carbonyl]-amino}-propionic acid | 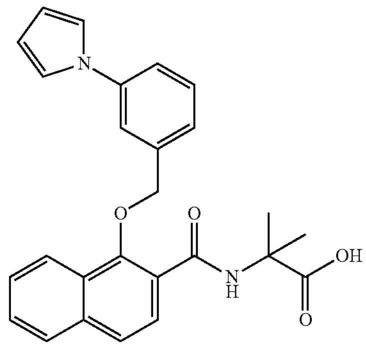 | 429.20 |
| 11 | 2-Methyl-2-{[1-(4-[1,2,4]triazol-1-yl-benzyloxy)-naphthalene-2-carbonyl]-amino}-propionic acid | 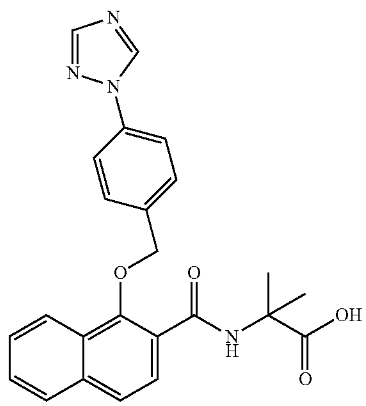 | 431.10 |
| 12 | 2-Methyl-2-{[1-(2-phenyl-oxazol-4-ylmethoxy)-naphthalene-2-carbonyl]-amino}-propionic acid | 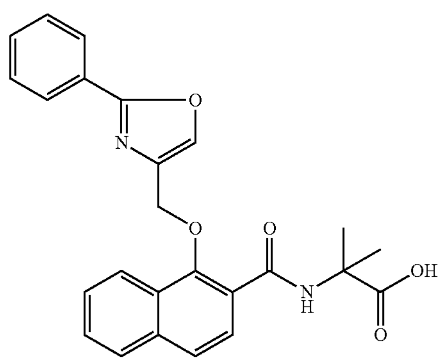 | 431.15 |
| 13 | 1-{[1-(Benzothiazol-2-ylmethoxy)-naphthalene-2-carbonyl]-amino}-cyclobutanecarboxylic acid | 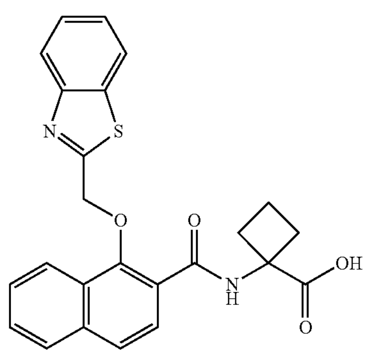 | 433.26 |

| No. | Chemical Name | Structure | ESI+ or ESI− |
|---|---|---|---|
| 14 | 2-Methyl-2-{[1-(6-trifluoromethyl-pyridin-3-ylmethoxy)-naphthalene-2-carbonyl]-amino}-propionic acid | 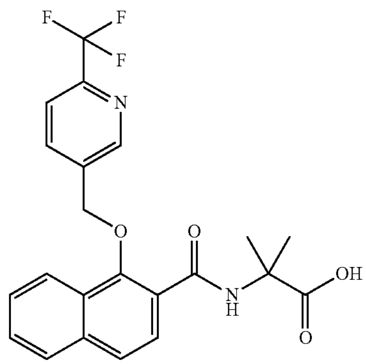 | 433.18 |
| 15 | 2-{[1-(Benzothiazol-2-ylmethoxy)-naphthalene-2-carbonyl]-amino}-2-methyl-butyric acid | 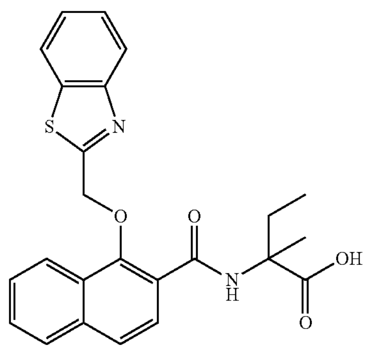 | 435.23 |
| 16 | 2-{[1-(5-Fluoro-benzothiazol-2-ylmethoxy)-naphthalene-2-carbonyl]-amino}-2-methyl-propionic acid | 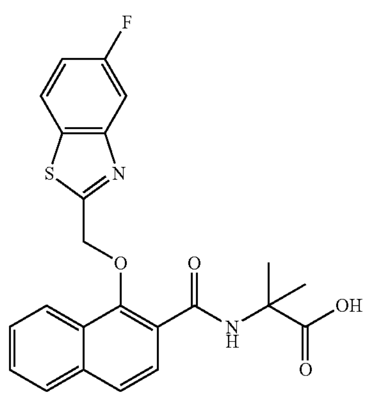 | 439.21 |
| 17 | 1-{[1-(Quinolin-2-ylmethoxy)-naphthalene-2-carbonyl]-amino}-cyclopentanecarboxylic acid | 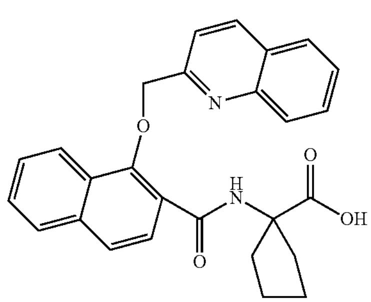 | 441.17 |

-continued

| No. | Chemical Name | Structure | ESI+ or ESI− |
|---|---|---|---|
| 18 | 2-{[1-(6-Bromo-pyridin-3-ylmethoxy)-naphthalene-2-carbonyl]-amino}-2-methyl-propionic acid | 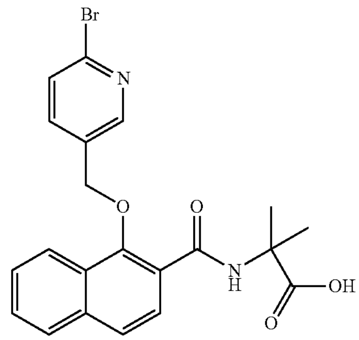 | 443.04 |
| 19 | 2-Methyl-2-{[1-(5-methyl-2-phenyl-2H-[1,2,3]triazol-4-ylmethoxy)-naphthalene-2-carbonyl]-amino}-propionic acid | 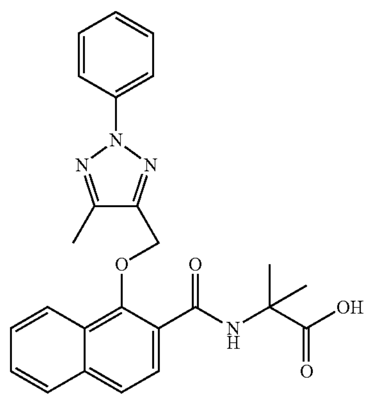 | 445.15 |
| 20 | 2-Methyl-2-{[1-(6-trifluoromethyl-pyridin-3-ylmethoxy)-naphthalene-2-carbonyl]-amino}-butyric acid | 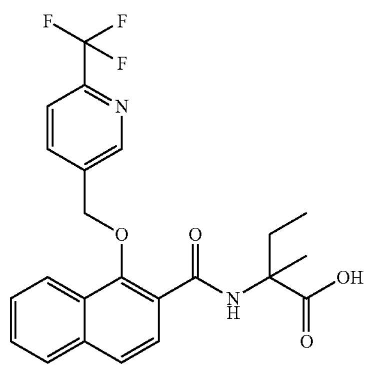 | 447.21 |
| 21 | 1-{[1-(Benzothiazol-2-ylmethoxy)-naphthalene-2-carbonyl]-amino}-cyclopentanecarboxylic acid | 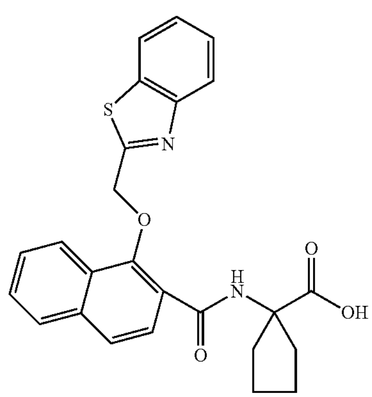 | 447.11 |

| No. | Chemical Name | Structure | ESI+ or ESI− |
|---|---|---|---|
| 22 | 2-{[1-(5-Fluoro-benzothiazol-2-ylmethoxy)-naphthalene-2-carbonyl]-amino}-2-methyl-butyric acid | 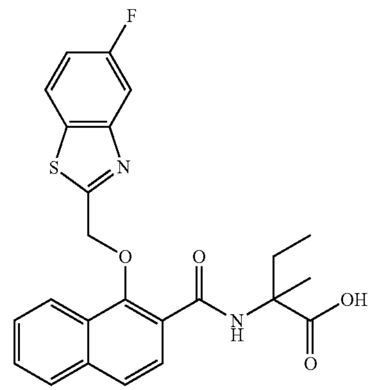 | 453.22 |
| 23 | 2-{[1-(Benzothiazol-2-ylmethoxy)-4-chloro-naphthalene-2-carbonyl]-amino}-2-methyl-propionic acid | 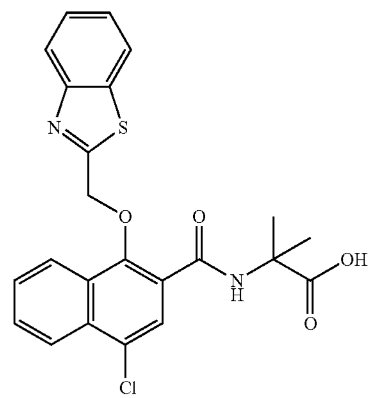 | 455.15 |
| 24 | 2-{[1-(5,6-Difluoro-benzothiazol-2-ylmethoxy)-naphthalene-2-carbonyl]-amino}-2-methyl-propionic acid | 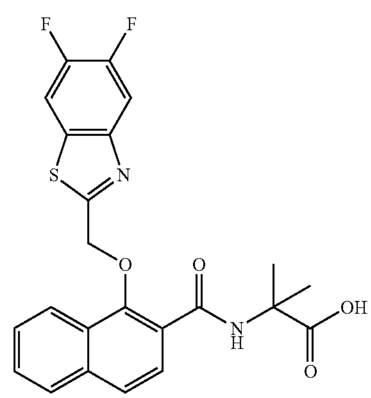 | 457.19 |
| 25 | 2-{[4-(Benzothiazol-2-ylmethoxy)-7-chloro-quinoline-3-carbonyl]-amino}-2-methyl-propionic acid | 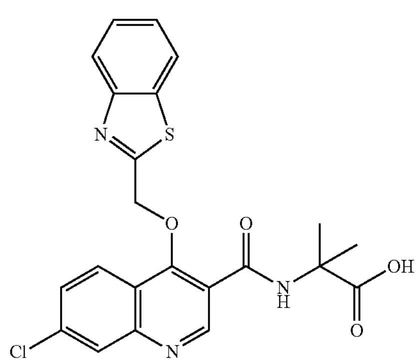 | 456.13 |

| No. | Chemical Name | Structure | ESI+ or ESI– |
|---|---|---|---|
| 26 | 1-{[1-(6-Trifluoromethyl-pyridin-3-ylmethoxy)-naphthalene-2-carbonyl]-amino}-cyclopentanecarboxylic acid | 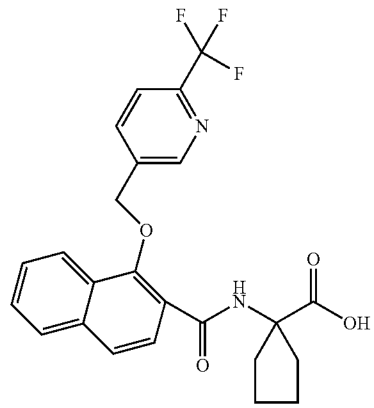 | 459.19 |
| 27 | 2-({1-[5-(4-Chloro-phenyl)-oxazol-2-ylmethoxy]-naphthalene-2-carbonyl}-amino)-2-methyl-propionic acid | 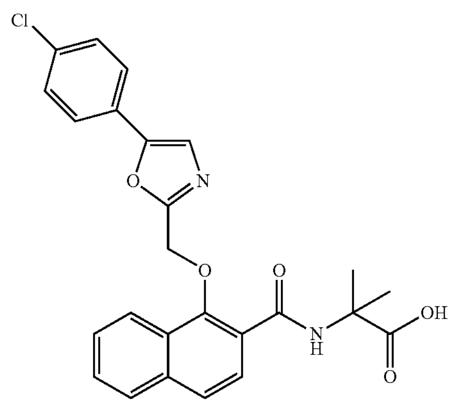 | 465.24 |
| 28 | 2-({1-[2-(4-Chloro-phenyl)-oxazol-5-ylmethoxy]-naphthalene-2-carbonyl}-amino)-2-methyl-propionic acid | 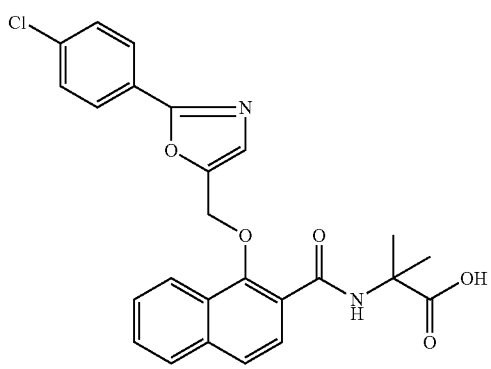 | 465.23 |
| 29 | 2-{[4-Chloro-1-(6-trifluoromethyl-pyridin-3-ylmethoxy)-naphthalene-2-carbonyl]-amino}-2-methyl-propionic acid | 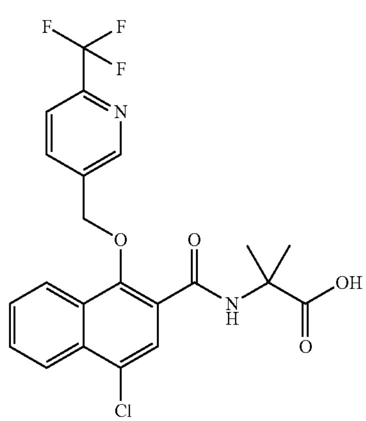 | 467.16 |

| No. | Chemical Name | Structure | ESI+ or ESI− |
|---|---|---|---|
| 30 | 2-{[7-Chloro-4-(6-trifluoromethyl-pyridin-3-ylmethoxy)-quinoline-3-carbonyl]-amino}-2-methyl-propionic acid | 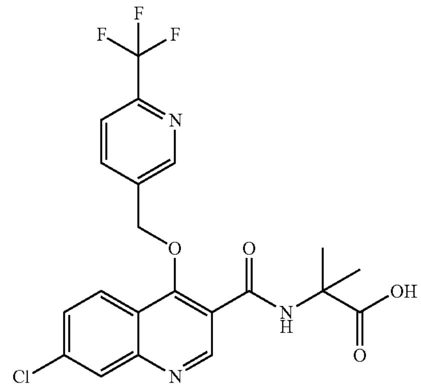 | 468.14 |
| 31 | 2-{[1-(Benzothiazol-2-ylmethoxy)-4-chloro-naphthalene-2-carbonyl]-amino}-2-methyl-butyric acid | 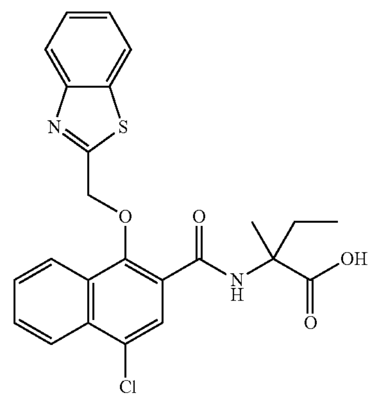 | 469.11 |
| 32 | 2-{[1-(5,6-Difluoro-benzothiazol-2-ylmethoxy)-naphthalene-2-carbonyl]-amino}-2-methyl-butyric acid | 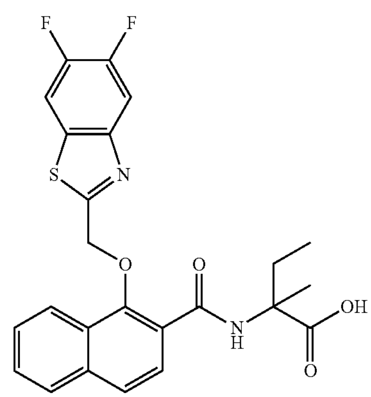 | 471.23 |
| 33 | 2-{[1-(5-Bromo-4-methoxy-pyridin-2-ylmethoxy)-naphthalene-2-carbonyl]-amino}-2-methyl-propionic acid | 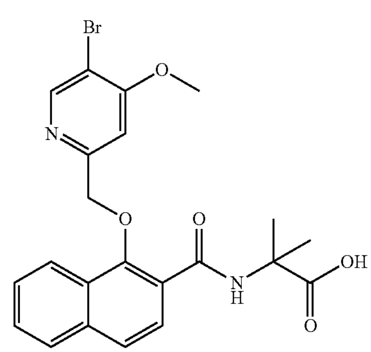 | 473.17 |

| No. | Chemical Name | Structure | ESI+ or ESI− |
|---|---|---|---|
| 34 | 2-Methyl-2-({1-[3-methyl-4-(2,2,2-trifluoro-ethoxy)-pyridin-2-ylmethoxy]-naphthalene-2-carbonyl}-amino)-propionic acid | 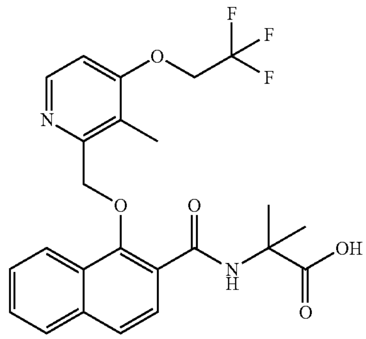 | 477.25 |
| 35 | 2-{[4-Chloro-1-(4-trifluoromethyl-benzyloxy)-naphthalene-2-carbonyl]-amino}-2-methyl-butyric acid | 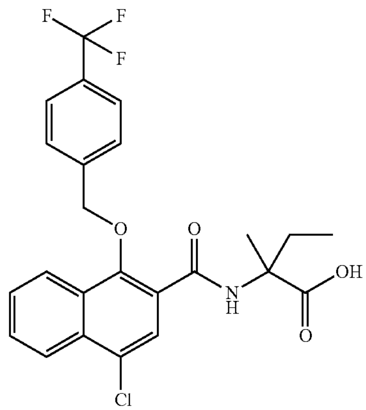 | 480.15 |
| 36 | 2-{[4-Chloro-1-(6-trifluoromethyl-pyridin-3-ylmethoxy)-naphthalene-2-carbonyl]-amino}-2-methyl-butyric acid | 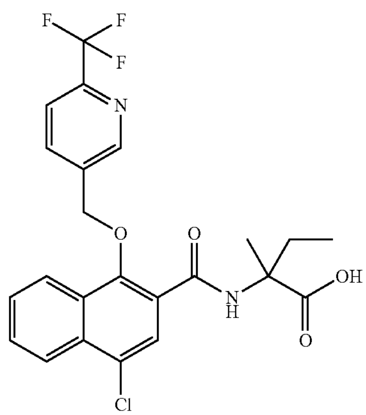 | 481.19 |
| 37 | 2-{[1-(3-Chloro-4-trifluoromethoxy-benzyloxy)-naphthalene-2-carbonyl]-amino}-2-methyl-propionic acid | 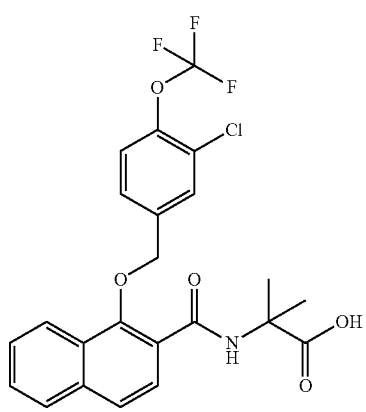 | 482.10 |

-continued

| No. | Chemical Name | Structure | ESI+ or ESI− |
|---|---|---|---|
| 38 | 2-Methyl-2-{[1-(5-trifluoromethyl-benzothiazol-2-ylmethoxy)-naphthalene-2-carbonyl]-amino}-propionic acid | 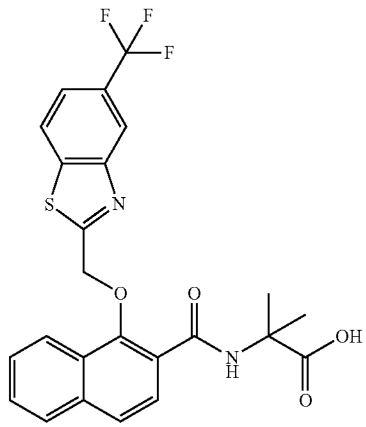 | 489.19 |
| 39 | 2-({1-[3-Methoxy-4-(2,2,2-trifluoro-ethoxy)pyridin-2-ylmethoxy]-naphthalene-2-carbonyl}-amino)-2-methyl-propionic acid | 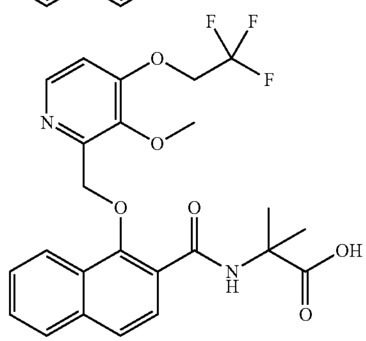 | 493.29 |
| 40 | 2-Methyl-2-{[1-(5-trifluoromethyl-benzothiazol-2-ylmethoxy)-naphthalene-2-carbonyl]-amino}-butyric acid | 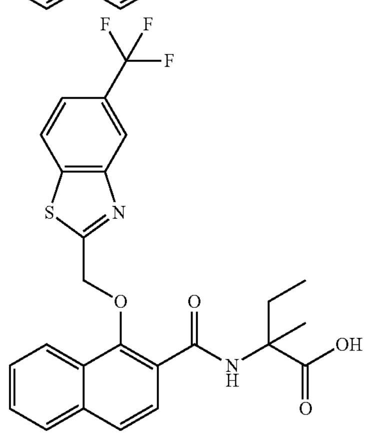 | 503.23 |
| 41 | 2-{[4-Chloro-1-(5,6-difluoro-benzothiazol-2-ylmethoxy)-naphthalene-2-carbonyl]-amino}-2-methyl-butyric acid | 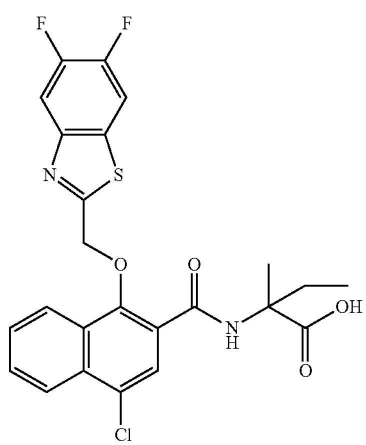 | 505.16 |

-continued

| No. | Chemical Name | Structure | ESI+ or ESI− |
|---|---|---|---|
| 42 | 2-{[4-Bromo-1-(4-trifluoromethoxy-benzyloxy)-naphthalene-2-carbonyl]-amino}-2-methyl-propionic acid | 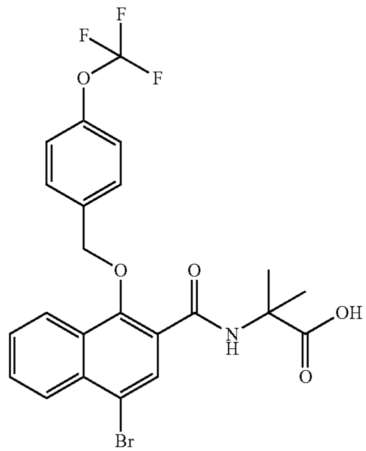 | 526.05 |

The following examples were prepared in analogy to example 2:

| No | Chemical Name | Structure | ESI+ or ESI− |
|---|---|---|---|
| 43 | 2-[(1-Benzyloxy-naphthalene-2-carbonyl)-amino]-2-methyl-propionic acid | 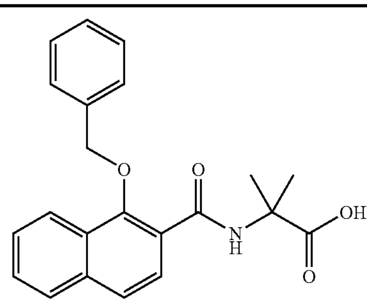 | 364.06 |
| 44 | 2-[(1-Cyclohexylmethoxy-naphthalene-2-carbonyl)-amino]-2-methyl-propionic acid | 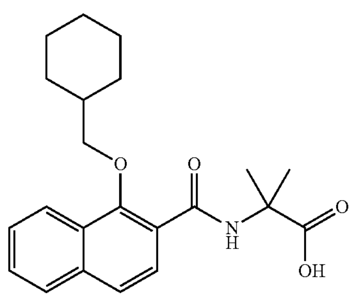 | 370.26 |
| 45 | 2-Methyl-2-{[1-(4-methyl-benzyloxy)-naphthalene-2-carbonyl]-amino}-propionic acid | 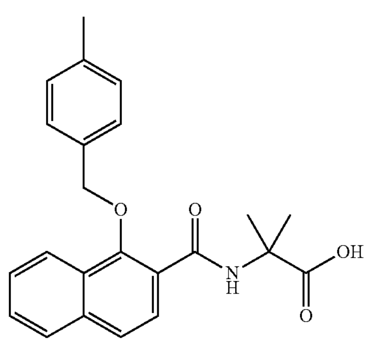 | 378.09 |

-continued

| No | Chemical Name | Structure | ESI+ or ESI− |
|---|---|---|---|
| 46 | 2-{[1-(1-Ethyl-1H-pyrazol-4-ylmethoxy)-naphthalene-2-carbonyl]-amino}-2-methyl-propionic acid | 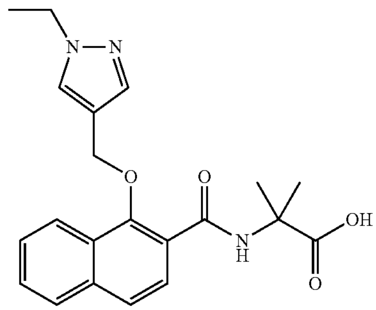 | 382.15 |
| 47 | (rac)-2-Methyl-2-{[1-(4-methyl-cyclohexylmethoxy)-naphthalene-2-carbonyl]-amino}-propionic acid | 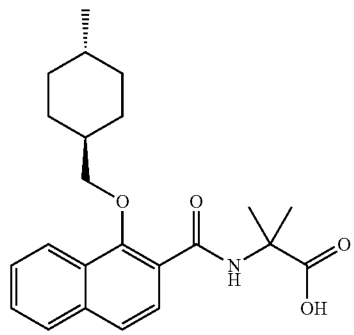 | 384.34 |
| 48 | (rac)-2-Methyl-2-{[1-(4-methyl-cyclohexylmethoxy)-naphthalene-2-carbonyl]-amino}-propionic acid | 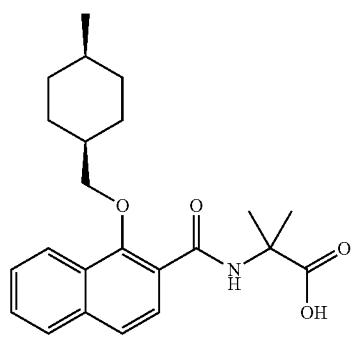 | 384.34 |
| 49 | 2-{[1-(4-Ethyl-benzyloxy)-naphthalene-2-carbonyl]-amino}-2-methyl-propionic acid | 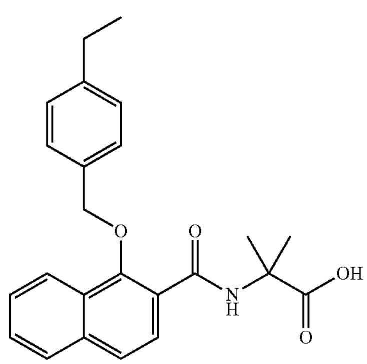 | 392.10 |

| No | Chemical Name | Structure | ESI+ or ESI- |
|---|---|---|---|
| 50 | 2-{[1-(4-Chloro-benzyloxy)-naphthalene-2-carbonyl]-amino}-2-methyl-propionic acid | 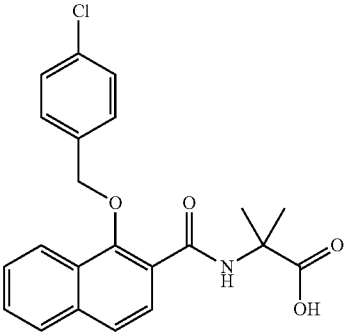 | 398.18 |
| 51 | 2-{[1-(6-Chloro-pyridin-3-ylmethoxy)-naphthalene-2-carbonyl]-amino}-2-methyl-propionic acid | 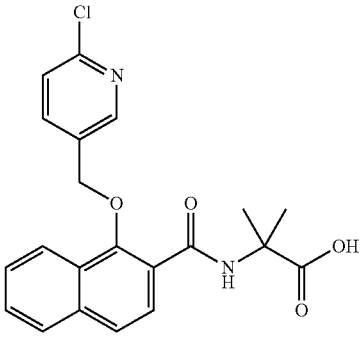 | 399.07 |
| 52 | 2-{[1-(Indan-5-ylmethoxy)-naphthalene-2-carbonyl]-amino}-2-methyl-propionic acid | 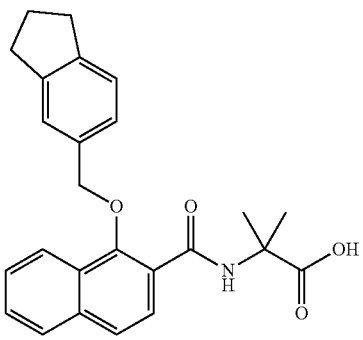 | 404.15 |
| 53 | 2-Methyl-2-{[1-(2,4,6-trimethyl-benzyloxy)-naphthalene-2-carbonyl]-amino}-propionic acid | 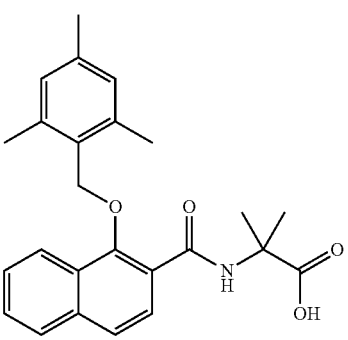 | 406.23 |

-continued

| No | Chemical Name | Structure | ESI+ or ESI− |
|---|---|---|---|
| 54 | 2-{[1-(4-Isopropyl-benzyloxy)-naphthalene-2-carbonyl]-amino}-2-methyl-propionic acid | 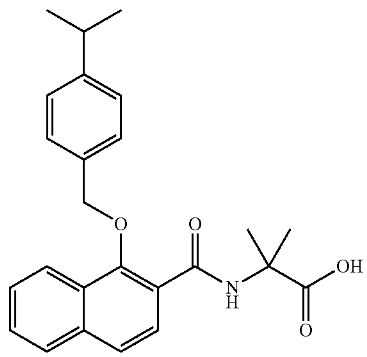 | 406.20 |
| 55 | 2-{[1-Benzo[1,3]dioxol-5-ylmethoxy)-naphthalene-2-carbonyl]-amino}-2-methyl-propionic acid | 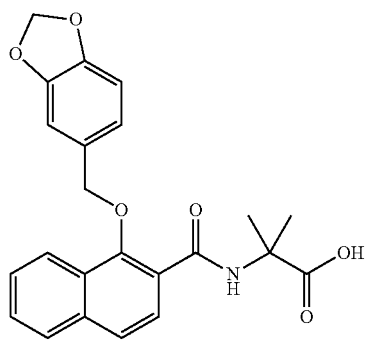 | 408.13 |
| 56 | 2-Methyl-2-{[1-(4-nitro-benzyloxy)-naphthalene-2-carbonyl]-amino}-propionic acid | 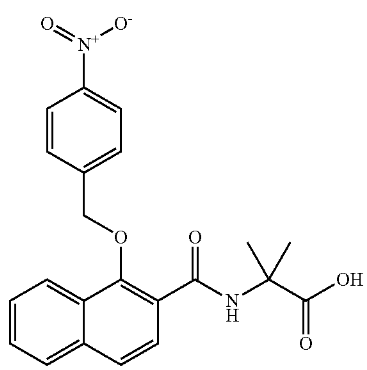 | 409.12 |
| 57 | 2-Methyl-2-{[1-(4-methylsulfanyl-benzyloxy)-naphthalene-2-carbonyl]-amino}-propionic acid | 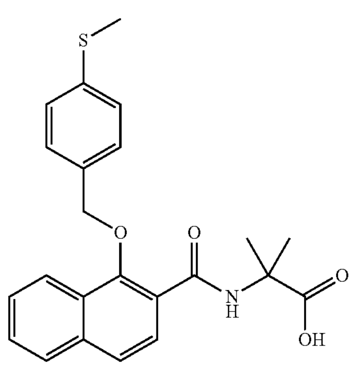 | 410.22 |

-continued

| No | Chemical Name | Structure | ESI+ or ESI- |
|---|---|---|---|
| 58 | 2-Methyl-2-{[1-(2,4,6-trimethyl-cyclohexylmethoxy)-naphthalene-2-carbonyl]-amino}-propionic acid | 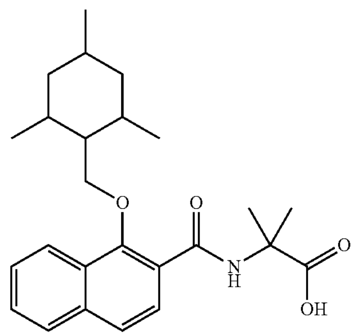 | 412.37 |
| 59 | 2-({1-[1-(4-Chloro-phenyl)-ethoxy]-naphthalene-2-carbonyl}-amino)-2-methyl-propionic acid | 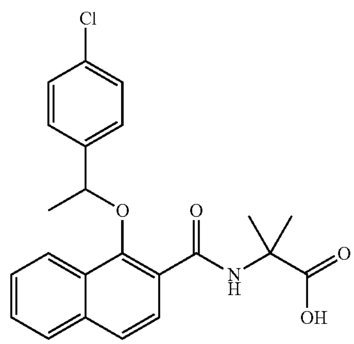 | 412.21 |
| 60 | 2-Methyl-2-{[1-(naphthalen-2-ylmethoxy)-naphthalene-2-carbonyl]-amino}-propionic acid | 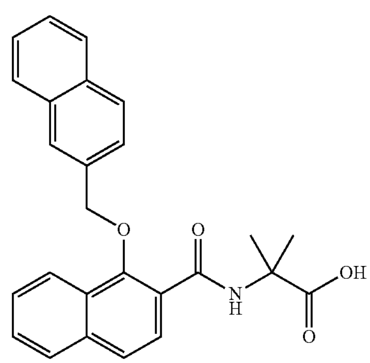 | 414.13 |
| 61 | 2-{[1-(4-Chloro-2-fluoro-benzyloxy)-naphthalene-2-carbonyl]-amino}-2-methyl-propionic acid | 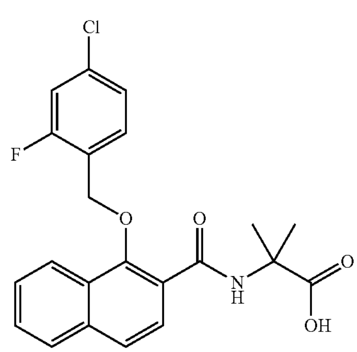 | 416.15 |

-continued

| No | Chemical Name | Structure | ESI+ or ESI− |
|---|---|---|---|
| 62 | 2-{[1-(4-Chloro-3-fluoro-benzyloxy)-naphthalene-2-carbonyl]-amino}-2-methyl-propionic acid | 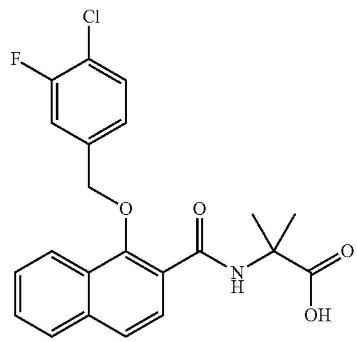 | 416.16 |
| 63 | 2-{[1-(Benzo[b]thiophen-2-ylmethoxy)-naphthalene-2-carbonyl]-amino}-2-methyl-propionic acid | 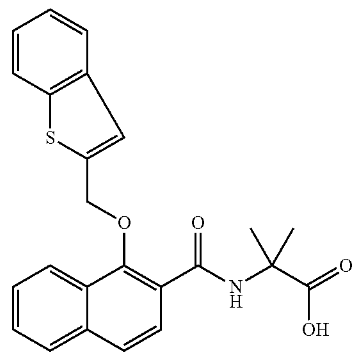 | 420.16 |
| 64 | 2-{[1-(Benzo[b]thiophen-3-ylmethoxy)-naphthalene-2-carbonyl]-amino}-2-methyl-propionic acid | 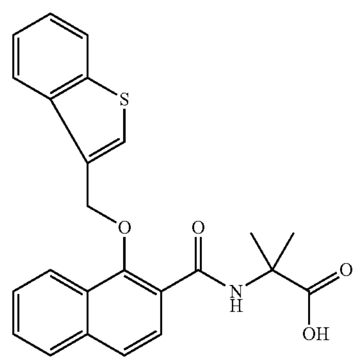 | 420.17 |
| 65 | 2-{[1-(4-tert-Butyl-benzyloxy)-naphthalene-2-carbonyl]-amino}-2-methyl-propionic acid | 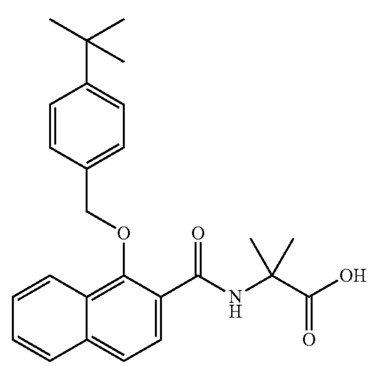 | 420.26 |

-continued

| No | Chemical Name | Structure | ESI+ or ESI− |
|---|---|---|---|
| 66 | 2-{[1-(4-Butyl-benzyloxy)-naphthalene-2-carbonyl]-amino}-2-methyl-propionic acid | 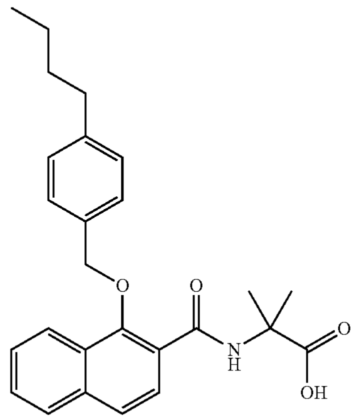 | 420.35 |
| 67 | 2-{[1-(2,3-Dihydro-benzo[1,4]dioxin-6-ylmethoxy)-naphthalene-2-carbonyl]-amino}-2-methyl-propionic acid | 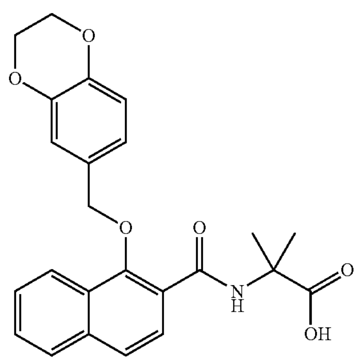 | 422.23 |
| 68 | 2-{[1-(4-Difluoromethoxy-benzyloxy)-naphthalene-2-carbonyl]-amino}-2-methyl-propionic acid | 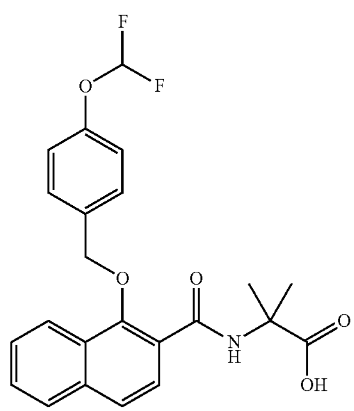 | 430.26 |
| 69 | 2-Methyl-2-{[1-(3-trifluoromethyl-benzyloxy)-naphthalene-2-carbonyl]-amino}-propionic acid | 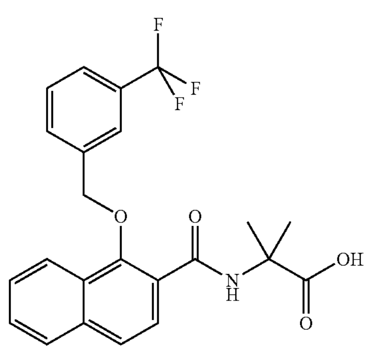 | 432.31 |

-continued

| No | Chemical Name | Structure | ESI+ or ESI− |
|---|---|---|---|
| 70 | 2-Methyl-2-{[1-(4-trifluoromethyl-benzyloxy)-naphthalene-2-carbonyl]-amino}-propionic acid | 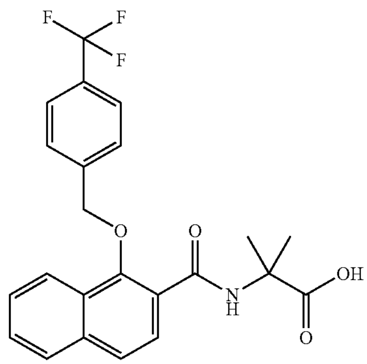 | 432.06 |
| 71 | 2-{[1-(3,4-Dichloro-benzyloxy)-naphthalene-2-carbonyl]-amino}-2-methyl-propionic acid | 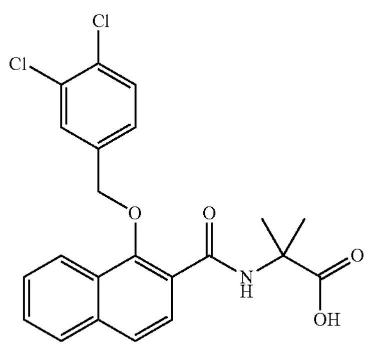 | 432.19 |
| 72 | 2-{[1-(2,4-Dichloro-benzyloxy)-naphthalene-2-carbonyl]-amino}-2-methyl-propionic acid | 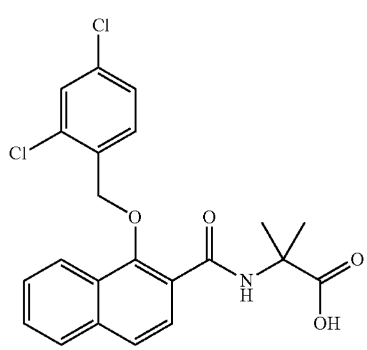 | 432.19 |
| 73 | 2-{[1-(5,6-Dichloro-pyridin-3-ylmethoxy)-naphthalene-2-carbonyl]-amino}-2-methyl-propionic acid | 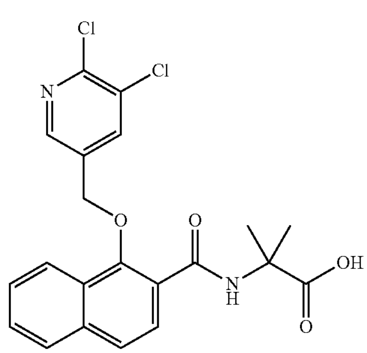 | 433.10 |

| No | Chemical Name | Structure | ESI+ or ESI- |
|---|---|---|---|
| 74 | 2-{[1-(Benzo[b]thiophen-2-ylmethoxy)-naphthalene-2-carbonyl]-amino}-2-methyl-butyric acid | 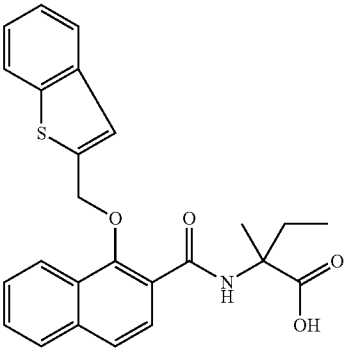 | 434.24 |
| 75 | 2-{[1-Benzo[b]thiophen-3-ylmethoxy)-naphthalene-2-carbonyl]-amino}-2-methyl-butyric acid | 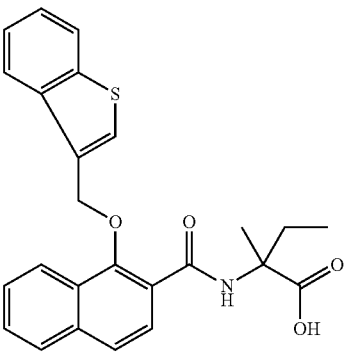 | 434.26 |
| 76 | 2-{[1-Biphenyl-4-ylmethoxy)-naphthalene-2-carbonyl]-amino}-2-methyl-propionic acid | 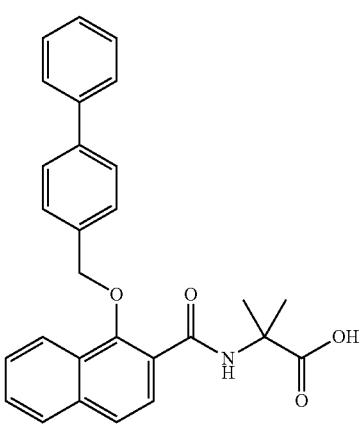 | 440.15 |
| 77 | 2-{[1-(4-Methanesulfonyl-benzyloxy)-naphthalene-2-carbonyl]-amino}-2-methyl-propionic acid | 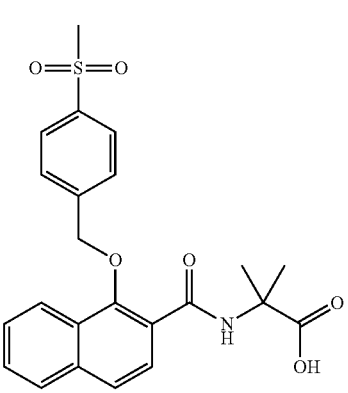 | 442.17 |

| No | Chemical Name | Structure | ESI+ or ESI− |
|---|---|---|---|
| 78 | 2-{[1-(6-Chloro-benzo[1,3]dioxol-5-ylmethoxy)-naphthalene-2-carbonyl]-amino}-2-methyl-propionic acid | 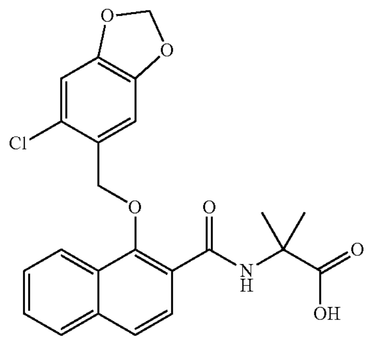 | 442.19 |
| 79 | 2-{[1-(3-Bromo-benzyloxy)-naphthalene-2-carbonyl]-amino}-2-methyl-propionic acid | 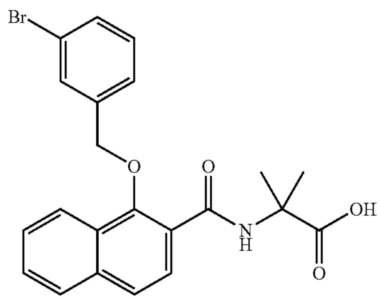 | 442.09 |
| 80 | 2-{[1-(4-Difluoromethoxy-benzyloxy)-naphthalnene-2-carbonyl]-amino}-2-methyl-butyric acid | 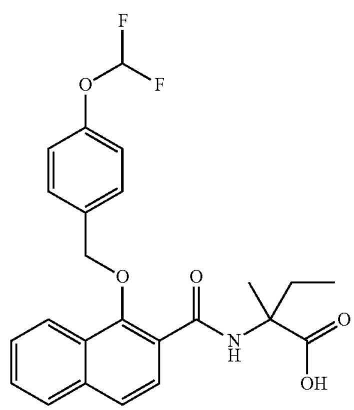 | 444.23 |
| 81 | 2-{[1-(5-Benzyl-furan-3-ylmethoxy)-naphthalene-2-carbonyl]-amino}-2-methyl-propionic acid | 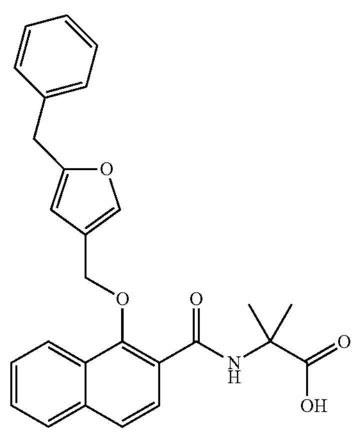 | 442.31 |

-continued

| No | Chemical Name | Structure | ESI+ or ESI− |
|---|---|---|---|
| 82 | 2-{[1-(5-Cyano-benzo[b]thiophen-2-ylmethoxy)-naphthalene-2-carbonyl]-amino}-2-methyl-propionic acid | 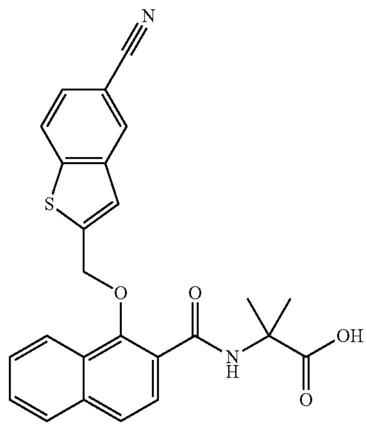 | 443.17 |
| 83 | 2-Methyl-2-({1-[1-(4-trifluoromethyl-phenyl)-ethoxy]-naphthalene-2-carbonyl}-amino)-propionic acid | 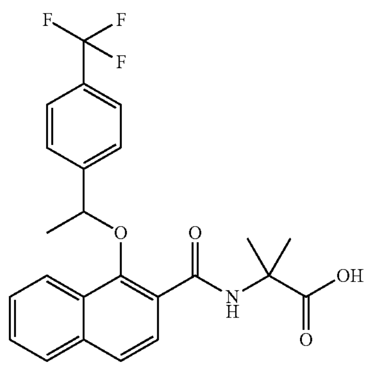 | 446.15 |
| 84 | 2-Methyl-2-({1-[1-(3-trifluoromethyl-phenyl)-ethoxy]-naphthalene-2-carbonyl}-amino)-propionic acid | 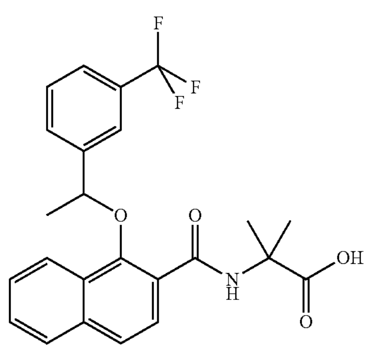 | 446.12 |
| 85 | 2-Methyl-2-({1-[1-(2-trifluoromethyl-phenyl)-ethoxy]-naphthalene-2-carbonyl}-amino)-propionic acid | 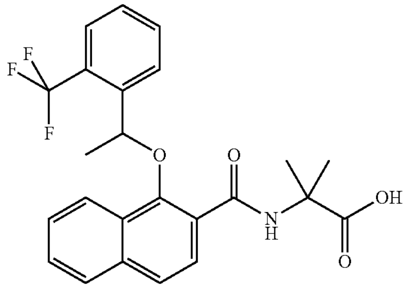 | 446.06 |

-continued

| No | Chemical Name | Structure | ESI+ or ESI− |
|---|---|---|---|
| 86 | 2-({1-[1-(3,4-Dichloro-phenyl)-ethoxy]-naphthalene-2-carbonyl}-amino)-2-methyl-propionic acid | 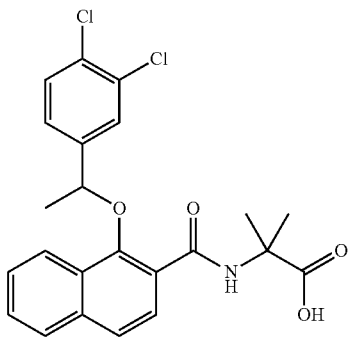 | 446.16 |
| 87 | 2-Methyl-2-{[1-(2-phenyl-thiazol-4-ylmethoxy)-naphthalene-2-carbonyl]-amino}-propionic acid | 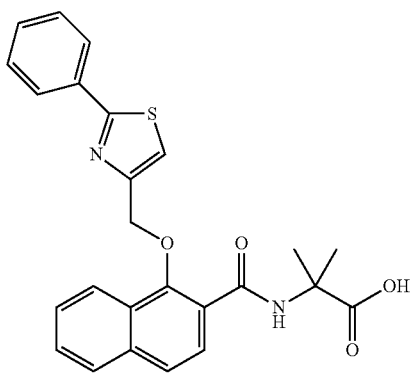 | 447.10 |
| 88 | 2-Methyl-2-{[1-(4-trifluoromethoxy-benzyloxy)-naphthalene-2-carbonyl]-amino}-propionic acid | 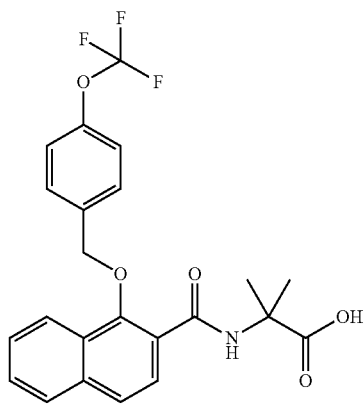 | 448.03 |
| 89 | 2-Methyl-2-{[1-(3-trifluoromethoxy-benzyloxy)-naphthalene-2-carbonyl]-amino}-propionic acid | 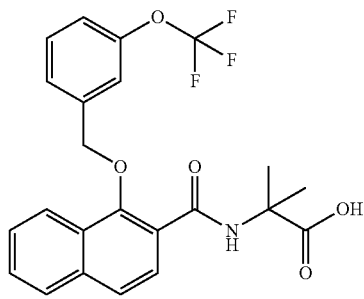 | 448.05 |

-continued

| No | Chemical Name | Structure | ESI+ or ESI– |
|---|---|---|---|
| 90 | 2-{[1-(2-Fluoro-4-trifluoromethyl-benzyloxy)-naphthalene-2-carbonyl]-amino}-2-methyl-propionic acid | 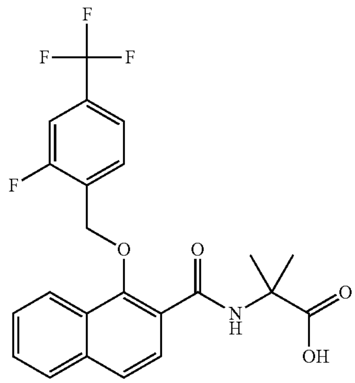 | 450.19 |
| 91 | 2-{[1-(4-Methanesulfonyl-benzyloxy)-naphthalene-2-carbonyl]-amino}-2-methyl-butyric acid | 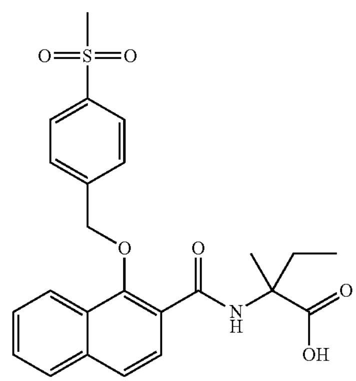 | 456.26 |
| 92 | 2-{[4-Chloro-1-(5-trifluoromethyl-furan-2-ylmethoxy)-naphthalene-2-carbonyl]-amino}-2-methyl-propionic acid | 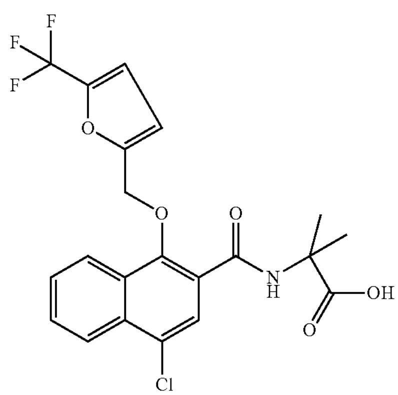 | 456.10 |
| 93 | 2-({1-[1-(4-Bromo-phenyl)-ethoxy]-naphthalene-2-carbonyl}-amino)-2-methyl-propionic acid | 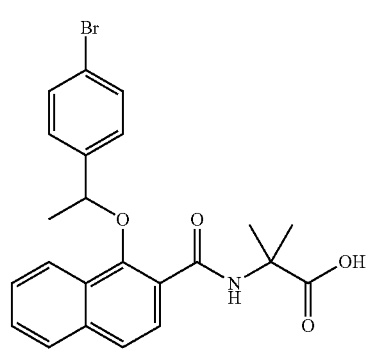 | 456.07 |

-continued

| No | Chemical Name | Structure | ESI+ or ESI− |
|---|---|---|---|
| 94 | 2-({1-[1-(3-Bromo-phenyl)-ethoxy]-naphthalene-2-carbonyl}-amino)-2-methyl-propionic acid | 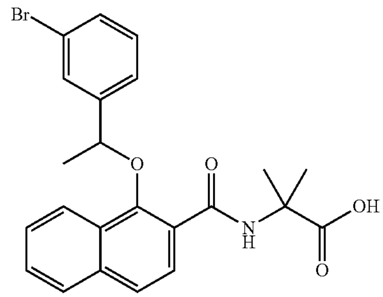 | 456.07 |
| 95 | 2-{[1-(4-Bromo-2-fluoro-benzyloxy)-naphthalene-2-carbonyl]-amino}-2-methyl-propionic acid | 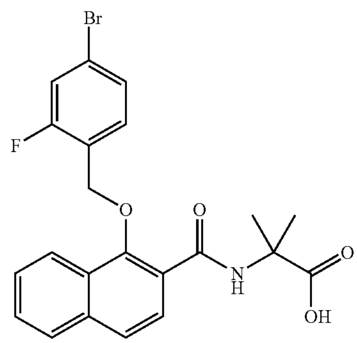 | 460.10 |
| 96 | 2-{[1-(4-Methoxy-3-trifluoromethyl-benzyloxy)-naphthalene-2-carbonyl]-amino}-2-methyl-propionic acid | 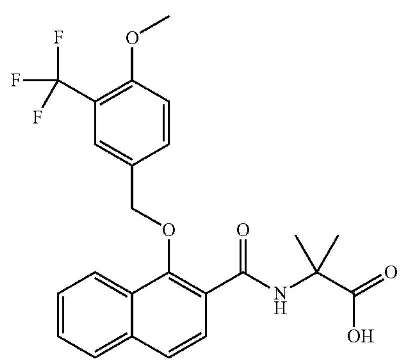 | 462.21 |
| 97 | 2-Methyl-2-{[1-(3-trifluoromethoxy-benzyloxy)-naphthalene-2-carbonyl]-amino}-butyric acid | 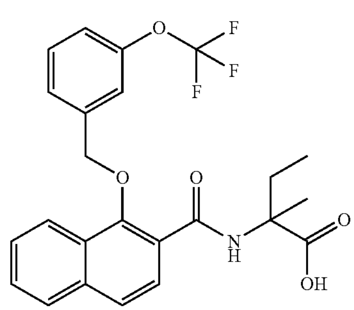 | 462.11 |

| No | Chemical Name | Structure | ESI+ or ESI- |
|----|---------------|-----------|--------------|
| 98 | 2-{[1-(2-Fluoro-4-trifluoromethyl-benzyloxy)-naphthalene-2-carbonyl]-amino}-2-methyl-butyric acid | 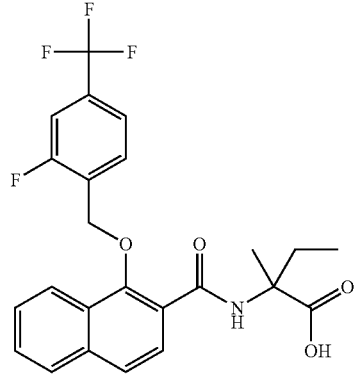 | 464.21 |
| 99 | 2-Methyl-2-{[1-(4-trifluoromethylsulfanyl-benzyloxy)-naphthalene-2-carbonyl]-amino}-propionic acid | 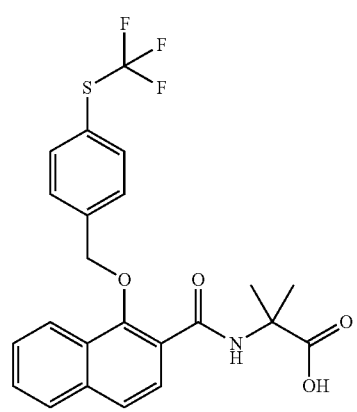 | 464.18 |
| 100 | 2-{[1-(2,3-Difluoro-4-trifluoromethyl-benzyloxy)-naphthalene-2-carbonyl]-amino}-2-methyl-propionic acid | 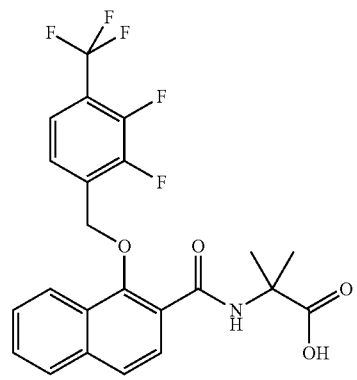 | 468.15 |
| 101 | 2-{[1-(4-Bromo-2-fluoro-benzyloxy)-naphthalene-2-carbonyl]-amino}-2-methyl-butyric acid | 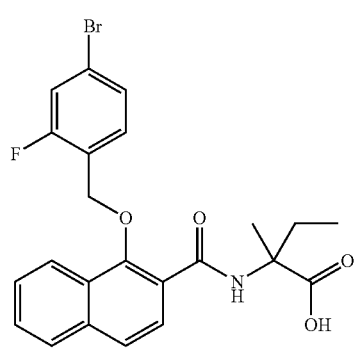 | 474.16 |

-continued

| No | Chemical Name | Structure | ESI+ or ESI− |
|----|---------------|-----------|--------------|
| 102 | 2-Methyl-2-{[1-(4-trifluoromethylsulfanyl-benzyloxy)-naphthalene-2-carbonyl]-amino}-butyric acid | 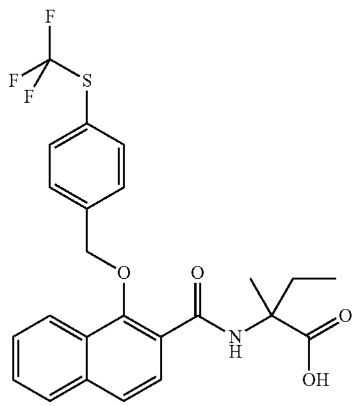 | 478.29 |
| 103 | 2-({1-[1-(4-Chloro-benzyl)-1H-imidazol-2-ylmethoxy]-naphthalene-2-carbonyl}-amino)-2-methyl-propionic acid | 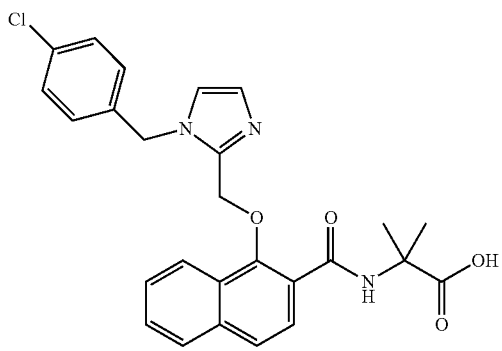 | 478.15 |
| 104 | 2-{[1-(2,3-Difluoro-4-trifluoromethyl-benzyloxy)-naphthalene-2-carbonyl]-amino}-2-methyl-butyric acid | 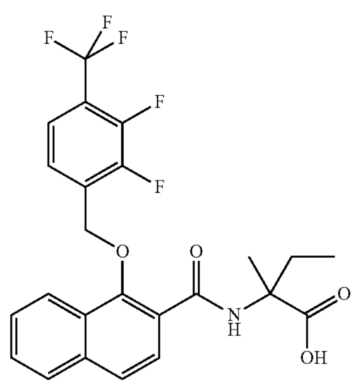 | 482.28 |
| 105 | 2-{[1-(3-Chloro-4-trifluoromethoxy-benzyloxy)-naphthalene-2-carbonyl]-amino}-2-methyl-butyric acid | 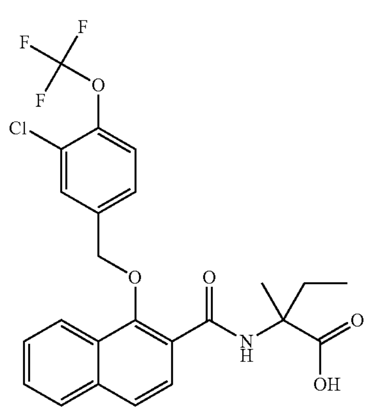 | 496.26 |

-continued

| No | Chemical Name | Structure | ESI+ or ESI– |
|---|---|---|---|
| 106 | 2-{[1-(3,4-Bis-trifluoromethyl-benzyloxy)-naphthalene-2-carbonyl]-amino}-2-methyl-propionic acid | 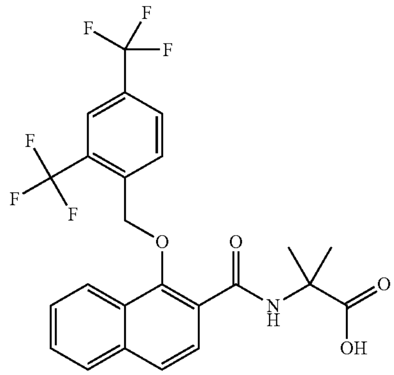 | 500.23 |

20

The following examples were prepared in analogy to example 3:

| No | Chemical Name | Structure | ESI+ or ESI– |
|---|---|---|---|
| 107 | 2-Methyl-2-{[1-(pyridin-2-ylmethoxy)-naphthalene-2-carbonyl]-amino}-propionic acid | 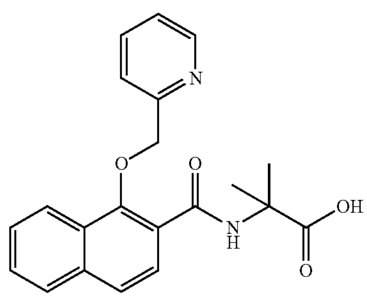 | 365.10 |
| 108 | 2-[(3-Benzyloxy-benzo[b]thiophene-2-carbonyl)-amino]-2-methyl-propionic acid | 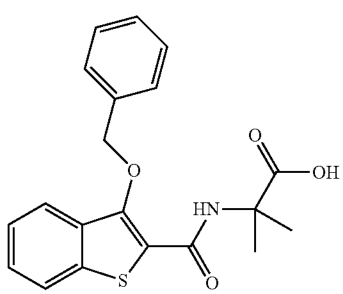 | 370.12 |
| 109 | 2-{[1-(3-Hydroxy-pyridin-2-ylmethoxy)-naphthalene-2-carbonyl]-amino}-2-methyl-propionic acid | 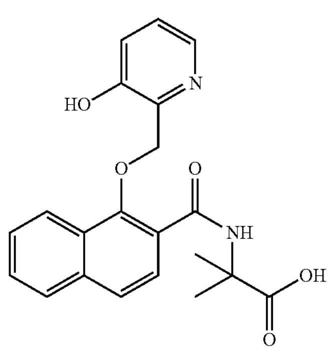 | 381.13 |

-continued

| No | Chemical Name | Structure | ESI+ or ESI− |
|---|---|---|---|
| 110 | 2-{[1-(4-Trifluoromethyl-benzyloxy)-naphthalene-2-carbonyl]-amino}-propionic acid | 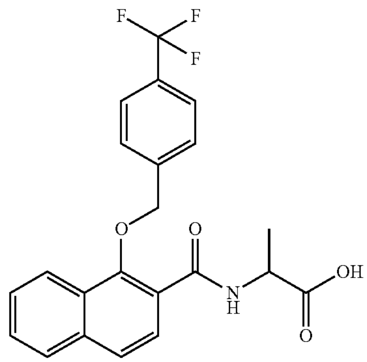 | 418.07 |
| 111 | 2-Methyl-2-{[3-(quinolin-2-ylmethoxy)-benzo[b]thiophene-2-carbonyl]-amino}-propionic acid | 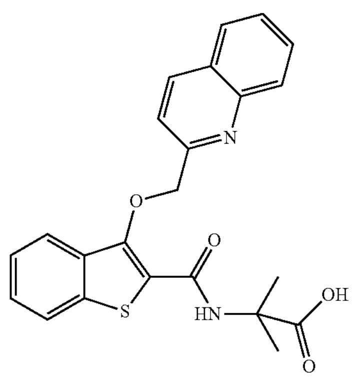 | 421.25 |
| 112 | 2-{[1-(2,3-Dihydro-benzo[1,4]dioxin-2-ylmethoxy)-naphthalene-2-carbonyl]-amino}-2-methyl-propionic acid | 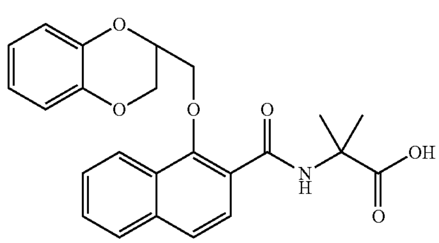 | 422.15 |
| 113 | 2-{[3-(Benzothiazol-2-ylmethoxy)-benzo[b]thiophene-2-carbonyl]-amino}-2-methyl-propionic acid | 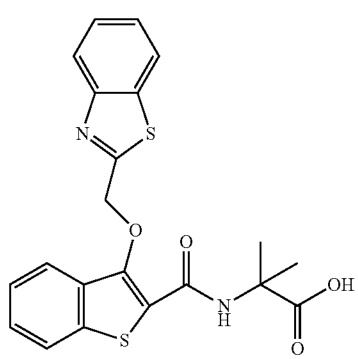 | 427.10 |

| No | Chemical Name | Structure | ESI+ or ESI− |
|---|---|---|---|
| 114 | 2-{[3-(Benzothiazol-2-ylmethoxy)-thieno[2,3-b]pyridine-2-carbonyl]-amino}-2-methyl-propionic acid | 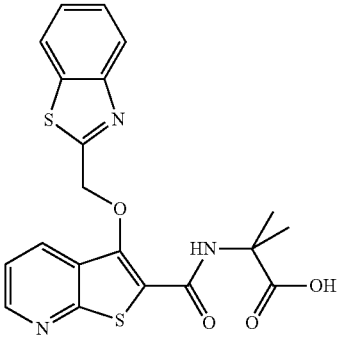 | 427.95 |
| 115 | 1-{[1-(4-Trifluoromethyl-benzyloxy)-naphthalene-2-carbonyl]-amino}-cyclopropanecarboxylic acid | 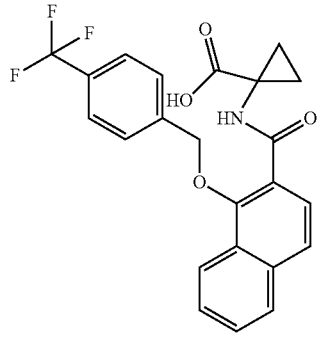 | 430.07 |
| 116 | 2-Methyl-2-{[4-(4-trifluoromethyl-benzyloxy)-isoquinolin-3-carbonyl]-amino}-propionic acid | 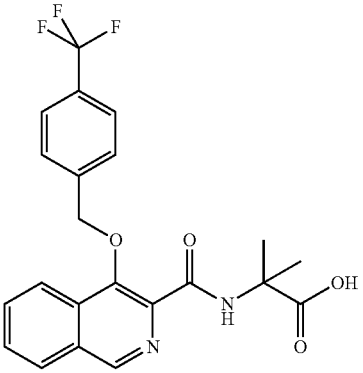 | 433.15 |
| 117 | 2-Methyl-2-{[3-(quinolin-2-ylmethoxy)-benzo[b]thiophene-2-carbonyl]-amino}-butyric acid | 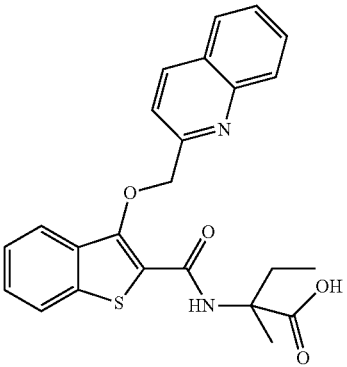 | 435.26 |

-continued

| No | Chemical Name | Structure | ESI+ or ESI− |
|---|---|---|---|
| 118 | 2-{[1-(2,3-Dihydro-benzo[1,4]dioxin-2-ylmethoxy)-naphthalene-2-carbonyl]-amino}-2-methyl-butyric acid | 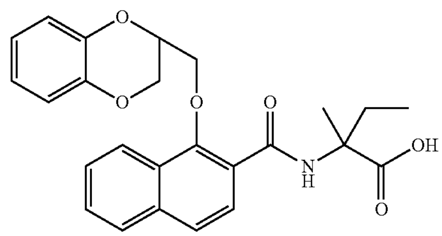 | 436.10 |
| 119 | 2-Methyl-2-{[3-(4-trifluoromethyl-benzyloxy)-benzo[b]thiophene-2-carbonyl]-amino}-propionic acid | 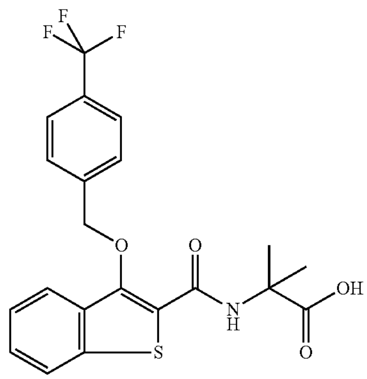 | 438.03 |
| 120 | 2-Methyl-2-{[3-(6-trifluoromethyl-pyridin-3-ylmethoxy)-benzo[b]thiophene-2-carbonyl]-amino}-propionic acid | 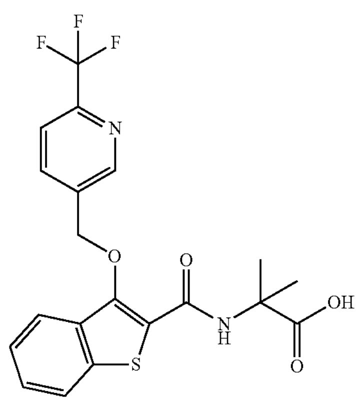 | 439.15 |
| 121 | 2-{[3-(Benzothiazol-2-ylmethoxy)-benzo[b]thiophene-2-carbonyl]-amino}-2-methyl-butyric acid | 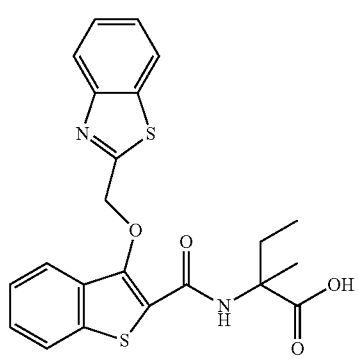 | 441.05 |

-continued

| No | Chemical Name | Structure | ESI+ or ESI− |
|---|---|---|---|
| 122 | 2-Methyl-2-{[1-(4-trifluoromethyl-benzyloxy)-naphthalene-2-carbonyl]-amino}-butyric acid | 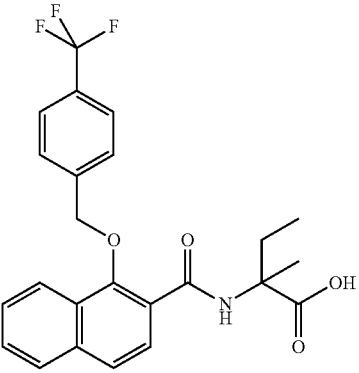 | 446.14 |
| 123 | 1-{[3-(Quinolin-2-ylmethoxy)-benzo[b]thiophene-2-carbonyl]-amino}-cyclopentanecarboxylic acid | 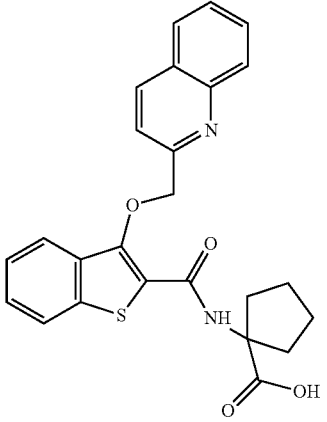 | 447.27 |
| 124 | 2-Methyl-2-{[3-(4-trifluoromethyl-benzyloxy)-benzo[b]thiophene-2-carbonyl]-amino}-butyric acid | 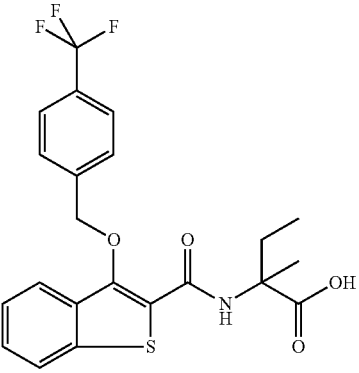 | 452.05 |
| 125 | 2-Methyl-2-{[3-(6-trifluoromethyl-pyridin-3-ylmethoxy)-benzo[b]thiophene-2-carbonyl]-amino}-butyric acid | 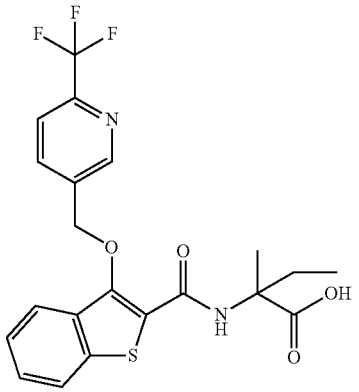 | 453.17 |

| No | Chemical Name | Structure | ESI+ or ESI- |
|----|---------------|-----------|--------------|
| 126 | 2-Methyl-2-{[3-(4-trifluoromethoxy-benzyloxy)-benzo[b]thiophene-2-carbonyl]-amino}-propionic acid | 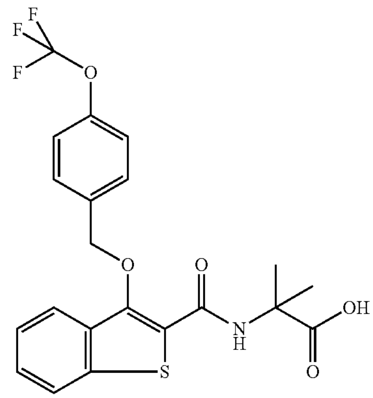 | 454.02 |
| 127 | 1-{[1-(4-Trifluoromethyl-benzyloxy)-naphthalene-2-carbonyl]-amino}-cyclopentanecarboxylic acid | 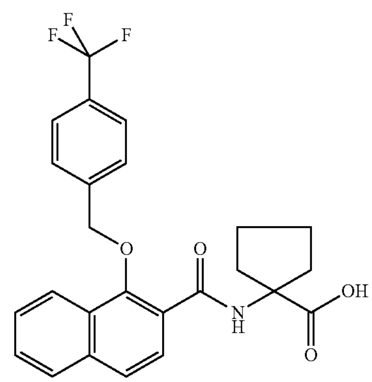 | 458.14 |
| 128 | 2,3-Dimethyl-2-{[1-(4-trifluoromethyl-benzyloxy)-naphthalene-2-carbonyl]-amino}-butyric acid | 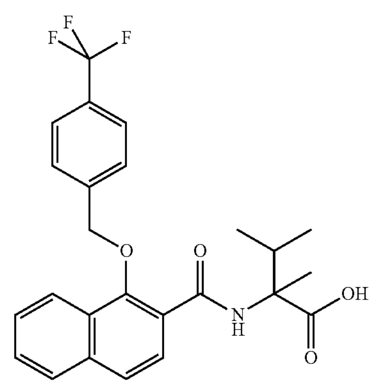 | 460.14 |
| 129 | 2-Methyl-2-{[1-(4-trifluoromethoxy-benzyloxy)-naphthalene-2-carbonyl]-amino}-butyric acid | 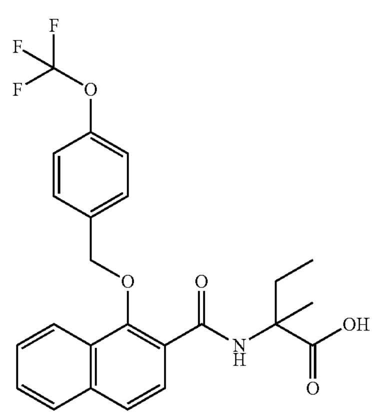 | 462.14 |

-continued

| No | Chemical Name | Structure | ESI+ or ESI− |
|---|---|---|---|
| 130 | 1-{[3-(4-Trifluoromethyl-benzyloxy)-benzo[b]thiophene-2-carbonyl]-amino}-cyclopentanecarboxylic acid | 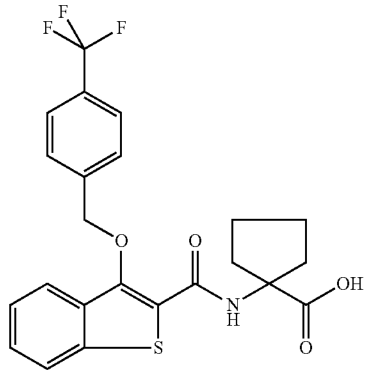 | 464.03 |
| 131 | 2,3-Dimethyl-2-{[3-(4-trifluoromethyl-benzyloxy)-benzo[b]thiophene-2-carbonyl]-amino}-butyric acid | 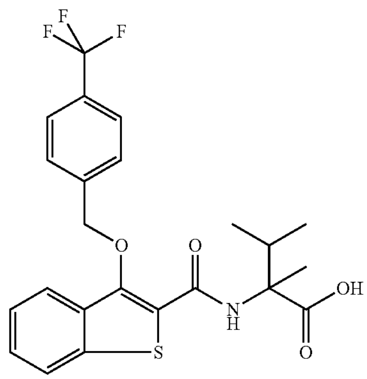 | 466.06 |
| 132 | 2-{[4-Chloro-1-(4-trifluoromethyl-benzyloxy)-naphthalene-2-carbonyl]-amino}-2-methyl-propionic acid | 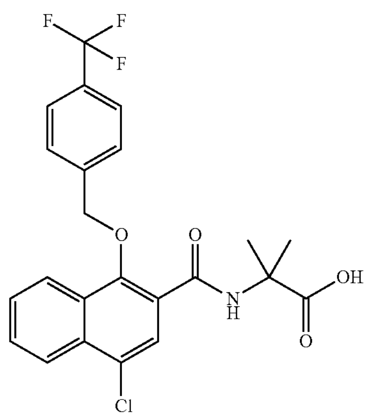 | 466.05 |
| 133 | 2-Methyl-2-{[3-(4-trifluoromethoxy-benzyloxy)-benzo[b]thiophene-2-carbonyl]-amino}-butyric acid | 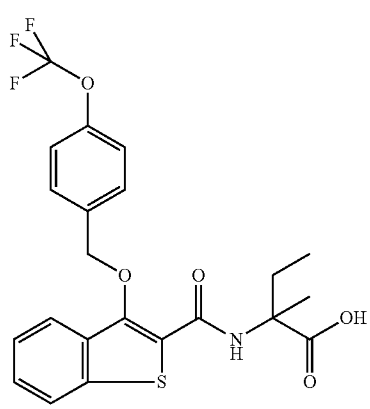 | 468.10 |

| No | Chemical Name | Structure | ESI+ or ESI− |
|---|---|---|---|
| 134 | 1-{[1-(4-Trifluoromethoxy-benzyloxy)-naphthalene-2-carbonyl]-amino}-cyclopentanecarboxylic acid | 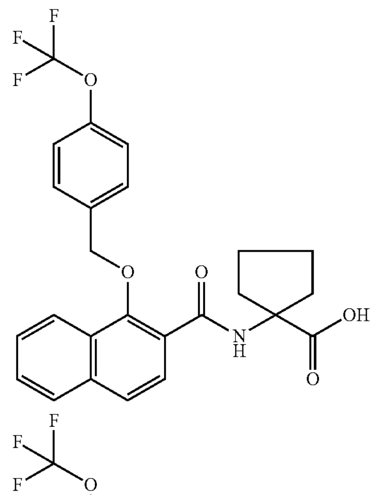 | 474.15 |
| 135 | 2,3-Dimethyl-2-{[1-(4-trifluoromethoxy-benzyloxy)-naphthalene-2-carbonyl]-amino}-butyric acid | 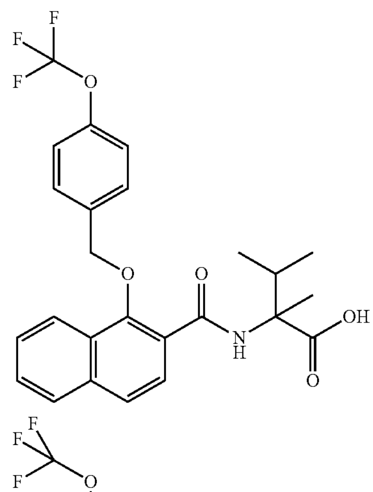 | 476.21 |
| 136 | 1-{[3-(4-Trifluoromethoxy-benzyloxy)-benzo[b]thiophene-2-carbonyl]-amino}-cyclopentanecarboxylic acid | 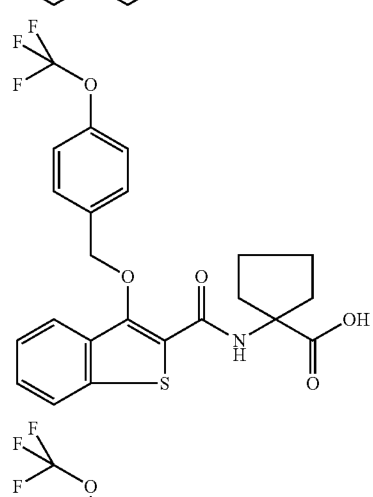 | 480.09 |
| 137 | 2,3-Dimethyl-2-{[3-(4-trifluoromethoxy-benzyloxy)-benzo[b]thiophene-2-carbonyl]-amino}-butyric acid | 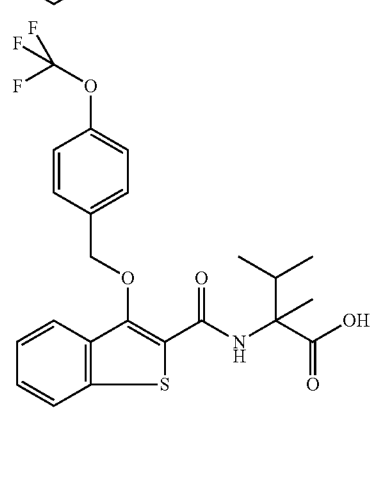 | 482.15 |

-continued
| No | Chemical Name | Structure | ESI+ or ESI− |
|----|---------------|-----------|--------------|
| 138 | 2-{[4-Chloro-1-(4-trifluoromethoxy-benzyloxy)-naphthalene-2-carbonyl]-amino}-2-methyl-propionic acid | 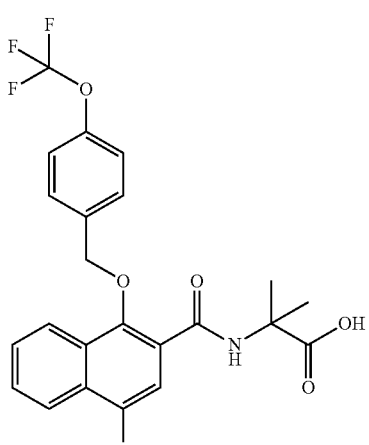 | 482.24 |
| 139 | 2-{[4-Chloro-1-(2-fluoro-4-trifluoromethyl-benzyloxy)-naphthalene-2-carbonyl]-amino}-2-methyl-propionic acid | 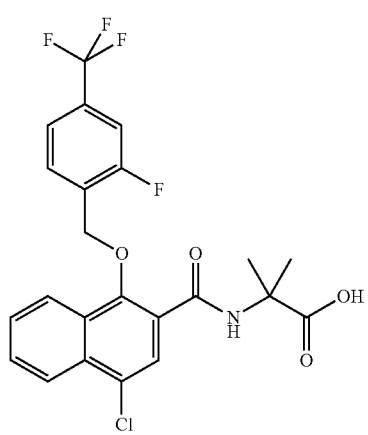 | 484.10 |
| 140 | 1-{[4-Chloro-1-(4-trifluoromethyl-benzyloxy)-naphthalene-2-carbonyl]-amino}-cyclopentanecarboxylic acid | 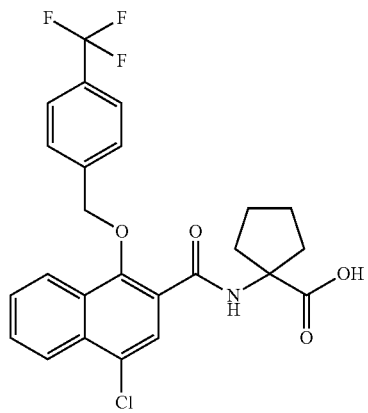 | 492.10 |

-continued

| No | Chemical Name | Structure | ESI+ or ESI– |
|---|---|---|---|
| 141 | 2-{[4-Chloro-1-(4-trifluoromethoxy-benzyloxy)-naphthalene-2-carbonyl]-amino}-2-methyl-butyric acid | 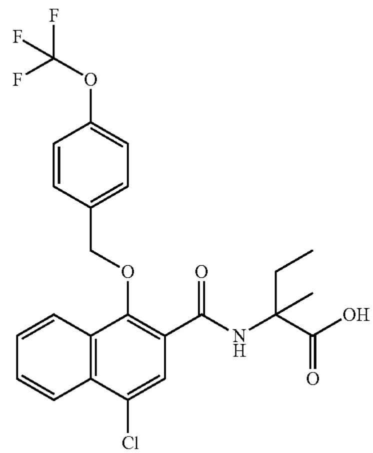 | 496.29 |
| 142 | 2-{[4-Chloro-1-(6-chloro-quinolin-2-ylmethoxy)-naphthalene-2-carbonyl]-amino}-2-methyl-butyric acid | 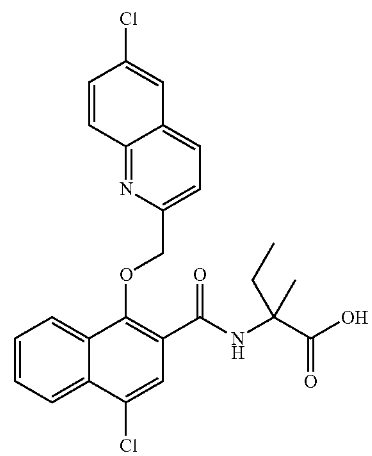 | 497.10 |
| 143 | 3-(3-Hydroxy-phenyl)-2-methyl-2-{[1-(4-trifluoromethyl-benzyloxy)-naphthalene-2-carbonyl]-amino}-propionic acid | 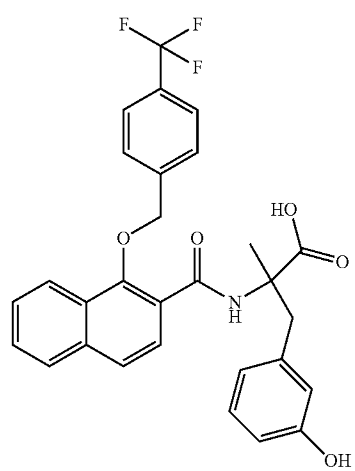 | 524.11 |

Example 144

1-(6-Trifluoromethyl-pyridin-3-ylmethoxy)-naphthalene-2-carboxylic acid (2-methylsulfonylamino-1,1-dimethyl-2-oxo-ethyl)-amide

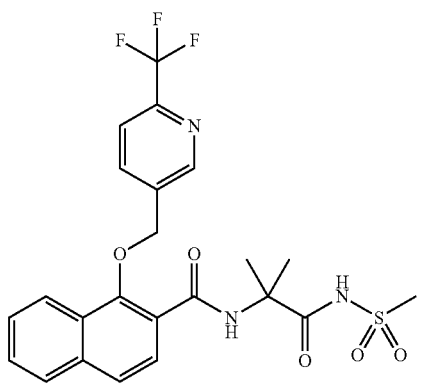

0.10 ml oxalyl chloride and DMF (0.1 ml) were added to a room temperature solution of 0.050 g 2-methyl-2-{[1-6-trifluoromethyl-pyridin-3-ylmethoxy-naphthalene-2-carbonyl]-amino}-propionic acid in 1,2-dichloroethane (2 ml). The resulting mixture was stirred at room temperature for 1 h, then concentrated in vacuo to give an orange oil. The residue was re-dissolved in THF (2 ml), and treated with a room temperature suspension of 0.033 g sodium hydride (60% dispersion in oil) and 0.040 g methylsulfonamide in THF (2 ml). The resulting mixture was heated in microwave reactor for 10 min at 150° C. The reaction mixture was cooled to room temperature, diluted with ethyl acetate (100 ml), and was washed with 1% aq. HCl (2×100 ml) and brine (100 ml). The aqueous layers were re-extracted with ethyl acetate (2×100 ml). The organic layers were combined, dried (sodium sulphate), and concentrated in vacuo to give 0.22 g of an amber oil. The residue was purified by flash chromatography (20 g SiO$_2$ column, 0-20% MeOH/dichloromethane to afford 50 mg of 1-(6-trifluoromethyl-pyridin-3-ylmethoxy)-naphthalene-2-carboxylic acid (2-methylsulfonylamino-1,1-dimethyl-2-oxo-ethyl)-amide.

$C_{23}H_{22}F_3N_3O_5S$ (509.50) LCMS (ESI): 510.09 (MH$^+$)

The following examples were prepared in analogy to example 144:

| No | Chemical Name | Structure | ESI+ or ESI− |
|---|---|---|---|
| 145 | 1-(6-Trifluoromethyl-pyridin-3-ylmethoxy)-naphthalene-2-carboxylic acid (2-benzenesulfonylamino-1,1-dimethyl-2-oxo-ethyl)-amide | 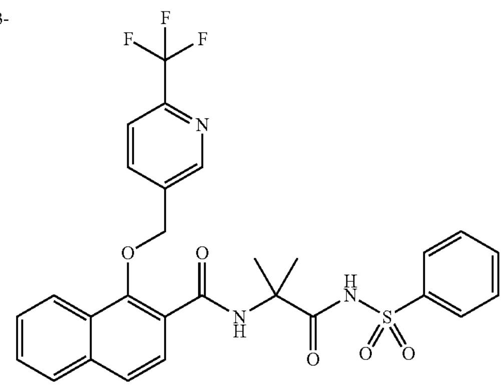 | 572.22 |
| 146 | 1-(6-Trifluoromethyl-pyridin-3-ylmethoxy)-naphthalene-2-carboxylic acid (2-tert-butylsulfonylamino-1,1-dimethyl-2-oxo-ethyl)-amide | 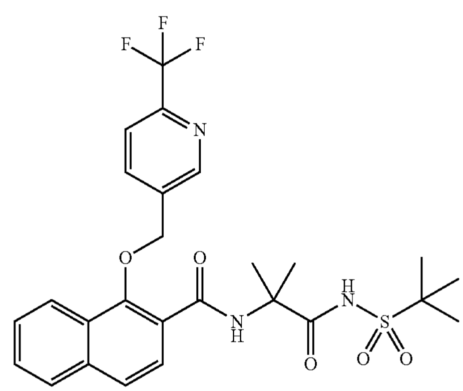 | 552.18 |

Example 147

2-{[4-Fluoro-1-(4-methyl-benzyloxy)-naphthalene-2-carbonyl]-amino}-2-methyl-propionic acid

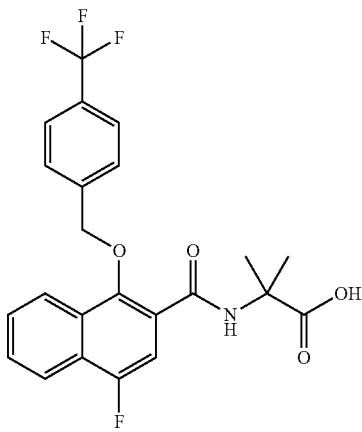

a) 1-Acetoxy-4-fluoro-naphthalene

To a rapidly stirred solution of 1.5 g of bis[3,5-bis(trifluoromethyl)phenyl]diselenide (prepared as described in H. J. Reich et al., JACS, 1975, 5441) in 50 ml of trifluoroethanol under nitrogen was added 3.5 ml of 50% hydrogen peroxide followed by 5.0 g of 1-acetyl-4-fluoro-naphthalene. The mixture was stirred at room temperature for 20 h. To the mixture was added an additional 1.75 ml of 50% hydrogen peroxide after which the mixture was stirred at ambient temperature for 24 h. The mixture was poured into cold water, extracted with dichloromethane, washed with 10% sodium bisulfite, 10% sodium bicarbonate and brine, dried (magnesium sulfate), filtered and concentrated to an orange solid. The material was purified by chromatography on silica gel, eluting with ethyl acetate/heptanes to provide 1.82 g of 1-acetoxy-4-fluoro-naphthalene as an off-white solid.

$C_{12}H_9FO_2$ (204.06), LCMS (Cl): 205.06 (M H$^+$)

b) 4-Fluoro-1-hydroxynaphthalene

To a stirred solution of 2.71 g of 1-acetoxy-4-fluoro-naphthalene in 142 ml of degassed methanol was added a solution of 9.2 g of potassium carbonate in 95 ml of degassed water. The mixture was stirred at room temperature for 5 h. The mixture was cooled with ice, acidified to pH1-2 with conc. HCL, extracted with dichloromethane, dried (magnesium sulphate), filtered and concentrated to an orange solid. The material was purified by chromatography on silica gel eluting with dichloromethane/heptanes/toluene to provide 1.98 g of 4-fluoro-1-hydroxynaphthalene as a white solid.

$C_{10}H_7FO$ (162.05), LCMS (ESI-): 161.01 (M-H)

c) 4-Fluoro-1-methoxymethoxynaphthalene

To a stirred solution of 1.91 g of 4-fluoro-1-hydroxynaphthalene in 40 ml of dry dichloromethane in an ice/salt bath was added by syringe 2.64 ml of diisopropylethylamine followed by 1.11 ml of methoxymethylchloride. The mixture was stirred at 0° C. for 0.5 h, allowed to warm to ambient temperature and stirred for 14 h. The reaction mixture was poured into saturated sodium bicarbonate, extracted with dichloromethane, dried (sodium sulphate), filtered and concentrated to a yellow oil. The material was purified by flash chromatography on silica gel eluting with toluene/heptanes to provide 1.98 g of 4-fluoro-1-methoxymethoxynaphthalene.

$C_{12}H_{11}FO_2$ (206.07), LCMS (Cl): 206.01 (M$^+$)

d) 4-Fluoro-1-methoxymethoxynaphthalene-2-carboxylic acid methyl ester

To a stirred solution of 0.30 g of 4-fluoro-1-methoxymethoxy-naphthalene in 21 ml of dry THF was added 1.8 ml of TMEDA. The mixture was cooled to −18 to −22° C. (carbon tetrachloride bath) after which was added 2.46 ml of 1.6 M n-butyl-lithium. The mixture was stirred at −20° C. for 0.5 h after which it was cooled to −75° C. To the mixture was added a solution of 0.60 ml of methyl chloroformate in 6 ml of THF. The mixture was stirred at −75 to −78° C. for 0.5 h, poured into brine, extracted twice with ether, dried (sodium sulphate), filtered and concentrated to an orange oil. The oil was dissolved in dichloromethane and purified by flash chromatography on silica gel, eluting with ethyl acetate/heptanes to provide 0.162 g of 4-fluoro-1-methoxymethoxynaphthalene-2-carboxylic acid methyl ester as an off-white solid.

$C_{14}H_{13}FO_4$ (264.08), LCMS (Cl): 264.01 (M$^+$)

e) 4-Fluoro-1-hydroxynaphthalene-2-carboxylic acid methyl ester

To a mixture of 0.375 g of 4-fluoro-1-methoxymethoxynaphthalene-2-carboxylic acid methyl ester and 375 mg of montmorillonite K-10 clay was added 10 ml of dry dichloromethane. The mixture was stirred at room temperature for 35 minutes. The suspension was diluted with dry dichloromethane and filtered. The residue was washed with ethyl acetate and the combined filtrate concentrated to a white solid. The material was purified by flash chromatography on silica gel, eluting with ethyl acetate/heptanes to provide 0.191 g of 4-fluoro-1-hydroxynaphthalene-2-carboxylic acid, methyl ester.

$C_{12}H_9FO_3$ (220.05), LCMS (Cl): 221.07 (MH$^+$)

f) 4-Fluoro-1-[4-(trifluoromethyl)benzyloxy]naphthalene-2-carboxylic acid methyl ester To 0.190 g of 4-fluoro-1-hydroxynaphthalene-2-carboxylic acid methyl ester in 4 ml of dry DMF 560 mg of Cesium carbonate and 31 mg of potassium iodide was added. The mixture was stirred at ambient temperature for 20 minutes after which was added a solution of 0.31 g of 4-(trifluoromethyl)benzyl bromide in 2 ml of DMF. The mixture was stirred at room temperature for 3 h, poured into saturated sodium bicarbonate, extracted with ethyl acetate, washed with water, brine, dried (sodium sulphate), filtered and concentrated to a white solid. The material was purified by flash chromatography on silica gel eluting with ethyl acetate/heptanes to provide 0.231 g of 4-fluoro-1-[4-(trifluoromethyl)benzyloxy]naphthalene-2-carboxylic acid methyl ester as a white solid.

$C_{20}H_{14}F_4O_3$ (378.09), LCMS (Cl): 378.99 (MH$^+$)

g) 4-Fluoro-1-[4-(trifluoromethyl)benzyloxy]-naphthalene-2-carboxylic acid

To a stirred solution of 0.22 g of 4-fluoro-1-[4-(trifluoromethyl)benzyloxy]-naphthalene-2-carboxylic acid, methyl ester in 4.5 ml of THF and 0.86 ml of methanol was added 1.7 ml of 1M sodium hydroxide. The mixture was stirred at ambient temperature for 11 h. The mixture was diluted with water, acidified to pH 1-2 with 1M HCl, extracted twice with ethyl acetate, dried (sodium sulphate), filtered and concentrated to provide 0.21 g of 4-fluoro-1-[4-(trifluoromethyl) benzyloxy]naphthalene-2-carboxylic acid as a white solid.

$C_{19}H_{12}F_4O_3$ (364.07), LCMS (ESI): 365.04 (MH$^+$)

h) 2-{[4-fluoro-1-(4-trifluoromethyl-benzyloxy)-naphthalene-2-carbonyl]-amino}-2-methyl-propionic acid methyl ester To 0.2 g of 4-fluoro-1-[4-(trifluoromethyl)benzyloxy] naphthalene-2-carboxylic acid, 158 mg of EDC, 104 mg of 1-hydroxybenzotriazole and 102 mg of 2,2-dimethylglycine methyl ester hydrochloride was added 5.3 ml of DMF followed by 0.29 ml of diisopropylethylamine. The mixture was stirred for 16 h at room temperature. The mixture was poured into cold water, acidified to pH 2-3 with 1M HCl, extracted with ethyl acetate, washed with water, brine, dried (sodium sulphate) filtered and concentrated to an oil. The material was flash chromatographed on silica gel eluting with ethyl acetate/heptanes to provide 0.207 g of 2-{[4-fluoro-1-(4-trifluoromethyl-benzyloxy)-naphthalene-2-carbonyl]-amino}-2-methyl-propionic acid methyl ester as a colorless oil.

$C_{24}H_{21}F_4NO_4$ (463.14), LCMS (ESI): 464.2 (MH$^+$).

i) 2-{[4-Fluoro-1-(4-trifluoromethyl-benzyloxy)-naphthalene-2-carbonyl]-amino}-2-methyl-propionic acid To 0.198 g of 2-{[4-fluoro-1-(4-trifluoromethyl-benzyloxy)-naphthalene-2-carbonyl]-amino}-2-methyl-propionic acid methyl ester was added 15 ml of THF and 5 ml of methanol followed by 5 ml of 1 M NaOH. The solution was stirred at ambient temperature for 12 h. The reaction mixture was poured into water/ethyl acetate, acidified to pH 1-2 with 1M HCl, extracted with ethyl acetate, washed with water, dried (sodium sulphate), filtered and concentrated to a colorless oil which crystallized on standing. The material was triturated with ether, filtered and dried at 50° C. for 1.5 h to provide 45 mg of 2-{[4-fluoro-1-(4-trifluoromethyl-benzyloxy)-naphthalene-2-carbonyl]-amino}-2-methyl-propionic acid as a white solid.

$C_{24}H_{21}F_4NO_4$ (449.12), LCMS (ESI): 450.09 (MH$^+$).

Example 148

2-{[1-(5-Chloro-6-methoxy-pyridin-3-ylmethoxy)-naphthalene-2-carbonyl]-amino}-2-methyl-propionic acid

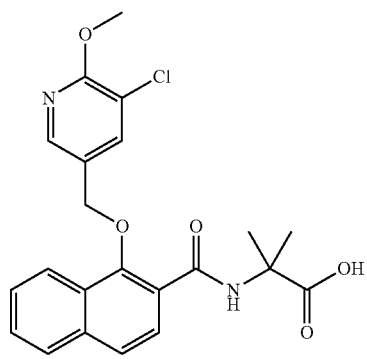

a) 2-{[1-(5,6-Dichloro-pyridin-3-ylmethoxy)-naphthalene-2-carbonyl]-amino}-2-methyl-propionic acid methyl ester To a solution of 80 mg of 2-[(1-hydroxy-naphthalene-2-carbonyl)-amino]-2-methyl-propionic acid methyl ester, 50 mg 5,6-dichloro-3-pyridine methanol and 73 mg triphenyl phosphine in 3 ml of dry THF 56 mg of diisopropylazodicarboxylate were added. After 16 h at room temperature the reaction was concentrated in vacuo and after chromatography on silica (ethyl acetate/heptane) 96 mg of 2-{[1-(5,6-dichloro-pyridin-3-ylmethoxy)-naphthalene-2-carbonyl]-amino}-2-methyl-propionic acid methyl ester were obtained.

$C_{22}H_{20}Cl_2N_2O_4$ (447.32), LCMS (ESI): 447.07, 449.06 (MH$^+$, di-Cl-pattern).

b) 2-{[1-(5-Chloro-6-methoxy-pyridin-3-ylmethoxy)-naphthalene-2-carbonyl]-amino}-2-methyl-propionic acid 82 mg 2-{[1-(5,6-dichloro-pyridin-3-ylmethoxy)-naphthalene-2-carbonyl]-amino}-2-methyl-propionic acid methyl ester in 0.5 ml MeOH and 0.5 ml 2 M aqueous sodium hydroxide solution were heated to 120° C. for 3 min using a microwave reactor. The reaction mixture was acidified with 2 M HCl and the precipitated solid was collected by filtration and purified by RP-HPLC to yield 36 mg 2-{[1-(5-chloro-6-methoxy-pyridin-3-ylmethoxy)-naphthalene-2-carbonyl]-amino}-2-methyl-propionic acid.

$C_{22}H_{21}ClN_2O_5$ (428.88), LCMS (ESI): 429.13 (MH$^+$).

Example 149

2-{[1-(5-Chloro-6-ethoxy-pyridin-3-ylmethoxy)-naphthalene-2-carbonyl]-amino}-2-methyl-propionic acid

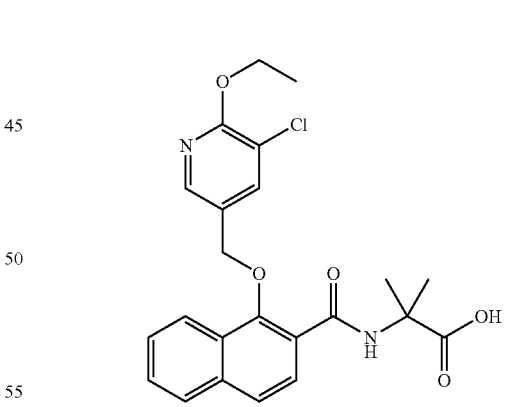

A solution of 50 mg 2-{[1-(5,6-dichloro-pyridin-3-ylmethoxy)-naphthalene-2-carbonyl]-amino}-2-methyl-propionic acid methyl ester and 30 mg sodium ethoxide in 3 ml EtOH containing 5% of water was heated to 120° C. for 2 min using a microwave reactor. The reaction mixture was acidified to pH 4 with 2 M HCl and the precipitated solid was collected by filtration and purified by RP-HPLC to yield 40 mg 2-{[1-(5-chloro-6-ethoxy-pyridin-3-ylmethoxy)-naphthalene-2-carbonyl]-amino}-2-methyl-propionic acid.

$C_{23}H_{23}ClN_2O_5$ (442.90), LCMS (ESI): 443.05 (MH$^+$).

Example 150

2-({1-[6-(2,2,2-trifluoro-ethoxy)-pyridin-3-yl-methoxy]-naphtha-lene-2-carbonyl}-amino)-2-methyl-propionic acid

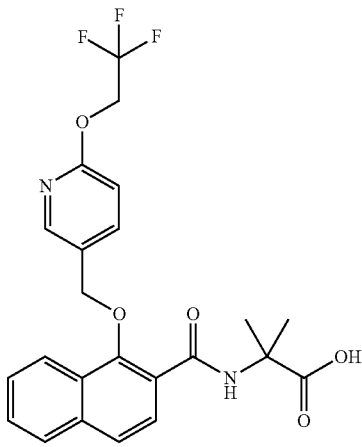

a) 1-(6-Chloro-pyridin-3-ylmethoxy)-naphthalene-2-carboxylic acid methyl ester To a solution of 1.0 g 1-hydroxy-2-naphthoic acid methyl ester in 20 ml abs. DMF 3.22 g cesium carbonate was added, followed by addition of 0.16 g potassium iodide and 0.96 g 2-chloro-5-chloromethyl-pyridine. Under argon-atmosphere the reaction mixture was heated to 60° C. for 1 h. The mixture was then poured into water and extracted with ethyl acetate at pH9 three times. The combined organic layers were dried over magnesium sulphate, filtrated and after removal of the solvent a crude product was obtained which was recrystallized from diethyl ether to yield 1.62 g 1-(6-chloro-pyridin-3-ylmethoxy)-naphthalene-2-carboxylic acid methyl ester.

$C_{18}H_{14}ClNO_3$ (327.77), LCMS (ESI): 328.05 (MH$^+$).

b) 1-[6-(2,2,2-Trifluoro-ethoxy)-pyridin-3-yl-methoxy]-naphthalene-2-carboxylic acid To a solution of 0.30 g of 1-(6-chloro-pyridin-3-ylmethoxy)-naphthalene-2-carboxylic acid methyl ester in 4 ml 2,2,2-trifluoroethanol containing 5% of water was added 0.55 g sodium methoxide. The reaction was heated to 165° C. for 1 h using a microwave reactor. The reaction was then poured into ice-water, the pH was adjusted to 4 using 2 M hydrochloric acid and the precipitated product was collected by filtration and dried in vacuo yielding 0.22 g of 1-[6-(2,2,2-trifluoro-ethoxy)-pyridin-3-ylmethoxy]-naphthalene-2-carboxylic acid.

$C_{19}H_{14}F_3NO_4$ (377.32), LCMS (ESI): 378.05 (MH$^+$).

c) 2-Methyl-2-({1-[6-(2,2,2-trifluoro-ethoxy)-pyridin-3-ylmethoxy]-naphthalene-2-carbonyl}-amino)-propionic acid methyl ester At 0° C. to 115 mg 1-[6-(2,2,2-trifluoro-ethoxy)-pyridin-3-ylmethoxy]-naphthalene-2-carboxylic acid in 2 mL of abs. DMF 82 mg EDC, 45 mg 1-hydroxybenzotriazole and 49 mg N,N-diisopropylethylamine were added. After 30 min at 0° C. 56 mg of 2,2-dimethylglycine methyl ester hydrochloride and 49 mg N,N-diisopropylethylamine were added. The mixture was stirred for 16 h at room temperature. The mixture was poured into cold water, acidified to pH 3 with 2M HCl, extracted with ethyl acetate, washed with sat. sodium hydrogen carbonate solution and brine, dried over magnesium sulphate, filtrated and concentrated in vacuo to provide 124 mg of 2-methyl-2-({1-[6-(2,2,2-trifluoro-ethoxy)-pyridin-3-ylmethoxy]-naphthalene-2-carbonyl}-amino)-propionic acid methyl ester.

$C_{24}H_{23}F_3N_2O_5$ (476.46), LCMS (ESI): 477.10 (MH$^+$).

d) 2-({1-[6-(2,2,2-Trifluoro-ethoxy)-pyridin-3-yl-methoxy]-naphthalene-2-carbonyl}-amino)-2-methyl-propionic acid To 124 mg 2-methyl-2-({1-[6-(2,2,2-trifluoro-ethoxy)-pyridin-3-ylmethoxy]-naphthalene-2-carbonyl}-amino)-propionic acid methyl ester in 4 mL THF and 1 mL methanol was added 1.3 mL of 1 M aqueous sodium hydroxide solution. After stirring at room temperature for 1 h the mixture was poured into cold water, acidified to pH 2 with 2 M HCl and extracted with ethyl acetate three times. The combined organic layers were dried over magnesium sulphate, filtrated and concentrated to provide a yellow oil, which could be crystallized from diisopropylether to yield 43 mg of 2-methyl-2-({1-[6-(2,2,2-trifluoro-ethoxy)-pyridin-3-yl-methoxy]-naphthalene-2-carbonyl}-amino)-propionic acid.

$C_{23}H_{21}F_3N_2O_5$ (462.43), LCMS (ESI): 463.19 (MH$^+$).

Example 151

2-Methyl-2-({1-[6-(2,2,2-trifluoro-ethoxy)-pyridin-3-ylmethoxy]-naphtha-lene-2-carbonyl}-amino)-butyric acid

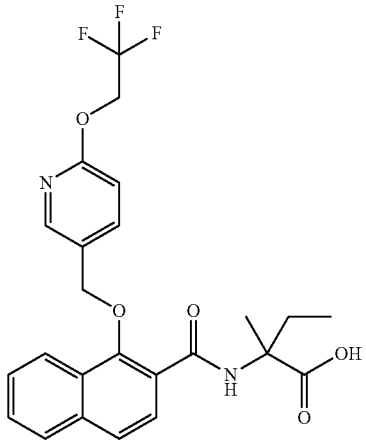

2-Methyl-2-({1-[6-(2,2,2-trifluoro-ethoxy)-pyridin-3-yl-methoxy]-naphtha-lene-2-carbonyl}-amino)-butyric acid was prepared in similar manner as 2-methyl-2-({1-[6-(2,2,2-trifluoro-ethoxy)-pyridin-3-ylmethoxy]-naphthalene-2-carbonyl}-amino)-propionic acid (example 150) via 2-methyl-2-({1-[6-(2,2,2-trifluoro-ethoxy)-pyridin-3-ylmethoxy]-naphthalene-2-carbonyl}-amino)-butyric acid methyl ester ($C_{25}H_{25}F_3N_2O_5$ (490.48), LCMS (ESI): 491.15 (MH$^+$)).

$C_{24}H_{23}F_3N_2O_5$ (476.46), LCMS (ESI): 477.10 (MH$^+$).

Example 152

2-{[1-(6-Methoxy)-pyridin-3-ylmethoxy)-naphthalene-2-carbonyl]-amino}-2-methyl-propionic acid

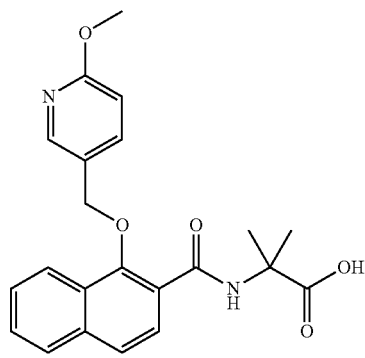

a) 1-(6-Methoxy-pyridin-3-ylmethoxy)-naphthalene-2-carboxylic acid

To a solution of 0.50 g of 1-(6-Chloro-pyridin-3-ylmethoxy)-naphthalene-2-carboxylic acid methyl ester (example 150, step a)) in 10 ml methanol containing 5% of water was added 0.82 g sodium methoxide. The reaction was heated to 165° C. for 5 min using a microwave reactor. The reaction was then poured into ice-water, the pH was adjusted to 4 using 2 M hydrochloric acid, the precipitated product was collected by filtration and dried in vacuo yielding 0.27 g of 1-(6-methoxy-pyridin-3-ylmethoxy)-naphthalene-2-carboxylic acid.

$C_{18}H_{15}NO_4$ (309.32), LCMS (ESI): 310.17 (MH$^+$).

b) 2-{[1-(6-Methoxy-pyridin-3-ylmethoxy)-naphthalene-2-carbonyl]-amino}-2-methyl-propionic acid methyl ester At 0° C. to 150 mg 1-[6-methoxy-pyridin-3-ylmethoxy]-naphthalene-2-carboxylic acid in 2 mL of abs. DMF 130 mg EDC, 72 mg 1-hydroxybenzotriazole and 81 mg N,N-diisopropylethylamine were added. After 30 min at 0° C. 89 mg of 2,2-dimethylglycine methyl ester hydrochloride and 81 mg N,N-diisopropylethylamine were added. The mixture was stirred for 1 h at room temperature. The mixture was poured into cold water, acidified to pH 3 with 2 M HCl, extracted with ethyl acetate twice, washed with sat. sodium hydrogen carbonate solution and brine. The combined organic layers were dried over magnesium sulphate, filtrated and concentrated in vacuo to provide 191 mg of 2-{[1-(6-methoxy-pyridin-3-ylmethoxy)-naphthalene-2-carbonyl]-amino}-2-methyl-propionic acid methyl ester.

$C_{23}H_{24}N_2O_5$ (408.46), LCMS (ESI): 409.15 (MH$^+$).

c) 2-{[1-(6-Methoxy-pyridin-3-ylmethoxy)-naphthalene-2-carbonyl]-amino}-2-methyl-propionic acid To 191 mg 2-{[1-(6-Methoxy-pyridin-3-ylmethoxy)-naphthalene-2-carbonyl]-amino}-2-methyl-propionic acid methyl ester in 6 mL THF and 1 mL methanol was added 2.3 mL of 1 M aqueous sodium hydroxide solution. After stirring at room temperature for 4 h the mixture was poured into cold water, acidified to pH 4 with 2M HCl and extracted with ethyl acetate three times. The combined organic layers were dried over magnesium sulphate, filtrated and concentrated to provide a yellow oil, which could be crystallized from diethylether and methanol to yield 44 mg of 2-{[1-(6-methoxy-pyridin-3-ylmethoxy)-naphthalene-2-carbonyl]-amino}-2-methyl-propionic acid.

$C_{22}H_{22}N_2O_5$ (394.43), LCMS (ESI): 395.14 (MH$^+$).

Example 153

2-{[1-(6-Methoxy-pyridin-3-ylmethoxy)-naphthalene-2-carbonyl]-amino}-2-methyl-butyric acid

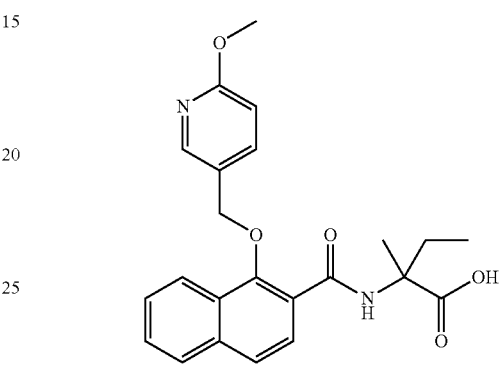

2-{[1-(6-Methoxy-pyridin-3-ylmethoxy)-naphthalene-2-carbonyl]-amino}-2-methyl-butyric acid was prepared in similar manner as 2-{[1-(6-methoxy-pyridin-3-ylmethoxy)-naphthalene-2-carbonyl]-amino}-2-methyl-propionic acid (example 152) via 2-{[1-(6-Methoxy-pyridin-3-ylmethoxy)-naphthalene-2-carbonyl]-amino}-2-methyl-butyric acid methyl ester ($C_{24}H_{26}N_2O_5$ (422.49), LCMS (ESI): 423.15 (MH$^+$)).

$C_{23}H_{24}N_2O_5$ (408.46), LCMS (ESI): 409.17 (MH$^+$).

Example 154

2-{[1-(1-Benzothiazol-2-yl-ethoxy)-naphthalene-2-carbonyl]-amino}-2-methyl-propionic acid

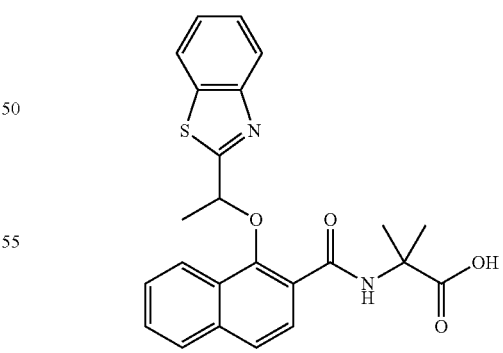

a) 2-{[1-(1-Benzothiazol-2-yl-ethoxy)-naphthalene-2-carbonyl]-amino}-2-methyl-propionic acid methyl ester To a solution of 108 mg 2-[(1-Hydroxy-naphthalene-2-carbonyl)-amino]-2-methyl-propionic acid methyl ester, 72 mg 1-benzothiazol-2-yl-ethanol and 372 mg diphenyl-[4-[1H,1H,2H,2H-perfluorodecyl]phenyl]phosphine in 2.5 mL dry THF a solution of 322 mg bis(1H,1H,2H,2H-perfluorooctyl)azodicarboxylate in 2.5 mL dry THF was added slowly at 0° C. After 16 h at room temperature and under argon atmosphere 372 mg diphenyl-[4-[1H,1H,2H,2H-perfluorodecyl]phenyl]phosphine and 322 mg bis(1H,1H,2H,2H-perfluorooctyl)azo-dicarboxylate were added. After additional 24 h the solvent was evaporated, the residue taken up in 5 mL methanol and purified using a FluoroFlash-SPE cartridge with methanol/water 80/20. After removal of methanol the remaining phase was extracted with ethyl acetate twice. The combined organic fractions were washed with 2 M sodium hydroxide and water, dried over magnesium sulphate, filtrated and condensed to yield 137 mg 2-{[1-(1-benzothiazol-2-yl-ethoxy)-naphthalene-2-carbonyl]-amino}-2-methyl-propionic acid methyl ester.

$C_{25}H_{24}N_2O_4S$ (448.55), LCMS (ESI): 449.15 (MH$^+$).

b) 2-{[1-(1-Benzothiazol-2-yl-ethoxy)-naphthalene-2-carbonyl]-amino}-2-methyl-propionic acid 135 mg 2-{[1-(1-Benzothiazol-2-yl-ethoxy)-naphthalene-2-carbonyl]-amino}-2-methyl-propionic acid methyl ester in 1 ml methanol and 1.5 ml 1 M aqueous sodium hydroxide solution were heated to 100° C. for 2 min in a microwave reactor. The reaction mixture was then acidified using 2 M hydrochloric acid and extracted with ethyl acetate twice. The combined organic layers were dried over magnesium sulphate, filtrated and concentrated in vacuo. Precipitation with pentane yielded 44 mg of 2-{[1-(1-Benzothiazol-2-yl-ethoxy)-naphthalene-2-carbonyl]-amino}-2-methyl-propionic acid as a colorless solid.

$C_{24}H_{22}N_2O_4S$ (434.52), LCMS (ESI): 435.08 (MH$^+$).

Example 155

1-(6-Trifluoromethyl-pyridin-3-ylmethoxy)-naphthalene-2-carboxylic acid [1-(N-hydroxycarbamimidoyl)-1-methyl-ethyl]-amide

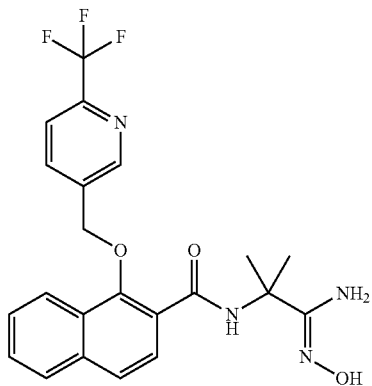

a) 1-(6-Trifluoromethyl-pyridin-3-ylmethoxy)-naphthalene-2-carboxylic acid (cyano-dimethyl-methyl)-amide In analogy to steps a) and b) of example 3 starting from 1-hydroxy-naphthalene-2-carboxylic acid methyl ester using 5-chloromethyl-2-trifluoromethyl-pyridine and and performing the amidation reaction using 2-amino-2-methyl-propionitrile 1-(6-trifluoromethyl-pyridin-3-ylmethoxy)-naphthalene-2-carboxylic acid (cyano-dimethyl-methyl)-amide was obtained as a brown oil.

$C_{22}H_{18}F_3N_3O_2$ (413.40), MS (ESI$^-$): 386 (M$^+$-CN).

b) 1-(6-Trifluoromethyl-pyridin-3-ylmethoxy)-naphthalene-2-carboxylic acid [1-(N-hydroxycarbamimidoyl)-1-methyl-ethyl]-amide 0.16 g hydroxylamine hydrochloride was added to a room temperature solution of 0.28 g 1-(6-trifluoromethyl-pyridin-3-yl-methoxy)-naphthalene-2-carboxylic acid (cyano-dimethyl-methyl)-amide and 0.50 g potassium carbonate in 5 ml 95% ethanol, and the resulting mixture was heated at reflux for 24 h. The reaction mixture was cooled to room temperature, diluted with 100 ml ethyl acetate, and was washed twice with 100 ml sat. sodium hydrogen carbonate solution and 100 ml brine. The combined organic layers were dried over sodium sulphate, and concentrated in vacuo to give an orange oil. Purification of the residue by RP-HPLC afforded 0.031 g of 1-(6-trifluoromethyl-pyridin-3-yl-methoxy)-naphthalene-2-carboxylic acid [1-(N-hydroxycarbamimidoyl)-1-methyl-ethyl]-amide as a colorless foam.

$C_{22}H_{21}F_3N_4O_2$ (446.43), LCMS (ESI): 447.16 (MH$^+$).

Examples 156 and 157

2-{[1-(4-Dimethylamino-2-trifluoromethyl-quinolin-6-ylmethoxy)-naphthalene-2-carbonyl]-amino}-2-methyl-propionic acid 2-{[1-(4-methoxy-2-trifluoromethyl-quinolin-6-ylmethoxy)-naphthalene-2-carbonyl]-amino}-2-methyl-propionic acid

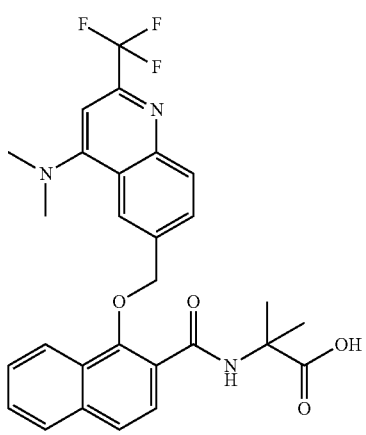

147
-continued

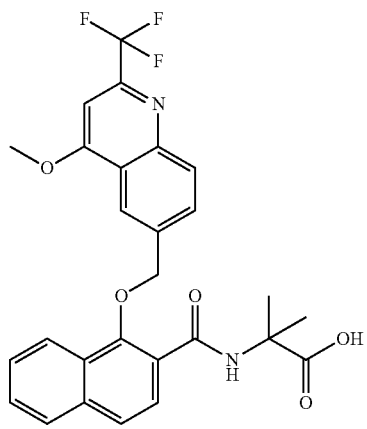

a) 2-{[1-(4-Chloro-2-trifluoromethyl-quinolin-6-ylmethoxy)-naphthalene-2-carbonyl]-amino}-2-methyl-propionic acid methyl ester To a solution of 100 mg 2-[(1-Hydroxy-naphthalene-2-carbonyl)-amino]-2-methyl-propionic acid methyl ester in 1 ml dry DMF 227 mg cesium carbonate and 135 mg 6-(bromomethyl)-4-chloro-2-(trifluoromethyl)-quinoline were added. After 16 h at room temperature the reaction mixture was taken up in ethyl acetate and water. The phases were separated and the aqueous phase was extracted with water twice. The combined organic phases were dried over magnesium sulphate, filtrated and concentrated to yield 292 mg of a crude product containing 2-{[1-(4-Chloro-2-trifluoromethyl-quinolin-6-ylmethoxy)-naphthalene-2-carbonyl]-amino}-2-methyl-propionic acid methyl ester.

$C_{27}H_{22}ClF_3N_2O_4$ (530.94), LCMS (ESI): 531.15 (MH$^+$).

b) 2-{[1-(4-Dimethylamino-2-trifluoromethyl-quinolin-6-ylmethoxy)-naphthalene-2-carbonyl]-amino}-2-methyl-propionic acid and 2-{[1-(4-methoxy-2-trifluoromethyl-quinolin-6-ylmethoxy)-naphthalene-2-carbonyl]-amino}-2-methyl-propionic acid 180 mg 2-{[1-(4-Chloro-2-trifluoromethyl-quinolin-6-ylmethoxy)-naphthalene-2-carbonyl]-amino}-2-methyl-propionic acid methyl ester in 0.66 ml methanol, 1.26 ml THF and 0.42 ml 2 M aqueous sodium hydroxide solution were reacted for 16 h at room temperature. The reaction mixture was then acidified using 2 M hydrochloric acid and extracted with ethyl acetate twice. The combined organic layers were dried over magnesium sulphate, filtrated and concentrated in vacuo. After preparative RP-HPLC 20 mg 2-{[1-(4-dimethylamino-2-trifluoromethyl-quinolin-6-ylmethoxy)-naphthalene-2-carbonyl]-amino}-2-methyl-propionic acid and 25 mg 2-{[1-(4-methoxy-2-trifluoromethyl-quinolin-6-ylmethoxy)-naphthalene-2-carbonyl]-amino}-2-methyl-propionic acid were obtained.

$C_{28}H_{26}F_3N_3O_4$ (525.53), LCMS (ESI): 526.17 (MH$^+$).
$C_{27}H_{23}F_3N_2O_5$ (512.49), LCMS (ESI): 513.11 (MH$^+$).

148

Example 158

2-{[3-(Benzothiazol-2-ylmethoxy)-5-fluoro-benzo[b]thiophene-2-carbonyl]-amino}-2-methyl-propionic acid

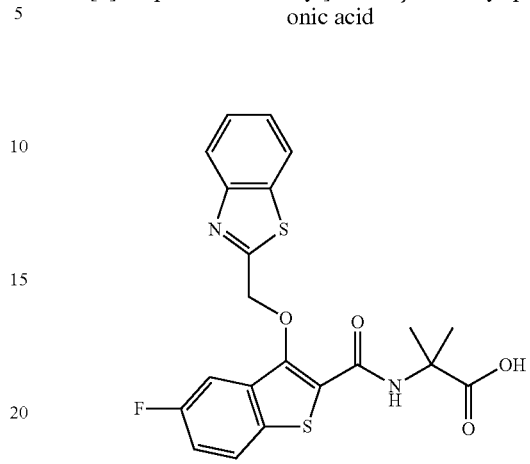

a) 2-(2-Chloro-acetylamino)-2-methyl-propionic acid methyl ester

To a solution of 0.95 g chloro acetic acid in 20 ml of dry THF 1.78 g N,N'-carbonyl-diimidazole were added. After 0.5 h at room temperature and under argon atmosphere 1.69 g 2-amino-2-methyl-propionic acid methyl ester and 1.29 g N,N-diisopropyl-ethyl-amine were added and it was stirred for 3 h. Then the solvent was evaporated, the residue taken up in ethyl acetate and washed with 2 M hydrochloric acid, water and sat. aqueous sodium hydrogen carbonate solution. The combined organic fractions were dried over sodium sulphate, filtrated and concentrated. The resulting residue was crystallized from diethylether to yield 2-(2-chloro-acetylamino)-2-methyl-propionic acid methyl ester.

$C_7H_{12}ClNO_3$ (193.63), LCMS (ESI): 194.05 (MH$^+$).

b) 2-[(5-Fluoro-3-hydroxy-benzo[b]thiophene-2-carbonyl)-amino]-2-methyl-propionic acid methyl ester To a solution of 1.00 g 5-fluoro-2-mercaptobenzoic acid ethyl ester in 10 ml methanol 0.81 g of sodium methoxide were added portionwise, followed by addition of 0.97 g 2-(2-chloro-acetylamino)-2-methyl-propionic acid methyl ester. After refluxing the reaction under argon-atmosphere for 0.5 h the resulting mixture was filtrated, 20 ml water and 1.25 ml of acetic acid were added and the precipitated product was collected by filtration, washed with water, dissolved in ethyl acetate and THF, dried over sodium sulphate, filtrated and concentrated in vacuo. The resulting crude product was crystallized from diethylether to yield 1.10 g 2-[(5-fluoro-3-hydroxy-benzo[b]thio-phene-2-carbonyl)-amino]-2-methyl-propionic acid methyl ester.

$C_{14}H_{14}FNO_4S$ (311.33), LCMS (ESI): 312.00 (MH$^+$).

c) 2-{[3-(Benzothiazol-2-ylmethoxy)-5-fluoro-benzo[b]thiophene-2-carbonyl]-amino}-2-methyl-propionic acid methyl ester To a suspension of 250 mg of cesium carbonate in 2.8 ml dry DMF 218 mg 2-[(5-fluoro-3-hydroxy-benzo[b]thio-phene-2-carbonyl)-amino]-2-methyl-propionic acid methyl ester were added, after 0.5 h followed by the addition of 176 mg 2-(bromomethyl)-1,3-benzothiazole. After 2.5 h the reaction was poured into ice water and the resulting mixture was extracted with ethyl acetate twice. The combined organic phases were dried over sodium sulphate, filtrated, concentrated in vacuo, and the resulting crude product was crystallized from diethylether to yield 0.14 g 2-{[3-(benzo-thiazol-2-ylmethoxy)-5-fluoro-benzo[b]thiophene-2-carbonyl]-amino}-2-methyl-propionic acid methyl ester.

$C_{22}H_{19}FN_2O_4S_2$ (458.53), LCMS (ESI): 459.10 (MH$^+$).

d) 2-{[3-(Benzothiazol-2-ylmethoxy)-5-fluoro-benzo[b]thiophene-2-carbonyl]-amino}-2-methyl-propionic acid 138 mg 2-{[3-(Benzothiazol-2-ylmethoxy)-5-fluoro-benzo[b]thiophene-2-carbonyl]-amino}-2-methyl-propionic acid methyl ester in 2 ml methanol and 1 ml 1 M aqueous sodium hydroxide solution was refluxed for 0.5 h. The reaction was acidified with 2 M hydrochloric acid, and the precipitated product was collected by filtration, dissolved in ethyl acetate, dried over sodium sulphate adding also active charcoal, filtrated, concentrated in vacuo, and the resulting crude product was crystallized from diethylether to yield 0.08 g 2-{[3-(Benzothiazol-2-ylmethoxy)-5-fluoro-benzo[b]thiophene-2-carbonyl]-amino}-2-methyl-propionic acid.

$C_{21}H_{17}FN_2O_4S_2$ (444.51), LCMS (ESI): 444.93 (MH$^+$).

Example 159

2-{[5-Fluoro-3-(6-trifluoromethyl-pyridin-3-yl-methoxy)-benzo[b]thio-phene-2-carbonyl]-amino}-2-methyl-propionic acid

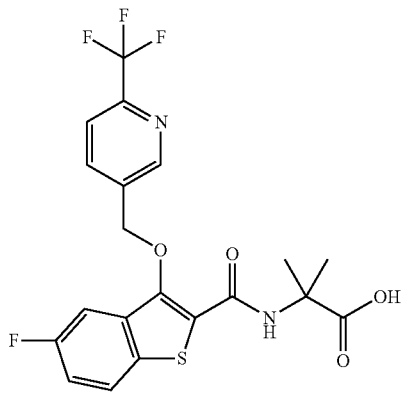

2-{[5-Fluoro-3-(6-trifluoromethyl-pyridin-3-ylmethoxy)-benzo[b]thio-phene-2-carbonyl]-amino}-2-methyl-propionic acid was prepared in similar manner as 2-{[3-(benzothiazol-2-ylmethoxy)-5-fluoro-benzo[b]thiophene-2-carbonyl]-amino}-2-methyl-propionic acid (example 158) via 2-{[5-fluoro-3-(6-trifluoromethyl-pyridin-3-yl-methoxy)-benzo[b]thio-phene-2-carbonyl]-amino}-2-methyl-propionic acid methyl ester ($C_{21}H_{18}F_4N_2O_4S$ (470.45), LCMS (ESI): 471.10 (MH$^+$)).

$C_{20}H_{16}F_4N_2O_4S$ (456.42), LCMS (ESI): 457.05 (MH$^+$).

Example 160

2-{[1-(1-Acetyl-piperidin-4-ylmethoxy)-4-chloro-naphthalene-2-carbonyl]-amino}-2-methyl-butyric acid

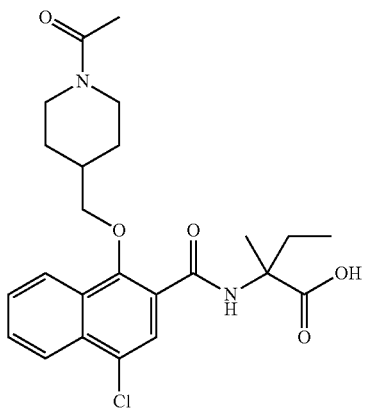

a) 4-[4-Chloro-2-(1-ethoxycarbonyl-1-methyl-propylcarbamoyl)-naphthalen-1-yloxymethyl]-piperidine-1-carboxylic acid tert-butyl ester To a solution of 0.95 g of 2-[(4-chloro-1-hydroxy-naphthalene-2-carbonyl)-amino]-2-methyl-butyric acid ethyl ester, 0.76 g 4-hydroxymethyl-piperidine-1-carboxylic acid tert-butyl ester and 1.43 g triphenylphosphine in 30 mL of dry THF, 1.10 g of diisopropylazodicarboxylate were added. After 18 h at room temperature 1.43 g of triphenylphosphine and 1.10 g of diisopropylazodicarboxylate were added, and after 3 h again 1.43 g of triphenylphosphine and 1.10 g of diisopropylazodicarboxylate were added. After an additional 24 h the reaction was concentrated. After chromatography on silica (ethyl acetate/heptane) 1.17 g of 4-[4-chloro-2-(1-ethoxycarbonyl-1-methyl-propylcarbamoyl)-naphthalen-1-yloxymethyl]-piperidine-1-carboxylic acid tert-butyl ester was obtained.

$C_{29}H_{39}ClN_2O_6$ (546.24), LCMS (ESI): 547.23 (MH$^+$).

b) 2-{[4-Chloro-1-(piperidin-4-yl-methoxy)-naphthalene-2-carbonyl]-amino}-2-methyl-butyric acid ethyl ester To a solution of 0.16 g of 4-[4-chloro-2-(1-ethoxycarbonyl-1-methyl-propylcarbamoyl)-naphthalen-1-yloxymethyl]-piperidine-1-carboxylic acid tert-butyl ester in 8 mL dichloromethane was added 4 mL of TFA at room temperature. This mixture was stirred at room temperature for 1 hour and then concentrated to dryness in vacuo. The residue was treated with 7 M NH3 in MeOH to adjust to pH 9. It was then chromatographed on silica with 7 N NH3 in MeOH/dichloromethane to provide 72 mg 2-{[4-chloro-1-(piperidin-4-yl-methoxy)-naphthalene-2-carbonyl]-amino}-2-methyl-butyric acid ethyl ester.

$C_{24}H_{31}ClN_2O_4$ (446.19), LCMS (ESI): 447.2 (MH$^+$).

c) 2-{[1-(1-Acetyl-piperidin-4-ylmethoxy)-4-chloro-naphthalene-2-carbonyl]-amino}-2-methyl-butyric acid ethyl ester To a solution of 70 mg of 2-{[4-chloro-1-(piperidin-4-yl-methoxy)-naphthalene-2-carbonyl]-amino}-2-methyl-butyric acid ethyl ester in 4 mL dichloromethane was added 0.026 ml of acetyl chloride followed by addition of 0.13 mL Et3N. This mixture was stirred overnight. The mixture was concentrated and chromatographed on silica with 7 N NH3 in MeOH/dichloromethane to give 76 mg of 2-{[1-(1-acetyl-piperidin-4-ylmethoxy)-4-chloro-naphthalene-2-carbonyl]-amino}-2-methyl-butyric acid ethyl ester.

$C_{26}H_{33}ClN_2O_5$ (488.20), LCMS (ESI): 489.2 (MH$^+$).

d) 2-{[1-(1-Acetyl-piperidin-4-ylmethoxy)-4-chloro-naphthalene-2-carbonyl]-amino}-2-methyl-butyric acid A solution of 70 mg of 2-{[1-(1-acetyl-piperidin-4-yl-methoxy)-4-chloro-naphthalene-2-carbonyl]-amino}-2-methyl-butyric acid ethyl ester in 4 mL THF and 1 mL MeOH was treated with 4 mL of 2 M aqueous sodium hydroxide. The reaction mixture was stirred at room temperature overnight. The organic solvent was removed in vacuo. The residue was taken up in 6 mL of water and washed with ethyl acetate. The aqueous phase was treated with 2 M hydrochloric acid to pH 4, then extracted with ethyl acetate. The organic phase was washed with brine, dried over sodium sulphate and concentrated to give 30 mg of 2-{[1-(1-acetyl-piperidin-4-yl-methoxy)-4-chloro-naphthalene-2-carbonyl]-amino}-2-methyl-butyric acid.

$C_{24}H_{29}ClN_2O_5$ (460.17), LCMS (ESI): 461.27 (MH$^+$).

The following examples were prepared in analogy to 2-{[1-(1-Acetyl-piperidin-4-ylmethoxy)-4-chloro-naphthalene-2-carbonyl]-amino}-2-methyl-butyric acid (example 160):

| No | Chemical Name | Structure | ESI+ or ESI– |
|---|---|---|---|
| 161 | 2-{[4-Chloro-1-(1-propionyl-piperidin-4-yl-methoxy)-naphthalene-2-carbonyl]-amino}-2-methyl-butyric acid | 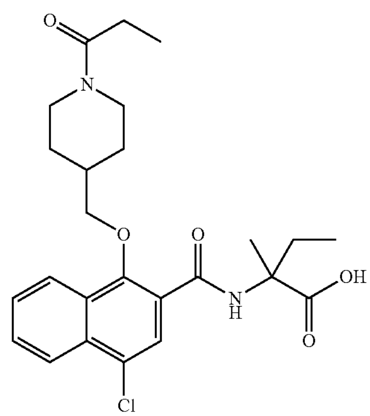 | 475.23 |
| 162 | 2-{[4-Chloro-1-(1-cyclopropanecarbonyl-piperidin-4-yl-methoxy)-naphthalene-2-carbonyl]-amino}-2-methyl-butyric acid | 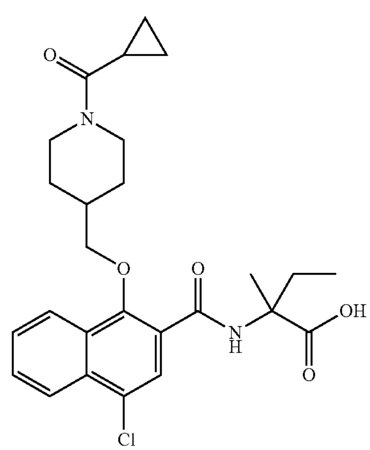 | 487.21 |

Example 163

4-[2-(1-Carboxy-1-methyl-propylcarbamoyl)-4-chloro-naphthalen-1-yloxymethyl]-piperidine-1-carboxylic acid tert-butyl ester

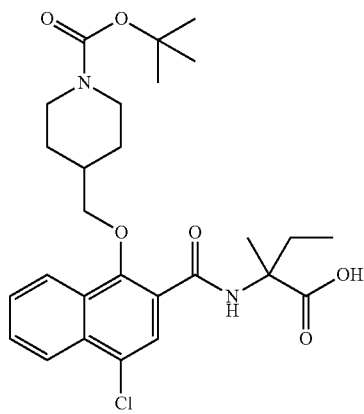

A solution of 41 mg of 4-[4-chloro-2-(1-ethoxycarbonyl-1-methyl-propylcarbamoyl)-naphthalen-1-yloxymethyl]-piperidine-1-carboxylic acid tert-butyl ester (see example 160, step a)) in 4 mL THF and 1 mL MeOH was treated with 4 mL of 2 M aqueous sodium hydroxide. The reaction mixture was stirred at room temperature overnight. The organic solvent was removed in vacuo. The residue was taken up in 6 ml of water and washed with ethyl acetate. It was treated with 2 M hydrochloric acid to adjust the pH to 5-6 and extracted with ethyl acetate. The organic phase was washed with brine, dried over sodium sulphate and concentrated to give 12 mg of 4-[2-(1-carboxy-1-methyl-propylcarbamoyl)-4-chloro-naphthalen-1-yloxymethyl]-piperidine-1-carboxylic acid tert-butyl ester.

$C_{27}H_{35}ClN_2O_6$ (518.21), LCMS (ESI): 519.34 (MH$^+$).

Example 164

2-{[4-Chloro-1-(piperidin-4-yl-methoxy)-naphthalene-2-carbonyl]-amino}-2-methyl-butyric acid

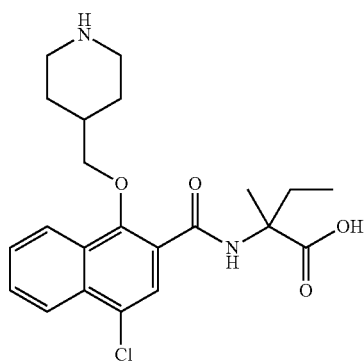

A solution of 70 mg of 2-{[4-chloro-1-(piperidin-4-yl-methoxy)-naphthalene-2-carbonyl]-amino}-2-methyl-butyric acid ethyl ester (see example 160, step b)) in 4 mL THF and 1 mL MeOH was treated with 4 mL of 2 M aqueous sodium hydroxide. The reaction mixture was stirred at room temperature overnight. The organic solvent was removed in vacuo. The residue was taken up in 6 ml of water and it was treated with 2 M hydrochloric acid to adjust the pH to 6~7, then extracted with ethyl acetate. The organic phase was washed with brine, dried over sodium sulphate and concentrated to give 32 mg of 2-{[4-chloro-1-(piperidin-4-yl-methoxy)-naphthalene-2-carbonyl]-amino}-2-methyl-butyric acid.

$C_{22}H_{27}ClN_2O_4$ (418.16), LCMS (ESI): 419.19 (MH$^+$).

Example 165

2-({4-Chloro-1-[1-(2,2,2-trifluoro-acetyl)-piperidin-4-yl-methoxy]-naphthalene-2-carbonyl}-amino)-2-methyl-butyric acid

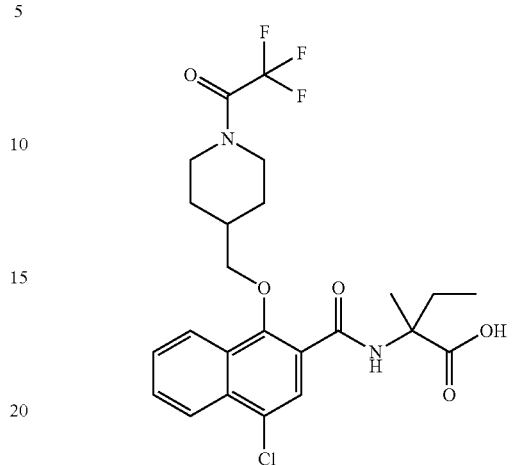

Trifluoroacetic anhydride (0.018 mL) was added to 2-{[4-chloro-1-(piperidin-4-yl-methoxy)-naphthalene-2-carbonyl]-amino}-2-methyl-butyric acid (see example 164, 0.050 g) at 0° C. with vigorous stirring. The mixture was stirred at 0° C. for 5 min. and a further portion of trifluoroacetic anhydride (0.003 mL) was then added. The mixture was stirred at 85° C. for 1.5 hour, then diluted with 1M HCl and extracted with diethyl ether. The organic phase was washed with brine, dried over sodium sulphate and concentrated in vacuo. The resulting residue was washed with 1 mL diethyl ether and dried in vacuo to give 26 mg of 2-({4-chloro-1-[1-(2,2,2-trifluoro-acetyl)-piperidin-4-yl-methoxy]-naphthalene-2-carbonyl}-amino)-2-methyl-butyric acid.

$C_{24}H_{26}ClF_3N_2O_5$ (514.14), LCMS (ESI): 515.13 (MH$^+$).

Example 166

2-{[4-Chloro-1-(1-isopropyl-piperidin-4-yl-methoxy)-naphthalene-2-carbonyl]-amino}-2-methyl-butyric acid

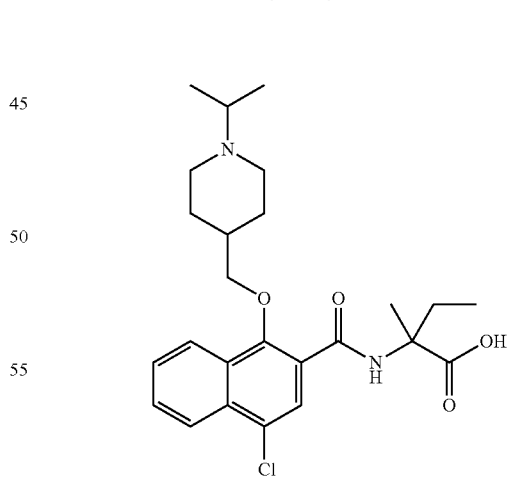

a) 2-{[4-Chloro-1-(1-isopropyl-piperidin-4-yl-methoxy)-naphthalene-2-carbonyl]-amino}-2-methyl-butyric acid ethyl ester To a solution containing 70 mg of 2-{[4-chloro-1-(piperidin-4-yl-methoxy)-naphthalene-2-carbonyl]-amino}-2-methyl-butyric acid ethyl ester (see example 160, step b)) and 9 mg of acetone in 6 mL dichloromethane was added 14 mg HOAc followed by addition of Na(OAc)3BH (46 mg). After 16 hours at room temperature, 9 mg of acetone, 14 mg of HOAc and 46 mg of Na(OAc)3BH were added. The reaction mixture was stirred at room temperature overnight. Aqueous sodium hydrogen carbonate solution was added and the mixture was extracted with dichloromethane. The organic phase was washed with brine, dried over sodium sulphate and concentrated in vacuo. The resulting residue was purified by flash chromatography (silica, 7N NH3 in MeOH/dichloromethane) to give 46 mg of 2-{[4-chloro-1-(1-isopropyl-piperidin-4-ylmethoxy)-naphthalene-2-carbonyl]-amino}-2-methyl-butyric acid ethyl ester.

$C_{27}H_{37}ClN_2O_4$ (488.24), LCMS (ESI): 489.26(MH$^+$).

b) 2-{[4-Chloro-1-(1-isopropyl-piperidin-4-yl-methoxy)-naphthalene-2-carbonyl]-amino}-2-methyl-butyric acid A solution of 36 mg of 2-{[4-chloro-1-(1-isopropyl-piperidin-4-ylmethoxy)-naphthalene-2-carbonyl]-amino}-2-methyl-butyric acid ethyl ester in 3 mL THF and 1 ml MeOH was treated with 3 mL of 2 M aqueous sodium hydroxide. The reaction mixture was stirred at room temperature for 40 hours. The organic solvent was removed in vacuo. The residue was taken up in 6 ml of water, treated with 2 M hydrochloric acid to adjust the pH to 6~7, then extracted with ethyl acetate. The organic phase was washed with brine, dried over sodium sulphate and concentrated to give 32 mg of 2-{[4-Chloro-1-(1-isopropyl-piperidin-4-ylmethoxy)-naphthalene-2-carbonyl]-amino}-2-methyl-butyric acid.

$C_{25}H_{33}ClN_2O_4$ (460.21), LCMS (ESI): 461.21 (MH$^+$).

Example 167

2-{[4-Chloro-1-(1-cyclopentyl-piperidin-4-yl-methoxy)-naphthalene-2-carbonyl]-amino}-2-methyl-butyric acid

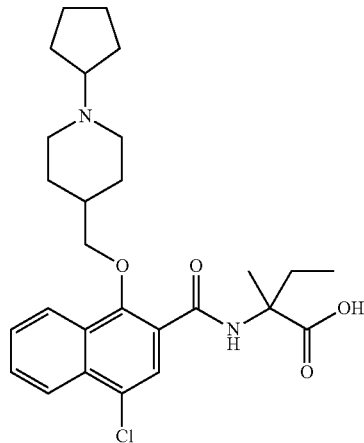

2-{[4-Chloro-1-(1-cyclopentyl-piperidin-4-ylmethoxy)-naphthalene-2-carbonyl]-amino}-2-methyl-butyric acid was prepared by a similar procedure as 2-{[4-Chloro-1-(1-isopropyl-piperidin-4-ylmethoxy)-naphthalene-2-carbonyl]-amino}-2-methyl-butyric acid (example 166).

$C_{27}H_{35}ClN_2O_4$ (486.22), LCMS (ESI): 487.22 (MH$^+$).

Example 168

1-{[1-(6-Trifluoromethyl-pyridin-3-ylmethoxy)-naphthalene-2-carbonyl]-amino}-cyclobutanecarboxylic acid

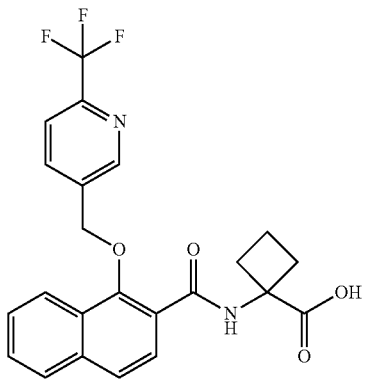

a) 1-{[1-(6-Trifluoromethyl-pyridin-3-ylmethoxy)-naphthalene-2-carbonyl]-amino}-cyclobutanecarboxylic acid ethyl ester 0.3 mmol 1-[(1-hydroxy-naphthalene-2-carbonyl)-amino]-cyclobutanecarboxylic acid ethyl ester (94 mg), 0.6 mmol cesium carbonate (196 mg) (0.75 mmol in case of non-benzylic halides, +1 eq. in case of hydrochlorides) and 0.03 mmol sodium iodide (4 mg) are stirred for 10 min in 3 ml dry DMF. 0.33 mmol 5-Chloromethyl-2-trifluoromethyl-pyridine (65 mg) (0.45 mmol in case of non-benzylic halides) is added and the mixture is stirred for 2 h at RT and then for 5 h at 80° C. The cooled mixture is filtered, the filter washed with 5 ml ethyl acetate, the filtrate diluted with 20 ml ethyl acetate and washed twice with 20 ml 5% brine. The organic phase is dried and evaporated to yield 140 mg of 1-{[1-(6-Tri-fluoromethyl-pyridin-3-ylmethoxy)-naphthalene-2-carbonyl]-amino}-cyclobutane-carboxylic acid ethyl ester.

$C_{25}H_{23}F_3N_2O_4$ (472.47), LCMS (ESI): 473.26 (MH$^+$).

b) 1-{[1-(6-Trifluoromethyl-pyridin-3-ylmethoxy)-naphthalene-2-carbonyl]-amino}-cyclobutanecarboxylic acid The crude product from the first step is dissolved in 2 ml methanol and 1 ml THF and 0.75 ml 2N NaOH (aq) is added. The mixture is stirred for 1 h at 45° C. and then over night by RT. (For 2-amino-2-ethyl-hexanoic acid ethyl ester derivatives 8 h at 65° C. were necessary to give complete conversion.) The solution was neutralized with 0.75 ml 2N HCl, evaporated, the residue was dissolved in 2 ml DMF and purified by prep. RP-HPLC, after which 11 mg 1-{[1-(6-trifluoromethyl-pyridin-3-ylmethoxy)-naphthalene-2-carbonyl]-amino}-cyclobutanecarboxylic acid were obtained.

$C_{23}H_{19}F_3N_2O_4$ (444.41), LCMS (ESI): 445.13 (MH$^+$).

The following examples were prepared in analogy to example 168:

| No | Chemical Name | Structure | ESI+ or ESI– |
|---|---|---|---|
| 169 | 1-{[1-(6-Chloro-pyridin-3-ylmethoxy)-naphthalene-2-carbonyl]-amino}-cyclobutanecarboxylic acid | 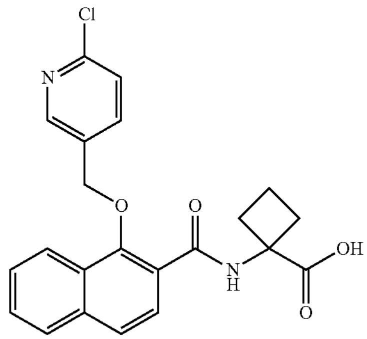 | 411.12 |
| 170 | 1-{[1-(Quinolin-2-ylmethoxy)-naphthalene-2-carbonyl]-amino}-cyclobutanecarboxylic acid | 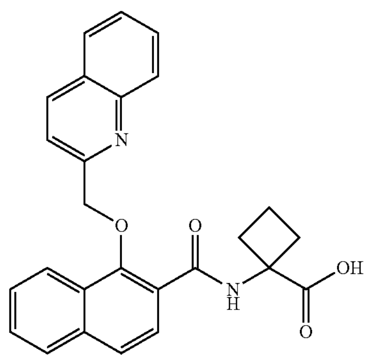 | 427.15 |
| 171 | 1-{[1-(2-Thiophen-2-yl-thiazol-4-ylmethoxy)-naphthalene-2-carbonyl]-amino}-cyclobutanecarboxylic acid | 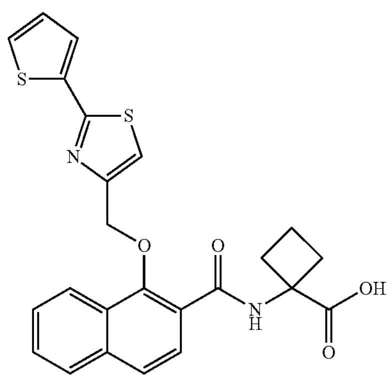 | 465.17 |
| 172 | 1-{[1-(4-Trifluoromethyl-benzyloxy)-naphthalene-2-carbonyl]-amino}-cyclobutanecarboxylic acid | 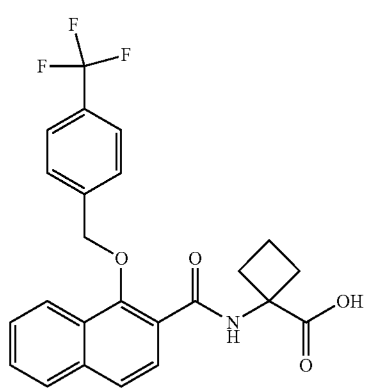 | 444.17 |

-continued

| No | Chemical Name | Structure | ESI+ or ESI− |
|---|---|---|---|
| 173 | 1-{[1-(2-Fluoro-4-trifluoromethyl-benzyloxy)-naphthalene-2-carbonyl]-amino}-cyclobutanecarboxylic acid | 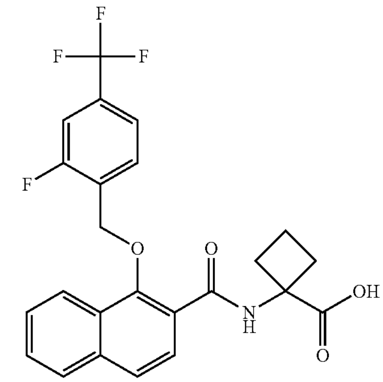 | 462.18 |
| 174 | 1-{[1-(2,4-Bis-trifluoromethyl-benzyloxy)-naphthalene-2-carbonyl]-amino}-cyclobutanecarboxylic acid | 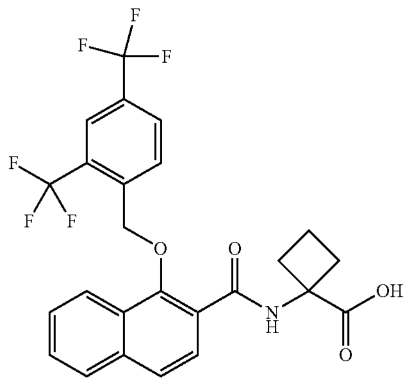 | 512.20 |
| 175 | 1-{[1-(4-Trifluoromethoxy-benzyloxy)-naphthalene-2-carbonyl]-amino}-cyclobutanecarboxylic acid | 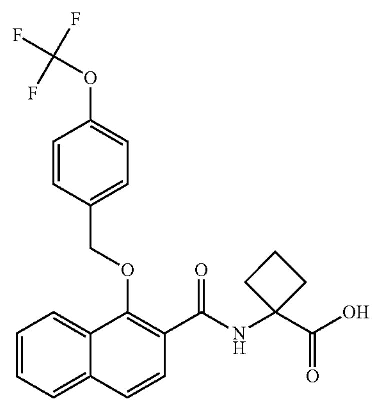 | 460.16 |
| 176 | 1-[(1-Benzyloxy-naphthalene-2-carbonyl)-amino]-cyclobutanecarboxylic acid | 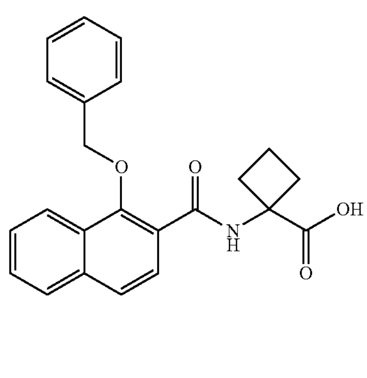 | 376.17 |

-continued

| No | Chemical Name | Structure | ESI+ or ESI− |
|---|---|---|---|
| 177 | 1-{[1-(4-Trifluoromethylsulfanyl-benzyloxy)-naphthalene-2-carbonyl]-amino}-cyclobutanecarboxylic acid | 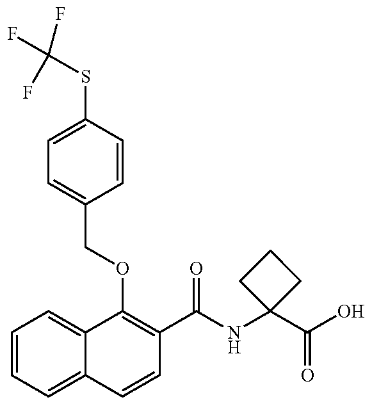 | 476.18 |
| 178 | 1-{[1-(4-Chloro-benzyloxy)-naphthalene-2-carbonyl]-amino}-cyclobutanecarboxylic acid | 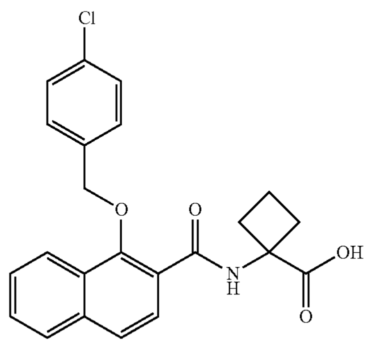 | 410.17 |
| 179 | 1-{[1-(4-Chloro-2-fluoro-benzyloxy)-naphthalene-2-carbonyl]-amino}-cyclobutanecarboxylic acid | 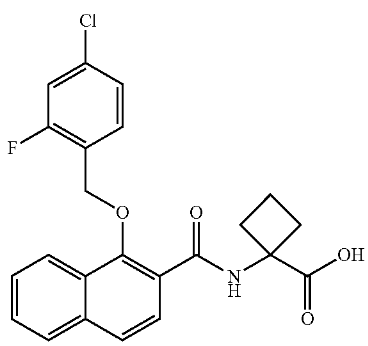 | 428.12 |
| 180 | 1-{[1-(4-Isopropyl-benzyloxy)-naphthalene-2-carbonyl]-amino}-cyclobutanecarboxylic acid | 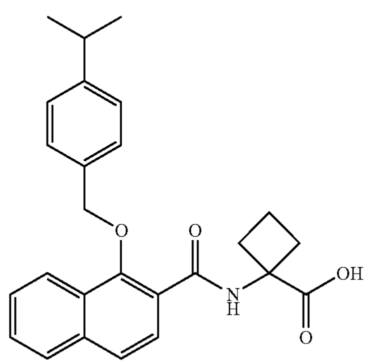 | 418.24 |

-continued

| No | Chemical Name | Structure | ESI+ or ESI− |
|---|---|---|---|
| 181 | 1-{[1-(4-Pyrazol-1-yl-benzyloxy)-naphthalene-2-carbonyl]-amino}-cyclobutanecarboxylic acid | 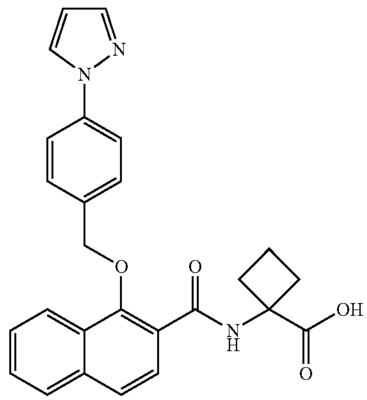 | 442.20 |
| 182 | 1-{[1-(2-Phenyl-thiazol-4-ylmethoxy)-naphthalene-2-carbonyl]-amino}-cyclobutanecarboxylic acid | 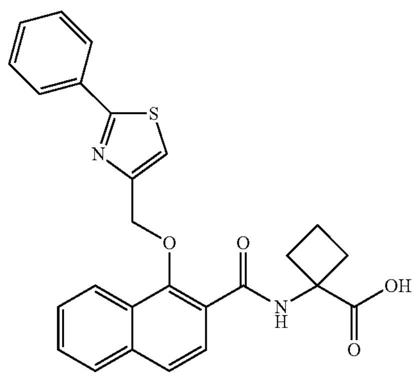 | 459.13 |
| 183 | 1-{[1-(2,4-Difluoro-benzyloxy)-naphthalene-2-carbonyl]-amino}-cyclobutanecarboxylic acid | 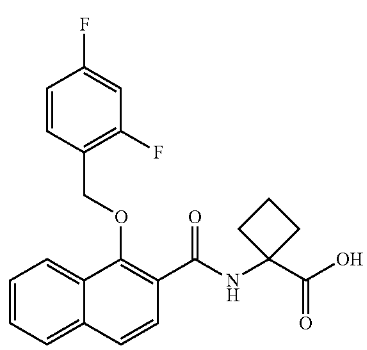 | 412.13 |
| 184 | 1-{[1-(4-Fluoro-benzyloxy)-naphthalene-2-carbonyl]-amino}-cyclobutanecarboxylic acid | 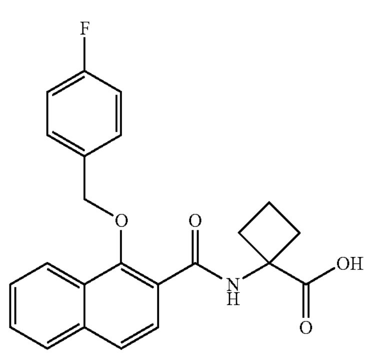 | 394.18 |

| No | Chemical Name | Structure | ESI+ or ESI− |
|---|---|---|---|
| 185 | 1-[(1-Cyclohexylmethoxy-naphthalene-2-carbonyl)-amino]-cyclobutanecarboxylic acid | 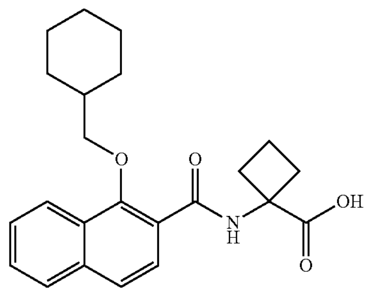 | 382.26 |
| 186 | 1-{[4-Chloro-1-(6-chloro-pyridin-3-ylmethoxy)-naphthalene-2-carbonyl]-amino}-cyclobutanecarboxylic acid | 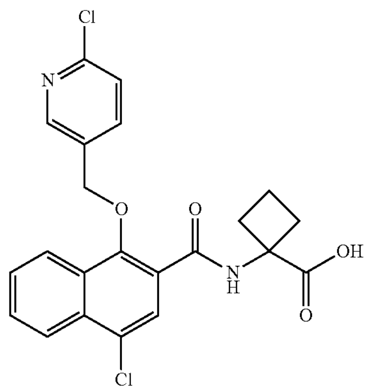 | 445.06 |
| 187 | 1-{[4-Chloro-1-(quinolin-2-ylmethoxy)-naphthalene-2-carbonyl]-amino}-cyclobutanecarboxylic acid | 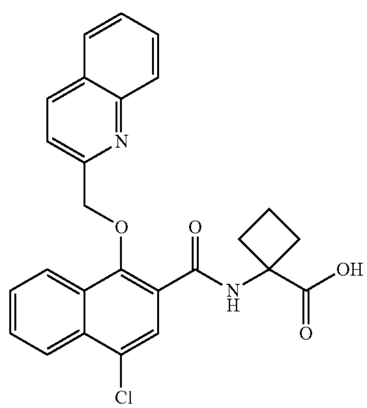 | 461.10 |
| 188 | 1-{[4-Chloro-1-(2-thiophen-2-yl-thiazol-4-ylmethoxy)-naphthalene-2-carbonyl]-amino}-cyclobutanecarboxylic acid | 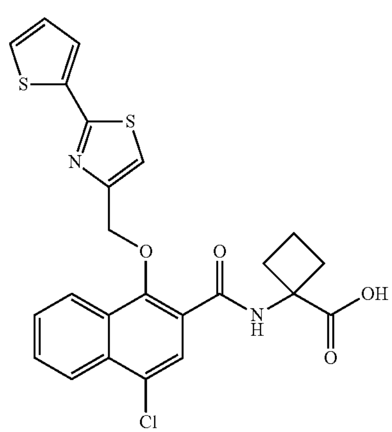 | 499.11 |

-continued

| No | Chemical Name | Structure | ESI+ or ESI− |
|---|---|---|---|
| 189 | 1-{[4-Chloro-1-(4-trifluoromethyl-benzyloxy)-naphthalene-2-carbonyl]-amino}-cyclobutanecarboxylic acid | 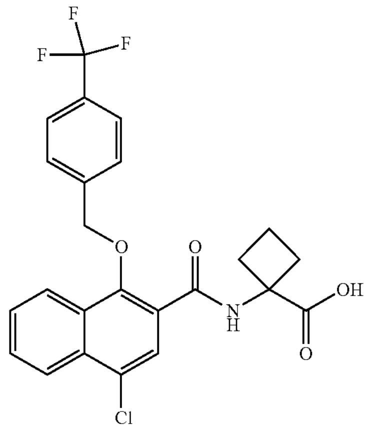 | 476.49 |
| 190 | 1-{[4-Chloro-1-(2-fluoro-4-trifluoromethyl-benzyloxy)-naphthalene-2-carbonyl]-amino}-cyclobutanecarboxylic acid | 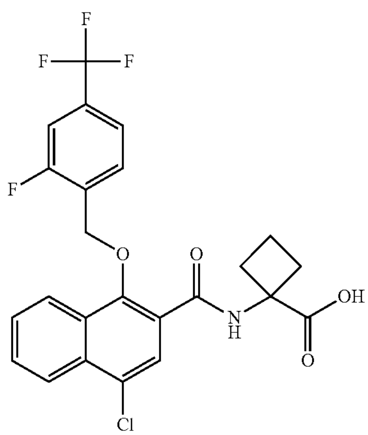 | 496.13 |
| 191 | 1-{[1-(2,4-Bis-trifluoromethyl-benzyloxy)-4-chloro-naphthalene-2-carbonyl]-amino}-cyclobutanecarboxylic acid | 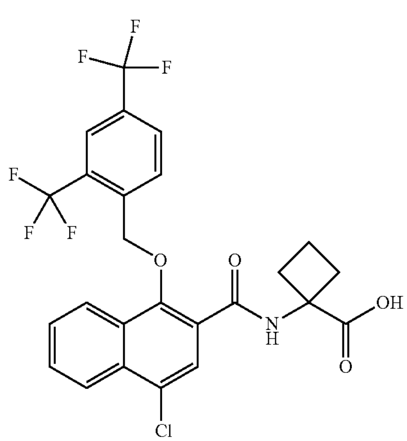 | 546.13 |

| No | Chemical Name | Structure | ESI+ or ESI− |
|---|---|---|---|
| 192 | 1-{[4-Chloro-1-(4-trifluoromethoxy-benzyloxy)-naphthalene-2-carbonyl]-amino}-cyclobutanecarboxylic acid | 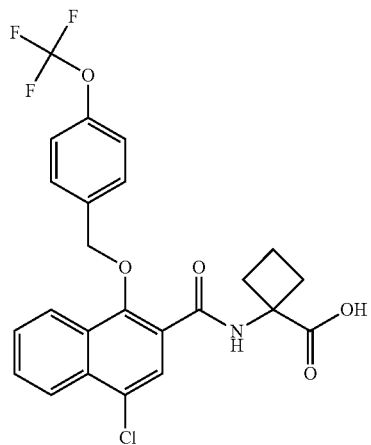 | 494.16 |
| 193 | 1-[(1-Benzyloxy-4-chloro-naphthalene-2-carbonyl)-amino]-cyclobutanecarboxylic acid | 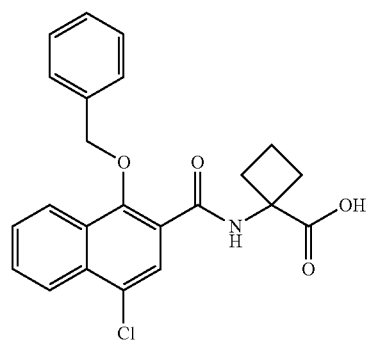 | 410.14 |
| 194 | 1-{[4-Chloro-1-(4-difluoromethoxy-benzyloxy)-naphthalene-2-carbonyl]-amino}-cyclobutanecarboxylic acid | 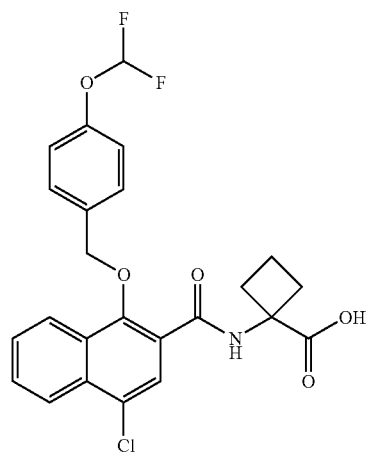 | 476.16 |

| No | Chemical Name | Structure | ESI+ or ESI− |
|---|---|---|---|
| 195 | 1-{[4-Chloro-1-(4-trifluoromethylsulfanyl-benzyloxy)-naphthalene-2-carbonyl]-amino}-cyclobutanecarboxylic acid | 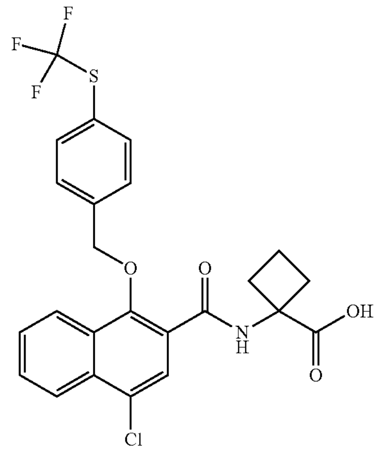 | 510.11 |
| 196 | 1-{[1-(4-Bromo-2-fluoro-benzyloxy)-4-chloro-naphthalene-2-carbonyl]-amino}-cyclobutanecarboxylic acid | 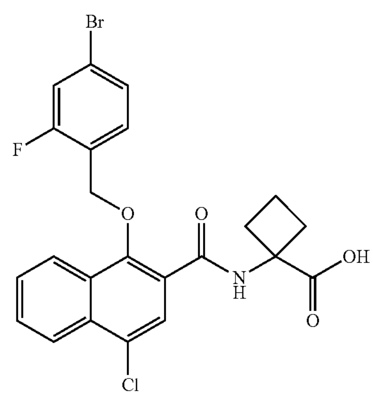 | 506.08 |
| 197 | 1-{[4-Chloro-1-(4-chloro-2-fluoro-benzyloxy)-naphthalene-2-carbonyl]-amino}-cyclobutanecarboxylic acid | 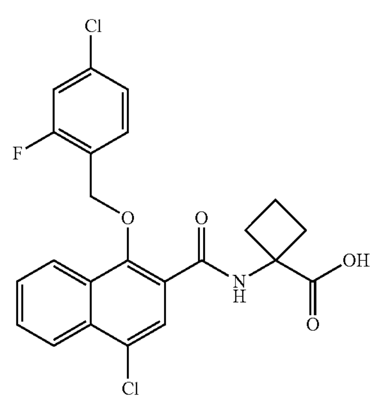 | 462.12 |

-continued

| No | Chemical Name | Structure | ESI+ or ESI− |
|----|---------------|-----------|--------------|
| 198 | 1-{[4-Chloro-1-(4-isopropyl-benzyloxy)-naphthalene-2-carbonyl]-amino}-cyclobutanecarboxylic acid | 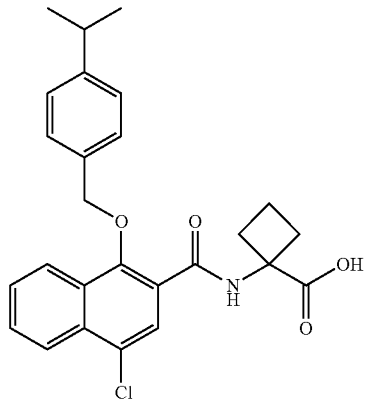 | 452.20 |
| 199 | 1-{[4-Chloro-1-(4-pyrazol-1-yl-benzyloxy)-naphthalene-2-carbonyl]-amino}-cyclobutanecarboxylic acid | 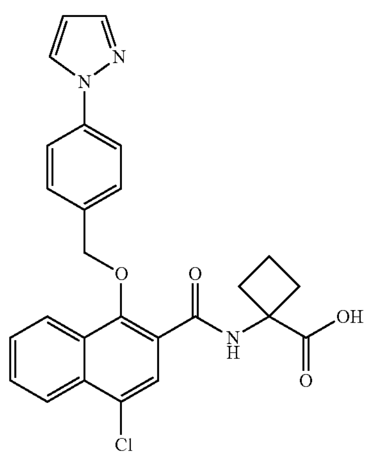 | 476.10 |
| 200 | 1-{[4-Chloro-1-(2-phenyl-thiazol-4-ylmethoxy)-naphthalene-2-carbonyl]-amino}-cyclobutanecarboxylic acid | 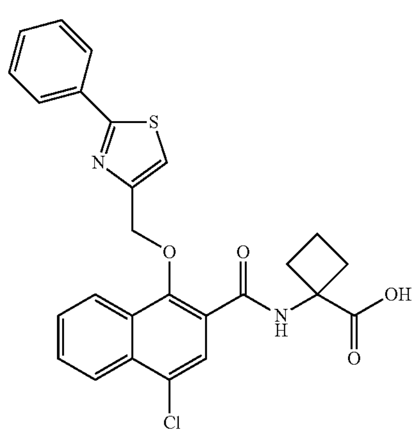 | 493.15 |

-continued

| No | Chemical Name | Structure | ESI+ or ESI− |
|---|---|---|---|
| 201 | 1-{[4-Chloro-1-(2,4-difluoro-benzyloxy)-naphthalene-2-carbonyl]-amino}-cyclobutanecarboxylic acid | 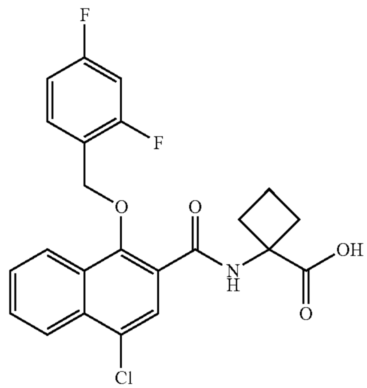 | 446.15 |
| 202 | 1-{[4-Chloro-1-(4-fluoro-benzyloxy)-naphthalene-2-carbonyl]-amino}-cyclobutanecarboxylic acid | 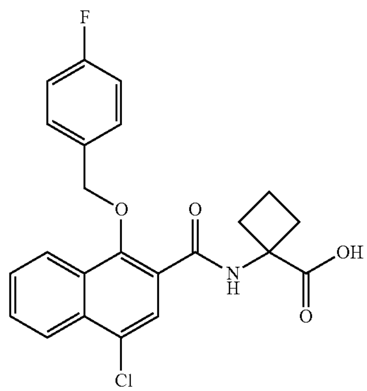 | 428.15 |
| 203 | 2-{[1-(2-Fluoro-4-trifluoromethyl-benzyloxy)-naphthalene-2-carbonyl]-amino}-butyric acid | 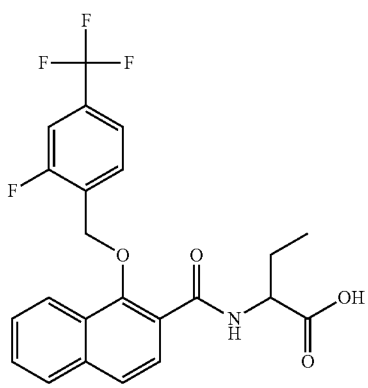 | 450.12 |
| 204 | 2-{[1-(4-Trifluoromethylsulfanyl-benzyloxy)-naphthalene-2-carbonyl]-amino}-butyric acid | 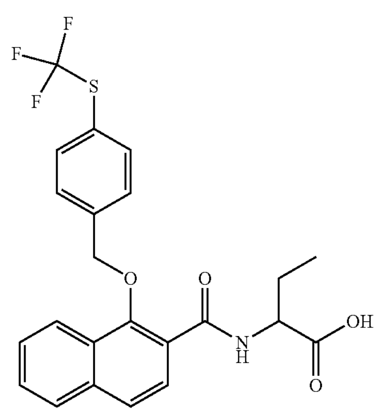 | 464.12 |

-continued

| No | Chemical Name | Structure | ESI+ or ESI− |
|---|---|---|---|
| 205 | 2-{[1-(Benzothiazol-2-ylmethoxy)-naphthalene-2-carbonyl]-amino}-2-ethyl-hexanoic acid | 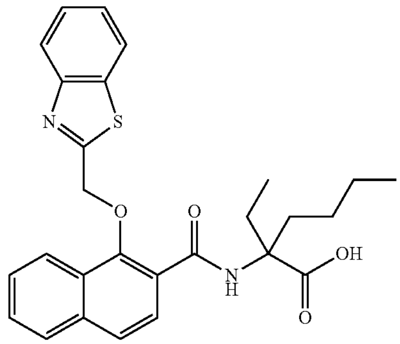 | 477.16 |
| 206 | 2-Ethyl-2-{[1-(6-trifluoromethyl-pyridin-3-ylmethoxy)-naphthalene-2-carbonyl]-amino}-hexanoic acid | 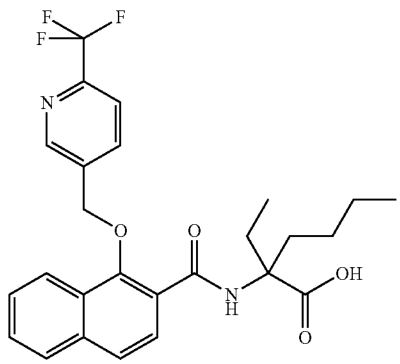 | 489.24 |
| 207 | 2-{[1-(6-Chloro-pyridin-3-ylmethoxy)-naphthalene-2-carbonyl]-amino}-2-ethyl-hexanoic acid | 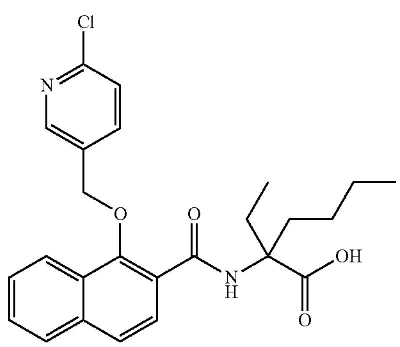 | 455.19 |
| 208 | 2-Ethyl-2-{[1-(quinolin-2-ylmethoxy)-naphthalene-2-carbonyl]-amino}-hexanoic acid | 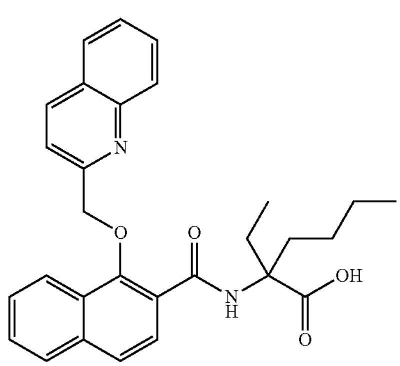 | 471.18 |

-continued

| No | Chemical Name | Structure | ESI+ or ESI− |
|----|---------------|-----------|--------------|
| 209 | 2-Ethyl-2-{[1-(2-thiophen-2-yl-thiazol-4-ylmethoxy)-naphthalene-2-carbonyl]-amino}-hexanoic acid | 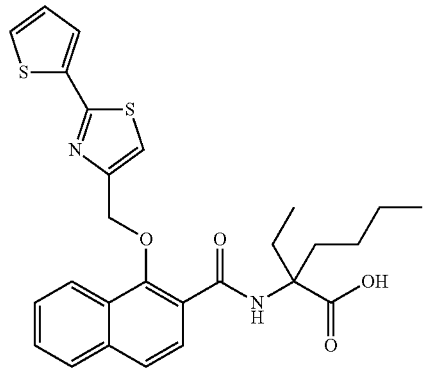 | 509.27 |
| 210 | 2-Ethyl-2-{[1-(4-trifluoromethyl-benzyloxy)-naphthalene-2-carbonyl]-amino}-hexanoic acid | 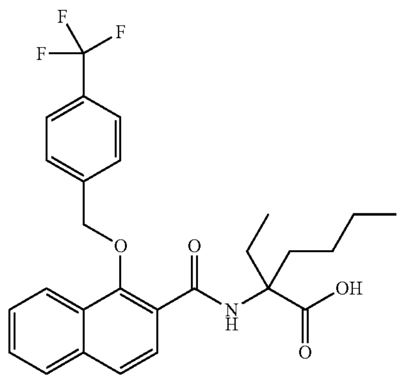 | 488.20 |
| 211 | 2-Ethyl-2-{[1-(2-fluoro-4-trifluoromethyl-benzyloxy)-naphthalene-2-carbonyl]-amino}-hexanoic acid | 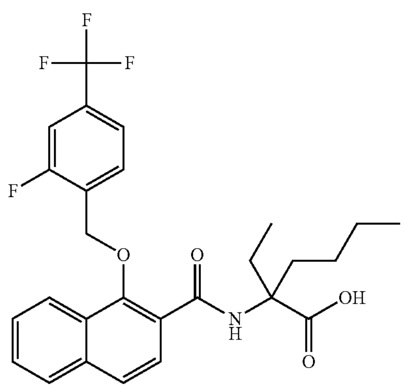 | 506.21 |
| 212 | 2-{[1-(2,4-Bis-trifluoromethyl-benzyloxy)-naphthalene-2-carbonyl]-amino}-2-ethyl-hexanoic acid | 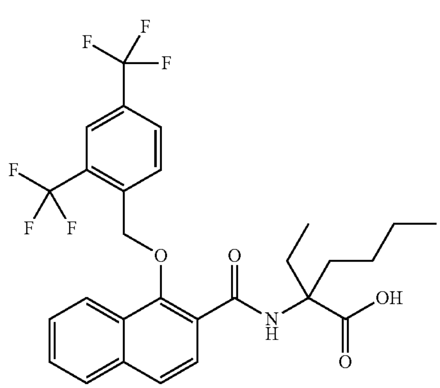 | 556.16 |

-continued

| No | Chemical Name | Structure | ESI+ or ESI− |
|---|---|---|---|
| 213 | 2-Ethyl-2-{[1-(4-trifluoromethoxy-benzyloxy)-naphthalene-2-carbonyl]-amino}-hexanoic acid | 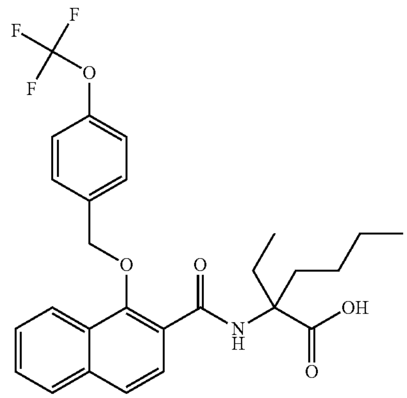 | 504.21 |
| 214 | 2-[(1-Benzyloxy-naphthalene-2-carbonyl)-amino]-2-ethyl-hexanoic acid | 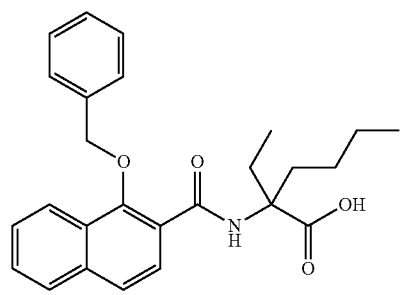 | 420.24 |
| 215 | 2-{[1-(4-Difluoromethoxy-benzyloxy)-naphthalene-2-carbonyl]-amino}-2-ethyl-hexanoic acid | 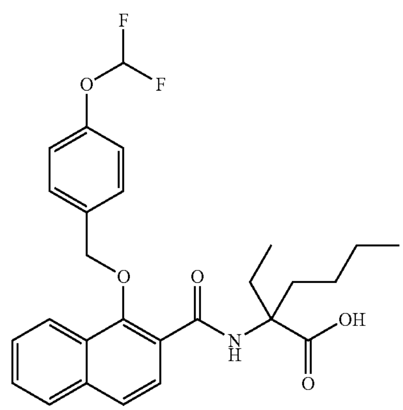 | 486.26 |
| 216 | 2-Ethyl-2-{[1-(4-trifluoromethylsulfanyl-benzyloxy)-naphthalene-2-carbonyl]-amino}-hexanoic acid | 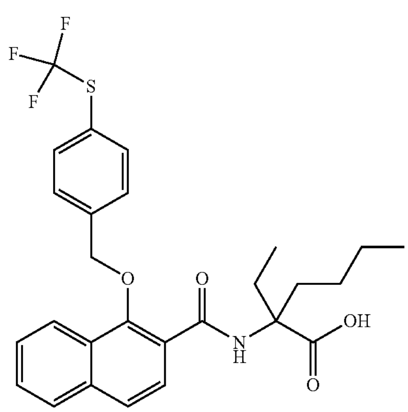 | 520.19 |

-continued
| No | Chemical Name | Structure | ESI+ or ESI− |
|---|---|---|---|
| 217 | 2-{[1-(4-Bromo-benzyloxy)-naphthalene-2-carbonyl]-amino}-2-ethyl-hexanoic acid | 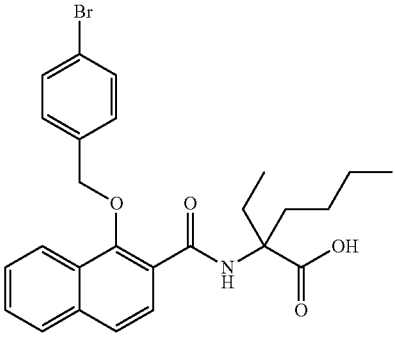 | 498.16 |
| 218 | 2-{[1-(4-Bromo-2-fluoro-benzyloxy)-naphthalene-2-carbonyl]-amino}-2-ethyl-hexanoic acid | 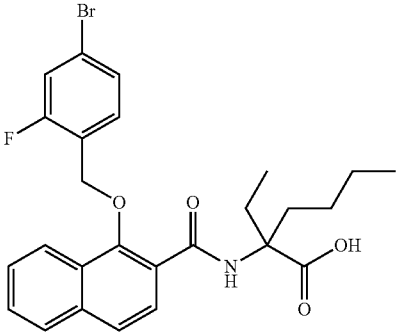 | 516.15 |
| 219 | 2-{[1-(4-Chloro-benzyloxy)-naphthalene-2-carbonyl]-amino}-2-ethyl-hexanoic acid | 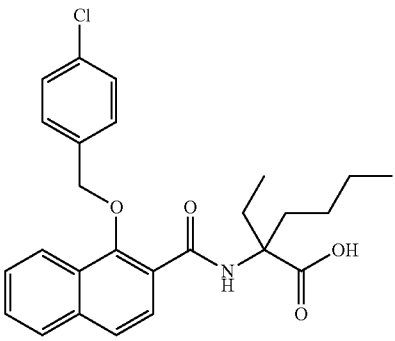 | 454.21 |
| 220 | 2-{[1-(4-Chloro-2-fluoro-benzyloxy)-naphthalene-2-carbonyl]-amino}-2-ethyl-hexanoic acid | 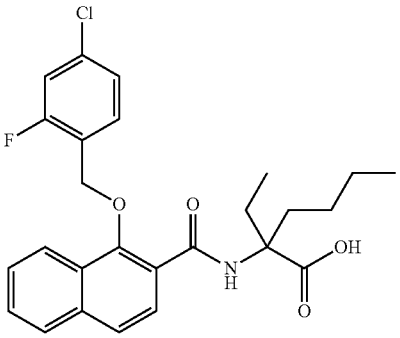 | 472.19 |

-continued

| No | Chemical Name | Structure | ESI+ or ESI− |
|---|---|---|---|
| 221 | 2-Ethyl-2-{[1-(4-isopropyl-benzyloxy)-naphthalene-2-carbonyl]-amino}-hexanoic acid | 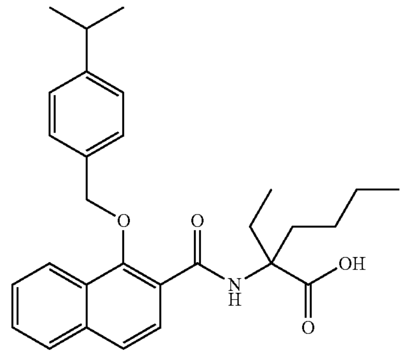 | 462.28 |
| 222 | 2-Ethyl-2-{[1-(4-pyrazol-1-yl-benzyloxy)-naphthalene-2-carbonyl]-amino}-hexanoic acid | 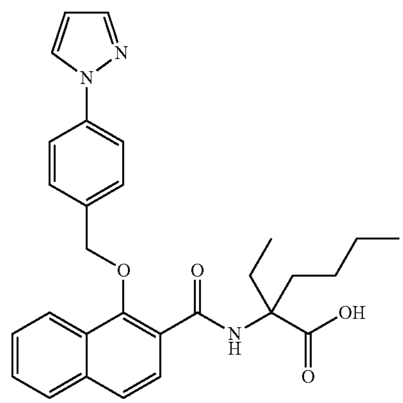 | 486.24 |
| 223 | 2-Ethyl-2-{[1-(2-phenyl-thiazol-4-ylmethoxy)-naphthalene-2-carbonyl]-amino}-hexanoic acid | 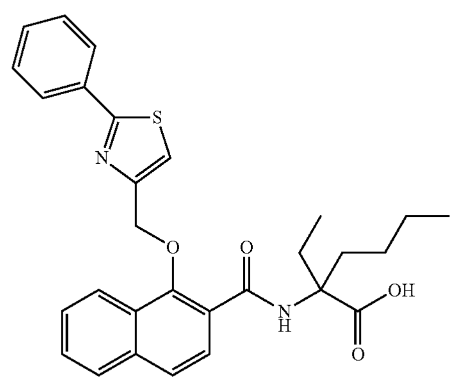 | 503.24 |
| 224 | 2-{[1-(2,4-Difluoro-benzyloxy)-naphthalene-2-carbonyl]-amino}-2-ethyl-hexanoic acid | 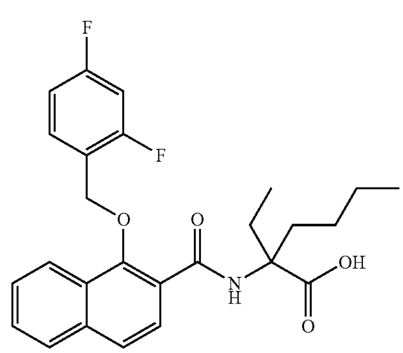 | 456.25 |

Example 225

2-{[1-(1H-Benzoimidazol-2-ylmethoxy)-naphthalene-2-carbonyl]-amino}-2-methyl-propionic acid

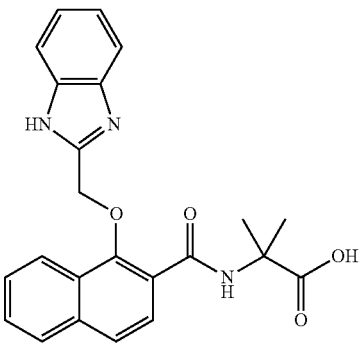

a) Wang-resin-bound 2-[(1-Hydroxy-naphthalene-2-carbonyl)-amino]-2-methyl-propionic acid 8.0 g of Wang resin (loading: 1.4 mmol/g) was placed in a solid phase fritted reaction vessel with 75 ml of dimethylformamide. After 5 minutes of swelling, 7.01 ml, of N,N'-diisopropyl carbodiimide, 0.136 g of 4-dimethylaminopyridine and 14.58 g of 2-(9H-Fluoren-9-ylmethoxy-carbonylamino)-2-methyl-propionic acid were added. The reaction was placed in an orbital shaker for 2 days, after which it was filtered, washed 4 times each with dimethylformamide, methanol and dichloromethane. Next, the resin was swollen in 50 ml of dichloromethane, 5.26 ml of acetic anhydride and 19.5 ml of N,N-diisopropylethylamine were added (to cap any unreacted hydroxyl group). It was filtered, washed 4 times each with dimethylformamide, methanol and dichloromethane and dried in vacuo. The loading was checked using a Perkin Elmer UV instrument (Fmoc-Echo test) to give 0.71 mmol/g (theoretical: 0.98 mmol/g). To 11 g (0.71 mmol/g) of the Wang-resin carrying Fmoc-2-Amino-2-methyl-propionic acid was added 140 ml of 20% piperidine in dimethylformamide. It was left in the orbital shaker for 1 hour, after which it was washed four times each with dimethylformamide, methanol and dichloromethane and dried in vacuo. To this Fmoc-deproteced resin was added 150 ml of dimethylformamide, 6.34 ml (40.5 mmol) of N,N'-diisopropyl carbodiimide, 7.62 g of 1-hydroxy-2-naphthoic acid and 5.47 g of 1-hydroxy-benzotriazole. The solid phase reaction was left 2 days in an orbital shaker. Since the reaction was not complete by resin colorimetric tests (Bromophenol blue test for presence of primary amines), once filtered, the same amounts of reagents were re-added to the resin and placed in a flex rotating oven for 4 hours at 55° C. and then left overnight at room temperature. Then it was filtered, washed four times each with dimethylformamide, methanol and dichloromethane and dried in vacuo. (Bromophenol blue test was negative). 10 g of the Wang-resin-bound 2-[(1-hydroxy-naphthalene-2-carbonyl)-amino]-2-methyl-propionic acid were obtained.

b) 2-{[1-(1H-Benzoimidazol-2-ylmethoxy) naphthalene-2-carbonyl]-amino}-2-methyl-propionic acid 0.45 g of the Wang-resin-bound 2-[(1-hydroxy-naphthalene-2-carbonyl)-amino]-2-methyl-propionic acid (loading 0.35 mmol/g) was placed in a reaction vessel with 3 ml of dimethylformamide. To this was added 0.058 g of 2-chloromethyl-1H-benzoimidazole, 0.228 g of cesium carbonate and 0.023 g of potassium iodide. The reaction was then placed in a vortex shaker overnight. The resin was filtered, washed four times each with dimethylformamide, methanol and dichloromethane. To this was added a solution of 30% trifluoroacetic acid, 65% dichloromethane and 5% triethylsilane and left in vortex shaker for 1.5 hours. The resin was filtered and the filtrate concentrated in vacuo. Purification by flash chromatography on silica with dichloromethane/methanol afforded 25 mg of 2-{[1-(1H-Benzoimidazol-2-ylmethoxy) naphthalene-2-carbonyl]-amino}-2-methyl-propionic acid.

$C_{23}H_{21}N_3O_4$ (403.44), LCMS (ESI): 404.10 (MH$^+$).

The following examples were prepared in analogy to example 225 using Wang-resin-bound 2-[(1-Hydroxy-naphthalene-2-carbonyl)-amino]-2-methyl-propionic acid or Wang-resin-bound 2-[(4-Fluoro-1-hydroxy-naphthalene-2-carbonyl)-amino]-2-methyl-propionic acid or Wang-resin bound 4,4,4-Trifluoro-2-[(4-fluoro-1-hydroxy-naphthalene-2-carbonyl)-amino]-butyric acid, which were prepared in analogy to Wang-resin-bound 2-[(1-Hydroxy-naphthalene-2-carbonyl)-amino]-2-methyl-propionic acid:

| No | Chemical Name | Structure | ESI+ or ESI− |
|---|---|---|---|
| 226 | 2-{[1-(6-Chloro-benzooxazol-2-ylmethoxy)-naphthalene-2-carbonyl]-amino}-2-methyl-propionic acid | 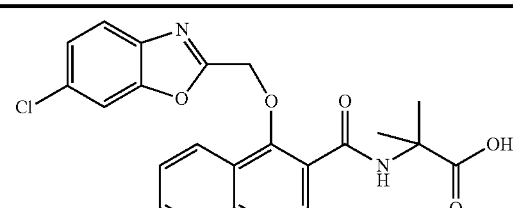 | 439.10 |
| 227 | 2-{[1-(5-tert-Butyl-benzooxazol-2-ylmethoxy)-naphthalene-2-carbonyl]-amino}-2-methyl-propionic acid | 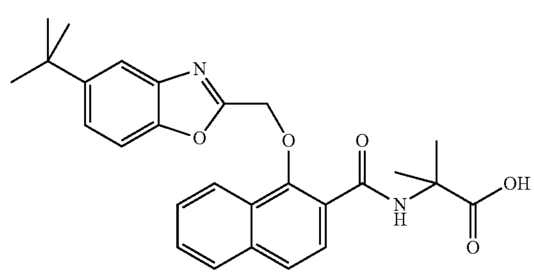 | 461.20 |

| No | Chemical Name | Structure | ESI+ or ESI– |
|---|---|---|---|
| 228 | 2-{[1-(5-Chloro-benzooxazol-2-ylmethoxy)-naphthalene-2-carbonyl]-amino}-2-methyl-propionic acid | 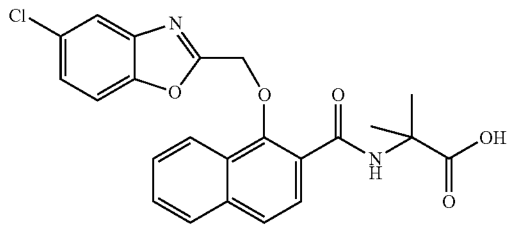 | 439.10 |
| 229 | 2-{[1-(5-Chloro-benzothiazol-2-ylmethoxy)-naphthalene-2-carbonyl]-amino}-2-methyl-propionic acid | 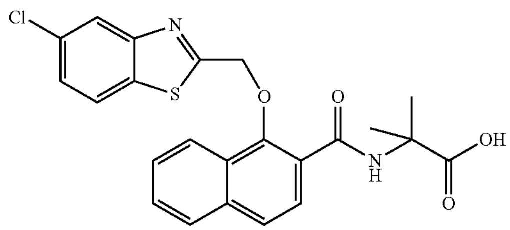 | 455.10 |
| 230 | 2-Methyl-2-{[1-(1-methyl-1H-benzoimidazol-2-ylmethoxy)-naphthalene-2-carbonyl]-amino}-propionic acid | 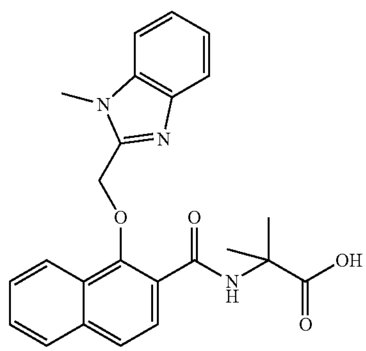 | 418.20 |
| 231 | 2-{[1-(5,6-Dichloro-1H-benzoimidazol-2-ylmethoxy)-naphthalene-2-carbonyl]-amino}-2-methyl-propionic acid | 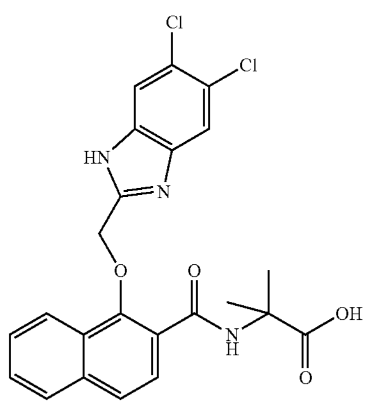 | 472.10 |
| 232 | 2-{[1-(5-Chloro-1H-benzoimidazol-2-ylmethoxy)-naphthalene-2-carbonyl]-amino}-2-methyl-propionic acid | 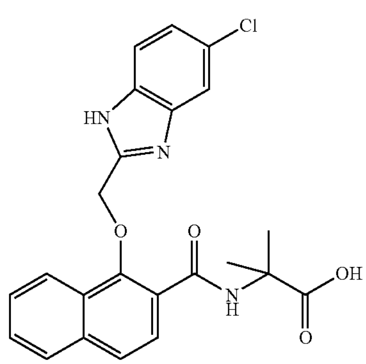 | 438.20 |

| No | Chemical Name | Structure | ESI+ or ESI− |
|---|---|---|---|
| 233 | 2-Methyl-2-{[1-(5-phenyl-[1,3,4]oxadiazol-2-ylmethoxy)-naphthalene-2-carbonyl]-amino}-propionic acid | 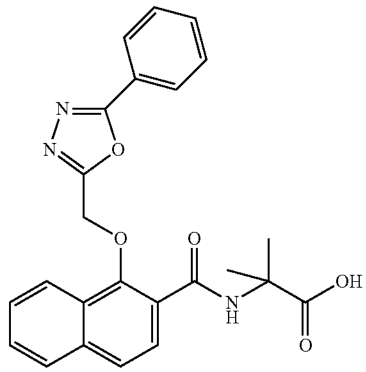 | 432.15 |
| 234 | 2-{[1-(5-Chloro-benzothiazol-2-ylmethoxy)-4-fluoro-naphthalene-2-carbonyl]-amino}-2-methyl-propionic acid | 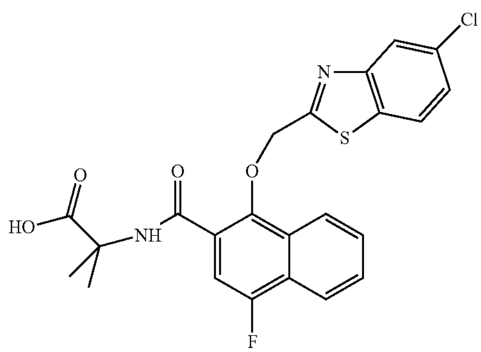 | 473.09 |
| 235 | 2-{[4-Fluoro-1-(5-fluoro-benzothiazol-2-ylmethoxy)-naphthalene-2-carbonyl]-amino}-2-methyl-propionic acid | 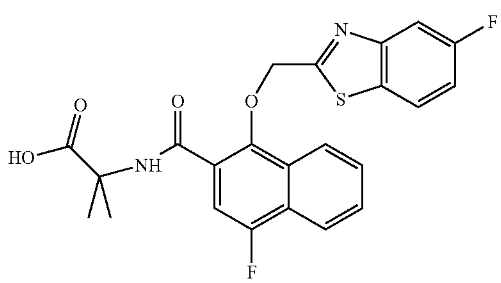 | 457.13 |
| 236 | 2-{[4-Fluoro-1-(2-phenyl-thiazol-4-ylmethoxy)-naphthalene-2-carbonyl]-amino}-2-methyl-propionic acid | 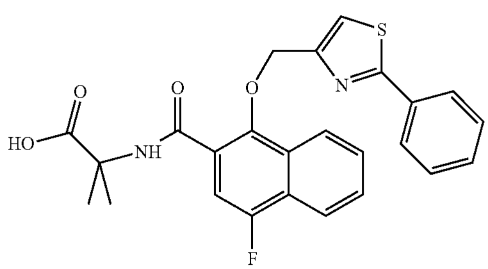 | 465.13 |
| 237 | 2-{[4-Fluoro-1-(5-thiophen-2-yl-[1,2,4]oxadiazol-3-ylmethoxy)-naphthalene-2-carbonyl]-amino}-2-methyl-propionic acid | 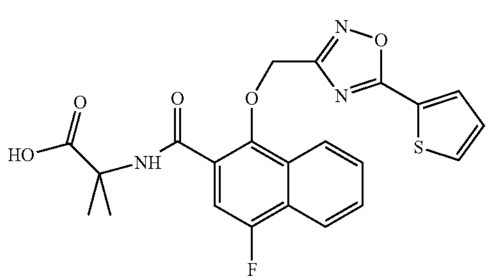 | 456.12 |

| No | Chemical Name | Structure | ESI+ or ESI– |
|---|---|---|---|
| 238 | 2-{[1-(Benzothiazol-2-ylmethoxy)-4-fluoro-naphthalene-2-carbonyl]-amino}-4,4,4-trifluoro-butyric acid | 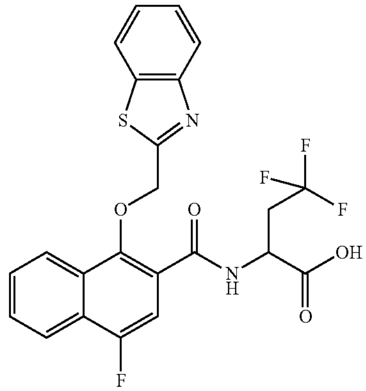 | 493.17 |
| 239 | 4,4,4-Trifluoro-2-{[4-fluoro-1-(4-trifluoromethyl-benzyloxy)-naphthalene-2-carbonyl]-amino}-butyric acid | 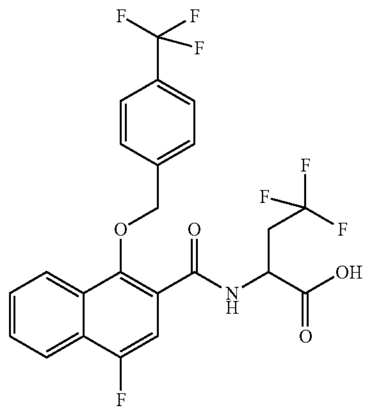 | 504.20 |

Example 240

2-{[4-Chloro-1-(2-trifluoromethyl-pyrimidin-5-ylmethoxy)-naphthalene-2-carbonyl]-amino}-2-methyl-propionic acid

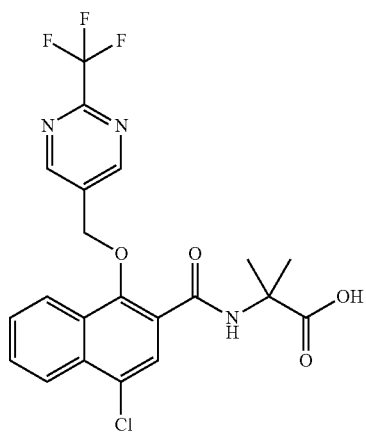

a) 2-[(4-Chloro-1-hydroxy-naphthalene-2-carbonyl)-amino]-2-methyl-propionic acid tert-butyl ester 2.25 g of 4-chloro-1-hydroxy-naphthalene-2-carboxylic acid, 3.57 2-amino-2-methyl-propionic acid tert-butyl ester hydrochloride, 6.93 g HATU and 5.29 mL of N,N'diisopropylethylamine were dissolved in 100 mL of dimethylformamide. The reaction was heated at 60° C. for 1.5 hour followed by room temperature overnight. Water was added and the mixture was extracted with diethyl ether twice. The combined organic layers were dried with magnesium sulfate and concentrated in vacuo. Purification by flash chromatography on silica with heptanes/ethyl acetate afforded 1.016 g (28%) of 2-[(4-chloro-1-hydroxy-naphthalene-2-carbonyl)-amino]-2-methyl-propionic acid tert-butyl ester as a beige solid.

$C_{19}H_{22}ClNO_4$ (363.12) LCMS (ES+): 386.10 (M+Na).

b) 2-{[4-Chloro-1-(2-trifluoromethyl-pyrimidin-5-ylmethoxy)-naphthalene-2-carbonyl]-amino}-2-methyl-propionic acid tert-butyl ester 0.092 g 2-[(4-chloro-1-hydroxy-naphthalene-2-carbonyl)-amino]-2-methyl-propionic acid tert-butyl ester was dissolved in 4 mL of tetrahydrofuran, after which, 0.09 g crude 2-trifluoromethyl-pyrimidin-5-yl)-methanol, 0.133 g triphenylphosphine and 0.1 mL of diisopropylazodicarboxylate were added to the reaction mixture, which was left stirring overnight at room temperature under nitrogen-atmosphere. The reaction mixture was then concentrated in vacuo, water was added and it was extracted with ethyl acetate, dried with magnesium sulfate, filtered and concentrated. Purification by flash chromatography on silica with ethyl acetate/heptanes afforded 0.015 g (11%) of 2-{[4-Chloro-1-(2-trifluoromethyl-pyrimidin-5-ylmethoxy)-naphthalene-2-carbonyl]-amino}-2-methyl-propionic acid tert-butyl ester.

$C_{25}H_{25}ClF_3N_3O_4$ (523.15) LCMS (ESI): 524.21(MH$^+$).

c) 2-{[4-Chloro-1-(2-trifluoromethyl-pyrimidin-5-ylmethoxy)-naphthalene-2-carbonyl]-amino}-2-methyl-propionic acid 0.015 g 2-{[4-chloro-1-(2-trifluoromethyl-pyrimidin-5-ylmethoxy)-naphthalene-2-carbonyl]amino}-2-methyl-propionic acid tert-butyl ester was dissolved in 5 mL of a mixture consisting of 95% trifluoroacetic acid, 2.5% triethylsilanes and 2.5% of water. This was left stirring at room temperature for 30 minutes, and then it was concentrated in vacuo. Purification was performed by flash chromatography on silica using methanol/dichloromethane to give 0.007 g (53%) of 2-{[4-Chloro-1-(2-trifluoromethyl-pyrimidin-5-ylmethoxy)-naphthalene-2-carbonyl]-amino}-2-methyl-propionic acid.

$C_{21}H_{17}ClF_3N_3O_4$ (467.08) LCMS (ESI): 468.11(MH$^+$).

The following examples were prepared in analogy to 2-{[4-chloro-1-(2-trifluoromethyl-pyrimidin-5-ylmethoxy)-naphthalene-2-carbonyl]-amino}-2-methyl-propionic acid (example 240):

| No | Chemical Name | Structure | ESI+ or ESI− |
|---|---|---|---|
| 241 | 2-{[4-Chloro-1-(2-methylsulfanyl-pyrimidin-5-ylmethoxy)-naphthalene-2-carbonyl]-amino}-2-methyl-propionic acid | 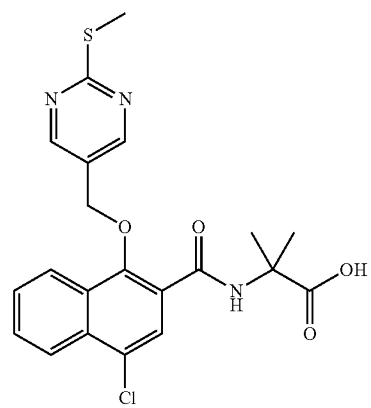 | 446.07 |
| 242 | 2-{[4-Chloro-1-(2-cyclopropyl-pyrimidin-5-ylmethoxy)-naphthalene-2-carbonyl]-amino}-2-methyl-propionic acid | 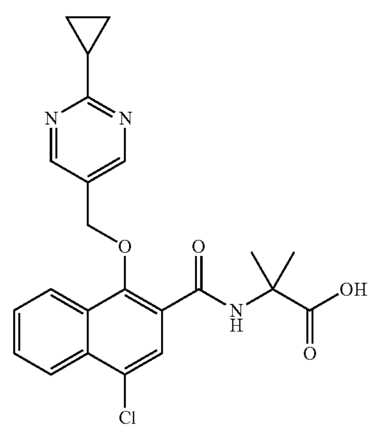 | 440.12 |

-continued

| No | Chemical Name | Structure | ESI+ or ESI− |
|---|---|---|---|
| 243 | 2-{[4-Chloro-1-(2-isopropyl-pyrimidin-5-ylmethoxy)-naphthalene-2-carbonyl]-amino}-2-methyl-propionic acid | 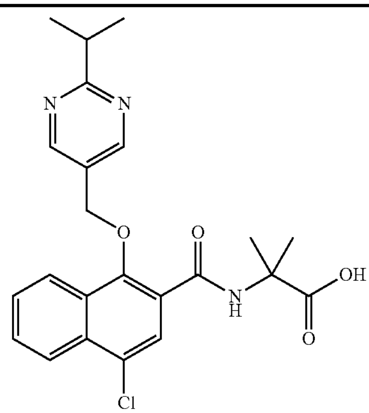 | 442.16 |

The following enantiomers were obtained after separation of the racemates by preparative HPLC using a Waters Alliance 2695 system and chiral columns and solvent mixtures at a flow rate of 1 ml/min as given in the following table.

| Exp. No. | Structure of racemate | Conditions of separation | No. of enantiomer | Rt [min] | % ee |
|---|---|---|---|---|---|
| 244 | | Chiralcel OJ 250 × 4.6 mm; heptane/EtOH/MeOH 25/1/1 + 0.1% TFA | 1 | 7.269 | >99.9% |
| 245 | | | 2 | 9.561 | 82% |
| 246 | | Chiralpak ADH 250 × 4.6 mm, EtOH/MeOH 1/1 + 0.1% TFA | 1 | 3.775 | >99.9% |
| 247 | | | 2 | 5.129 | 98% |

-continued
| Exp. No. | Structure of racemate | Conditions of separation | No. of enantiomer | Rt [min] | % ee |
|---|---|---|---|---|---|
| 248 249 | 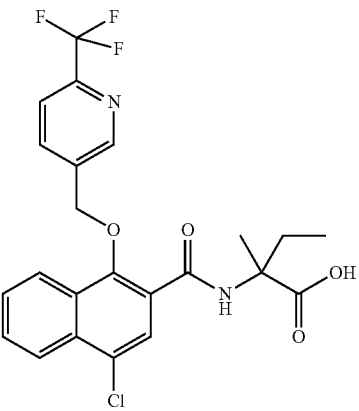 | Chirlapak AD-H 250 × 4.6 mm, heptane/EtOH/ ACN 50/5/1 | 1 2 | 8.458 19.57 | >99.9% >99.9% |
| 250 251 | 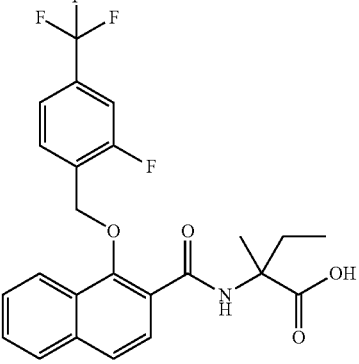 | Chiracel OD-H 250 × 4.6 mm, heptane/EtOH 10/1 + 0.1% TFA | 1 2 | 6.08 7.64 | >99.9% 96% |
| 252 253 | 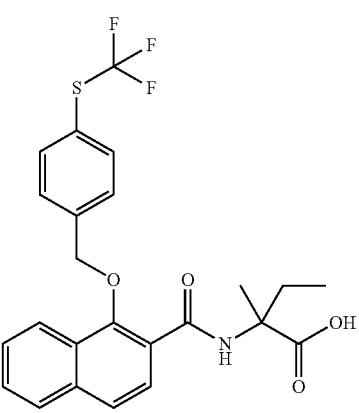 | Chiracel OD-H 250 × 4.6 mm, heptane/EtOH 10/1 + 0.1% TFA | 1 2 | 6.917 8.435 | >99.9% 96% |

-continued

| Exp. No. | Structure of racemate | Conditions of separation | No. of enantiomer | Rt [min] | % ee |
|---|---|---|---|---|---|
| 254 | 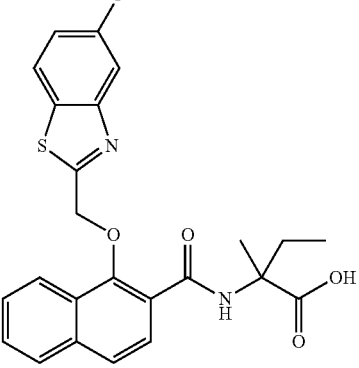 | Chiralpak ADH 250 × 4.6 mm, EtOH/MeOH 1/1 | 1 | 5.696 | >99.9% |
| 255 | | | 2 | 6.890 | 98% |
| 256 | 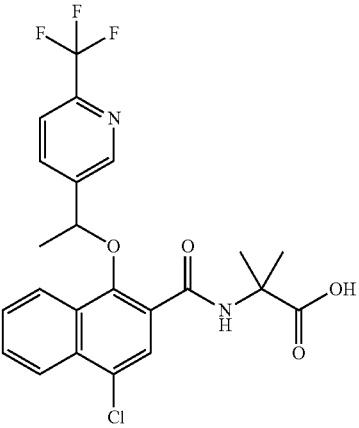 | Chiralpak AD-H 250 × 4.6 mm, heptane/EtOH/ MeOH 8/1/1 | 1 | 5.895 | >99.9% |
| 257 | | | 2 | 12.347 | >99.9% |

The following examples were prepared in analogy to example 1 via a sequence of a coupling of a suitable (ortho-) hydroxy-arene-carboxylic acid with a corresponding amino acid ester using coupling reagents as for example EDC/HOBT, DIC/HOBT, HATU, TBTU/DMAP, followed by an alkylation reaction to attach a suitably substituted alkylating agent to the aromatic hydroxy group and finally a basic hydrolysis of the amino acid ester to the free amino acid:

| No. | Chemical Name | Structure | ESI+ or ESI− |
|---|---|---|---|
| 258 | 2-Methyl-3-phenyl-2-{[1-(4-trifluoromethyl-benzyloxy)-naphthalene-2-carbonyl]-amino}-propionic acid | 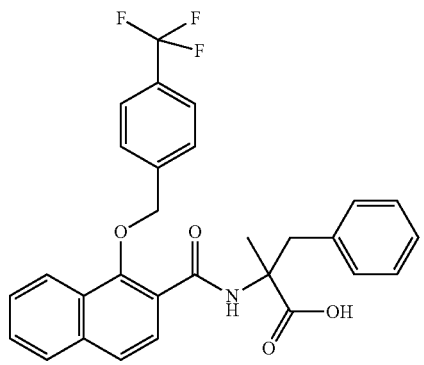 | 508.45 |

-continued
| No. | Chemical Name | Structure | ESI+ or ESI- |
|---|---|---|---|
| 259 | 2-{[1-(Benzothiazol-2-ylmethoxy)-naphthalene-2-carbonyl]-amino}-2-methyl-3-phenyl-propionic acid | 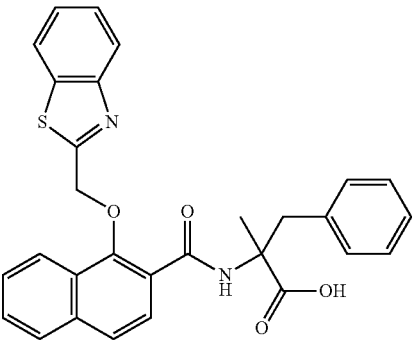 | 497.41 |
| 260 | 2-Methyl-2-{[1-(6-trifluoromethyl-1H-benzoimidazol-2-ylmethoxy)-naphthalene-2-carbonyl]-amino}-propionic acid | 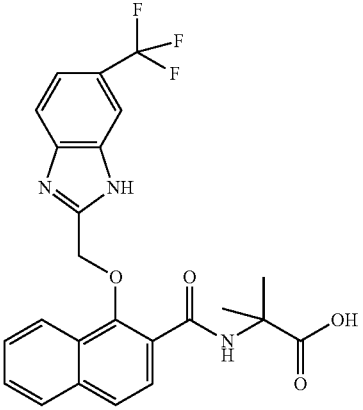 | 472.12 |
| 261 | 2-{[1-(4-Chloro-6-trifluoromethyl-1H-benzoimidazol-2-ylmethoxy)-naphthalene-2-carbonyl]-amino}-2-methyl-propionic acid | 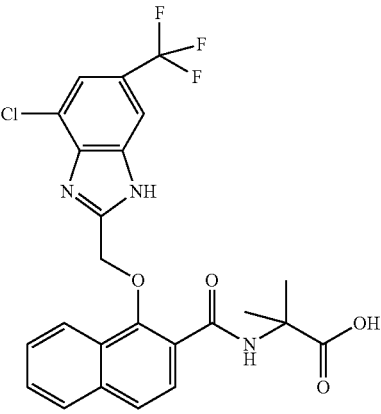 | 506.08 |

-continued

| No. | Chemical Name | Structure | ESI+ or ESI− |
|---|---|---|---|
| 262 | 2-{[1-(6-Cyano-1H-benzoimidazol-2-ylmethoxy)-naphthalene-2-carbonyl]-amino}-2-methyl-propionic acid | 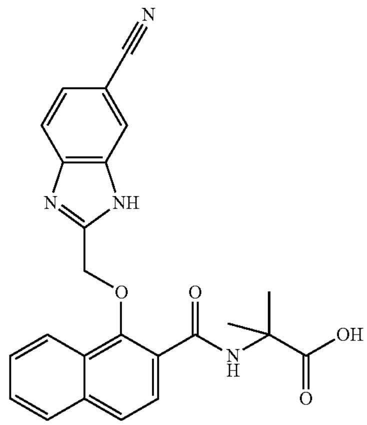 | 429.20 |
| 263 | 2-({4-Chloro-1-[1-(4-trifluoromethyl-phenyl)-ethoxy]-naphthalene-2-carbonyl}-amino)-2-methyl-propionic acid | 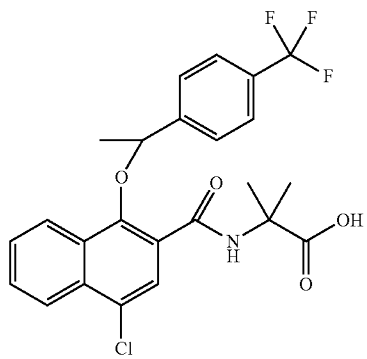 | 480.13 |
| 264 | 2-{[4-Chloro-1-(quinolin-2-ylmethoxy)-naphthalene-2-carbonyl]-amino}-2-methyl-propionic acid | 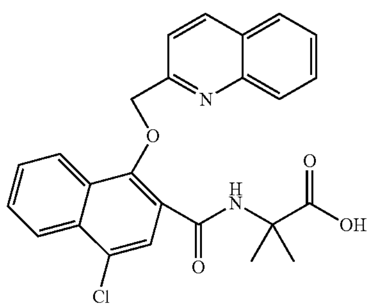 | 449.10 |
| 265 | 2-{[4-Chloro-1-(5-thiophen-2-yl-[1,2,4]oxadiazol-3-ylmethoxy)-naphthalene-2-carbonyl]-amino}-2-methyl-propionic acid | 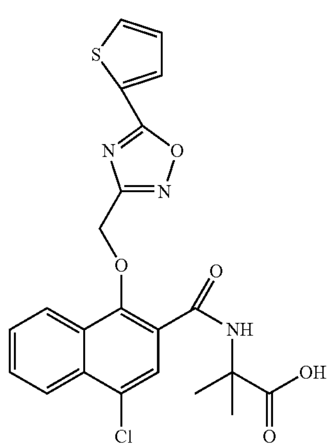 | 472.10 |

| No. | Chemical Name | Structure | ESI+ or ESI− |
|---|---|---|---|
| 266 | 2-({4-Chloro-1-[5-(4-trifluoromethyl-phenyl)-[1,2,4]oxadiazol-3-ylmethoxy]-naphthalene-2-carbonyl}-amino)-2-methyl-propionic acid | 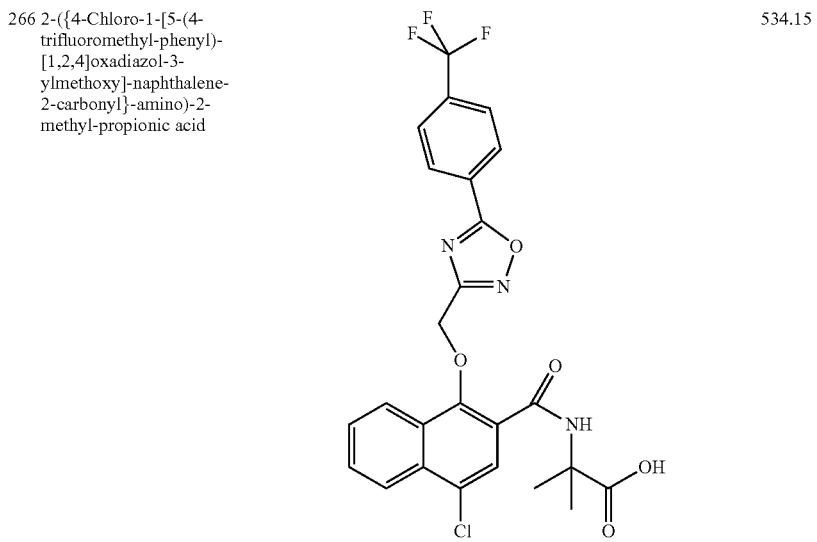 | 534.15 |
| 267 | 2-{[4-Chloro-1-(3-thiophen-2-yl-[1,2,4]oxadiazol-5-ylmethoxy)-naphthalene-2-carbonyl]-amino}-2-methyl-propionic acid | 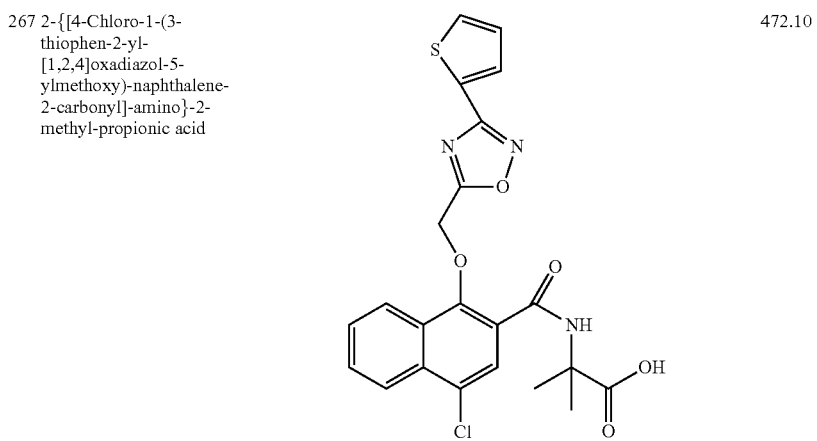 | 472.10 |
| 268 | (R)-2-{[1-(Benzothiazol-2-ylmethoxy)-4-chloro-naphthalene-2-carbonyl]-amino}-2-methyl-butyric acid | CHIRAL 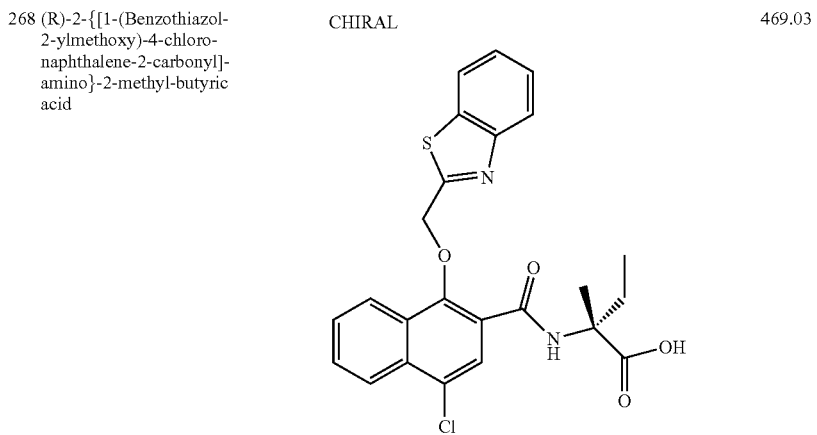 | 469.03 |

| No. | Chemical Name | Structure | ESI+ or ESI– |
|---|---|---|---|
| 269 | (S)-2-{[1-(Benzothiazol-2-ylmethoxy)-4-chloro-naphthalene-2-carbonyl]-amino}-2-methyl-butyric acid | CHIRAL 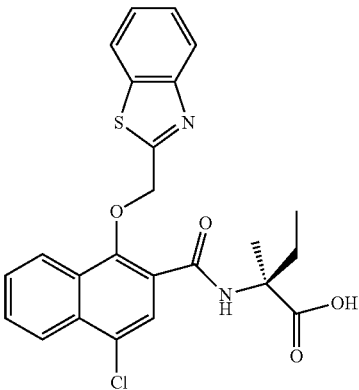 | 469.03 |
| 270 | 2-{[4-Chloro-1-(5-cyclopropyl-[1,3,4]thiadiazol-2-ylmethoxy)-naphthalene-2-carbonyl]-amino}-2-methyl-butyric acid | 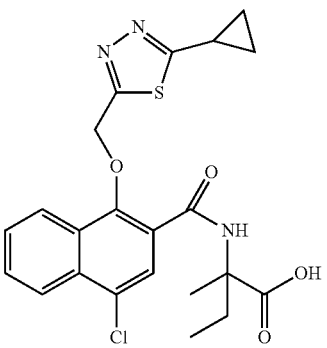 | 460.10 |
| 271 | 1-{[4-Chloro-1-(6-trifluoromethyl-pyridin-3-ylmethoxy)-naphthalene-2-carbonyl]-amino}-cyclopentanecarboxylic acid | 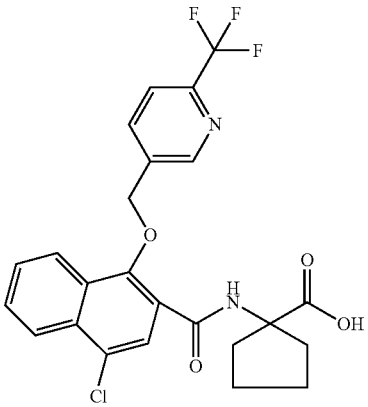 | 493.10 |
| 272 | 1-{[1-(Benzothiazol-2-ylmethoxy)-4-chloro-naphthalene-2-carbonyl]-amino}-cyclopentanecarboxylic acid | 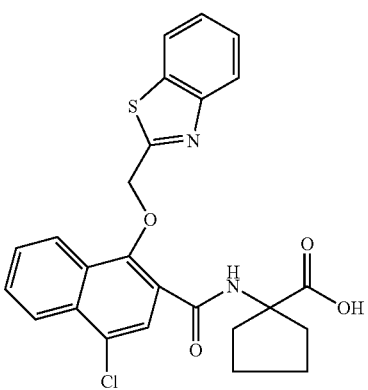 | 481.10 |

| No. | Chemical Name | Structure | ESI+ or ESI− |
|---|---|---|---|
| 273 | 1-{[4-Chloro-1-(quinolin-2-ylmethoxy)-naphthalene-2-carbonyl]-amino}-cyclopentanecarboxylic acid | 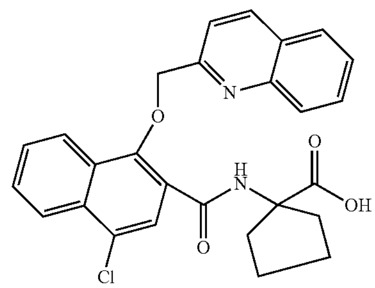 | 475.15 |
| 274 | 2-{[4-Chloro-1-(2-thiophen-2-yl-pyrimidin-5-ylmethoxy)-naphthalene-2-carbonyl]-amino}-2-methyl-propionic acid | 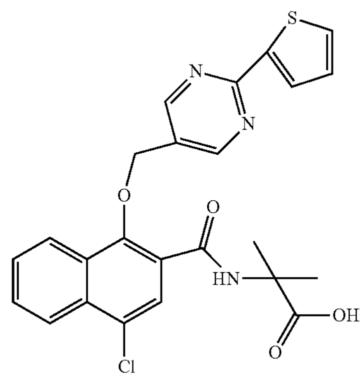 | 482.04 |
| 275 | 1-{[4-Chloro-1-(5-trifluoromethyl-pyridin-2-ylmethoxy)-naphthalene-2-carbonyl]-amino}-cyclopentanecarboxylic acid | 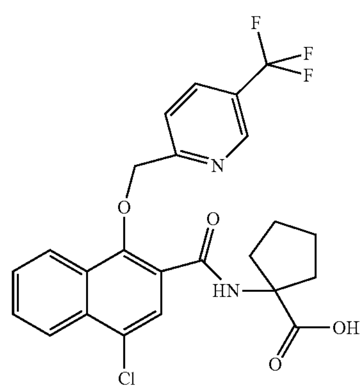 | 493.05 |
| 276 | 1-{[1-(5-Trifluoromethyl-pyridin-2-ylmethoxy)-naphthalene-2-carbonyl]-amino}-cyclopentanecarboxylic acid | 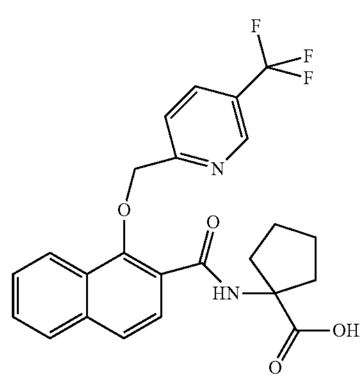 | 459.12 |

| No. Chemical Name | Structure | ESI+ or ESI− |
|---|---|---|
| 277 2-Methyl-2-{[1-(5-trifluoromethyl-pyridin-2-ylmethoxy)-naphthalene-2-carbonyl]-amino}-butyric acid | | 447.15 |
| 278 1-{[1-(4-Trifluoromethylsulfanyl-benzyloxy)-naphthalene-2-carbonyl]-amino}-cyclopentanecarboxylic acid | | 490.08 |
| 279 1-{[1-(2-Fluoro-4-trifluoromethyl-benzyloxy)-naphthalene-2-carbonyl]-amino}-cyclopentanecarboxylic acid | | 476.00 |
| 280 1-{[4-Chloro-1-(4-trifluoromethylsulfanyl-benzyloxy)-naphthalene-2-carbonyl]-amino}-cyclopentanecarboxylic acid | | 524.05 |

| No. | Chemical Name | Structure | ESI+ or ESI− |
|---|---|---|---|
| 281 | 1-{[4-Chloro-1-(2-fluoro-4-trifluoromethyl-benzyloxy)-naphthalene-2-carbonyl]-amino}-cyclopentanecarboxylic acid | 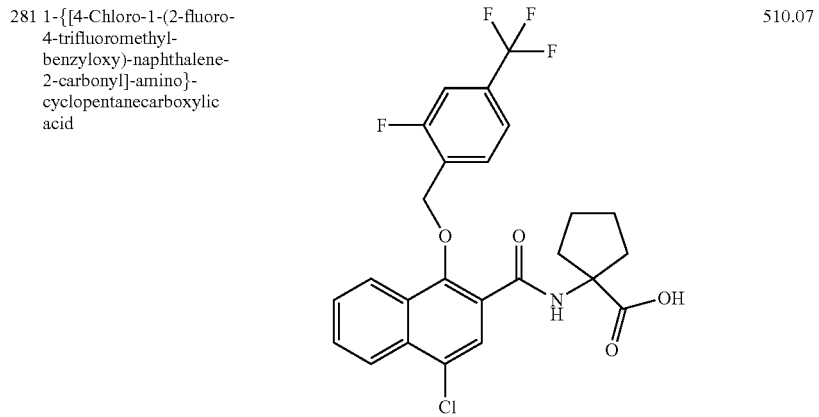 | 510.07 |
| 282 | 1-({4-Chloro-1-[1-(4-trifluoromethyl-phenyl)-ethoxy]-naphthalene-2-carbonyl}-amino)-cyclopentanecarboxylic acid | 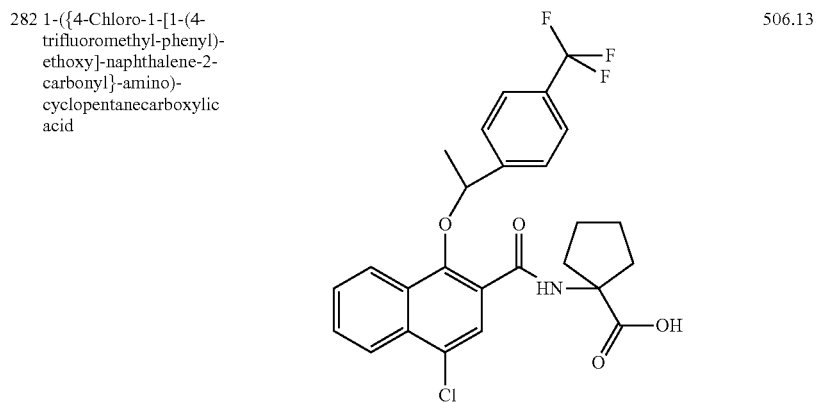 | 506.13 |
| 283 | 1-{[4-Chloro-1-(2-isopropyl-pyrimidin-5-ylmethoxy)-naphthalene-2-carbonyl]-amino}-cyclopentanecarboxylic acid | 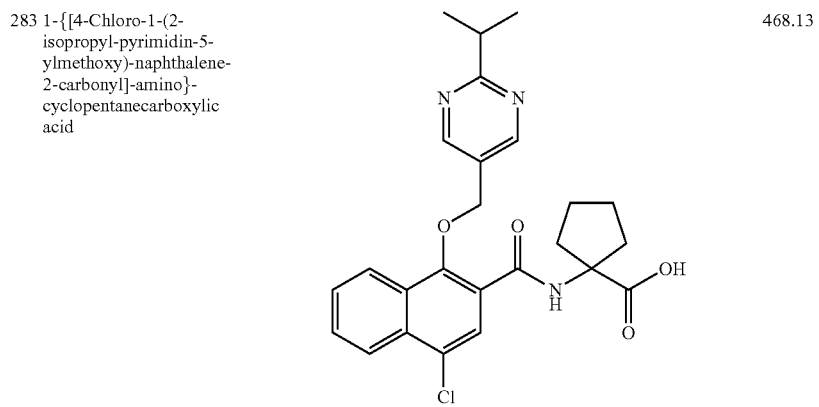 | 468.13 |

-continued

| No. | Chemical Name | Structure | ESI+ or ESI− |
|---|---|---|---|
| 284 | (S)-2-{[4-Fluoro-1-(4-trifluoromethyl-benzyloxy)-naphthalene-2-carbonyl]-amino}-2-methyl-butyric acid | CHIRAL | 464.15 |
| 285 | 2-{[1-(4-Bromo-benzyloxy)-4-fluoro-naphthalene-2-carbonyl]-amino}-2-methyl-propionic acid | 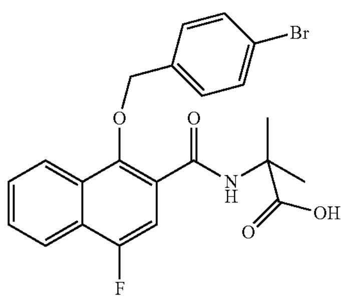 | 460.02 |
| 286 | 2-{[1-(2,4-Dichloro-benzyloxy)-4-fluoro-naphthalene-2-carbonyl]-amino}-2-methyl-propionic acid | 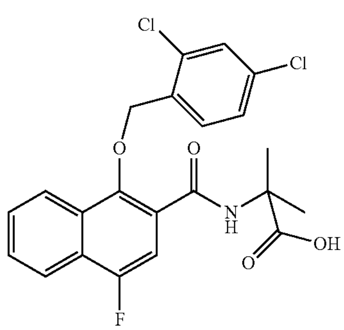 | 450.00 |
| 287 | 2-{[4-Fluoro-1-(quinolin-2-ylmethoxy)-naphthalene-2-carbonyl]-amino}-2-methyl-propionic acid | 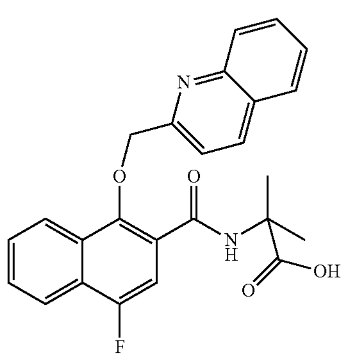 | 433.11 |

| No. | Chemical Name | Structure | ESI+ or ESI− |
|---|---|---|---|
| 288 | 2-{[1-(4-Bromo-benzyloxy)-4-fluoro-naphthalene-2-carbonyl]-amino}-2-methyl-butyric acid | 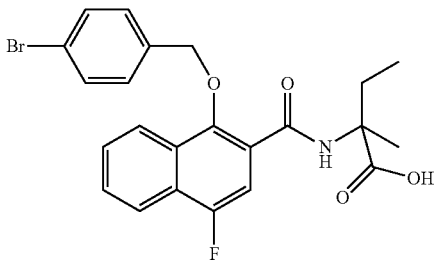 | 474.04 |
| 289 | 2-{[1-(4-Difluoromethoxy-benzyloxy)-4-fluoro-naphthalene-2-carbonyl]-amino}-2-methyl-butyric acid | 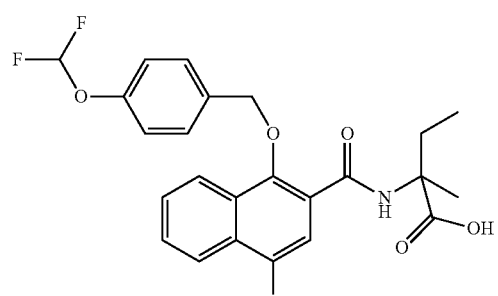 | 462.12 |
| 290 | 2-{[4-Fluoro-1-(quinolin-2-ylmethoxy)-naphthalene-2-carbonyl]-amino}-2-methyl-butyric acid | 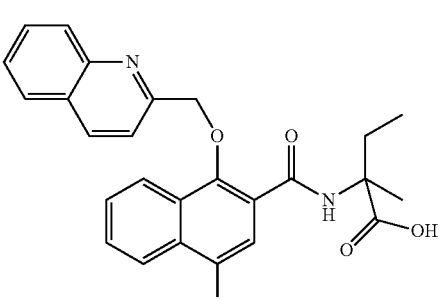 | 447.14 |
| 291 | 2-{[1-(2,4-Dichloro-benzyloxy)-4-fluoro-naphthalene-2-carbonyl]-amino}-2-methyl-butyric acid | 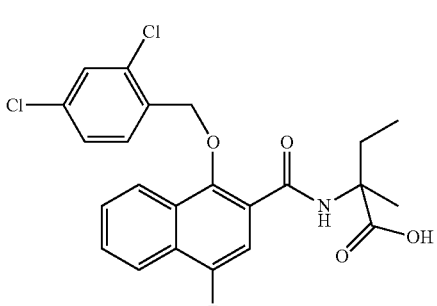 | 464.06 |
| 292 | 2-{[4-Fluoro-1-(2-phenyl-thiazol-4-ylmethoxy)-naphthalene-2-carbonyl]-amino}-2-methyl-butyric acid | 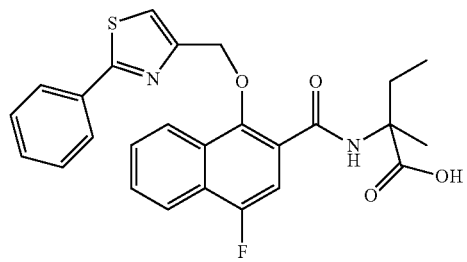 | 479.09 |

| No. | Chemical Name | Structure | ESI+ or ESI− |
|---|---|---|---|
| 293 | (R)-2-{[4-Fluoro-1-(4-trifluoromethyl-benzyloxy)-naphthalene-2-carbonyl]-amino}-2-methyl-butyric acid | CHIRAL | 464.14 |
| 294 | 2-{[4-Fluoro-1-(4-pyrrol-1-yl-benzyloxy)-naphthalene-2-carbonyl]-amino}-2-methyl-propionic acid | 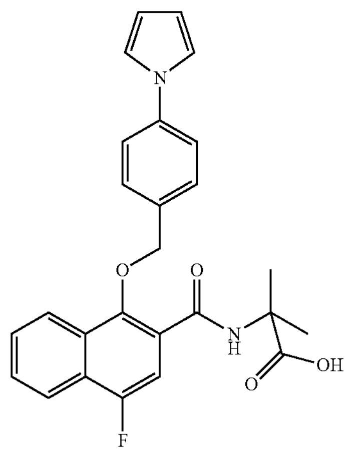 | 447.20 |
| 295 | 1-{[1-(Benzothiazol-2-ylmethoxy)-4-fluoro-naphthalene-2-carbonyl]-amino}-cyclobutanecarboxylic acid | 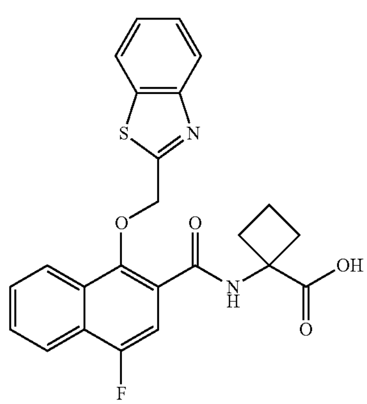 | 451.11 |

-continued

| No. | Chemical Name | Structure | ESI+ or ESI− |
|---|---|---|---|
| 296 | 1-{[4-Fluoro-1-(6-trifluoromethyl-pyridin-3-ylmethoxy)-naphthalene-2-carbonyl]-amino}-cyclobutanecarboxylic acid | 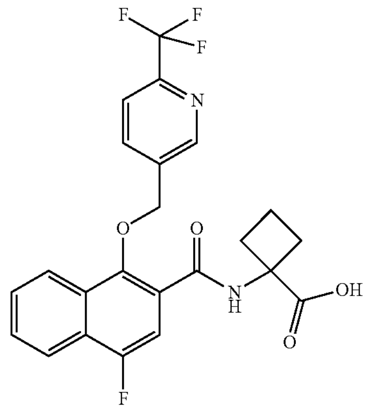 | 463.07 |
| 297 | 1-{[4-Fluoro-1-(4-trifluoromethyl-benzyloxy)-naphthalene-2-carbonyl]-amino}-cyclobutanecarboxylic acid | 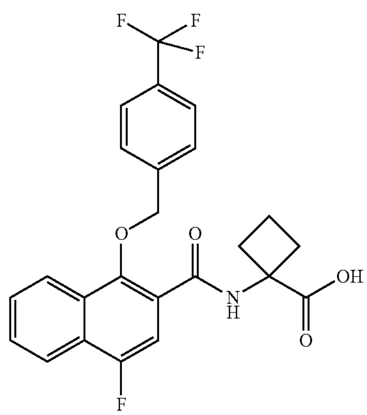 | 462.12 |
| 298 | 1-{[4-Fluoro-1-(5-trifluoromethyl-pyridin-2-ylmethoxy)-naphthalene-2-carbonyl]-amino}-cyclobutanecarboxylic acid | 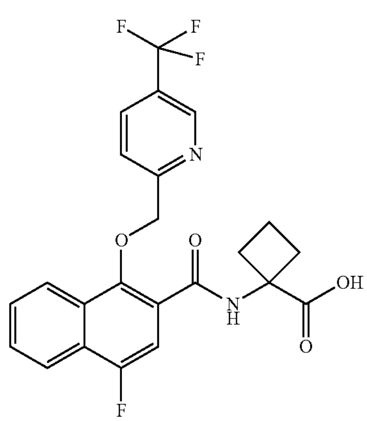 | 463.11 |

-continued

| No. | Chemical Name | Structure | ESI+ or ESI− |
|---|---|---|---|
| 299 | 2-{[4-Fluoro-1-(2-fluoro-4-trifluoromethyl-benzyloxy)-naphthalene-2-carbonyl]-amino}-2-methyl-propionic acid | 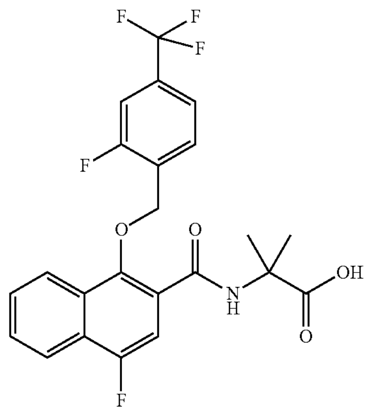 | 467.12 |
| 300 | 2-{[1-(4-Chloro-benzyloxy)-4-fluoro-naphthalene-2-carbonyl]-amino}-2-methyl-propionic acid | 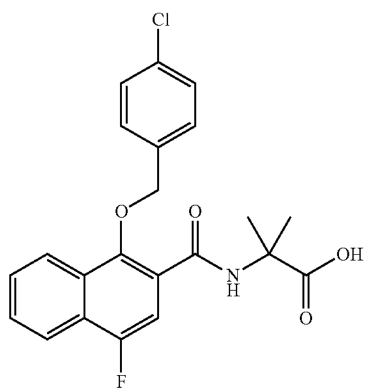 | 416.06 |
| 301 | 2-[(1-Cyclohexylmethoxy-4-fluoro-naphthalene-2-carbonyl)-amino]-2-methyl-propionic acid | 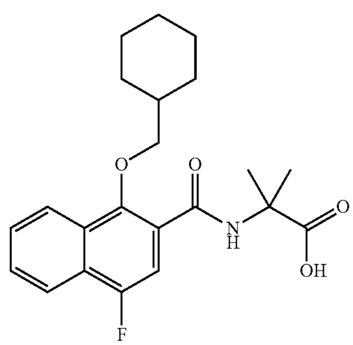 | 388.17 |
| 302 | 2-{[4-Fluoro-1-(4-fluoro-benzyloxy)-naphthalene-2-carbonyl]-amino}-2-methyl-propionic acid | 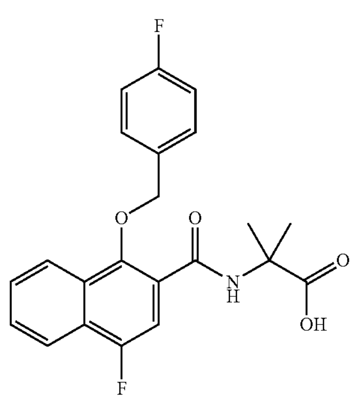 | 400.14 |

-continued

| No. | Chemical Name | Structure | ESI+ or ESI− |
|---|---|---|---|
| 303 | 2-{[4-Fluoro-1-(4-trifluoromethoxy-benzyloxy)-naphthalene-2-carbonyl]-amino}-2-methyl-propionic acid | 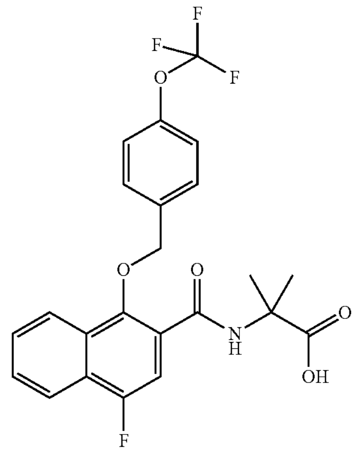 | 466.08 |
| 304 | 2-{[4-Fluoro-1-(tetrahydro-pyran-4-ylmethoxy)-naphthalene-2-carbonyl]-amino}-2-methyl-propionic acid | 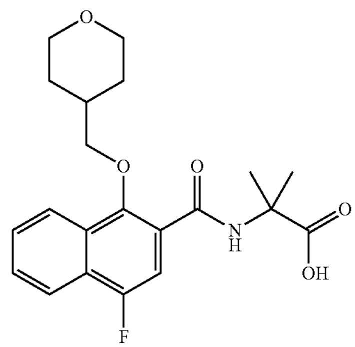 | 390.17 |
| 305 | 2-{[4-Fluoro-1-(4-isopropyl-benzyloxy)-naphthalene-2-carbonyl]-amino}-2-methyl-propionic acid | 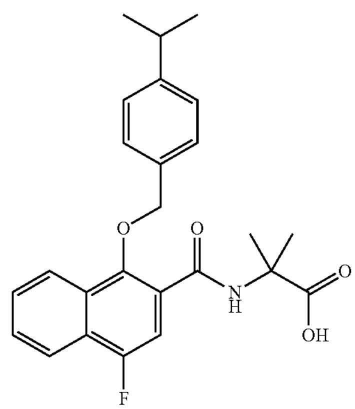 | 424.22 |
| 306 | 2-{[1-(4-Ethyl-benzyloxy)-4-fluoro-naphthalene-2-carbonyl]-amino}-2-methyl-propionic acid | 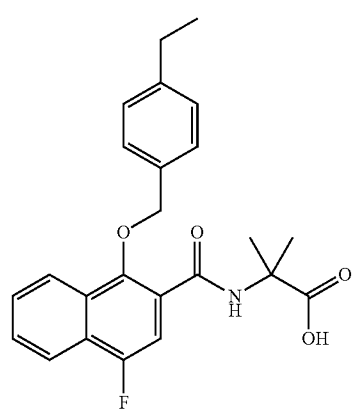 | 408.20 |

| No. | Chemical Name | Structure | ESI+ or ESI− |
|---|---|---|---|
| 307 | 2-Methyl-2-{[3-(6-trifluoromethyl-pyridin-3-ylmethoxy)-1H-indole-2-carbonyl]-amino}-propionic acid | 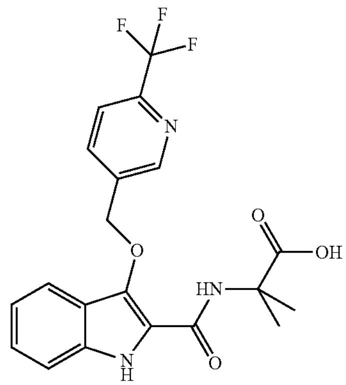 | 422.10 |
| 308 | 4,4,4-Trifluoro-2-{[1-(4-trifluoromethyl-benzyloxy)-naphthalene-2-carbonyl]-amino}-butyric acid | 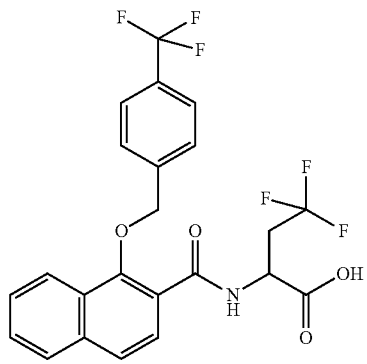 | 486.09 |
| 309 | 2-{[1-(6-Methanesulfonyl-pyridin-3-ylmethoxy)-naphthalene-2-carbonyl]-amino}-2-methyl-propionic acid | 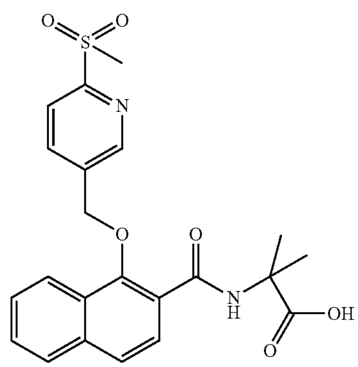 | 443.10 |
| 310 | 2-{[1-(6-Methanesulfinyl-pyridin-3-ylmethoxy)-naphthalene-2-carbonyl]-amino}-2-methyl-propionic acid | 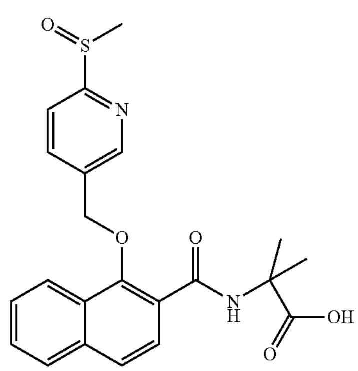 | 427.20 |

| No. | Chemical Name | Structure | ESI+ or ESI− |
|---|---|---|---|
| 311 | 2-({4-Chloro-1-[1-(6-trifluoromethyl-pyridin-3-yl)-ethoxy]-naphthalene-2-carbonyl}-amino)-2-methyl-propionic acid | 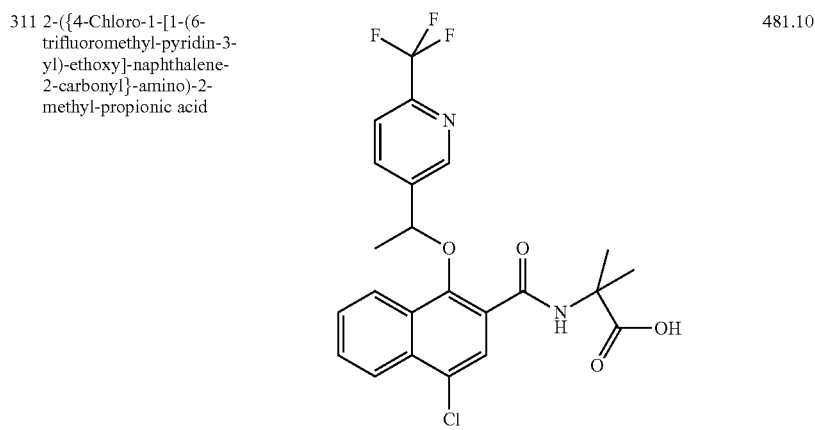 | 481.10 |
| 312 | 2-{[1-(6-Bromo-pyridin-3-ylmethoxy)-4-chloro-naphthalene-2-carbonyl]-amino}-2-methyl-propionic acid | 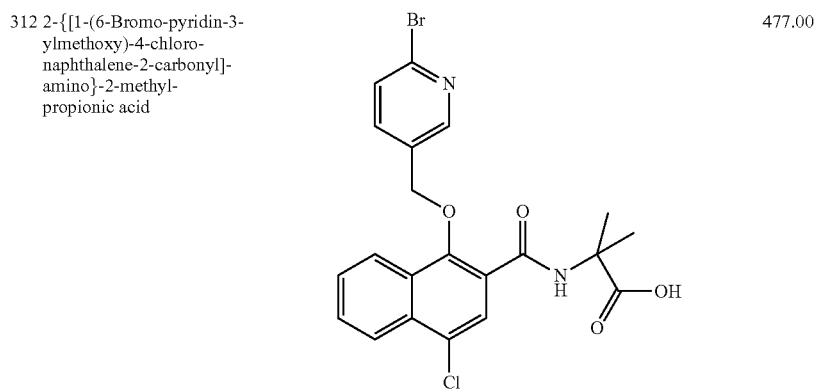 | 477.00 |
| 313 | 2-{[4-Chloro-1-(4-pentafluorothio-benzyloxy)-naphthalene-2-carbonyl]-amino}-2-methyl-butyric acid | 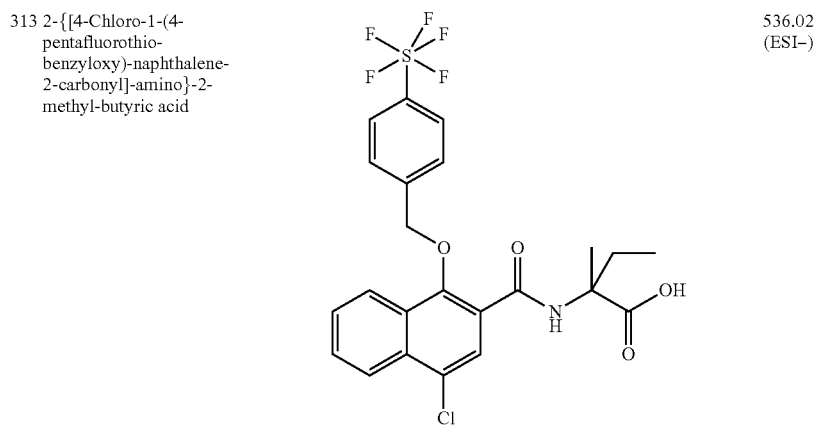 | 536.02 (ESI−) |

| No. | Chemical Name | Structure | ESI+ or ESI− |
|---|---|---|---|
| 314 | 2-{[1-(Benzothiazol-2-ylmethoxy)-4-fluoro-naphthalene-2-carbonyl]-amino}-2-methyl-butyric acid | 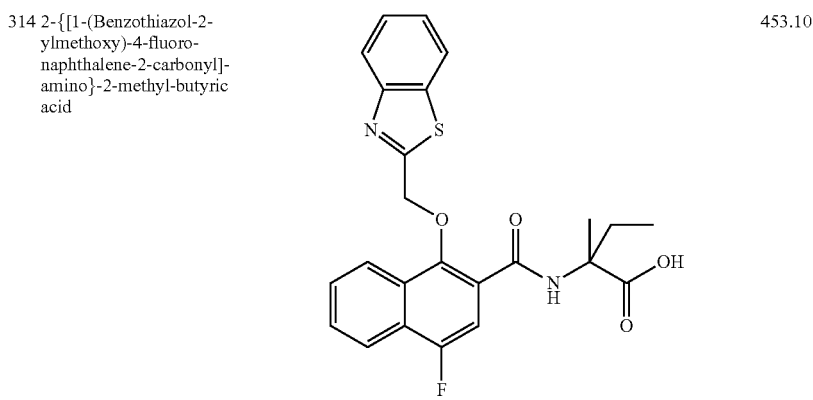 | 453.10 |
| 315 | 2-{[4-Fluoro-1-(5-trifluoromethyl-pyridin-2-ylmethoxy)-naphthalene-2-carbonyl]-amino}-2-methyl-butyric acid | 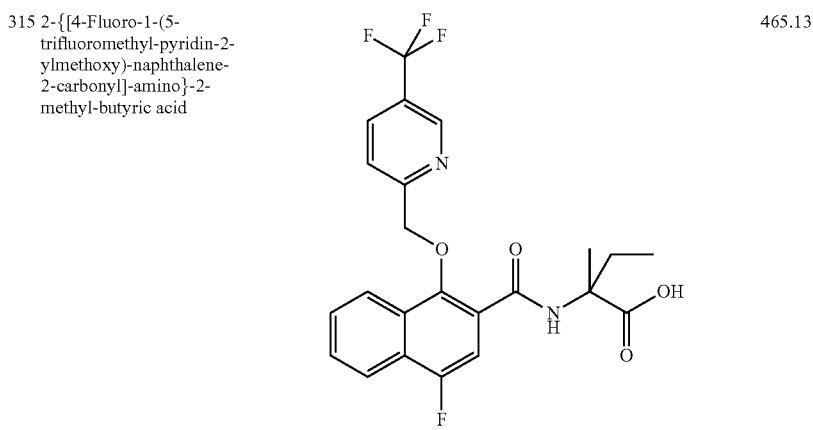 | 465.13 |
| 316 | 2-{[4-Fluoro-1-(6-trifluoromethyl-pyridin-3-ylmethoxy)-naphthalene-2-carbonyl]-amino}-2-methyl-butyric acid | 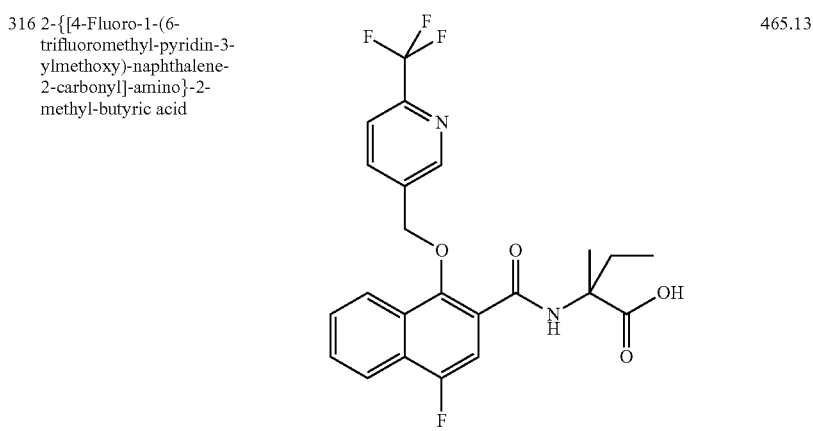 | 465.13 |

| No. | Chemical Name | Structure | ESI+ or ESI− |
|---|---|---|---|
| 317 | 2-{[4-Fluoro-1-(4-trifluoromethyl-benzyloxy)-naphthalene-2-carbonyl]-amino}-2-methyl-butyric acid | 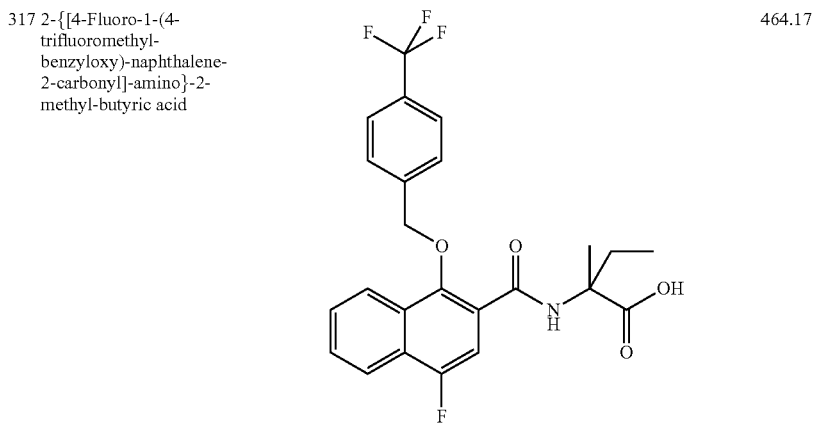 | 464.17 |
| 318 | 2-{[4-Fluoro-1-(5-trifluoromethyl-pyridin-2-ylmethoxy)-naphthalene-2-carbonyl]-amino}-2-methyl-propionic acid | 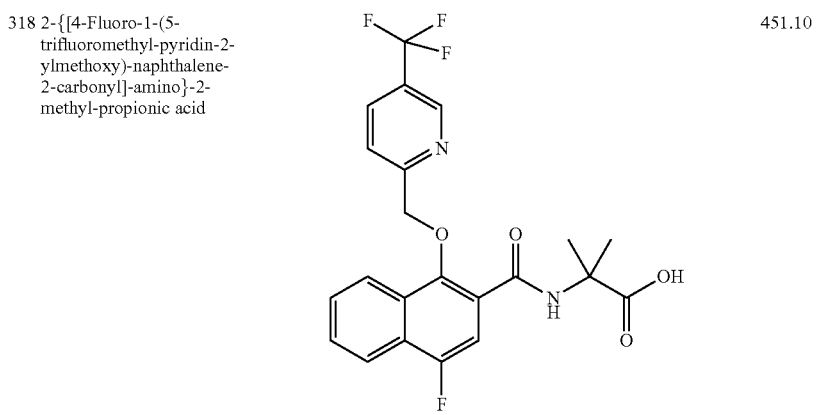 | 451.10 |
| 319 | 1-{[4-Fluoro-1-(5-trifluoromethyl-pyridin-2-ylmethoxy)-naphthalene-2-carbonyl]-amino}-cyclopentanecarboxylic acid | 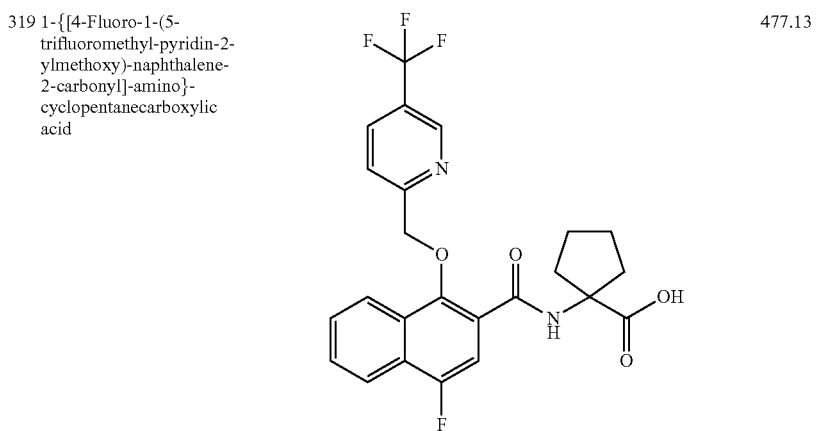 | 477.13 |

-continued
| No. | Chemical Name | Structure | ESI+ or ESI− |
|---|---|---|---|
| 320 | (R)-2-{[4-Fluoro-1-(5-trifluoromethyl-pyridin-2-ylmethoxy)-naphthalene-2-carbonyl]-amino}-2-methyl-butyric acid | 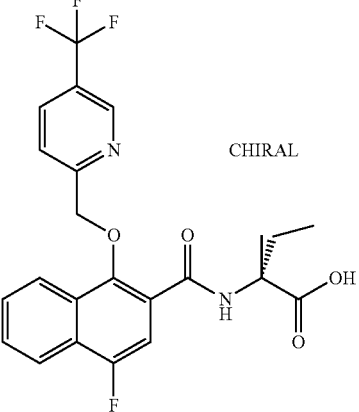 | 463.14 (ESI−) |
| 321 | (S)-2-{[4-Fluoro-1-(5-trifluoromethyl-pyridin-2-ylmethoxy)-naphthalene-2-carbonyl]-amino}-2-methyl-butyric acid | 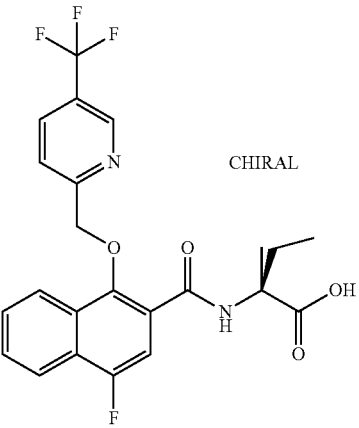 | 465.13 |
| 322 | (S)-2-{[1-(Benzothiazol-2-ylmethoxy)-4-fluoro-naphthalene-2-carbonyl]-amino}-2-methyl-butyric acid | 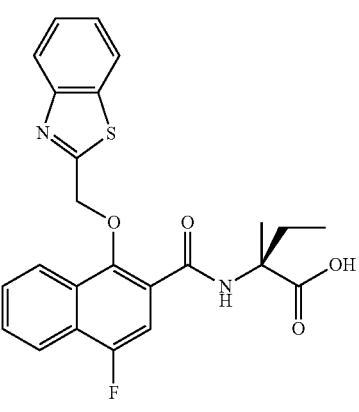 | 451.19 (ESI−) |

| No. | Chemical Name | Structure | ESI+ or ESI− |
|---|---|---|---|
| 323 | (R)-2-{[1-(Benzothiazol-2-ylmethoxy)-4-fluoro-naphthalene-2-carbonyl]-amino}-2-methyl-butyric acid | CHIRAL | 451.19 (ESI−) |
| 324 | 2-{[4-Fluoro-1-(6-trifluoromethyl-pyridin-3-ylmethoxy)-naphthalene-2-carbonyl]-amino}-2-methyl-propionic acid | 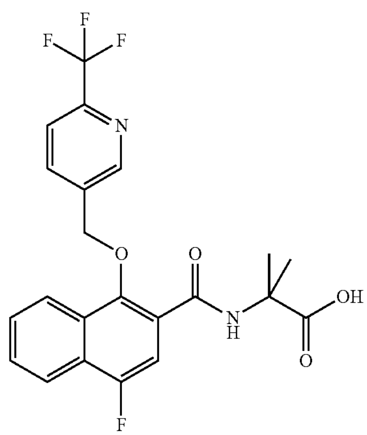 | 451.10 |
| 325 | (S)-2-{[4-Fluoro-1-(6-trifluoromethyl-pyridin-3-ylmethoxy)-naphthalene-2-carbonyl]-amino}-2-methyl-butyric acid | CHIRAL | 465.12 |

| No. | Chemical Name | Structure | ESI+ or ESI− |
|---|---|---|---|
| 326 | (R)-2-{[4-Fluoro-1-(6-trifluoromethyl-pyridin-3-ylmethoxy)-naphthalene-2-carbonyl]-amino}-2-methyl-butyric acid | 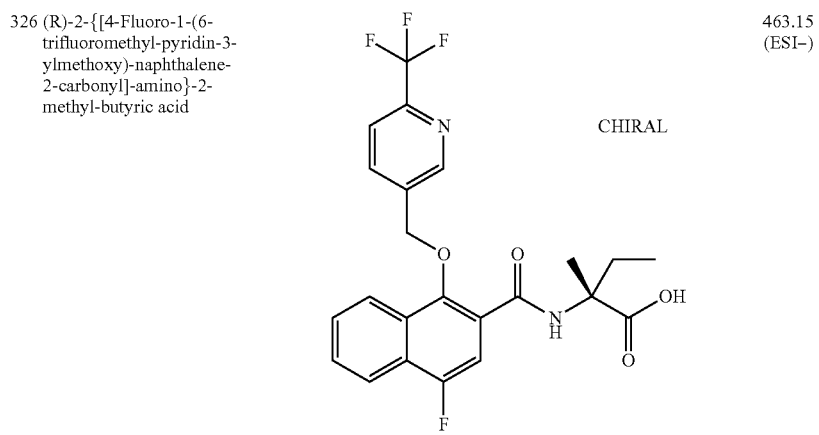 CHIRAL | 463.15 (ESI−) |
| 327 | 2-{[4-Fluoro-1-(4-pentafluorothio-benzyloxy)-naphthalene-2-carbonyl]-amino}-2-methyl-butyric acid | 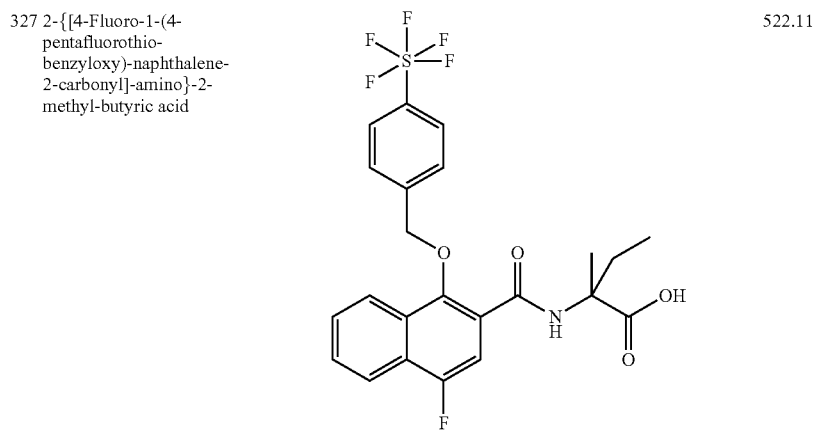 | 522.11 |
| 328 | 2-{[1-(4-Chloro-3-fluoro-benzyloxy)-4-fluoro-naphthalene-2-carbonyl]-amino}-2-methyl-propionic acid | 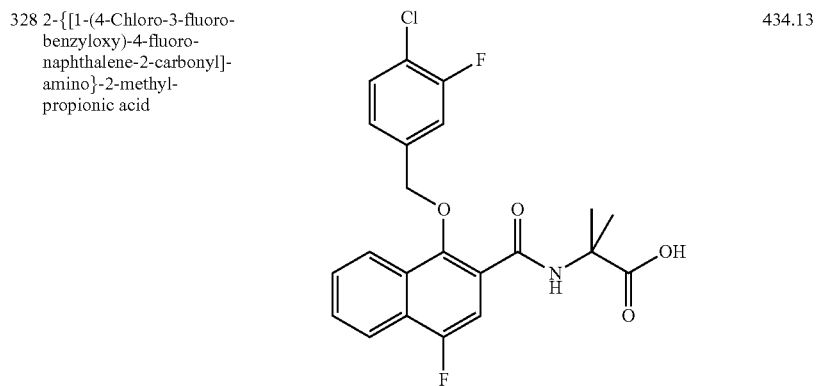 | 434.13 |

-continued

| No. Chemical Name | Structure | ESI+ or ESI− |
|---|---|---|
| 329 2-{[1-(4-Chloro-2-fluoro-benzyloxy)-4-fluoro-naphthalene-2-carbonyl]-amino}-2-methyl-propionic acid | | 434.12 |
| 330 2-{[1-(Benzothiazol-2-ylmethoxy)-4-fluoro-naphthalene-2-carbonyl]-amino}-2-methyl-propionic acid | | 439.09 |
| 331 2-{[4-Fluoro-1-(4-trifluoromethylsulfanyl-benzyloxy)-naphthalene-2-carbonyl]-amino}-2-methyl-butyric acid | | 494.13 (ESI−) |

| No. | Chemical Name | Structure | ESI+ or ESI− |
|---|---|---|---|
| 332 | 2-{[4-Fluoro-1-(2-fluoro-4-trifluoromethyl-benzyloxy)-naphthalene-2-carbonyl]-amino}-2-methyl-butyric acid | 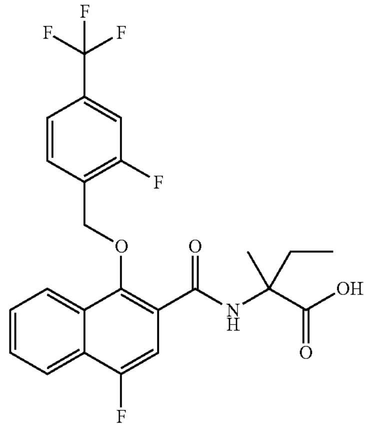 | 482.13 |
| 333 | 2-{[4-Fluoro-1-(4-pentafluorothio-benzyloxy)-naphthalene-2-carbonyl]-amino}-2-methyl-propionic acid | 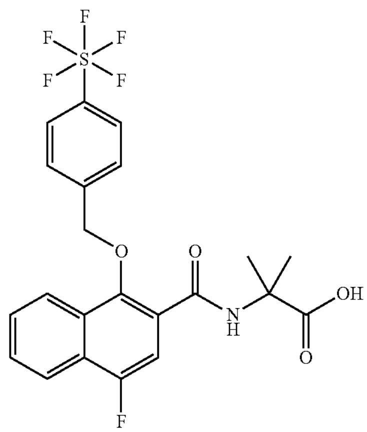 | 506.09 (ESI−) |
| 334 | 2-{[5-Fluoro-1-(6-trifluoromethyl-pyridin-3-ylmethoxy)-naphthalene-2-carbonyl]-amino}-2-methyl-propionic acid | 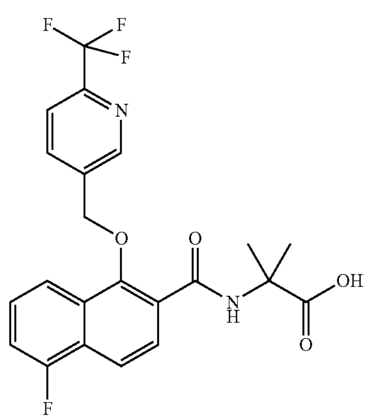 | 449.08 (ESI−) |

The following examples were prepared in analogy to example 2 via a sequence of a coupling of a suitable (ortho-) hydroxy-arene-carboxylic acid with a corresponding amino acid ester using coupling reagents as for example EDC/HOBT, DIC/HOBT, HATU, TBTU/DMAP, followed by a Mitsunobu reaction to attach a suitably substituted alcohol to the aromatic hydroxy group and finally a basic hydrolysis of the amino acid ester to the free amino acid:

| No. | Chemical Name | Structure | ESI+ or ESI− |
|---|---|---|---|
| 335 | 2-{[4-Chloro-1-(4-chloro-pyridin-2-ylmethoxy)-naphthalene-2-carbonyl]-amino}-2-methyl-propionic acid | 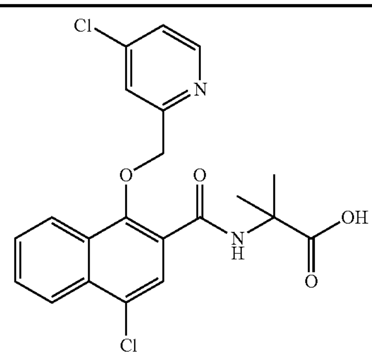 | 433.03 |
| 336 | 2-{[4-Fluoro-1-(4-trifluoromethyl-thiazol-2-ylmethoxy)-naphthalene-2-carbonyl]-amino}-2-methyl-propionic acid | 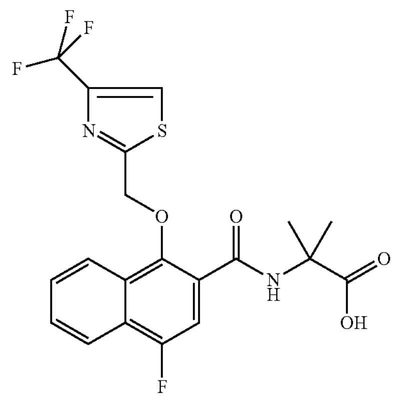 | 457.13 |
| 337 | 2-{[1-(4-Chloro-pyridin-2-ylmethoxy)-4-fluoro-naphthalene-2-carbonyl]-amino}-2-methyl-propionic acid | 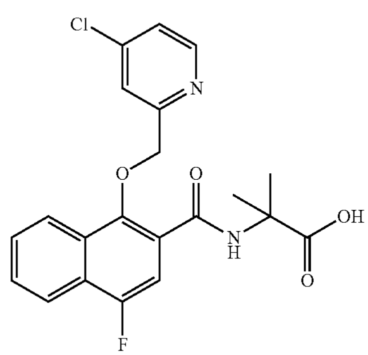 | 417.06 |
| 338 | 2-Methyl-2-{[1-(6-methyl-pyridin-2-ylmethoxy)-naphthalene-2-carbonyl]-amino}-propionic acid | 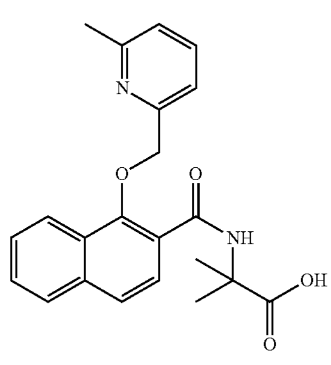 | 379.10 |

| No. | Chemical Name | Structure | ESI+ or ESI− |
|---|---|---|---|
| 339 | 2-{[4-Chloro-1-(4-trifluoromethylsulfanyl-benzyloxy)-naphthalene-2-carbonyl]-amino}-2-methyl-propionic acid | 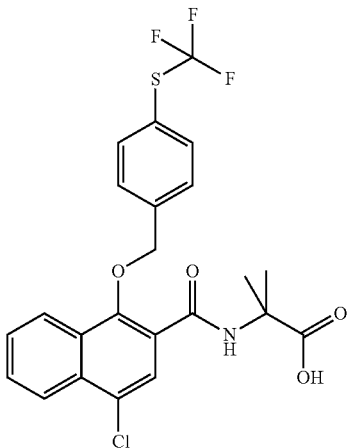 | 498.08 |
| 340 | 2-{[4-Chloro-1-(4-trifluoromethylsulfanyl-benzyloxy)-naphthalene-2-carbonyl]-amino}-2-methyl-butyric acid | 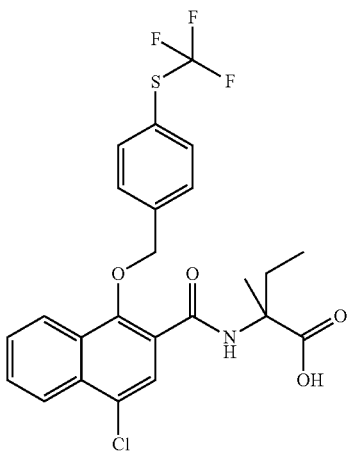 | 512.11 |
| 341 | 2-{[1-(5-Bromo-pyridin-2-ylmethoxy)-4-chloro-naphthalene-2-carbonyl]-amino}-2-methyl-propionic acid | 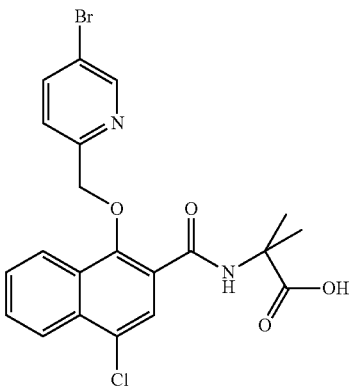 | 477.00 |

-continued

| No. | Chemical Name | Structure | ESI+ or ESI− |
|---|---|---|---|
| 342 | 2-{[4-Chloro-1-(5-trifluoromethyl-pyridin-2-ylmethoxy)-naphthalene-2-carbonyl]-amino}-2-methyl-propionic acid | 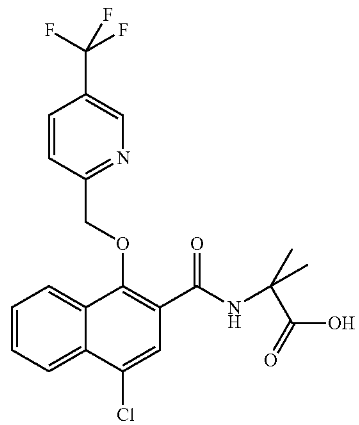 | 467.07 |
| 343 | 2-{[4-Chloro-1-(5-methyl-isoxazol-3-ylmethoxy)-naphthalene-2-carbonyl]-amino}-2-methyl-propionic acid | 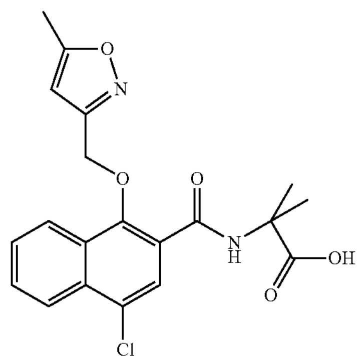 | 403.08 |
| 344 | 2-Methyl-2-{[1-(5-trifluoromethyl-pyridin-2-ylmethoxy)-naphthalene-2-carbonyl]-amino}-butyric acid | 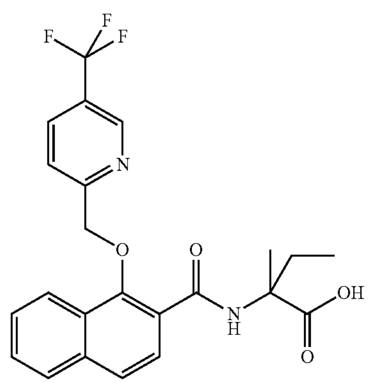 | 447.09 |
| 345 | 2-{[4-Chloro-1-(5-trifluoromethyl-pyridin-2-ylmethoxy)-naphthalene-2-carbonyl]-amino}-2-methyl-butyric acid | 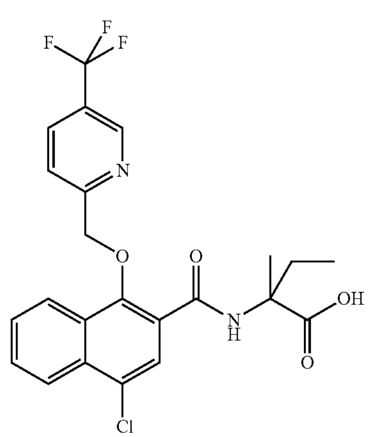 | 481.13 |

| No. | Chemical Name | Structure | ESI+ or ESI− |
|---|---|---|---|
| 346 | 2-({4-Fluoro-1-[1-(4-trifluoromethyl-phenyl)-ethoxy]-naphthalene-2-carbonyl}-amino)-2-methyl-propionic acid | 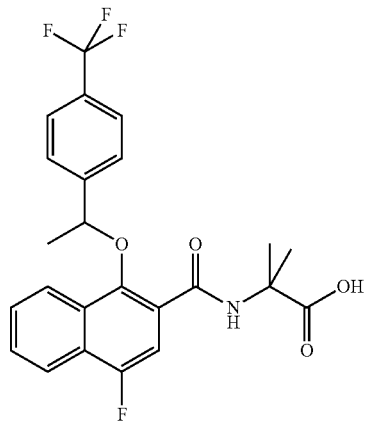 | 464.17 |
| 347 | 2-{[1-(4-Pentafluorothio)-benzyloxy)-naphthalene-2-carbonyl]-amino}-2-methyl-propionic acid | 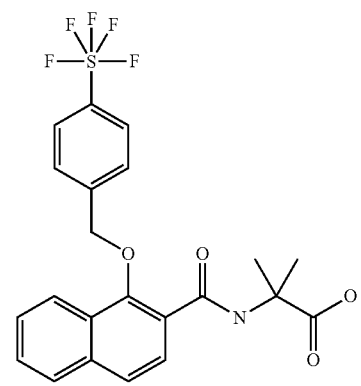 | 490.40 |

The following examples were prepared in analogy to example 3 via a sequence of an alkylation of a suitable (ortho-)hydroxy-arene-carboxylic ester with a corresponding alkylating agent, followed by a basic hydrolysis of this ester, and a coupling of the resulting acid with a corresponding amino acid ester using coupling reagents as for example EDC/HOBT, DIC/HOBT, HATU, TBTU/DMAP, and finally a basic hydrolysis of the amino acid ester to the free amino acid:

| No. | Chemical Name | Structure | ESI+ or ESI− |
|---|---|---|---|
| 348 | 1-{[3-(Benzothiazol-2-ylmethoxy)-benzo[b]thiophene-2-carbonyl]-amino}-cyclobutanecarboxylic acid | 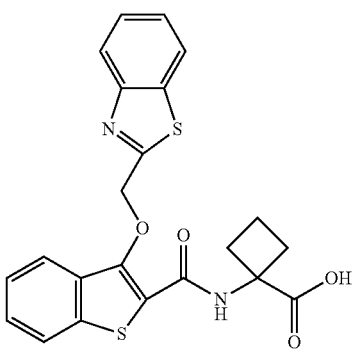 | 438.97 |

-continued

| No. | Chemical Name | Structure | ESI+ or ESI− |
|---|---|---|---|
| 349 | 2-{[3-(5-Fluoro-benzothiazol-2-ylmethoxy)-benzo[b]thiophene-2-carbonyl]-amino}-2-methyl-propionic acid | 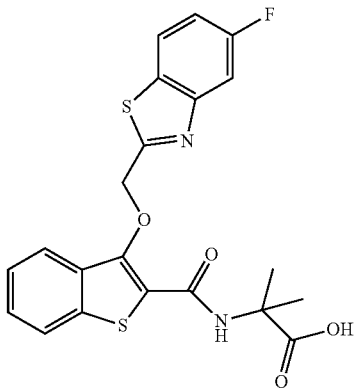 | 445.19 |
| 350 | 2-{[3-(Imidazo[1,2-a]pyridin-2-ylmethoxy)-benzo[b]thiophene-2-carbonyl]-amino}-2-methyl-propionic acid | 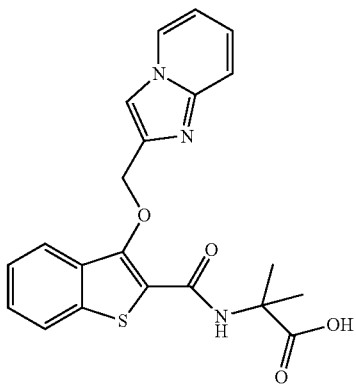 | 410.23 |
| 351 | 2-Methyl-2-({3-[1-(4-trifluoromethyl-phenyl)-ethoxy]-benzo[b]thiophene-2-carbonyl}-amino)-propionic acid | 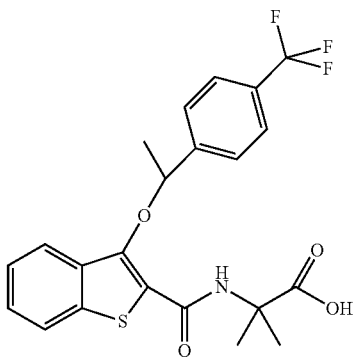 | 452.13 |
| 352 | 2-Methyl-2-({3-[1-(4-trifluoromethyl-phenyl)-ethoxy]-benzo[b]thiophene-2-carbonyl}-amino)-butyric acid | 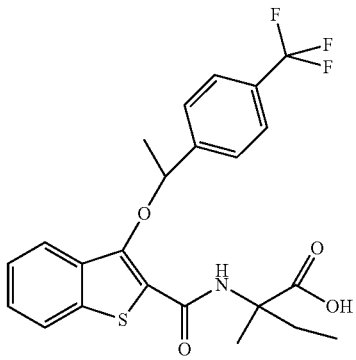 | 466.10 |

-continued
| No. Chemical Name | Structure | ESI+ or ESI− |
|---|---|---|
| 353 2-{[1-(Benzothiazol-2-ylmethoxy)-4-chloro-naphthalene-2-carbonyl]-amino}-2-ethyl-butyric acid | 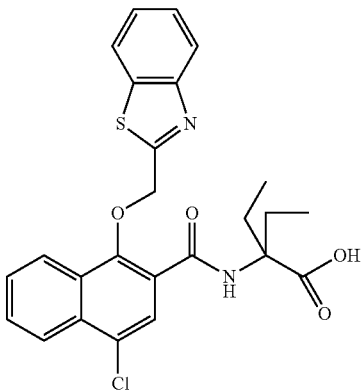 | 483.08 |
| 354 2-{[1-(Benzothiazol-2-ylmethoxy)-naphthalene-2-carbonyl]-amino}-2-ethyl-butyric acid | 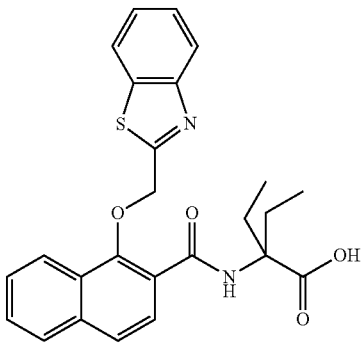 | 449.12 |
| 355 2-{[4-Chloro-1-(2-fluoro-4-trifluoromethyl-benzyloxy)-naphthalene-2-carbonyl]-amino}-2-methyl-butyric acid | 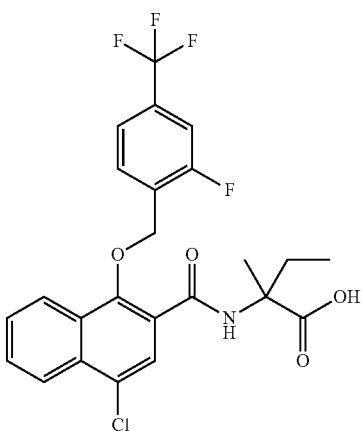 | 498.12 |

-continued

| No. | Chemical Name | Structure | ESI+ or ESI− |
|---|---|---|---|
| 356 | 2-{[4-Chloro-1-(6-trifluoromethyl-pyridin-3-ylmethoxy)-naphthalene-2-carbonyl]-amino}-2-ethyl-butyric acid | 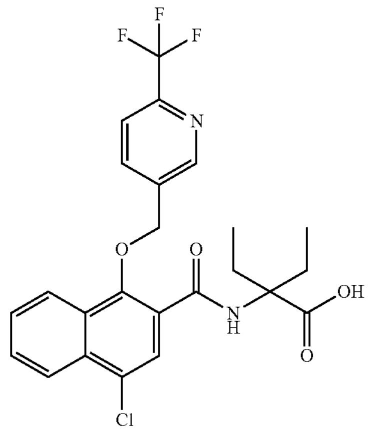 | 495.10 |
| 357 | 2-Ethyl-2-{[1-(6-trifluoromethyl-pyridin-3-ylmethoxy)-naphthalene-2-carbonyl]-amino}-butyric acid | 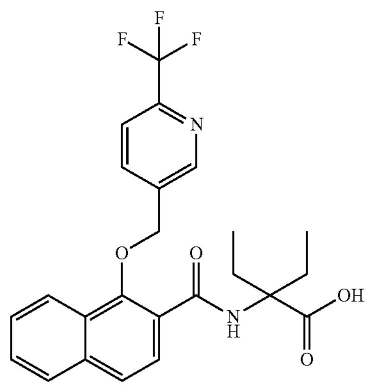 | 461.14 |
| 358 | 2-{[4-Fluoro-1-(4-trifluoromethylsulfanyl-benzyloxy)-naphthalene-2-carbonyl]-amino}-2-methyl-propionic acid | 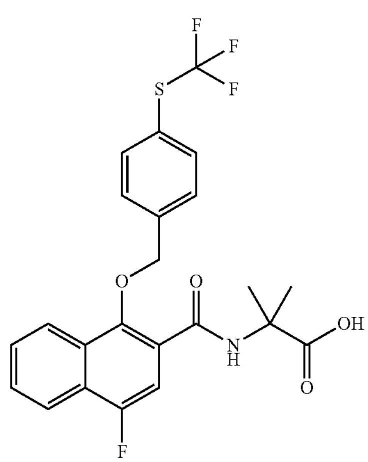 | 480.08 (ESI−) |

| No. | Chemical Name | Structure | ESI+ or ESI− |
|---|---|---|---|
| 359 | 2-{[1-(4-Trifluoromethyl-benzyloxy)-naphthalene-2-carbonyl]-amino}-pentanoic acid | 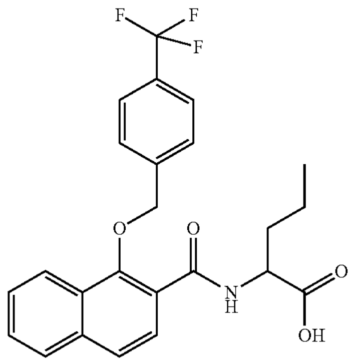 | 446.09 |
| 360 | 3-Thiophen-2-yl-2-{[1-(4-trifluoromethyl-benzyloxy)-naphthalene-2-carbonyl]-amino}-propionic acid | 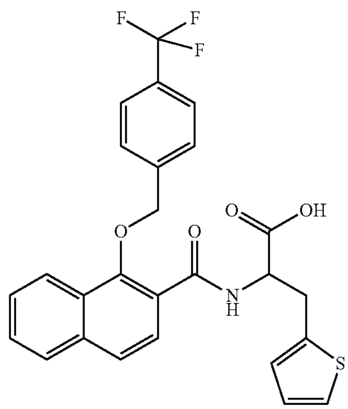 | 500.01 |
| 361 | (S)-3-Methyl-2-{[1-(4-trifluoromethyl-benzyloxy)-naphthalene-2-carbonyl]-amino}-butyric acid | CHIRAL | 446.09 |
| 362 | (S)-4-Methylsulfanyl-2-{[1-(4-trifluoromethyl-benzyloxy)-naphthalene-2-carbonyl]-amino}-butyric acid | CHIRAL | 478.06 |

Example 363

2-{[1-(Phenylethynyl)-naphthalene-2-carbonyl]-amino}-2-methyl-propionic acid

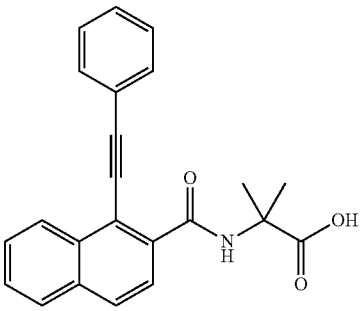

a) 2-{[1-(Phenylethynyl)-naphthalene-2-carbonyl]-amino}-2-methyl-propionic acid methyl ester 40 mg 2-[(1-Bromo-naphthalene-2-carbonyl)amino]-2-methyl-propionic acid methyl ester and 2 mg Bis(triphenylphosphine)palladium(II)chloride were suspended in 2 ml of DMF and deoxygenated with Argon. 0.26 ml of TMEDA were added, the mixture was again bubbled with Argon, and then 14 mg (0.137 mmol) phenylacetylene were added. After 14 h at 80° the reaction was filtered, purified by RP-HPLC and freeze-dried to give 8 mg of 2-{[1-(Phenylethynyl)-naphthalene-2-carbonyl]-amino}-2-methyl-propionic acid methyl ester (19%).

b) 2-{[1-(Phenylethynyl)-naphthalene-2-carbonyl]-amino}-2-methyl-propionic acid 8 mg 2-{[1-(phenylethynyl)-naphthalene-2-carbonyl]-amino}-2-methyl-propionic acid methyl ester were dissolved in 3 ml of MeOH and 1 ml of water was added. After addition of 1.95 mg of LiOH.H$_2$O the reaction was stirred at room temperature for 14 h. Filtration of the crude mixture, RP-HPLC and freeze-drying gave 6.8 mg of 2-{[1-(phenylethynyl)-naphthalene-2-carbonyl]-amino}-2-methyl-propionic acid (89%).

$C_{23}H_{19}NO_3$ (357.41), LCMS (ESI): 358.19 (MH$^+$).

The following examples were prepared in analogy to example 363:

| No | Chemical Name | Structure | ESI+ or ESI− |
|---|---|---|---|
| 364 | (S)-2-[(1-Phenylethynyl-naphthalene-2-carbonyl)-amino]-propionic acid | 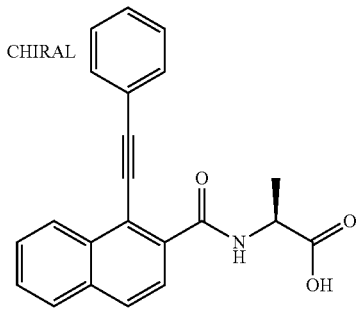 CHIRAL | 344.18 |
| 365 | 2-{[1-(4-Chloro-phenylethynyl)-naphthalene-2-carbonyl]-amino}-2-methyl-propionic acid | 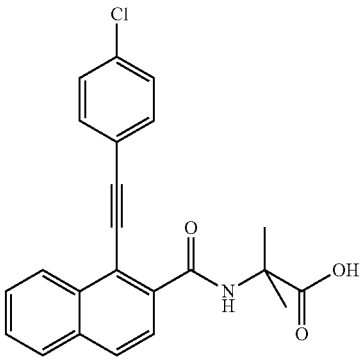 | 392.19 |

-continued

| No | Chemical Name | Structure | ESI+ or ESI− |
|----|---------------|-----------|--------------|
| 366 | (S)-2-{[1-(4-Chloro-phenylethynyl)-naphthalene-2-carbonyl]-amino}-propionic acid | 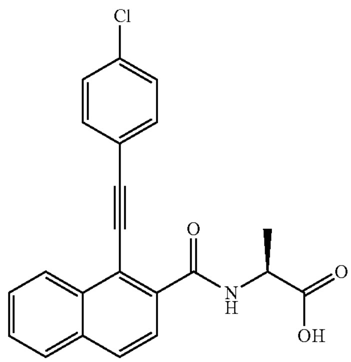 | 378.17 |
| 367 | 2-{[1-(4-Fluoro-phenylethynyl)-naphthalene-2-carbonyl]-amino}-2-methyl-propionic acid | 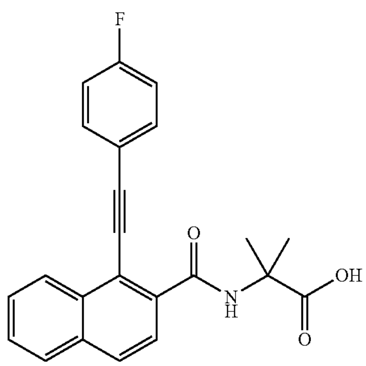 | 376.19 |
| 368 | 2-{[1-(4-Methoxy-phenylethynyl)-naphthalene-2-carbonyl]-amino}-2-methyl-propionic acid | 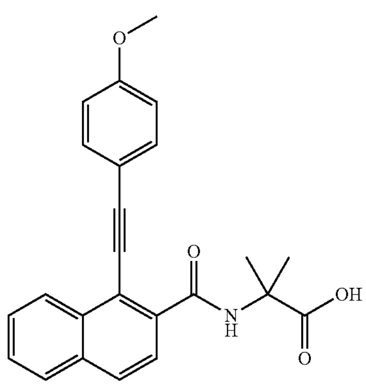 | 388.21 |
| 369 | 1-{[1-(4-Chloro-phenylethynyl)-naphthalene-2-carbonyl]-amino}-cyclopentanecarboxylic acid | 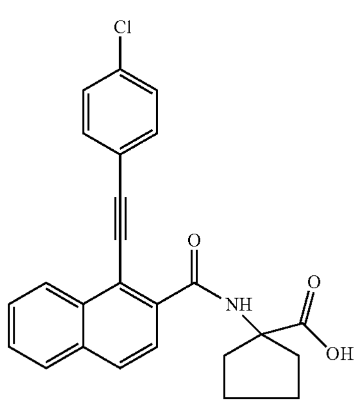 | 418.23 |

-continued
| No | Chemical Name | Structure | ESI+ or ESI– |
|---|---|---|---|
| 370 | (S)-2-{[1-(4-Chloro-phenylethynyl)-naphthalene-2-carbonyl]-amino}-3-methyl-butyric acid | 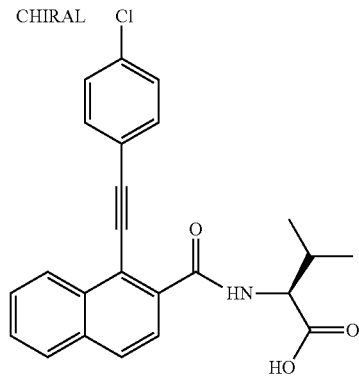 | 406.17 |
| 371 | (S)-2-{[1-(4-Methoxy-phenylethynyl)-naphthalene-2-carbonyl]-amino}-3-methyl-butyric acid | 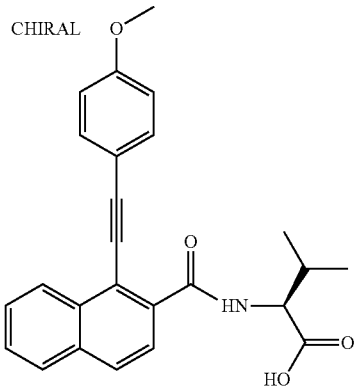 | 402.26 |
| 372 | 1-[(1-Phenylethynyl-naphthalene-2-carbonyl)-amino]-cyclopentanecarboxylic acid | 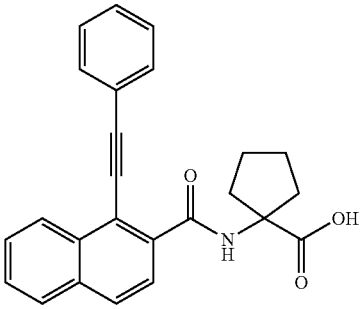 | 384.11 |
| 373 | 1-{[1-(4-Methoxy-phenylethynyl)-naphthalene-2-carbonyl]-amino}-cyclopentanecarboxylic acid | 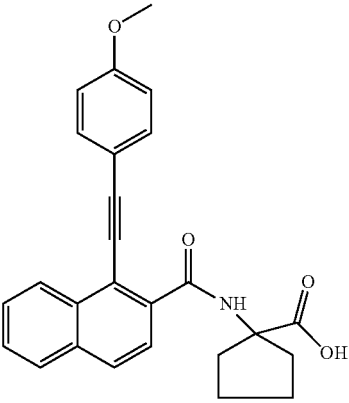 | 414.32 |

Example 374

2-Methyl-2-[(1-phenethyl-naphthalene-2-carbonyl)-amino]-propionic acid

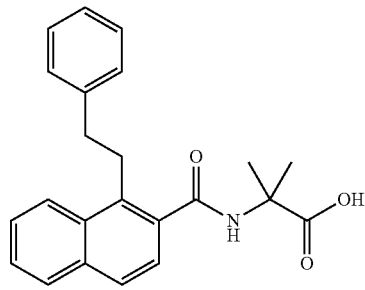

17 mg 2-{[1-(phenylethynyl)-naphthalene-2-carbonyl]-amino}-2-methyl-propionic acid were dissolved in 4 ml of MeOH, 19 mg 10% Pd on charcoal were added and the mixture hydrogenated at room temperature for 14 h. Filtration, RP-HPLC and freeze-drying gave 3.2 mg of 2-Methyl-2-[(1-phenethyl-naphthalene-2-carbonyl)-amino]-propionic acid (18%).

$C_{23}H_{23}NO_3$ (361.44), LCMS (ESI): 362.15 (MH$^+$).

The following examples were prepared in analogy to example 374:

Example 377

2-({1-[(E)-2-(4-Chloro-phenyl)-vinyl]-naphthalene-2-carbonyl}-amino)-2-methyl-propionic acid

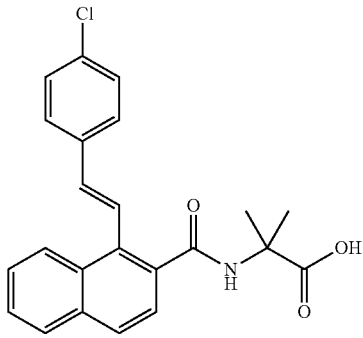

a) 2-({1-[(E)-2-(4-Chloro-phenyl)-vinyl]-naphtha-lene-2-carbonyl}-amino)-2-methyl-propionic acid methyl ester 50 mg 2-[(1-bromo-naphthalene-2-carbonyl)amino]-2-methyl-propionic acid methyl ester, 49.5 mg tetrakis(triph-enylphosphine)palladium (0), 28.7 mg trans-2-(4-chloro-phenyl)vinylboronic acid and 43 mg CsF were suspended in 1 ml of MeOH and 3 ml of dimethoxyethane, deoxygenated with Argon, and heated to 80° for 14 h. The reaction was

| No | Chemical Name | Structure | ESI+ or ESI− |
|---|---|---|---|
| 375 | 1-[(1-Phenethyl-naphthalene-2-carbonyl)-amino]-cyclopentanecarboxylic acid | 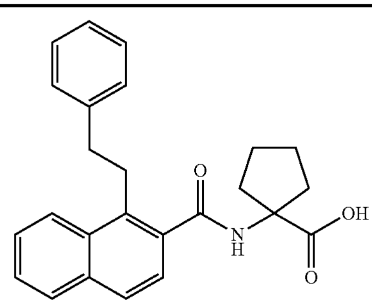 | 388.13 |
| 376 | 2-({1-[2-(4-Methoxy-phenyl)-ethyl]-naphthalene-2-carbonyl}-amino)-2-methyl-propionic acid | | 392.12 | filtered, purified by RP-HPLC and freeze-dried to give 38 mg of 2-({1-[(E)-2-(4-Chloro-phenyl)-vinyl]-naphthalene-2-carbonyl}-amino)-2-methyl-propionic acid methyl ester (65%).

b) 2-({1-[(E)-2-(4-Chloro-phenyl)-vinyl]-naphthalene-2-carbonyl}-amino)-2-methyl-propionic acid 38 mg 2-({1-[(E)-2-(4-chloro-phenyl)-vinyl]-naphthalene-2-carbonyl}-amino)-2-methyl-propionic acid methyl ester were dissolved in 3 ml of MeOH and 1 ml of water was added. After addition of 5 mg of LiOH.H$_2$O the reaction was stirred at room temperature for 14 h. Filtration of the crude mixture, RP-HPLC and freeze-drying gave 35 mg of 2-({1-[(E)-2-(4-Chloro-phenyl)-vinyl]-naphthalene-2-carbonyl}-amino)-2-methyl-propionic acid (96%).

C$_{23}$H$_{20}$ClNO$_3$ (393.87), LCMS (ESI): 394.07 (MH$^+$).

Example 378

2-({1-[(E)-2-(4-Fluoro-phenyl)-vinyl]-naphthalene-2-carbonyl}-amino)-2-methyl-propionic acid

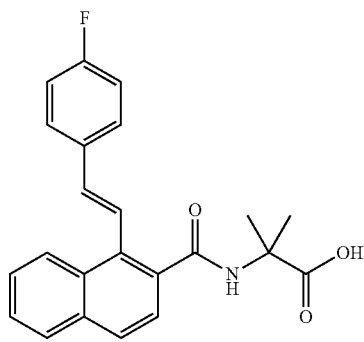

2-({1-[(E)-2-(4-Fluoro-phenyl)-vinyl]-naphthalene-2-carbonyl}-amino)-2-methyl-propionic acid was prepared in analogy to example 377 (2-({1-[(E)-2-(4-Chloro-phenyl)-vinyl]-naphthalene-2-carbonyl}-amino)-2-methyl-propionic acid)

C$_{23}$H$_{20}$FNO$_3$ (377.42), LCMS (ESI): 378.09 (MH$^+$).

Example 379

2-({1-[(E)-2-(4-Isopropyl-phenyl)-vinyl]-naphthalene-2-carbonyl}-amino)-2-methyl-propionic acid

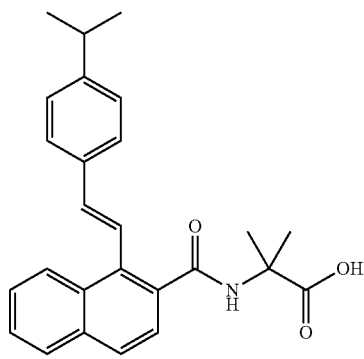

a) 2-({1-[(E)-2-(4-Isopropyl-phenyl)-vinyl]-naphthalene-2-carbonyl}-amino)-2-methyl-propionic acid methyl ester According to the general procedure described in Org. Lett. 2001, 3(26), 4295-4298 26.6 mg Pd2(dba)3 and 17.1 mg [(tBu)3PH]BF4 were evacuated and flushed with argon several times. Then 205 mg 2-[(1-bromo-naphthalene-2-carbonyl)-amino]-2-methyl-propionic acid methyl ester were dissolved in 2 ml of dioxane, 171 mg 4-isopropylstyrene and 126 mg (0.645 mmol) dicyclohexylmethylamine were added, and the mixture was deoxygenated with argon. This mixture was added to the mixture of catalyst and phosphine at room temperature, and the resulting reaction stirred at room temperature for 14 h. The reaction mixture was directly purified on silica gel to yield 210 mg 2-({1-[(E)-2-(4-Isopropyl-phenyl)-vinyl]-naphthalene-2-carbonyl}-amino)-2-methyl-propionic acid methyl ester (86%).

b) 2-({1-[(E)-2-(4-Isopropyl-phenyl)-vinyl]-naphthalene-2-carbonyl}-amino)-2-methyl-propionic acid 207 mg 2-({1-[(E)-2-(4-isopropyl-phenyl)-vinyl]-naphthalene-2-carbonyl}-amino)-2-methyl-propionic acid methyl ester were dissolved in 6 ml of MeOH and 2 ml of water was added. After addition of 114 mg of LiOH.H$_2$O the reaction was stirred at room temperature for 14 h. Filtration of the crude mixture, RP-HPLC and freeze-drying gave 104 mg of 2-({1-[(E)-2-(4-isopropyl-phenyl)-vinyl]-naphthalene-2-carbonyl}-amino)-2-methyl-propionic acid (42%).

C$_{26}$H$_{27}$NO$_3$ (401.51), LCMS (ESI): 402.12 (MH$^+$).

The following examples were prepared in analogy to example 379:

| Chemical No Name | Structure | ESI+ or ESI− |
|---|---|---|
| 380 2-({1-[(E)-2-(4-Methoxy-phenyl)-vinyl]-naphthalene-2-carbonyl}-amino)-2-methyl-propionic acid | | 390.10 |

-continued

| No | Chemical Name | Structure | ESI+ or ESI− |
|---|---|---|---|
| 381 | 2-({1-[(E)-2-(4-Ethoxy-phenyl)-vinyl]-naphthalene-2-carbonyl}-amino)-2-methyl-propionic acid | 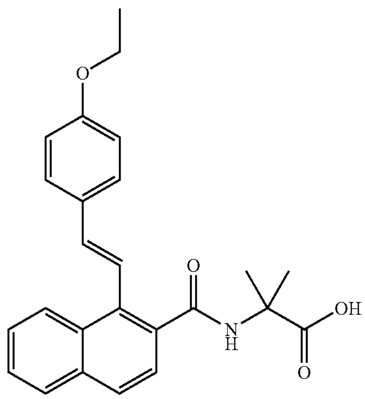 | 404.15 |
| 382 | 2-Methyl-2-({1-[(E)-2-(4-trifluoro-methyl-phenyl)-vinyl]-naphthalene-2-carbonyl}-amino)-propionic acid | 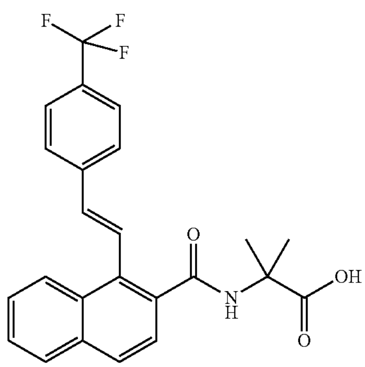 | 428.08 |
| 383 | 2-Methyl-2-{[1-(4-trifluoro-methyl-phenyl-ethynyl)-naphthalene-2-carbonyl]-amino}-propionic acid | 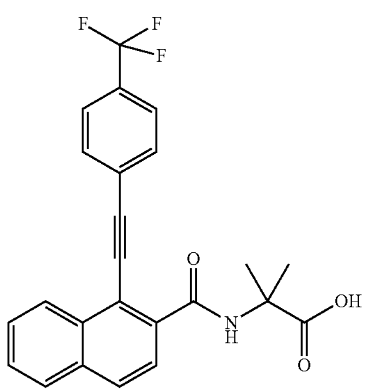 | 426.05 |

Example 384

2-Methyl-2-{[1-(4-trifluoromethyl-benzylamino)-naphthalene-2-carbonyl]-amino}-propionic acid

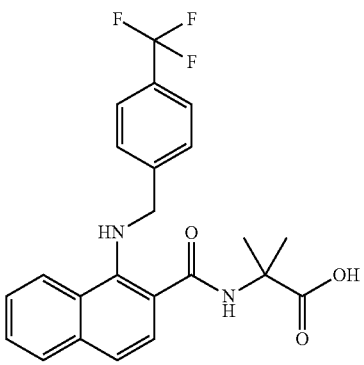

a) 2-Methyl-2-[(1-trifluoromethanesulfonyloxy-naphthalene-2-carbonyl)-amino]-propionic acid methyl ester 2-[(1-Hydroxy-naphthalene-2-carbonyl)-amino]-2-methyl-propionic acid methyl ester (1.07 g) was dissolved in dichloromethane (15 ml). At 0° C. trifluoromethane sulfonic acid anhydride (0.785 ml) was added, followed by slow addition of triethylamine (1.03 ml). The reaction was kept under stirring for 30 min. It was diluted with dichloro-methane (100 ml), which was washed with 5% NaHCO$_3$ (25 ml), 1N hydrochloric acid (25 ml) and brine (25 ml), and then dried over sodium sulphate. The solvent was removed in vacuo, and the residue was purified by silica gel chromatography. 1.00 g of 2-methyl-2-[(1-trifluoromethanesulfonyloxy-naphthalene-2-carbonyl)-amino]-propionic acid methyl ester was obtained as a white solid.

$C_{17}H_{16}F_3NO_6S$ (419.38), LCMS (ESI): 420.06 (MH$^+$).

b) 2-Methyl-2-{[1-(4-trifluoromethyl-benzylamino)-naphthalene-2-carbonyl]-amino}-propionic acid methyl ester 2-Methyl-2-[(1-trifluoromethanesulfonyloxy-naphthalene-2-carbonyl)-amino]-propionic acid methyl ester (142 mg), 4-trifluoromethyl benzyl amine (119 mg) and a catalytic amount of palladium acetate and BINAP, together with cesium carbonate (277 mg) in THF (3 ml) were heated in a microwave reactor for 55 min at 80° C. The reaction mixture was diluted with ethyl acetate (60 ml), which was washed with water (25 ml) and brine (10 ml) and then dried over sodium sulfate. The solvent was removed in vacuo, and the residue was purified by silica gel chromatography. 142 mg of 2-methyl-2-{[1-(4-trifluoromethyl-benzylamino)-naphthalene-2-carbonyl]-amino}-propionic acid methyl ester was obtained as light yellow oil.

$C_{24}H_{23}F_3N_2O_3$ (444.46), LCMS (ESI): 445.13 (MH$^+$).

c) 2-Methyl-2-{[1-(4-trifluoromethyl-benzylamino)-naphthalene-2-carbonyl]-amino}-propionic acid 140 mg 2-methyl-2-{[1-(4-trifluoromethyl-benzylamino)-naphthalene-2-carbonyl]-amino}-propionic acid methyl ester in 2 ml methanol and 1 ml 1 M aqueous sodium hydroxide solution was refluxed for 0.5 h. The reaction was acidified with 2 M hydrochloric acid, and the precipitated product was collected by filtration, dissolved in ethyl acetate, dried over sodium sulphate, filtrated, concentrated in vacuo, and the resulting crude product was purified by silica gel chromatography to yield 0.09 g 2-methyl-2-{[1-(4-trifluoromethyl-benzylamino)-naphthalene-2-carbonyl]-amino}-propionic acid.

$C_{23}H_{21}F_3N_2O_3$ (430.43), LCMS (ESI): 431.13 (MH$^+$).

Preparation of Intermediates:

(R)-2-Amino-2-methyl-butyric acid methyl ester hydrochloride

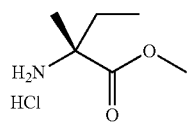

(R)-2-Amino-2-methyl-butyric acid was prepared according to the method described in Synlett, 1996, 1051 a) (R)-3-Methyl-5-phenyl-5,6-dihydro-[1,4]oxazin-2-one

Ethyl pyruvate (10.0 g) was added to a room temperature solution of (R)-phenylglycinol (10.0 g) over 4 A mol. sieves (36.5 g) in 2,2,2-trifluoroethanol (100 mL). The resulting mixture was heated at reflux for 72 h. The reaction mixture was cooled to room temperature, filtered, and concentrated in vacuo to give 18.3 g of a brown oil. Purification of the residue by flash chromatography (silica, ethyl acetate/heptane) afforded 4.70 g (34% yield) of (R)-3-methyl-5-phenyl-5,6-dihydro-[1,4]oxazin-2-one as an orange glass.

$C_{11}H_{11}NO_2$ (189.22) MS (ESI): 190 (MH+).

b) (3R,5R)-3-Ethyl-3-methyl-5-phenyl-morpholin-2-one

Freshly distilled boron trifluoride etherate (5.20 mL) was added to a solution of (R)-3-methyl-5-phenyl-5,6-dihydro-[1,4]oxazin-2-one (2.57 g) in THF (60 mL) at −78° C. The resulting mixture was stirred at −78° C. for 1 h, then it was treated with ethyl magnesium bromide (40.0 mL of a 1.0 M solution in THF). The reaction mixture was stirred at −78° C. for 2 h, and then allowed to warm to room temperature and stirred for 24 h. The reaction mixture was quenched with water, diluted with ethyl acetate (200 mL) and was washed with aqueous sat. sodium hydrogen carbonate solution (2×200 mL) and brine (200 mL). The aqueous layers were re-extracted with ethyl acetate (2×200 mL). The combined organic layers were dried (sodium sulphate), combined, and concentrated in vacuo to give 3.60 g of a brown oil. Purification of the residue by flash chromatography (silica, ethyl acetate/heptanes) afforded 2.09 g (70% yield) of (3R,5R)-3-Ethyl-3-methyl-5-phenyl-morpholin-2-one as an off-white powder.

$C_{13}H_{17}NO_2$ (219.29) LCMS (ESI): 220 (MH$^+$).

c) (R)-2-Amino-2-methyl-butyric acid

Palladium hydroxide (0.15 g) was added under N$_2$ to a room temperature solution of (3R,5R)-3-ethyl-3-methyl-5-phenyl-morpholin-2-one (0.15 g) in MeOH (10 mL), H$_2$O (1 mL) and TFA (0.060 mL). The resulting mixture was hydrogenated at 65 psi for 48 h. The reaction mixture was filtered through a short pad of celite and concentrated in vacuo to give 0.22 g of a brown oil. Purification of the residue by flash chromatography (silica, MeOH/ethyl acetate) afforded 0.075 g (91% yield) of (R)-2-amino-2-methyl-butyric acid as a colorless solid.

$C_5H_{11}NO_2$ (117.15) LCMS (ESI): 118 (MH$^+$).

d) (R)-2-amino-2-methyl-butyric acid methyl ester hydrochloride

Thionyl chloride (0.50 mL) was added dropwise to dry MeOH (2 mL) at −10° C. After stirring at −10° C. for 1 h, a 0° C. solution of (R)-2-amino-2-methyl-butyric acid (0.068 g) in MeOH (1 mL) was added, and the mixture was allowed to warm to room temperature, and was stirred for an additional 24 h. The reaction mixture was concentrated in vacuo, repeatedly diluted with toluene (50 mL) and reconcentrated in vacuo to give 0.076 g (quant. yield) of (R)-2-amino-2-methyl-butyric acid methyl ester hydrochloride as a light yellow solid.

$C_6H_{13}NO_2$ (131.18) MS (ESI): 132 (MH$^+$).

(S)-2-Amino-2-methyl-butyric acid methyl ester hydrochloride

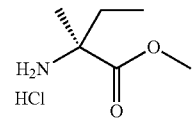

(S)-2-Amino-2-methyl-butyric acid methyl ester hydrochloride was prepared in analogous manner to (R)-2-amino-2-methyl-butyric acid methyl ester hydrochloride using (S)-phenylglycinol.

$C_6H_{13}NO_2$ (131.18) MS (ESI): 132 (MH$^+$).

4-Fluoro-1-hydroxynaphthalene-2-carboxylic acid

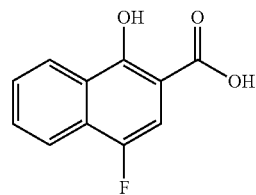

a) 4-Fluoro-naphthalene-1-carbaldehyde 19.9 g Dichloromethyl methyl ether and 45.7 g tin chloride were dissolved in 70 mL dichloromethane. The solution was cooled to +5° C. and 20.0 g fluoronaphthalene in dichloromethane (49 mL) was added over a 60 min period, while keeping the temperature at 5° C. The reaction was brought to room temperature after the addition. After 4 h the reaction was quenched by slowly pouring it into an ice/water mixture. This mixture was stirred for 15 min and left standing overnight. The dichloromethane layer was washed with water, dried (sodium sulfate), filtered through celite and concentrated in vacuo to obtain 24.0 g of 4-fluoro-naphthalene-1-carbaldehyde as an off white solid.

b) 4-Fluoro-naphthalen-1-ol 23.3 g of 4-fluoro-naphthalene-1-carbaldehyde were dissolved in 200 mL dichloromethane. 65.9 g MCPBA was added neat in portions over a 15 min period, 70 mL additional dichloromethane was added and the reaction was stirred overnight at ambient temperature. Then, the reaction mixture was filtered and the solid was washed with dichloromethane. Heptane was added and the mixture filtrated several times, then the combined filtrates were concentrated and taken up in ethyl acetate. This was shaken with 10% sodium thiosulfate (100 mL). The organic layer was separated, washed water and brine, dried over sodium sulfate, filtered and concentrated to yield 27.3 g of the formate ester as a viscous oil, which was dissolved in MeOH (80 mL), treated with KOH (7.5 g) in a methanol solution (30 mL) for 15 min at 5° C. and was then left stirring at ambient temperature for 3 h, before the solvent was removed in vacuo. The resulting oil was treated with 6N HCl (40 mL) to obtain a pH of 2-3. Water (60 mL) was added) and the aqueous phase was extracted 3× with ethyl acetate (35 mL). The extracts were washed with water (2×20 mL) and concentrated to yield 23.7 g of 4-fluoro-naphthalen-1-ol, which was used without further purification.

c) 4-Fluoro-1-methoxynaphthalene 21.7 g of 4-Fluoro-naphthalen-1-ol were dissolved in 250 mL acetone. 39.0 g of potassium carbonate and 14.6 mL dimethyl sulfate were added at room temperature. The reaction was placed under nitrogen and stirred for 72 h. The mixture was filtrated, the solid washed with acetone, and the filtrate was concentrated to a viscous oil, which was taken up in ethyl acetate. This was washed with water and with brine, dried over sodium sulfate, filtered through celite and concentrated. The resulting oil was distilled using a Kugelrohr-apparatus, yielding 11.4 g of 4-fluoro-1-methoxynaphthalene.

d) 4-Fluoro-1-methoxynaphthalene-2-carbaldehyde 5.25 mL of dichloromethyl methyl ether were dissolved in 40 mL dichloromethane and cooled to +5° C. 6.75 mL tin(IV) chloride were added neat over 45 min to the solution. After the addition the mixture was stirred for 45 min at 5° C. 11.4 g 4-fluoro-1-methoxynaphthalene in 30 mL dichloromethane was added over 1 h. Then the cooling bath was removed, and the mixture was stirred for 2 h at ambient temperature. It was then poured into ice/water. The dichloromethane layer was separated and the aqueous phase was extracted with dichloromethane. The combined dichloromethane layers were washed with water, dried over sodium sulfate, filtered through celite and concentrated in vacuo. The residue was treated with pentane to yield 9.3 g of 4-fluoro-1-methoxynaphthalene-2-carbaldehyde as a brown solid.

e) 4-Fluoro-1-methoxynaphthalene-2-carboxylic acid 9.3 g of 4-fluoro-1-methoxynaphthalene-2-carbaldehyde were dissolved in 100 mL of acetonitrile. 2.1 g sodium dihydrogenphosphate monohydrate in 10 mL of water were added, followed by the addition of 9.5 mL hydrogen peroxide (30%). 8.9 g sodium chlorite, dissolved in 20 mL water were added dropwise while maintaining an internal temperature between 5° C. and 15° C. The reaction was then allowed to come to room temp over 2.5 h. The precipitated solid was filtered with suction, and the solid was washed with water, and dried in vacuo at 40° C. to yield 9.4 g of 4-fluoro-1-methoxynaphthalene-2-carboxylic acid. The filtrate was treated with 60 mL of cold 10% aqueous sodium bisulfite solution. The aqueous layer was extracted with ethyl acetate. The combined organic layers were washed with water and brine. The organic layer was washed with 0.2 N NaOH twice. The washes were acidified with 6 N HCl to pH 3, whereupon crystallization occurred. The precipitating product was filtered, washed with water and dried in vacuo at 40° C. to yield a second batch of 1.0 g of 4-fluoro-1-methoxynaphthalene-2-carboxylic acid.

f) 4-Fluoro-1-hydroxynaphthalene-2-carboxylic acid

To 10.1 g 4-fluoro-1-methoxynaphthalene-2-carboxylic acid 55 mL HBr/HOAc were added and the mixture was stirred and heated. After 30 min at 60° C. another 7.5 mL of HBr/HOAc were added, and after an additional 30 min at 80° C. the mixture was cooled to ambient temperature and left standing overnight. The reaction was then poured into ice/water and the precipitated solid was filtered and washed with water, followed by 1% ether in heptane and then by heptane. The solid was dried in vacuo at 40° C. to yield 7.7 g 4-fluoro-1-hydroxynaphthalene-2-carboxylic acid.

$C_{11}H_7FO_3$ (206.18), LCMS: (ESI$^+$): 207.2 (MH$^+$).

4-Chloro-1-hydroxy-naphthalene-2-carboxylic acid

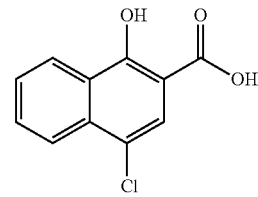

To a suspension of 30.0 g 1-Hydroxy-naphthalene-2-carboxylic acid in 600 ml chloroform a mixture of 14.9 ml sulfuryl chloride and 20 ml chloroform was added dropwise. After stirring the reaction for 8 h at room temperature the precipitated product was isolated by filtration, washed with dichloromethane and recrystallized from isopropanol/water to yield 25.1 g of 4-chloro-1-hydroxy-naphthalene-2-carboxylic acid as off-white solid.

$C_{11}H_7ClO_3$ (222.63, LCMS (ESI): 223.00 (MH$^+$).

4-Bromo-1-hydroxy-naphthalene-2-carboxylic acid

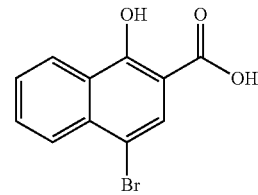

To a solution of 2.50 g 1-hydroxy-2-naphthoic acid in 50 mL chloroform a solution of 0.68 mL bromine in 5 mL chloroform was added dropwise. After 16 h the reaction was concentrated to yield 3.40 g 4-bromo-1-hydroxy-naphthalene-2-carboxylic acid.

$C_{11}H_7BrO_3$ (267.08, LCMS (ESI): 268.95 (MH$^+$).

2-[(1-Bromo-naphthalene-2-carbonyl)amino]-2-methyl-propionic acid methyl ester

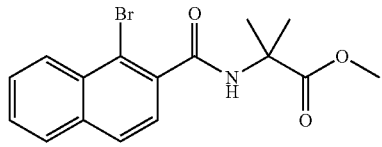

1.0 g 1-Bromo-naphthalene-2-carboxylic acid and 0.61 g 2,2-dimethylglycine methyl ester hydrochloride were suspended in 30 ml of dichloromethane and 10 ml of DMF. 1.31 ml N-methylmorpholine, 0.70 g 1-hydroxybenzotriazole and, finally, 0.99 g 1-(3-dimethylaminopropyl)-3-ethylcarbodiimide hydrochloride were added and the reaction stirred at room temperature for 14 h. The reaction mixture was chromatographed on silica gel without aqueous work-up to give 1.3 g 2-[(1-bromo-naphthalene-2-carbonyl)-amino]-2-methyl-propionic acid methyl ester (93%).

(S)-2-[(1-Bromo-naphthalene-2-carbonyl)amino]-propionic acid methyl ester, (S)-2-[(1-Bromo-naphthalene-2-carbonyl)amino]-3-methyl-butyric acid methyl ester and 1-[(1-Bromo-naphthalene-2-carbonyl)-amino]-cyclopentanecarboxylic acid methyl ester were prepared in analogous manner.

The following intermediates were prepared in analogy to the preparation of Example 1, step a) (2-[(4-Bromo-1-hydroxy-naphthalene-2-carbonyl)-amino]-2-methyl-propionic acid methyl ester) from the corresponding 1-Hydroxy-naphthalene-2-carboxylic acids and the corresponding alpha-amino acid methyl or ethyl esters:

4,4,4-Trifluoro-2-[(1-hydroxy-naphthalene-2-carbonyl)-amino]-butyric acid methyl ester

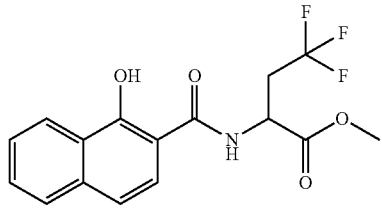

$C_{16}H_{14}F_3NO_4$ (341.29), LCMS (ESI): 342.35 (MH$^+$).

2-[(1-Hydroxy-naphthalene-2-carbonyl)-amino]-butyric acid ethyl ester

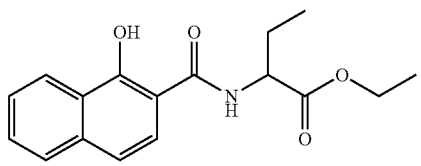

$C_{17}H_{19}NO_4$ (301.35), LCMS (ESI): 302.08 (MH$^+$).

2-[(1-Hydroxy-naphthalene-2-carbonyl)-amino]-2-methyl-butyric acid methyl ester

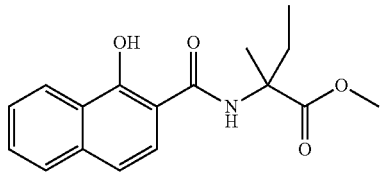

$C_{17}H_{19}NO_4$ (301.35), LCMS (ESI): 302.15 (MH$^+$).

(R)-2-[(1-Hydroxy-naphthalene-2-carbonyl)-amino]-2-methyl-butyric acid methyl ester

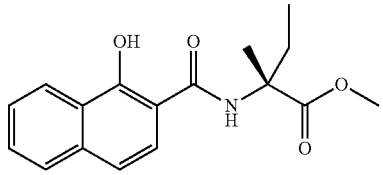

$C_{17}H_{19}NO_4$ (301.35), LCMS (ESI): 302.15 (MH$^+$).

(S)-2-[(1-Hydroxy-naphthalene-2-carbonyl)-amino]-2-methyl-butyric acid methyl ester

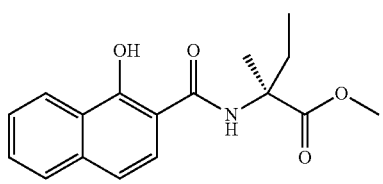

$C_{17}H_{19}NO_4$ (301.35), LCMS (ESI): 302.15 (MH$^+$).

2-[(1-Hydroxy-naphthalene-2-carbonyl)-amino]-2,3-dimethyl-butyric acid methyl ester

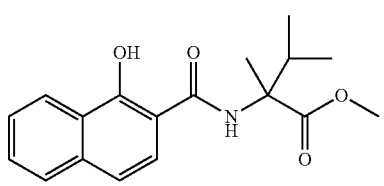

$C_{18}H_{21}NO_4$ (315.37), LCMS (ESI): 316.2 (MH$^+$).

2-Ethyl-2-[(1-hydroxy-naphthalene-2-carbonyl)-
amino]-hexanoic acid ethyl ester

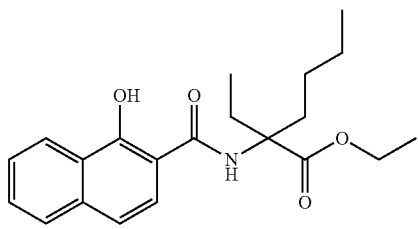

C₂₁H₂₇NO₄ (357.45), LCMS (ESI): 358.21 (MH⁺).

2-[(1-Hydroxy-naphthalene-2-carbonyl)-amino]-2-
methyl-3-phenyl-propionic acid methyl ester

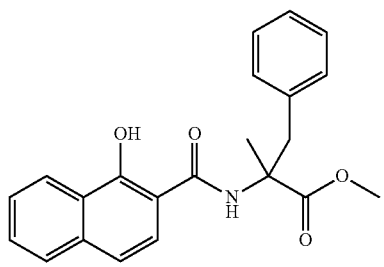

C₂₂H₂₁NO₄ (363.42), LCMS (ESI): 364.10 (MH⁺).

1-[(1-Hydroxy-naphthalene-2-carbonyl)-amino]-
cyclopropanecarboxylic acid ethyl ester

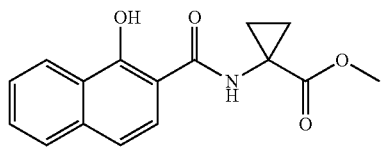

C₁₆H₁₅NO₄ (285.30), LCMS (ESI): 286.1 (MH⁺).

1-[(1-Hydroxy-naphthalene-2-carbonyl)-amino]-
cyclobutanecarboxylic acid ethyl ester

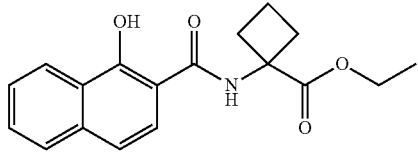

C₁₈H₁₉NO₄ (313.36), LCMS (ESI): 314.12 (MH⁺).

2-[(4-Chloro-1-hydroxy-naphthalene-2-carbonyl)-
amino]-2-methyl-propionic acid methyl ester

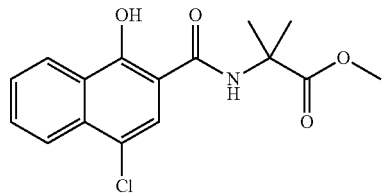

C₁₆H₁₆ClNO₄ (321.76, LCMS (ESI): 322.05 (MH⁺).

2-[(4-Chloro-1-hydroxy-naphthalene-2-carbonyl)-
amino]-2-methyl-butyric acid methyl ester

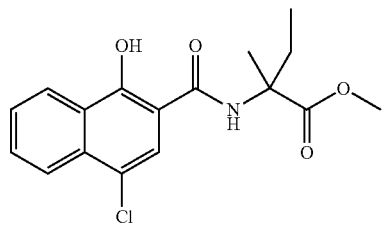

C₁₇H₁₈ClNO₄ (335.79), LCMS (ESI): 336.05 (MH⁺).

1-[(4-Chloro-1-hydroxy-naphthalene-2-carbonyl)-
amino]-cyclobutanecarboxylic acid ethyl ester

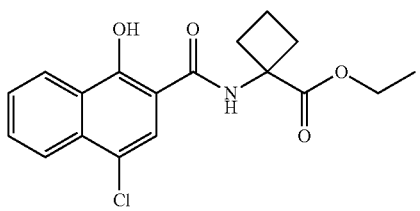

C₁₈H₁₈ClNO₄ (347.80), LCMS (ESI): 348.05 (MH⁺).

1-[(1-Hydroxy-naphthalene-2-carbonyl)-amino]-
cyclopentanecarboxylic acid methyl ester

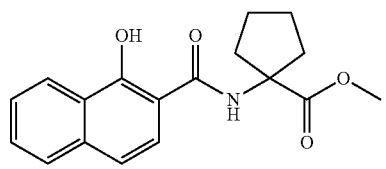

1.00 g 1-amino-cyclopentanecarboxylic acid methyl ester hydrochloride, 0.698 g 1-hydroxy-2-naphthoic acid, 2.12 g HATU and 1.94 ml N,N'diisopropyl-ethylamine in 40 ml of dimethylformamide were stirred at 65° C. for 1 hour, followed by room temperature for 2 days. Water was added and the mixture was extracted with diethyl ether three times. The combined organic layers were dried with magnesium sulfate and concentrated in vacuo. Purification by flash chromatography on silica with heptane/ethyl acetate afforded 0.5 g of 1-[(1-Hydroxy-naphthalene-2-carbonyl)-amino]-cyclopentanecarboxylic acid methyl ester.

$C_{18}H_{19}NO_4$ (313.36), LCMS (ESI): 314.2 (MH$^+$).

The following intermediates were prepared in analogy to the preparation of 1-[(1-Hydroxy-naphthalene-2-carbonyl)-amino]-cyclopentanecarboxylic acid methyl ester from the corresponding 1-Hydroxy-naphthalene-2-carboxylic acids and the corresponding alpha-amino acid methyl or ethyl esters:

1-[(4-Chloro-1-hydroxy-naphthalene-2-carbonyl)-amino]-cyclopentanecarboxylic acid methyl ester

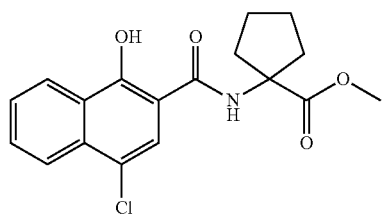

$C_{18}H_{18}ClNO_4$ (347.80), LCMS (ESI): 348.1 (MH$^+$).

2-[(4-Chloro-1-hydroxy-naphthalene-2-carbonyl)-amino]-2-methyl-butyric acid ethyl ester

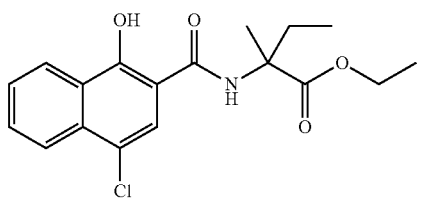

$C_{18}H_{20}ClNO_4$ (349.82), LCMS (ESI): 350.1 (MH$^+$).

(R)-2-[(4-Chloro-1-hydroxy-naphthalene-2-carbonyl)-amino]-2-methyl-butyric acid ethyl ester

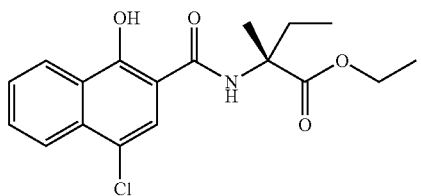

$C_{18}H_{20}ClNO_4$ (349.82), LCMS (ESI): 350.1 (MH$^+$).

(S)-2-[(4-Chloro-1-hydroxy-naphthalene-2-carbonyl)-amino]-2-methyl-butyric acid ethyl ester

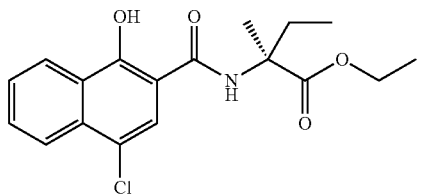

$C_{18}H_{20}ClNO_4$ (349.82), LCMS (ESI): 350.1 (MH$^+$).

2-{[4-Fluoro-1-(hydroxy)naphthalene-2-carbonyl]-amino}-2-methyl-propionic acid methyl ester

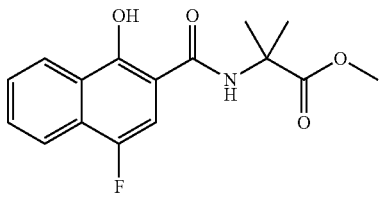

$C_{16}H_{16}FNO_4$ (305.31), LCMS: (ESI$^+$): 306.11 (MH$^+$).

2-[(4-Fluoro-1-hydroxy-naphthalene-2-carbonyl)-amino]-2-methyl-butyric acid methyl ester

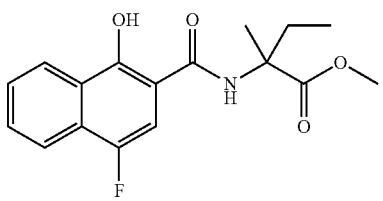

$C_{17}H_{18}FNO_4$ (319.34), LCMS: (ESI$^+$): 320.12 (MH$^+$).

(S)-2-[(4-Fluoro-1-hydroxy-naphthalene-2-carbonyl)-amino]-2-methyl-butyric acid methyl ester

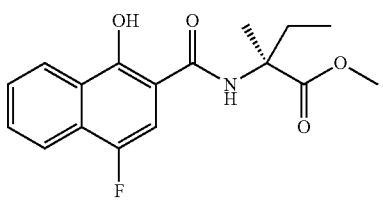

($C_{17}H_{18}FNO_4$ (319.34), LCMS: (ESI$^+$): 320.12 (MH$^+$).

(R)-2-[(4-Fluoro-1-hydroxy-naphthalene-2-carbonyl)-amino]-2-methyl-butyric acid methyl ester

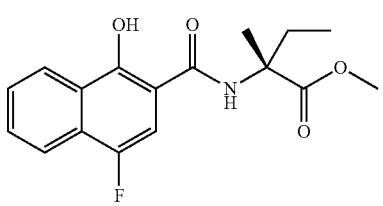

$C_{17}H_{18}FNO_4$ (319.34), LCMS: (ESI$^+$): 320.12(MH$^+$).

1-[(4-Fluoro-1-hydroxy-naphthalene-2-carbonyl)-amino]-cyclobutanecarboxylic acid ethyl ester

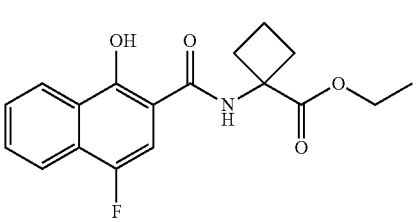

$C_{18}H_{18}FNO_4$ (331.35), LCMS: (ESI$^+$): 332.09 (MH$^+$).

1-[(4-Fluoro-1-hydroxy-naphthalene-2-carbonyl)-amino]-cyclopentanecarboxylic acid methyl ester

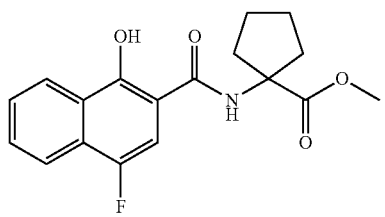

$C_{18}H_{18}FNO_4$ (331.35), LCMS: (ESI$^+$): 332.1 (MH$^+$).

2-{[5-Fluoro-1-(hydroxy)naphthalene-2-carbonyl]-amino}-2-methyl-propionic acid methyl ester

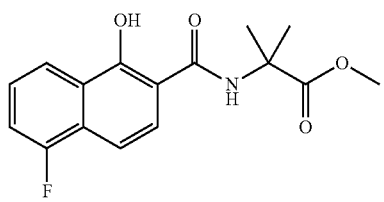

a) 5-Amino-1-methoxynaphthalene

To a mixture of 10 g of 5-amino-1-hydroxynaphthalene in 250 ml of acetonitrile and 25 ml of methanol was added 15 ml of diisopropylethylamine followed by 44 ml of 2M TMSCHN$_2$ in ether. The mixture was stirred at room temperature for 3.5 h after which it was concentrated to a dark oil. The material was purified by flash chromatography on silica gel, eluting with ethyl acetate/dichloromethane/heptane to provide 6.9 g (63%) of 5-amino-1-methoxynaphthalene.

$C_{11}H_{11}NO$ (173.08), LCMS: (ESI$^+$): 174.06 (MH$^+$).

b) 5-Fluoro-1-methoxynaphthalene

A stirred mixture of 6.8 g of 5-amino-1-methoxynaphthalene, 57 ml THF and 74 ml of 48-50% HBF$_4$ was cooled in an ice/salt bath. To the stirred suspension was added dropwise a solution of 3.00 g of sodium nitrite in 6 ml of water. The mixture was stirred at 0-5° C. for 30 minutes after which 300 ml of ether was added. The mixture was stirred at 0-5° C. for 45 minutes after which it was filtered and the residue washed three times with dry ether. The resulting dark red solid was air dried overnight to yield 12.2 g.

The material was dissolved in 70 ml of 1-ethyl-3-methylimidazolium tetrafluoroborate and heated at 70-80° C. for 2 h (gas evolution was observed). The mixture was allowed to cool to room temperature, extracted twice with ether, washed with brine, dried (magnesium sulphate), filtered and concentrated to an oil. The material was dissolved in dichloromethane and flash chromatographed on silica gel, eluting with ethyl acetate/heptane to provide 2.08 g (30%) of 5-fluoro-1-methoxynaphthalene.

$C_{11}H_9FO$ (176.06), LCMS: (CI): 177.04 (MH$^+$).

c) 5-Fluoro-1-hydroxynaphthalene

A stirred solution of 2.08 g of 5-fluoro-1-methoxynaphthalene in 42 ml of dry dichloromethane was cooled to −60 to −65° C. after which was added 13 ml of 1M BBr3 in dichloromethane. The mixture was allowed to warm to room temperature, and stirred at RT for 1 h. The reaction mixture was again cooled to −60 to −65° C. after which was added an additional 13 ml of 1M BBr3 in dichloromethane. The mixture was allowed to warm to RT and stirred at RT for 1.5 h. The mixture was poured into cold water, extracted twice with dichloromethane, dried (sodium sulphate), filtered and concentrated to a purple/white solid. The material was dissolved in a minimum volume of dichloromethane and flash chromatographed on silica gel, eluting with ethyl acetate/dichloromethane/heptane to provide 1.58 g (83%) of 5-fluoro-1-hydroxynaphthalene as a white solid.

$C_{10}H_7FO$ (162.05), LCMS: (ESI$^-$): 161.04 (M-H$^+$).

d) 5-Fluoro-1-methoxymethylnaphthalene

A solution of 0.257 g of 5-fluoro-1-hydroxynaphthalene in 6 ml of dry dichloromethane was cooled in an ice/salt bath after which was added 0.36 ml (2.07 mmol) of ethyl diisopropylamine followed by 0.15 ml (0.16 g, 1.96 mmol) of chloromethylmethyl ether. The mixture was stirred at 0° C. for 0.5 h after which it was allowed to warm to RT and stirred at RT for 11 h. The mixture was poured into saturated sodium carbonate solution, extracted twice with dichloromethane, dried, filtered and concentrated to an oil. The material was dissolved in a minimum volume of dichloromethane and flash chromatographed on silica gel, eluting with ethyl acetate/heptane to provide 0.260 g (79%) of 5-fluoro-1-methoxymethyloxynaphthalene.

e) 2-{[5-Fluoro-1-(hydroxy)naphthalene-2-carbonyl]-amino}-2-methyl-propionic acid methyl ester and 2-{[5-Fluoro-1-(methoxymethoxyl)naphthalene-2-carbonyl]-amino}-2-methyl-propionic acid methyl ester A stirred solution of 0.260 g of 5-fluoro-1-methoxymethyloxynaphthalene in 2.4 ml of dry THF was cooled to −75 to −78° C. after which was added by syringe 0.87 ml of 1.6 M n-BuLi in hexanes. The resulting mixture was stirred at −75 to −78° C. for 5 h. The mixture was poured onto freshly crushed dry ice and allowed to warm to RT. The resulting mixture was treated with ethyl acetate and washed with 0.3 N NaOH. The aqueous solution was acidified to pH 5 with citric acid, extracted twice with ethyl acetate, dried, filtered and concentrated to a white solid, the TLC of which indicates two lower eluting spots. The material was carried forward without further purification.

To 0.183 g of the white solid and 0.33 g of HATU was added 3 ml of DMF followed by 0.28 ml of diisopropylethylamine. The mixture was stirred for 10 minutes after which a solution of 0.135 g of 2,2-dimethylglycine methyl ester hydrochloride in 1.75 ml of dry DMF was added by syringe. The mixture was stirred at RT for 36 h after which it was poured into brine, extracted with ethyl acetate, washed with brine, dried, filtered and concentrated to an oil. The material was dissolved in a minimum volume of dichloromethane and flash chromatographed on silica gel eluting with ethyl acetate/dichloromethane/heptane to provide two batches of material: 0.037 g of 2-{[5-fluoro-1-(hydroxy)naphthalene-2-carbonyl]-amino}-2-methyl-propionic acid methyl ester; and 0.107 g of 2-{[5-fluoro-1-(methoxymethoxyl)naphthalene-2-carbonyl]-amino}-2-methyl-propionic acid methyl ester.

f) 2-{[5-Fluoro-1-(hydroxy)naphthalene-2-carbonyl]-amino}-2-methyl-propionic acid methyl ester To a stirred solution of 0.107 g of 2-{[5-fluoro-1-(methoxymethoxyl)-naphthalene-2-carbonyl]-amino}-2-methylpropionic acid methyl ester in 3 ml of dichloromethane at −65 to −70° C. was added by syringe 0.344 ml of 1M BCl3 in dichloromethane. The mixture was stirred for 10 minutes at −65 to −70° C. after which it was allowed to warm to RT and stirred at RT for 0.5 h. The mixture was poured into brine, extracted twice with ethyl acetate, dried, filtered and concentrated to an oil, which was chromatographed on silica gel eluting with ethyl acetate/dichloromethane/heptane to provide 0.088 g of 2-{[5-fluoro-1-(hydroxy)-naphthalene-2-carbonyl]-amino}-2-methyl-propionic acid methyl ester.

$C_{16}H_{16}FNO_4$ (305.10), LCMS (ESI+): 306.07 04 (MH+).

5-Chloro-2-chloromethyl-benzothiazole

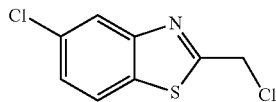

0.966 g of 2-amino-4-chloro-benzenethiol was dissolved in 10 ml of abs. ethanol. 1.44 g of 2-chloro-1,1,1-triethoxy-ethane were added and the reaction was heated at 60° C. overnight. The reaction mixture was then concentrated in vacuo, dissolved in diethyl ether and the organic phase was washed once each with 5% aqueous hydrochloric acid, followed by water and 10% aqueous sodium bicarbonate. The organic layer was dried with magnesium sulfate and concentrated in vacuo. Purification by flash chromatography on silica with heptanes/dichloromethane afforded 1.071 g of 5-chloro-2-chloromethyl benzothiazole as a yellow solid.

$C_8H_5Cl_2NS$ (218.11), LCMS (ESI): 218.00 (MH+).

The following intermediates were prepared in analogy to 5-Chloro-2-chloromethyl-benzothiazole:

| Chemical Name | Structure | ESI+ or ESI− |
|---|---|---|
| 5-tert-Butyl-2-chloromethyl-benzooxazole | 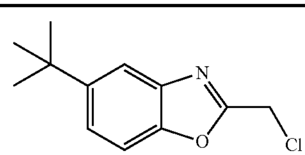 | 224.09 |
| 6-Chloro-2-chloromethyl-benzooxazole | 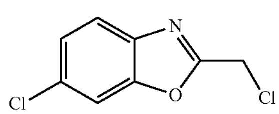 | 202.01 |
| 5,6-Dichloro-2-chloromethyl-1H-benzoimidazole | 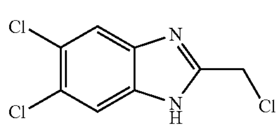 | 235.0 |
| 5-Chloro-2-chloromethyl-1H-benzoimidazole | 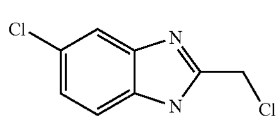 | 201.0 |
| 7-Chloro-2-chloromethyl-5-trifluoromethyl-1H-benzoimidazole | | 269.0 |
| 2-Chloromethyl-5-trifluoromethyl-1H-benzoimidazole | | 235.0 |
| 2-Chloromethyl-1H-benzoimidazole-5-carbonitrile | | 192.1 |

2-Chloromethyl-5-phenyl-[1,3,4]oxadiazole

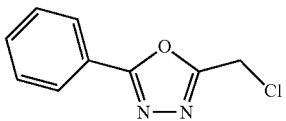

2-Chloromethyl-5-phenyl-[1,3,4]oxadiazole was prepared similarly to 5-chloro-2-chloromethyl-benzothiazole using benzoic acid hydrazide as the reagent.

$C_9H_7ClN_2O$ (194.02), LCMS (ESI): 194.95 (MH+).

(6-Bromo-pyridin-3-yl)-methanol

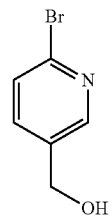

To a solution of 4.85 g of 6-bromo-pyridine-3-carboxaldehyde in 50 mL of MeOH at 0° C. was added 1.93 g of NaBH4. This mixture was allowed to warm to room temperature. Upon completion of the reaction, the reaction mixture was concentrated to a residue, which was partitioned between ethyl acetate and water and extracted with ethyl acetate. The organic layer was washed with brine and dried over sodium sulphate. Purification by flash chromatography (silica, heptanes/ethyl acetate) provided 4.83 g of (6-bromo-pyridin-3-yl)-methanol.

$C_6H_6BrNO$ (186.96), LCMS (ESI): 188.0 (MH+).

2-Bromo-5-bromomethyl-pyridine

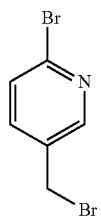

To a solution of 0.91 g (6-bromo-pyridin-3-yl)-methanol in 10 mL of dichloromethane was added 1.88 g of triphenyl phosphine and 2.38 g of carbon tetrabromide. This mixture was stirred at room temperature for 3 hours. It was then concentrated on silica gel, eluted with heptane/ethyl acetate to provide 0.91 g of 2-bromo-5-bromomethyl-pyridine.

$C_6H_5Br_2N$ (248.87), LCMS (ESI): 249.9 (MH+).

1-(6-Trifluoromethyl-pyridin-3-yl)-ethanol

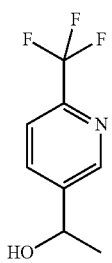

To a solution of 2.0 g 6-trifluoromethyl-pyridine-3-carboxaldehyde in 20 mL of dry THF under inert atmosphere at −78° C. was added dropwise 6 ml of MeMgCl (3 M in THF). This mixture was allowed to warm up to room temperature slowly. Aqueous ammonium chloride was added to reaction mixture. The whole was extracted with ethyl acetate. The organic phase was washed with brine, dried over sodium sulphate. Purification by flash chromatography (silica, haptane/ethyl acetate) provided 0.85 g of 1-(6-trifluoromethyl-pyridin-3-yl)-ethanol.

$C_8H_8F_3NO$ (191.05), LCMS (ESI): 192.1 (MH+).

5-(1-Chloroethyl)-2-trifluoromethyl-pyridine

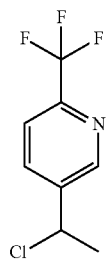

To a solution of 0.30 g of 1-(6-trifluoromethyl-pyridin-3-yl)-ethanol in 5 mL of dry dichloromethane was added 0.34 mL of SOCl2. The reaction mixture was refluxed for a half hour and then poured into ice-water, and extracted with dichloromethane. The organic phase was washed with 10% aqueous sodium hydrogen carbonate solution, dried over sodium sulphate and concentrated in vacuo. The resulting residue was purified by flash chromatography (silica, heptanes/ethyl acetate) to give 0.10 g of 5-(1-chloroethyl)-2-trifluoromethyl-pyridine.

$C_8H_7ClF_3N$ (209.02), LCMS (ESI): 210.0 (MH+).

4-Trifluoromethyl-thiazol-2-yl-methanol

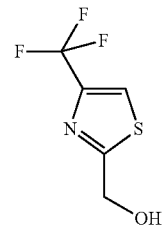

a) 4-Trifluoromethyl-thiazole-2-carboxylic acid ethyl ester

Ethyl thiooxamate (134 mg) and 3-bromo-1,1,1-trifluoroacetone (194 mg) were mixed together and kept under stirring for 5 min at 100° C. in a microwave reactor. The compound was extracted with ethyl acetate (100 ml), and it was washed with water (25 ml) and brine (25 ml) and then dried over sodium sulphate. 131.4 mg of 4-trifluoromethyl-thiazole-2-carboxylic acid ethyl ester was obtained.

$C_7H_6F_3NO2S$ (225.19), LCMS (ESI): 226.0 (MH+).

b) 4-Trifluoromethyl-thiazol-2-yl-methanol

4-Trifluoromethyl-thiazole-2-carboxylic acid ethyl ester (131 mg) was dissolved in THF (5 ml). The reaction mixture was then cooled to −78° C. DIBAL-H (4.7 ml, 1.0 M in tetrahydrofurane) was added slowly during a period of 10 min. The cooling bath was removed, and the solution was kept under stirring for 30 min at RT. The solution was then cooled to 0° C., and NaF (784 mg) was added, followed by the slow addition of 3 ml water. The product was extracted by ethyl acetate. The solvent was removed, and the crude product was used in alkylation reactions without further purification.

2-Bromomethyl-5-trifluoromethyl-pyridine

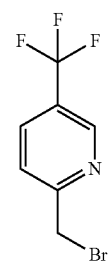

To (5-trifluoromethyl-pyridin-2-yl)-methanol (1.65 g) in dichloromethane (20 ml) at 0° C. (ice-bath) under nitrogen was added triphenylphosphine (3.66 g, 13.98 mmol) in portions, followed by addition of carbon tetrabromide (3.23 g) in portions. The ice-bath was removed and the flask was sealed with a glass stopper. The reaction mixture was gently stirred for 1 hour. The crude reaction mixture was loaded onto a silica gel column (120 g), and eluted with methyl acetate/hexane to give 2-bromomethyl-5-trifluoromethyl-pyridine as a light orange oil (1.65 g, 73%).

$C_7H_5BrF_3N$ (238.95), LCMS (ESI): 239.90 (MH$^+$).

(2-Thiophen-2-yl-pyrimidin-5-yl)-methanol

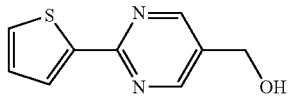

a) 2-Thiophen-2-yl-pyrimidine-5-carboxylic acid methyl ester 0.663 g of thiophene-2-carboxamide.HCl was dissolved in 10 mL of N,N-dimethyl formamide. 0.97 g of sodium 3,3-dimethoxy-2-methoxycarbonyl-propen-1-olate was added and the reaction was heated at 100° C. under nitrogen for 1 hour. The reaction mixture was then cooled to room temperature, and 30 mL of water were added to obtain a precipitate. The solid was filtered and was washed with 5 mL of water. After drying in vacuum overnight at 45° C. 0.65 g of 2-thiophen-2-yl-pyrimidine-5-carboxylic acid methyl ester were obtained as a white solid (73% yield).

$C_{10}H_8N_2O_2S$ (220.25) LCMS (ESI): 221.0 (MH$^+$).

b) (2-Thiophen-2-yl-pyrimidin-5-yl)-methanol 0.175 g of 2-thiophen-2-yl-pyrimidine-5-carboxylic acid methyl ester was dissolved in 3 mL of tetrahydrofuran. The reaction was cooled to 0° C. (ice-water bath) and then 2.39 mL of diisobutylaluminumhydride (1.0 M in tetrahydrofuran) were added dropwise. The reaction was left stirring at 0° C. for 30 minutes, then at room temperature overnight. Water was added, the mixture was extracted with ethylacetate, and the organic layer was dried with magnesium sulphate, filtered and concentrated to afford the crude (2-thiophen-2-yl-pyrimidin-5-yl)-methanol, which was used without purification for the next reactions.

$C_9H_8N_2OS$ (192.03) LCMS (ESI):193.0 (MH$^+$).

The following intermediates were prepared in analogy to (2-thiophen-2-yl-pyrimidin-5-yl)-methanol

| Chemical Name | Structure | ESI+ or ESI– |
|---|---|---|
| (2-Methylsulfanyl-pyrimidin-5-yl)-methanol | 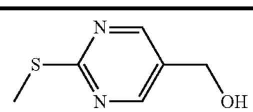 | 157.0 |
| (2-Cyclopropyl-pyrimidin-5-yl)-methanol | 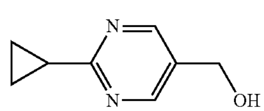 | 151.0 |
| (2-Isopropyl-pyrimidin-5-yl)-methanol | | 153.1 |

(2-Trifluoromethyl-pyrimidin-5-yl)-methanol

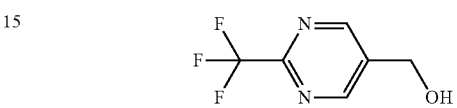

a) 2-Trifluoromethyl-pyrimidine-5-carboxylic acid 2,2,2,-Trifluoroacetamidine was reacted with sodium 3,3-dimethoxy-2-methoxycarbonyl-propen-1-olate in a similar way as described for the synthesis of (2-thiophen-2-yl-pyrimidin-5-yl)-methanol, step a), however 2-trifluoromethyl-pyrimidine-5-carboxylic acid was obtained instead of the ester after the work up as a yellow oil.

$C_6H_3F_3N_2O_2$ (192.01) LCMS (ESI–): 190.97 (M-H$^+$).

b) (2-Trifluoromethyl-pyrimidin-5-yl)-methanol

To 0.2 g of 2-trifluoromethyl-pyrimidine-5-carboxylic acid 2 mL of diethyl ether were added, and the solution was cooled in ice-water bath to 0° C. Then 0.126 mL of N-methylmorpholine were added, followed by 0.135 mL of isobutylchloroformate. The reaction was left stirring for one hour at room temperature. The yellow solid formed was filtered and washed with diethyl ether. To the filtrate, 0.115 g (3.12 mmol) of sodium borohydride was then added at 0° C. and left stirring at that temperature for one hour. 5 mL of a saturated aqueous solution of sodium and potassium tartrate were then added and the mixture was extracted twice with ethyl acetate, dried with magnesium sulphate, filtered and concentrated to afford 0.09 g of (2-Trifluoromethyl-pyrimidin-5-yl)-methanol as an oil, which was used without further purification.

C6H5F3N2O (178.11) LCMS (ESI) 179.0 (MH$^+$).

5-Bromomethyl-2-methanesulfinyl-pyridine

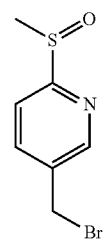

a) 5-Methyl-2-methylsulfanyl-pyridine

To a solution of 1.11 g of 2-fluoro-5-methyl-pyridine in 16 mL abs. NMP was added NaSMe (1.4 g). This mixture was heated to 90° C. for one minute in a microwave reactor. The reaction mixture was diluted with ethyl acetate and washed with water and brine. The organic layer was dried over sodium sulphate and concentrated in vacuo. The resulting residue was purified by flash chromatography (silica, heptane/ethyl acetate) to yield 1.39 g of 5-methyl-2-methylsulfanyl-pyridine.

$C_7H_9NS$ (139.04), LCMS (ESI): 140.0 (MH$^+$).

b) 2-Methanesulfinyl-5-methyl-pyridine and 2-methanesulfonyl-5-methyl-pyridine

To a solution of 0.69 g 5-methyl-2-methylsulfanyl-pyridine in 15 mL HOAc was added NaBO3.4H2O (1.92 g). This mixture was stirred at room temperature for 5 hours. The reaction mixture was then poured into ice. NaOH (10 M) was used to adjust the pH to 7. The mixture was extracted with ethyl acetate. The organic phase was dried over sodium sulphate and concentrated in vacuo. The residue was purified by flash chromatography (silica, heptane/ethyl acetate) to yield 0.51 g of 2-methanesulfinyl-5-methyl-pyridine and 0.27 g of 2-methanesulfonyl-5-methyl-pyridine.

$C_7H_9NOS$ (155.04), LCMS (ESI): 156.01 (MH$^+$).
$C_7H_9NO_2S$ (171.03), LCMS (ESI): 172.0 (MH$^+$).

c) 5-Bromomethyl-2-methanesulfinyl-pyridine

To a solution of 0.33 g of 2-methanesulfinyl-5-methyl-pyridine in 20 mL of carbon tetrachloride was added 0.40 g NBS and 6 mg benzoyl peroxide. This mixture was refluxed for 4 hours. The reaction mixture was cooled to room temperature, washed with aqueous sodium hydrogen carbonate solution, dried over sodium sulphate, and concentrated to dryness. Purification by flash chromatography (silica, heptane/ethyl acetate) provided 0.14 g of 5-bromomethyl-2-methanesulfinyl-pyridine.

$C_7H_8BrOS$ (232.95), LCMS (ESI+): 234.0 (MH$^+$).

5-Bromomethyl-2-methanesulfonyl-pyridine

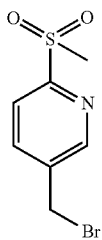

To a solution of 0.25 g of 2-methanesulfonyl-5-methyl-pyridine (from the preparation of 5-bromomethyl-2-methanesulfinyl-pyridine, step b)) in 20 mL carbon tetrachloride was added 0.27 g NBS and 4 mg benzoyl peroxide. This mixture was refluxed for 4 hours. The reaction mixture was cooled to room temperature, washed with aqueous sodium hydrogen carbonate solution, dried over sodium sulphate, and concentrated to dryness. Purification by flash chromatography (silica, heptane/ethyl acetate) provided 0.11 g of 5-bromomethyl-2-methanesulfonyl-pyridine.

$C_7H_8BrNO_2S$ (248.94), LCMS (ESI): 250.0 (MH$^+$).

Sulfurous acid bis-[4-(pentafluorothio)-benzyl]ester

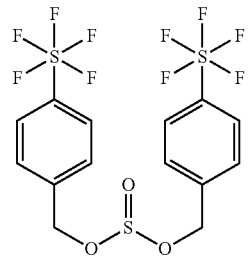

To a solution of 1.0 g of 4-pentafluorothiobenzaldehyde in 6 mL MeOH was added 0.17 g NaBH4. This mixture was stirred at room temperature overnight. The reaction mixture was concentrated and the residue was partitioned between ethyl acetate and water and extracted with ethyl acetate. The organic layer was washed with brine, dried over sodium sulphate and evaporated to yield 0.96 g of (4-pentafluorothiophenyl)-methanol as an oil.

The crude product was taken up directly in anhydrous toluene (10 mL) and SOCl2 (0.36 mL) was added dropwise over 1 minute. After being stirred for 5 minutes, the reaction mixture was concentrated. The residue was purified by flash chromatography (silica, heptanes/ethyl acetate) to provide 0.33 g of sulfurous acid bis-[4-(pentafluorothio)-benzyl]ester as colorless oil.

Determination of CXCR2 Inhibition: Calcium Fluorescence Assay (FLIPR)

The assay is based on the detection of intracellular calcium changes detected by the selective, calcium-chelating dye, Fluo-4 (Molecular Probes). A large fluorescence intensity increase is observed upon calcium association with Fluo-4. The dye is delivered to the cell interior using an acetoxymethylester form of Fluo-4, where the intracellular esterase activity results in the charged species being released and trapped within the cytoplasm of the cell. Hence, influx of calcium to this cytoplasmic pocket, via release from intracellular pools and the phospholipase C cascade can be detected. By co-expressing the CXCR2 receptor and the promiscuous $G_{\alpha 16}$ protein, activation of this chemokine receptor is directed into this phospholipase C cascade resulting in intracellular calcium mobilization.

The CHO—K1 cells stably transfected with human CXCR2 and the promiscuous $G_{\alpha 16}$ protein were maintained in a log phase of growth at 37° C. and 5% $CO_2$ in the following media: Iscove's, 10% FBS, 1× Penicillin-Streptomycin, 400 µg/mL G418 and 350 µg/mL Zeocin. Approximately 24-48 hours prior to the assay, 20,000-30,000 cells/well were plated onto a 96-well black/clear bottomed assay plate (Becton Dickinson) with a well volume of 180 µl. For dye-loading the culture medium was carefully removed and replaced by 100 µl/well dye solution (4 µM Fluo-4 in 135 mM NaCl, 5 mM KCl, 1 mM magnesium sulphate, 5 mM glucose, 20 mM Hepes, 2.5 mM probenecid; pH 7.4). Cells were incubated for 1 h at 37° C., and then washed 3× with buffer. After washing 90 µl buffer/well were left. Increasing concentrations of compound was added in 45 µl buffer (4× concentrated) followed by 10 min incubation at 37° C. Then the chemokine (10-100 nM) was applied in 45 µl buffer (4× concentrated) and the measurement performed for 2 min. The IC50 value of a compound was determined by calculation of % inhibition of total calcium response to the chemokine.

Compounds of this invention exhibit activity in the CXCR2-calcium fluorescence (FLIPR) assay in a range of about 0.01 nM to 30000 nM. Some compounds of the invention may additionally exhibit activity as modulators of CXCR1 and CX3CR1.

CXCR2 inhibition for selected example compounds:

| Example No. | IC50 [µM] |
|---|---|
| 5 | 3.213 |
| 42 | 0.972 |
| 74 | 0.980 |
| 105 | 1.625 |
| 110 | 0.700 |
| 120 | 4.445 |
| 127 | 0.996 |
| 131 | 0.200 |

What is claimed is:

1. A compound of formula I:

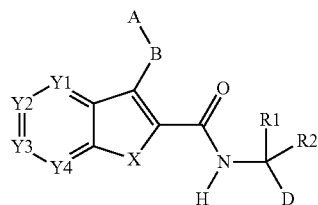

wherein:
X is —S—;
Y1, Y2, Y3 and Y4
 are —CR8—,
 R8 is hydrogen, F or Cl;
A is cyclohexyl, piperidyl, phenyl, naphthyl, indanyl, 2,3-dihydro-benzo[1,4]dioxanyl, benzo[1,3]-dioxolyl, furyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl, benzimidazolyl, benzoxadiazolyl, benzotriazolyl, benzo-1,1-dioxid-thiophenyl or quinolyl;
 in which cyclohexyl is unsubstituted or substituted by 1, 2 or 3 methyl radicals;
 in which piperidyl is unsubstituted or substituted by alkyl having 1, 2, 3 or 4 carbon atoms, —C(O)CH$_3$, —C(O)CH$_2$CH$_3$, —C(O)-cyclopropyl, —C(O)CF$_3$, —C(O)OC(CH$_3$)$_3$;
 in which the aryl or heteroaryl radical is unsubstituted or substituted by 1, 2 or 3 radicals selected from the group consisting of F, Cl, Br, CN, NO$_2$, SF$_5$,-N(CH$_3$)$_2$, methoxy, ethoxy, alkyl having 1, 2, 3 or 4 carbon atoms, CF$_3$, OCF$_3$, OCH$_2$CF$_3$, OCHF$_2$, SCH$_3$, SOCH$_3$, SO$_2$CH$_3$, SCF$_3$, phenyl, benzyl, pyrazolyl, pyrrolyl and triazolyl, in which phenyl can be substituted by Cl;
B is —O—C(R11R12)-;
 R11 is hydrogen;
 R12 is hydrogen or methyl;
D is C(O)OH;
R1 and R2
 are, independently of one another, alkyl having 1, 2 or 3 carbon atoms;
or
R1 and R2
 form, together with the carbon atom to which they are attached, a 3-, 4-, or 5-membered carbon ring;
and a pharmaceutically acceptable salt thereof.

2. A compound of the formula I according to claim 1 selected from the group consisting of:
 2-[(3-Benzyloxy-benzo[b]thiophen-2-carbonyl)-amino]-2-methyl-propionic acid;
 2-Methyl-2-{[3-(quinolin-2-ylmethoxy)-benzo[b]thiophene-2-carbonyl]-amino}-propionic acid;
 2-{[3-(Benzothiazol-2-ylmethoxy)-benzo[b]thiophene-2-carbonyl]-amino}-2-methyl-propionic acid;
 2-{[3-(Benzothiazol-2-ylmethoxy)-thieno[2,3-b]pyridine-2-carbonyl]-amino}-2-methyl-propionic acid;
 2-Methyl-2-{[3-(quinolin-2-ylmethoxy)-benzo[b]thiophene-2-carbonyl]-amino}-butyric acid;
 2-Methyl-2-{[3-(4-trifluoromethyl-benzyloxy)-benzo[b]thiophene-2-carbonyl]-amino}-propionic acid;
 2-Methyl-2-{[3-(6-trifluoromethyl-pyridin-3-ylmethoxy)-benzo[b]thiophene-2-carbonyl]-amino}-propionic acid;
 2-{[3-(Benzothiazol-2-ylmethoxy)-benzo[b]thiophene-2-carbonyl]-amino}-2-methyl-butyric acid;
 1-{[3-(Quinolin-2-ylmethoxy)-benzo[b]thiophene-2-carbonyl]-amino}-cyclopentanecarboxylic acid;
 2-Methyl-2-{[3-(4-trifluoromethyl-benzyloxy)-benzo[b]thiophene-2-carbonyl]-amino}-butyric acid;
 2-Methyl-2-{[3-(6-trifluoromethyl-pyridin-3-ylmethoxy)-benzo[b]thiophene-2-carbonyl]-amino}-butyric acid;
 2-Methyl-2-{[3-(4-trifluoromethoxy-benzyloxy)-benzo[b]thiophene-2-carbonyl]-amino}-propionic acid;
 1-{[3-(4-Trifluoromethyl-benzyloxy)-benzo[b]thiophene-2-carbonyl]-amino}-cyclopentanecarboxylic acid;
 2,3-Dimethyl-2-{[3-(4-trifluoromethyl-benzyloxy)-benzo[b]thiophene-2-carbonyl]-amino}-butyric acid;
 2-Methyl-2-{[3-(4-trifluoromethoxy-benzyloxy)-benzo[b]thiophene-2-carbonyl]-amino}-butyric acid;
 1-{[3-(4-Trifluoromethoxy-benzyloxy)-benzo[b]thiophene-2-carbonyl]-amino}-cyclopentanecarboxylic acid;
 2,3-Dimethyl-2-{[3-(4-trifluoromethoxy-benzyloxy)-benzo[b]thiophene-2-carbonyl]-amino}-butyric acid;
 2-{[3-(Benzothiazol-2-ylmethoxy)-5-fluoro-benzo[b]thiophene-2-carbonyl]-amino}-2-methyl-propionic acid;
 2-{[5-Fluoro-3-(6-trifluoromethyl-pyridin-3-ylmethoxy)-benzo[b]thiophene-2-carbonyl]-amino}-2-methyl-propionic acid;
 1-{[3-(Benzothiazol-2-ylmethoxy)-benzo[b]thiophene-2-carbonyl]-amino}-cyclobutanecarboxylic acid;
 2-{[3-(5-Fluoro-benzothiazol-2-ylmethoxy)-benzo[b]thiophene-2-carbonyl]-amino}-2-methyl-propionic acid;
 2-{[3-(Imidazo[1,2-a]pyridin-2-ylmethoxy)-benzo[b]thiophene-2-carbonyl]-amino}-2-methyl-propionic acid;
 2-Methyl-2-({3-[1-(4-trifluoromethyl-phenyl)-ethoxy]-benzo[b]thiophene-2-carbonyl}-amino)-propionic acid; and
 2-Methyl-2-({3-[1-(4-trifluoromethyl-phenyl)-ethoxy]-benzo[b]thiophene-2-carbonyl}-amino)-butyric acid;
or a pharmaceutically acceptable salt thereof.

* * * * *